(12) United States Patent
Inagaki et al.

(10) Patent No.: US 8,084,460 B2
(45) Date of Patent: Dec. 27, 2011

(54) 6,7-UNSATURATED-7-CARBAMOYL SUBSTITUTED MORPHINAN DERIVATIVE

(75) Inventors: Masanao Inagaki, Osaka (JP);
Shin-ichiro Hara, Osaka (JP);
Nobuhiro Haga, Osaka (JP); Yoshinori Tamura, Osaka (JP); Yoshihisa Goto, Amagasaki (JP); Tsuyoshi Hasegawa, Osaka (JP)

(73) Assignee: Shionogi & Co., Ltd., Osaka (JP)

(*) Notice: Subject to any disclaimer, the term of this patent is extended or adjusted under 35 U.S.C. 154(b) by 596 days.

(21) Appl. No.: 11/920,851

(22) PCT Filed: May 25, 2006

(86) PCT No.: PCT/JP2006/310454
§ 371 (c)(1),
(2), (4) Date: Mar. 10, 2009

(87) PCT Pub. No.: WO2006/126637
PCT Pub. Date: Nov. 30, 2006

(65) Prior Publication Data
US 2009/0203723 A1    Aug. 13, 2009

(30) Foreign Application Priority Data

May 25, 2005  (JP) .................... 2005-151864
Mar. 10, 2006  (JP) .................... 2006-065762
May 23, 2006  (WO) ............... PCT/JP2006/310231

(51) Int. Cl.
*C07D 489/00* (2006.01)
*C07D 489/08* (2006.01)
*A01N 43/42* (2006.01)
*A61K 31/44* (2006.01)

(52) U.S. Cl. ........................... 514/282; 546/46
(58) Field of Classification Search .............. 514/282; 546/46
See application file for complete search history.

(56) References Cited

U.S. PATENT DOCUMENTS

| | | | |
|---|---|---|---|
| 4,272,541 A | 6/1981 | Kotick et al. | |
| 4,275,205 A | 6/1981 | Kotick et al. | |
| 4,347,361 A | 8/1982 | Quick et al. | |
| 4,370,333 A | 1/1983 | Ghosh et al. | |
| 4,440,932 A | 4/1984 | Kotick et al. | |
| 4,443,605 A | 4/1984 | Kotick et al. | |
| 6,177,438 B1 | 1/2001 | Nagase et al. | |
| 2004/0019071 A1 | 1/2004 | Sakami et al. | |
| 2004/0024004 A1 | 2/2004 | Sherman et al. | |
| 2004/0157784 A1 | 8/2004 | Chopdekar et al. | |
| 2005/0038061 A1 | 2/2005 | Schutz et al. | |
| 2006/0052409 A1 | 3/2006 | Kawai et al. | |

FOREIGN PATENT DOCUMENTS

| | | |
|---|---|---|
| EP | 1 522 542 A1 | 4/2005 |
| JP | 56-15290 | 2/1981 |
| JP | 58-8067 | 1/1983 |
| JP | 2000/503019 | 3/2000 |
| JP | 2003/528819 | 9/2003 |
| JP | 2004-501094 | 1/2004 |
| JP | 2004/522706 | 7/2004 |
| JP | 2006/502190 | 1/2006 |
| WO | WO 95/13071 A2 | 5/1995 |
| WO | WO 97/25331 A1 | 7/1997 |
| WO | WO 01/37785 A2 | 5/2001 |
| WO | WO 01/37785 A3 | 5/2001 |
| WO | WO 01/37785 A9 | 5/2001 |
| WO | WO 01/85150 A2 | 11/2001 |
| WO | WO 01/85150 A3 | 11/2001 |
| WO | WO 01/85257 A2 | 11/2001 |
| WO | WO 01/85257 A3 | 11/2001 |
| WO | WO 02/36573 A2 | 5/2002 |
| WO | WO 02/42309 A1 | 5/2002 |
| WO | WO 2004/005294 A2 | 1/2004 |
| WO | WO 2004/007503 | 1/2004 |

(Continued)

OTHER PUBLICATIONS

West, Anthony R., Solid State Chemistry and its Applications, Wiley, New York, 1988, pp. 358 & 365.*
Chun-Su et al., The journal of Supportive Oncology, vol. 2(2), pp. 11-122, ( 2004 ).*
Ohkawa et al.; "7-Arylidenenaltrexones as Selective $\delta_1$ Opioid Receptor Antagonists", J. Med. Chem., vol. 41, pp. 4177-4180, (1998).
Fujii et al.; "The First Example of the Steroselective Synthesis of 7β-Carbamoyl-4,5α-Epdxymorphinan Via a Novel and Reactive γ-Lactone", Chem. Pharm. Bull., vol. 52, No. 6, pp. 747-750, (2004).

(Continued)

Primary Examiner — D M Seaman
Assistant Examiner — Niloofar Rahmani
(74) Attorney, Agent, or Firm — Finnegan, Henderson, Farabow, Garrett & Dunner, LLP

(57) ABSTRACT

A novel compound which is useful as an agent for treating and/or preventing emesis, vomiting and/or constipation.
A compound represented by the formula (I):

[Chemical formula 1]

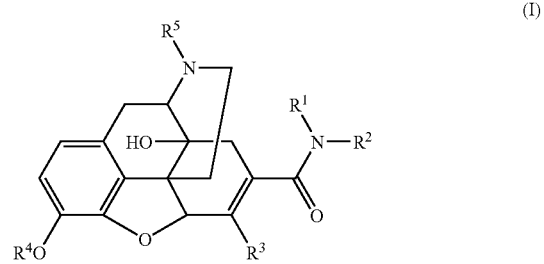

(I)

wherein $R^1$ and $R^2$ are each independently hydrogen, optionally substituted lower alkyl, optionally substituted lower alkenyl, optionally substituted cycloalkyl, optionally substituted aryl etc., $R^3$ is hydrogen, hydroxy, optionally substituted lower alkyl, optionally substituted lower alkenyl, optionally substituted lower alkynyl, optionally substituted lower alkoxy etc., $R^4$ is hydrogen or lower alkyl, $R^5$ is hydrogen, lower alkyl, cycloalkyl lower alkyl or lower alkenyl, or a pharmaceutically acceptably salt, or a solvate thereof is provided.

19 Claims, No Drawings

FOREIGN PATENT DOCUMENTS

| WO | WO 2004/026819 A2 | 4/2004 |
|---|---|---|
| WO | WO 2005/105093 A2 | 11/2005 |
| WO | WO 2005/105093 A3 | 11/2005 |
| WO | WO 2005/117589 A1 | 12/2005 |
| WO | WO 2006/034039 A2 | 3/2006 |
| WO | WO 2006/034309 A3 | 3/2006 |

OTHER PUBLICATIONS

Leland et al.; "Analgesic Narcotic Antagonists. 5. 7,7-Dimethyldihydrocodeinones and 7,7-Dimethyldihydromorphinones[1]", J. Med. Chem., American Chemical Society, vol. 24, pp. 717-721, (1981).

Kotick et al.; "Analgesic Narcotic Antagonists. 8. 7α-Alkyl-4,5α-Epoxymorphinan-6-Ones", J. Med. Chem., American Chemical Society, vol. 24, pp. 1445-1450, (1981).

Herlihy et al.; "Novel Opiates and Antagonists. 5. 7-Carbethoxy-N-(Cycloalkylmethyl)-3-Hydroxymorphinan-6-Ones and -Isomorphinan-6-Ones", American Chemical Society, J. Med. Chem., vol. 25, pp. 986-990, (1982).

Kotick et al.; "Analgesic Narcotic Antagonists. 15. Potent Narcotic Agonist 7β-(Arylalkyl)-4,5α-Epdxymorphinans", J. Med. Chem., American Chemical Society, vol. 26, pp. 1050-1056, (1983).

Koolpe et al.; "Opioid Agonists and Antagonists. 6-Desoxy-6-Substituted Lactone, Epoxide, and Glycidate Ester Derivatives of Naltrexone and Oxymorphone", J. Med. Chem., American Chemical Society, vol. 28, pp. 949-957, (1985).

Hernàndez-Gallegos et al.; "A Free-Wilson/Fujita-Ban Analysis and Prediction of the Analgesic Potency of Some 3-Hydroxy- and 3-Methoxy-N-Alkylmorphinan-6-One Opioids[1]", J. Med. Chem., American Chemical Society, vol. 33, pp. 2813-2817, (1990).

Portoghese et al.; "Synthesis of Naltrexone-Derived δ-Opioid Antagonists. Role of Conformation of the δ Address Moiety", J. Med. Chem., American Chemical Society, vol. 37, pp. 579-585, (1994).

Gao et al.; "Synthesis of 7-Arylmorphinans. Probing the "Address" Requirements for Selectivity at Opioid δ Receptors", J. Med. Chem., American Chemical Society, vol. 41, pp. 3091-3098, (1998).

Ananthan et al.; "Synthesis, Opioid Receptor Binding, and Biological Activities of Naltrexone-Derived Pyrido- and Pyrimidomorphinans", J. Med. Chem., American Chemical Society, vol. 42, pp. 3527-3538, (1999).

Nagase et al.; "Facile Intramolecular O-14 → C-7 Acetyl Transfer in Opiate 14-Acetate Esters", J. Org. Chem., American Chemical Society, vol. 55, pp. 365-367, (1990).

Leland et al.; "7α- Or 7β-(4-Phenylbutyl)Dihydrocodeine Derivatives", J. Org. Chem., American Chemical Society, vol. 48, pp. 1813-1819, (1983).

Gao et al.; "Monophenylation of Morphinan-6-Ones With Diphenyliodonium Iodide", J. Org. Chem., American Chemical Society, vol. 60, pp. 2276-2278, (1995).

Gao et al.; "Boron Tribromide-Catalyzed Rearrangement of 7,7-Diphenylhydromorphone to 6,7-Diphenylmorphine: A Novel Conversion of Ketones to Allylic Alcohols", J. Org. Chem., American Chemical Society, vol. 61, pp. 2466-2469, (1996).

Brandt; "A Uniform Molecular Model of δ Opioid Agonist and Antagonist Pharmacophore Conformations", Journal of Computer-Aided Molecular Design, Vo. 12, pp. 615-621, (1998).

Ronzoni et al.; "Synthesis and NMR Characterization of a Novel Class of Thienomorphinans", Organic Letters, vol. 1, No. 3, pp. 513-515, (1999).

Lester et al.; "Vilsmeier Reactions With 14-Hydroxy-Dihydrocodeinone and Derived Enol Ethers", Tetrahedron, vol. 20, pp. 1407-1417, (1964).

Lester et al.; "Vilsmeier Reactions With Cyclic Ketals of 14-Hydroxy-dihydrocodeinone and Some New Cyclic Derivatives of 14-Hydroxy-dihydrocodeinone", Tetrahedron, vol. 21, pp. 771-778, (1965).

Boche et al.; "Electrophilic Amination of Acyl Anion Equivalents: Mild Oxidation of Aldehydes to Amides Via 0-(Trimethylsilyl)Aldehyde Cyanohydrin Anions", Tetrahedron Letters, vol. 23, No. 32, pp. 3255-3256, (1982).

"Persistently Low Natural Killer Cell Activity", Life Science, vol. 48, No. 2, pp. 111-116, (1991).

Munson et al.; "Ligand: A Versatile Computerized Approach for Characterization of Ligand-Binding Systems", Analytical Biochemistry, vol. 107(1), pp. 220-239, (1980).

Dalzell et al.; "4,5-Alpha-Epoxy-3-Hydroxy-7,17-DI:Substd.-Morphinan-6-One(S)—Useful as Analgesics and/or Narcotic", Abstract, JP 57-122088, Jul. 29, 1982.

Portoghese, "The Role of Concepts in Structure-Activity Relationship Studies of Opiod Ligands," J. Med. Chem., 35(11):1927-1937 (1992).

International Search Report mailed Jun. 20, 2006, for Application No. PCT/JP2006/310454.

International Preliminary Report on Patentability issued Nov. 29, 2007, for Application No. PCT/JP2006/310454.

Supplementary European Search Report mailed Jul. 11, 2011, in European Application No. EP 06746833.0.

* cited by examiner

6,7-UNSATURATED-7-CARBAMOYL SUBSTITUTED MORPHINAN DERIVATIVE

This application is a 371 national phase filing of International Application No. PCT/JP2006/310454, filed May 25, 2006, now International Publication No. WO 2006/126637, which claims priority from Japanese Patent Application No. 2005-151864, filed May 25, 2005, Japanese Patent Application No. 2006-065762, filed Mar. 10, 2006, and International Application No. PCT/JP2006/310231, filed May 23, 2006, now International Publication No. WO 2006/126529, each of which are herein incorporated by reference for all purposes.

TECHNICAL FIELD

The present invention relates to a 6,7-unsaturated-7-carbamoyl-substituted morphinan derivatives, which are useful as an agent for treating and/or preventing nausea, emesis, vomiting and/or constipation, particularly as an agent for alleviating and/or preventing a side effect (emesis, vomiting and/or constipation etc.) induced by a compound having the opioid receptor (e.g. opioid μ receptor) agonistic activity.

BACKGROUND ART

An opioid receptor agonist such as morphine and the like which is used as an analgesic is very effective in a patient having cancer pain, but as a side effect, induces severe nausea, emesis, vomiting, constipation, anuresis, and itching. Various antiemetics and anti-constipation agents are clinically used, but it can not be said that any of them exhibits the sufficient effect, and an excellent side effect alleviating agent is also demanded for improving QOL of a patient.

Patent Literatures 1 and 2, and Non-patent Literature 1 describe to the effect that a morphinan derivative is effective in treating or preventing emesis and vomiting induced by an opioid μ agonist, and Non-Patent Literature 2 describes that a 6,7-saturated-7-carbamoyl-substituted-morphinan derivatives have the opioid δ receptor antagonism. However, none of them describes or suggests the present compound.

[Patent Literature 1] International Patent Application Publication WO 2004-007503
[Patent Literature 2] International Patent Application Publication WO 95/13071
[Non-Patent Literature 1] Journal of Medicinal Chemistry 41, 4177-4180 (1998)
[Non-Patent Literature 2] Chemical and Pharmaceutical Bulletin, 52 (66) 747-750 (2004)

DISCLOSURE OF INVENTION

Problems to be Solved by the Invention

We found 6,7-unsaturated-7-carbamoyl-substituted morphinan derivatives useful as a composition for treating and/or preventing emesis, vomiting and/or constipation.

Means to Solve the Problems

The present invention provides:

(1) a compound represented by the formula (I):

[Chemical formula 1]

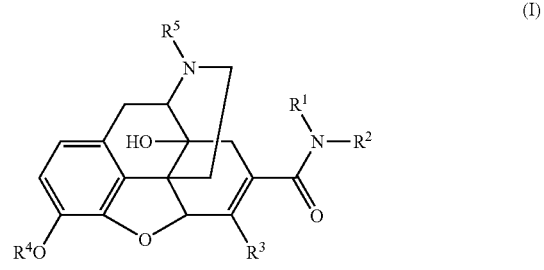

wherein $R^1$ and $R^2$ are each independently hydrogen, optionally substituted lower alkyl, optionally substituted lower alkenyl, optionally substituted lower alkynyl, optionally substituted lower alkylsulfonyl, optionally substituted acyl, optionally substituted cycloalkyl, optionally substituted cycloalkenyl, optionally substituted aryl, an optionally substituted heterocyclic group, or optionally substituted arylsulfonyl, or $R^1$ and $R^2$ are taken together with the nitrogen atom to which they are attached to form optionally substituted heterocycle;

$R^3$ is hydrogen, hydroxy, optionally substituted lower alkyl, lower optionally substituted lower alkenyl, optionally substituted lower alkynyl optionally substituted lower alkoxy, mercapto, optionally substituted lower alkylthio, optionally substituted amino, optionally substituted carbamoyl, optionally substituted acyl, optionally substituted acyloxy, optionally substituted aryl, or an optionally substituted heterocyclic group, a group represented by the formula:

[Chemical formula 2]

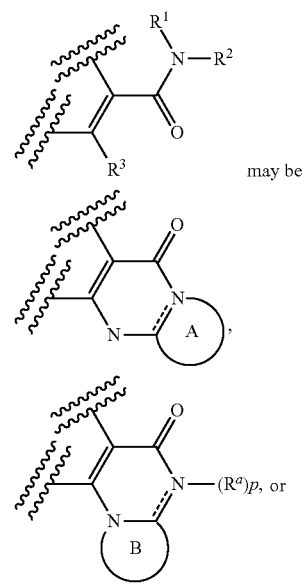

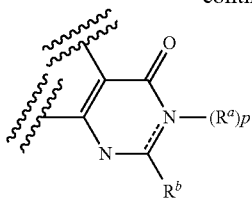

wherein ring A or ring B are each independently optionally substituted nitrogen-containing heterocycle optionally containing additional nitrogen atom, an oxygen atom, and/or a sulfur atom in the ring;
broken line indicates the presence or the absence of a bond;
when a broken line indicates the presence of a bond, p is 0;
when a broken line indicates the absence of a bond, p is 1;
$R^a$ is hydrogen, optionally substituted lower alkyl, optionally substituted lower alkenyl, or optionally substituted lower alkynyl;
and $R^b$ is hydrogen or oxo;
$R^4$ is hydrogen or lower alkyl;
$R^5$ is hydrogen, lower alkyl, cycloalkyl lower alkyl or lower alkenyl,
or a pharmaceutically acceptable salt, or a solvate thereof,
(1') a compound represented by the formula (I):

[Chemical formula 3]

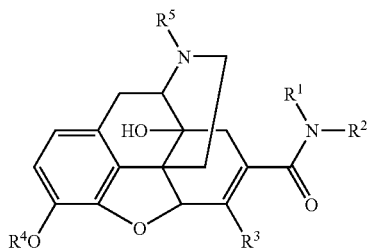
(I)

wherein $R^1$ and $R^2$ are each independently hydrogen, optionally substituted lower alkyl, optionally substituted lower alkenyl, optionally substituted cycloalkyl, optionally substituted aryl, or an optionally substituted heterocyclic group, or $R^1$ and $R^2$ are taken together with the nitrogen atom to which they are attached to form optionally substituted heterocycle;
$R^3$ is hydrogen, hydroxy, optionally substituted lower alkyl, optionally substituted lower alkenyl, optionally substituted lower alkynyl, optionally substituted lower alkoxy, mercapto, optionally substituted lower alkylthio, optionally substituted aryl, or an optionally substituted heterocyclic group;
$R^4$ is hydrogen or lower alkyl;
and $R^5$ is hydrogen, lower alkyl, cycloalkyl lower alkyl or lower alkenyl;
or a pharmaceutically acceptable salt, or a solvate thereof,
(2) the compound according to (1) or (1'), wherein $R^3$ is hydroxy,
or a pharmaceutically acceptable salt, or a solvate thereof,
(3) the compound according to (1) or (1'), wherein $R^3$ is optionally substituted amino,
or a pharmaceutically acceptable salt, or a solvate thereof,
(4) the compound according to (1) or (1'), wherein $R^3$ is amino substituted with optionally substituted arylsulfonyl,
or a pharmaceutically acceptable salt, or a solvate thereof,
(5) the compound according to any one of (1) to (4), and (1'), wherein $R^1$ is hydrogen or lower alkyl, $R^2$ is optionally substituted lower alkyl, optionally substituted phenyl, optionally substituted cycloalkyl, or an optionally substituted heterocyclic group, and $R^5$ is cyclopropylmethyl;
or a pharmaceutically acceptable salt, or a solvate thereof,
(6) the compound according to any of (1) to (5), and (1'), wherein $R^1$ is hydrogen, $R^2$ is lower alkyl optionally substituted with lower alkoxy or with a heterocyclic group that is optionally substituted with aryl, phenyl optionally substituted with lower alkyl or with lower alkoxy, cycloalkyl substituted with lower alkylcarbonyl, or a heterocyclic group substituted with lower alkoxy or with aryl, $R^4$ is hydrogen, and $R^5$ is cyclopropylmethyl, or a pharmaceutically acceptable salt, or a solvate thereof.
(7) a pharmaceutical composition containing the compound according to any one of (1) to (6), and (1'), or a pharmaceutically acceptable salt, or a solvate thereof,
(8) a composition having opioid receptor antagonistic activity containing the compound according to (1) to (6), and (1'), or a pharmaceutically acceptable salt, or a solvate thereof,
(9) a composition for treating and/or preventing emesis, vomiting and/or constipation containing the compound according to any one of (1) to (6), and (1'), or a pharmaceutically acceptable salt, or a solvate thereof,
(10) a composition for alleviating and/or preventing a side effect induced by a compound having the opioid receptor agonistic activity, containing the compound according to any one of (1) to (6), and (1'), or a pharmaceutically acceptable salt, or a solvate thereof,
(11) a composition for treatment and/or prevention according to (10), wherein the side effect is emesis, vomiting and/or constipation,
(12) an agent for treatment and/or prevention according to (10) or (11), wherein the compound having the opioid receptor agonistic activity is morphine, oxycodone, or a pharmaceutically acceptable salt, or a solvate thereof,
(13) use of the compound according to any one of (1) to (6), and (1'), or a pharmaceutically acceptable salt, or solvate thereof for producing a medicament for treating and/or preventing emesis, vomiting and/or constipation,
(14) use of the compound according to any one of (1) to (6), and (1'), or a pharmaceutically acceptable salt, or solvate thereof, for producing a medicament for alleviating and/or preventing a side effect induced by a compound having the opioid receptor agonistic activity,
(15) a method for treating and/or preventing emesis, vomiting and/or constipation, comprising administering the compound according to any one of (1) to (6) and (1'), or a pharmaceutically acceptable salt, or a solvate thereof,
(16) a method for alleviating and/or preventing a side effect induced by a compound having the opioid receptor agonistic activity, comprising administering the compound according to any one of (1) to (6) and (1'), its pharmaceutically acceptable salt, or a solvate thereof,
(17) a composition for analgesic containing
a compound having an opioid receptor agonistic activity,
and an effective amount of compound according to any one of (1) to (6) and (1'),
or a pharmaceutically acceptable salt, or a solvate thereof, for alleviating and/or preventing a side effect induced by administration of the compound having an opioid receptor agonistic activity,

(18) a composition for analgesic containing
a compound having an opioid receptor agonistic activity,
and an effective amount of compound according to any one of (1) to (6) and (1'),
or a pharmaceutically acceptable salt or a solvate thereof, for treating and/or preventing emesis, vomiting and/or constipation induced by administration of the compound having an opioid receptor agonistic activity,
(19) the analgesic according to (17) or (18), wherein the compound having the opioid receptor agonistic activity, is morphine, oxycodone, its pharmaceutically acceptable salt, or a solvate thereof.

EFFECT OF THE INVENTION

The compound (I) of the present invention has the activity of treating/or preventing emesis, vomiting and/or constipation, particularly emesis, vomiting and/or constipation induced by a compound having the opioid receptor (e.g. opioid μ receptor) agonistic activity, and is useful as a composition for alleviating a side effect of a patient to whom a compound having the opioid receptor agonistic activity is administered or is in the middle of administration.

BEST MODE FOR CARRYING OUT THE INVENTION

As used herein, the "halogen" includes fluorine, chlorine, bromine and iodine. A halogen part of the "halogeno lower alkyl", the "halogeno lower alkoxy", and the "halogeno lower alkylthio" is the same.

The "lower alkyl" includes a straight or branched alkyl of a carbon number of 1 to 10, preferably a carbon number of 1 to 6, further preferably 1 to 3, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl. Preferable are methyl, ethyl, isopropyl, n-butyl, sec-butyl, tert-butyl, and 1-ethylpropyl.

Examples of a substituent of the "optionally substituted lower alkyl" include halogen, hydroxy, lower alkoxy, halogeno lower alkoxy, hydroxy lower alkoxy, lower alkylthio, lower alkylamino, acylamino, acyl, acyloxy, cyano, carboxy, lower alkoxycarbonyl, carbamoyl, lower alkylcarbamoyl, cyanocarbamoyl, lower alkylsulfonylcarbamoyl, arylsulfonylcarbamoyl, sulfamoyl, lower alkylsulfamoyl, lower alkylsulfonyl, cycloalkyl optionally substituted with one or more substituents selected from Substituent group α(wherein Substituent group α is halogen, hydroxy, lower alkyl, halogeno lower alkyl, hydroxy lower alkyl, lower alkoxy lower alkyl, carboxy lower alkyl, lower alkoxycarbonyl lower alkyl, amino lower alkyl, lower alkylamino lower alkyl, acylamino lower alkyl, cyano lower alkyl, lower alkoxy, halogeno lower alkoxy, hydroxy lower alkoxy, lower alkylthio, halogeno lower alkylthio, acyl, acyloxy, amino, lower alkylamino, acylamino, cyano, carboxy, lower alkoxycarbonyl, carbamoyl, lower alkylcarbamoyl, arylcarbamoyl, cyanocarbamoyl, lower alkylsulfonylcarbamoyl, sulfamoyl, lower alkylsulfamoyl, lower alkylsulfonyl, aryl optionally substituted with lower alkylenedioxy, and a heterocyclic group), cycloalkenyl optionally substituted with one or more substituents selected from Substituent group α, aryl optionally substituted with one or more substituents selected from Substituent group α, aryloxy optionally substituted with one or more substituents selected from Substituent group α, arylthio optionally substituted with one or more substituents selected from Substituent group α, a heterocyclic group optionally substituted with one or more substituents selected from Substituent group α, and heterocyclic oxy optionally substituted with one or more substituents selected from Substituent group α.

A lower alkyl part of the "halogeno lower alkyl", the "hydroxy lower alkyl", the "amino lower alkyl", the "acylamino lower alkyl", the "acyloxy lower alkyl", the "cycloalkyl lower alkyl", the "lower alkoxy", the "halogeno lower alkoxy", the "hydroxy lower alkoxy", the "lower alkoxy lower alkyl", the "lower alkoxycarbonyl", the "carboxy lower alkyl", the "lower alkoxycarbonyl lower, alkyl", the "lower alkylthio", the "halogeno lower alkylthio", the "lower alkylamino", the "lower alkylamino lower alkyl", the "lower alkylcarbamoyl", the "lower alkylsulfamoyl", the "lower alkylsulfonyl", the "aryl lower alkyl", the "tri lower alkylsilyl", the "lower alkyldiarylsilyl", the "triaryl lower alkylsilyl", the "lower alkoxy lower alkoxy lower alkyl", the "lower alkylthio lower alkyl", the "aryl lower alkoxy lower alkyl", the "lower alkylsulfonyl", the "lower alkylsulfonylcarbamoyl", the "lower alkylcarbonyl", the "cyano lower alkyl", the "lower alkoxycarbonylamino", the "lower alkylenedioxy", and the "heterocyclic lower alkyl" is the same as that of the aforementioned "lower alkyl".

A substituent of the "optionally substituted lower alkoxy", the "optionally substituted lower alkylthio", and the "optionally substituted lower alkylsulfonyl" is the same as the aforementioned substituent of the "optionally substituted lower alkyl".

The "lower alkenyl" includes a straight or branched alkenyl of a carbon number of 2 to 10, preferably a carbon number of 2 to 8, further preferably a carbon number of 3 to 6 having one or more double bonds at an arbitrary position. Specifically, examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl. The lower alkenyl in $R^5$ is preferably allyl.

The substituent of the "optionally substituted lower alkenyl" is the same as that of the "optionally substituted lower alkyl".

The "lower alkynyl" includes straight or branched alkynyl of a carbon number of 2 to 10, preferably a carbon number of 2 to 8, further preferably a carbon number of 3 to 6 having one or more triple bonds at an arbitrary position. Specifically, examples include ethynyl, propynyl, butynyl, pentynyl, hexynyl, heptynyl, octynyl, nonynyl, and decynyl. These may further have a double bond at an arbitrary position.

The substituent of the "optionally substituted lower alkynyl" is the same as that of the "optionally substituted lower alkyl".

Examples of the substituent of the "optionally substituted amino" include lower alkyl optionally substituted with one or more substituents selected from Substituent group α, cycloalkyl optionally substituted with one or more substituents selected from Substituent group α, acyl optionally substituted with one or more substituents selected from Substituent group α, amino optionally substituted with one or more substituents selected from Substituent group α, aryl optionally substituted with one or more substituents selected from Substituent group α, sulfamoyl, lower alkylsulfamoyl optionally substituted with one or more substituents selected from Substituent group α, arylsulfamoyl optionally substituted with one or more substituents selected from Substituent group α, lower alkylsulfonyl optionally substituted with one or more substituents selected from Substituent group α, arylsulfonyl optionally substituted with one or more substituents selected from Substituent group α, arylamino optionally substituted with one or more substituents selected from Substituent group α, and a heterocyclic group optionally substituted with one or more substituents selected from Substituent group α.

The substituent of the "optionally substituted carbamoyl" is the same as that of the "optionally substituted amino".

The "cycloalkyl" is a carbocyclic group of a carbon number of 3 to 10, preferably a carbon number of 3 to 8, more preferably a carbon number of 4 to 8 and, for example, includes cyclopropyl, cyclobutyl, cyclopentyl, cyclohexyl, cycloheptyl, cyclooctyl, cyclononyl and cyclodecyl. These may be further condensed with "aryl" described later or "heterocyclic group" described later at an arbitrary position.

As the "cycloalkyl" in $R^1$ and $R^2$, cyclopropyl, cyclobutyl, cyclopentyl and cyclohexyl are preferable.

A cycloalkyl part of the "cycloalkyl lower alkyl" and the "cycloalkylcarbonyl" is the same as the aforementioned "cycloalkyl".

As the "cycloalkyl lower alkyl" in $R^5$, cyclopropylmethyl is preferable."

Examples of the substituent of the "optionally substituted cycloalkyl" include on or more substituents selected from the aforementioned Substituent group α. The substituent can replace at an arbitrary position, and may replace at a carbon atom having a bond of cycloalkyl.

The "cycloalkenyl" includes cycloalkenyl having one or more double bonds at an arbitrary position in a ring of the aforementioned cycloalkyl, and examples include cyclopropenyl, cyclobutenyl, cyclopentenyl, cyclohexenyl, cycloheptyl, cyclooctynyl and cyclohexadienyl.

As the "cycloalkenyl" in $R^1$ or $R^2$, cyclopropenyl, cyclobutenyl, cyclopentenyl, and cyclohexenyl are preferable.

A cycloalkenyl part of the "cycloalkenylcarbonyl" is the same as the aforementioned "cycloalkenyl".

The substituent of the "optionally substituted cycloalkenyl" is the same as that of the aforementioned "optionally substituted cycloalkyl".

The "aryl" includes phenyl, naphthyl, anthryl and phenanthryl, and phenyl is particularly preferable.

An aryl part of the "aryloxy", the "arylthio", the "aryl lower alkyl", the "lower alkyldiarylsilyl", the "triaryl lower alkylsilyl", the "aryl lower alkyloxy lower alkyl", the "arylsulfonyl", the "arylsofamoyl", the "arylamino", the "arylcarbamoyl", and the "arylsulfonylcarbamoyl" is the same as the aforementioned "aryl".

Examples of the substituent of the "optionally substituted aryl", the "optionally substituted phenyl", and the "optionally substituted arylsulfonyl" include the Substituent group α, phenyl substituted with one or more groups selected from Substituent group α, phenoxy substituted with one or more groups selected from Substituent group α, and lower alkylenedioxy.

The "heterocyclic group" includes a heterocyclic group having one or more heteroatoms arbitrarily selected from O, S and N in a ring, and specifically includes a 5- to 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl; a bicyclic condensed heterocyclic group such as indolyl, isoindolyl, indazolyl, indolidinyl, indolinyl, isoindolinyl, quinolyl, isoquinolyl, cinnolinyl, phthalazinyl, quinazolinyl, naphthridinyl, quinoxalinyl, purinyl, pteridinyl, benzopyranyl, benzimidazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, quinazolinyl, quinolyl, isoquinolyl, naphthyridinyl, dihydropyridyl, tetrahydroquinolyl, and tetrahydrobenzothienyl; a tricyclic condensed heterocyclic group such as carbazolyl, acridinyl, xanthenyl, phenothiazinyl, phenoxathiinyl, phenoxazinyl, and dibenzofuryl; a non-aromatic heterocyclic group such as dioxanyl, thiiranyl, thioranyl, thietanyl, oxilanyl, oxetanyl, oxathioranyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, dihydrofuryl, tetrahydrofuryl, tetrahydropyranyl, tetrahydrothiazolyl, and tetrahydroisothiazolyl. Preferable is a 5- to 6-membered heteroaryl or a non-aromatic heterocyclic group.

As the "heterocyclic group" in $R^1$ and $R^2$, pyrazolyl, pyridyl, pyridazinyl, pyrimidinyl, pyrazinyl, isoxazolyl, thiazolyl, thiadiazolyl, furyl, thienyl, indolyl, indazolyl, quinolyl, isoquinolyl, benzoxazolyl, benzothiazolyl, oxetanyl, tetrahydrofuryl, and tetrahydropyranyl are preferable. Pyridyl, pyridazinyl, pyrimidinyl, and pyrazinyl are more preferable. Pyridyl and pyrimidinyl are particularly preferable.

As the heterocyclic group of the "optionally substituted lower alkyl" in $R^1$ and $R^2$, isoxazolyl, oxazolyl, and oxadiazolyl are preferable. Oxadiazolyl is particularly preferable.

A heterocyclic part of the "heterocyclic oxy" and the "heterocyclic lower alkyl" is the same as the aforementioned "heterocyclic group".

Examples of the substituent of the "optionally substituted heterocyclic group" include one or more groups selected from the group consisting of the Substituent group α and oxo. The substituent can replace at an arbitrary position, or may replace at a carbon atom or a nitrogen atom having a bond of the heterocyclic group.

The "acyl" includes straight or branched chain-like aliphatic acyl of a carbon number of 1 to 10, preferably a carbon number of 1 to 6, further preferably a carbon number of 1 to 4, cyclic aliphatic acyl of a carbon number of 4 to 9, preferably a carbon number of 4 to 7, aroyl and heterocyclic carbonyl. Herein, the "chain-like aliphatic" includes the aforementioned "lower alkyl", the aforementioned "lower alkenyl", and the aforementioned "lower alkynyl". The "cyclic aliphatic" includes the aforementioned "cycloalkyl" and the aforementioned "cycloalkenyl". A heterocyclic part of the heterocyclic carbonyl is the same as the aforementioned "heterocyclic group". Examples of the acyl include formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl, pyridine carbonyl, piperidinecarbonyl, piperazinecarbonyl, morpholinocarbonyl, and the like.

An acyl part of the "acylaxy", the "acylamino", the "acylamino lower alkyl" and the "acyloxy lower alkyl" is the same as the aforementioned "acyl".

The substituent of the "optionally substituted acyl" or the "optionally substituted" is the same as the substituent of the aforementioned "optionally substituted lower alkyl" when the "acyl" is chain-like aliphatic acyl, and includes one or more groups selected from the Substituent group a when the "acyl" is cyclic aliphatic acyl, aroyl or heterocyclic carbonyl.

The "optionally substituted heterocycle" formed when $R^1$ and $R^2$ are taken together with the nitrogen atom to which they are attached, includes a 5-membered or 6-membered heterocycle containing the nitrogen atom to which $R^1$ and $R^2$ are attached and, further, optionally containing one or more heteroatoms selected from N, S and O. For example, the case where

[Chemical formula 4]

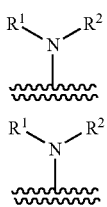

is a saturated heterocycle group such as

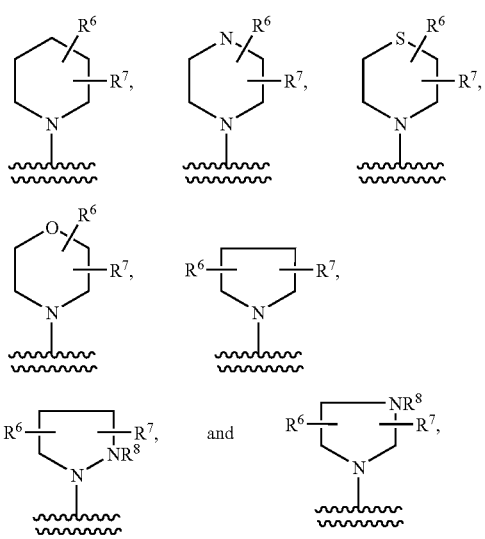

, or an unsaturated heterocycle group such as

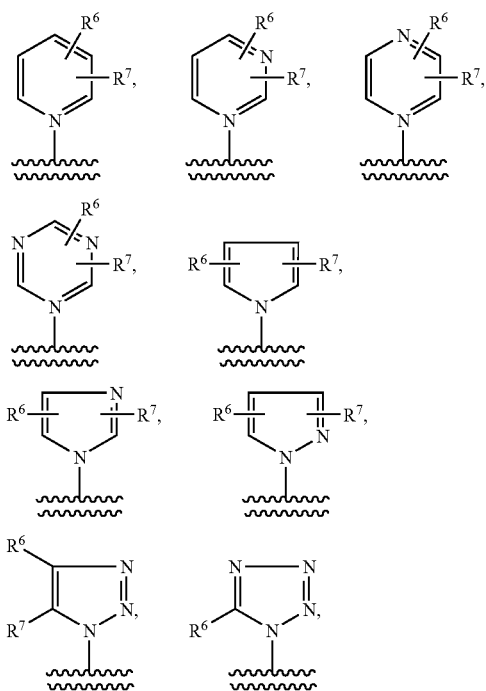

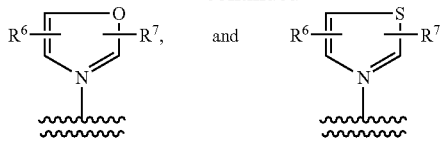

wherein $R^6$, $R^7$ and $R^8$ are each independently hydrogen, halogen, hydroxy, lower alkyl, lower alkoxy, lower alkylthio, acyl, acyloxy, amino, lower alkylamino, acylamino, lower alkoxycarbonylamino, carboxy or lower alkoxycarbonyl, is included and the preferable is a saturated heterocycle group such as morpholine ring, pyrrolidine ring, piperidine ring, piperazine ring, and the like optionally substituted with hydrogen, halogen, hydroxy or lower alkyl.

The substituent of the "optionally substituted heterocycle, which is formed when $R^1$ and $R^2$ are taken together with the nitrogen atom to which they are attached" is the same as the substituent of the "optionally substituted heterocyclic group".

[Chemical formula 5]

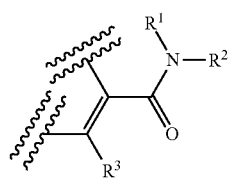

is

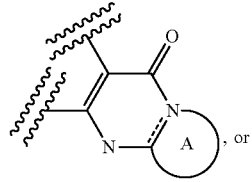

, or

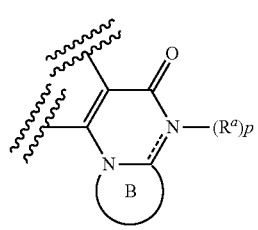

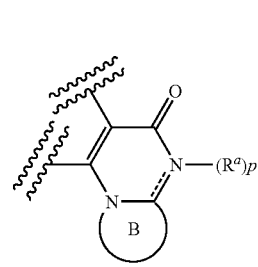

includes, for example, the following:
[Chemical formula 6]
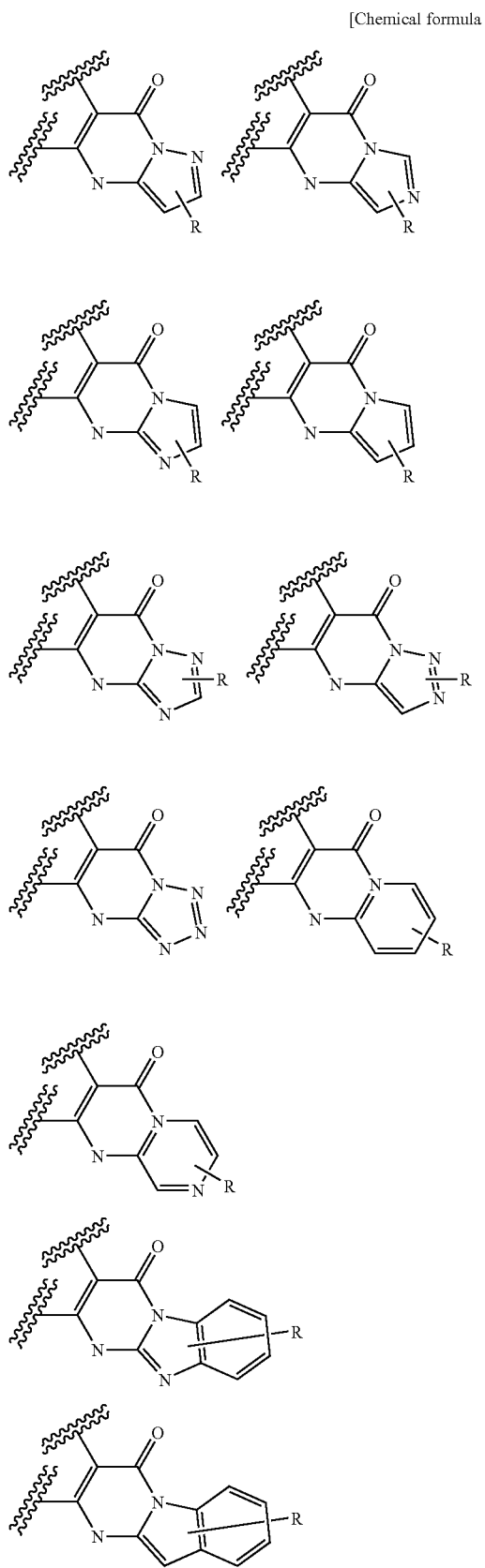
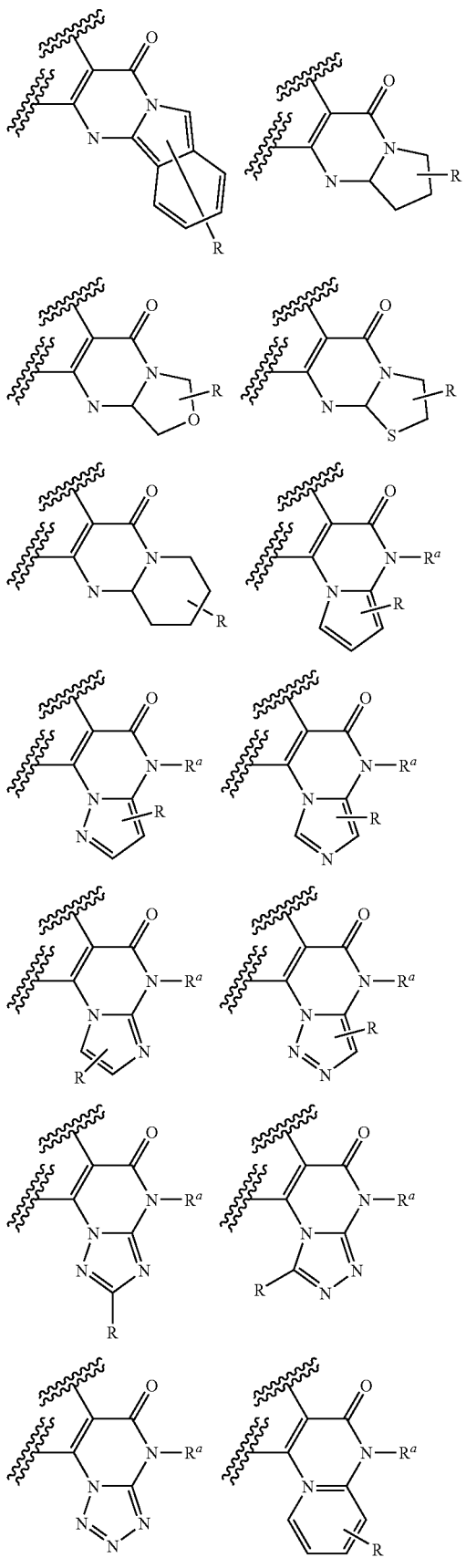

-continued

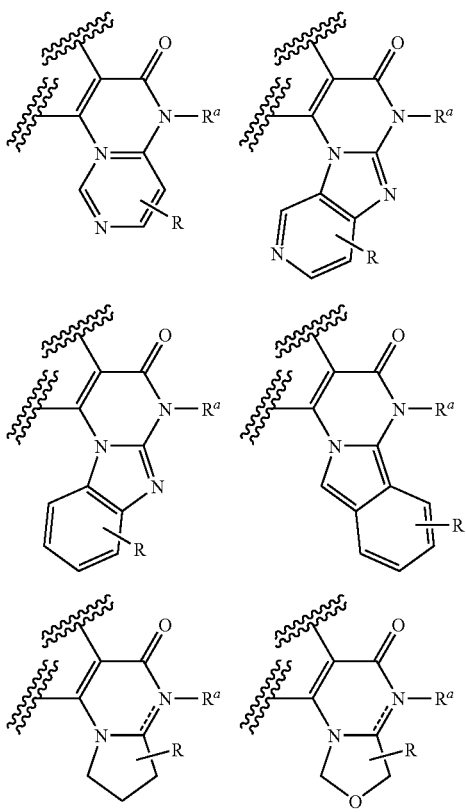

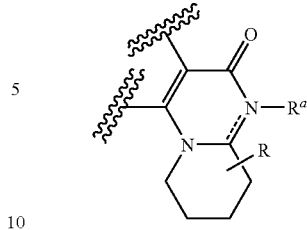

wherein $R^a$ is as defined above, and R is hydrogen or a group selected from Substituent group α.

Herein, the "solvate" includes, for example, a solvate with an organic solvent, a hydrate and the like. When a hydrate is formed, any number of water molecules may be coordinated.

The compound (I) includes a pharmaceutically acceptable salt. Examples include salts with alkali metals (lithium, sodium or potassium), alkaline earth metals (magnesium or calcium), ammonium, organic bases or amino acids, and salts with inorganic acids (hydrochloric acid, sulfuric acid, nitric acid, hydrobromic acid, phosphoric acid and hydroiodic acid), or organic acids (acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzenesulfonic acid, p-toluenesulfonic acid, methanesulfonic acid, or ethanesulfonic acid). Particularly, hydrochloric acid, phosphoric acid, tartaric acid, or methanesulfonic acid is preferable. These salts can be formed by a conventional method.

In addition, the compound (I) is not limited to a specific isomer, but includes all possible isomers and racemates. For example, when $R^3$ of the compound (I) is hydroxy, the compound (I) includes other tautomer, that is, the following compound (I').

[Chemical formula 7]

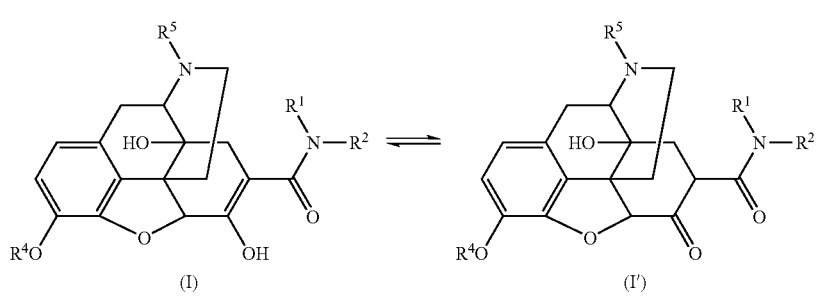

The present compound (I) can be produced by the following process.

(A process)

[Chemical formula 8]

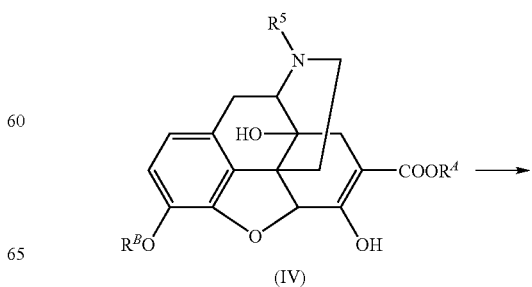

-continued

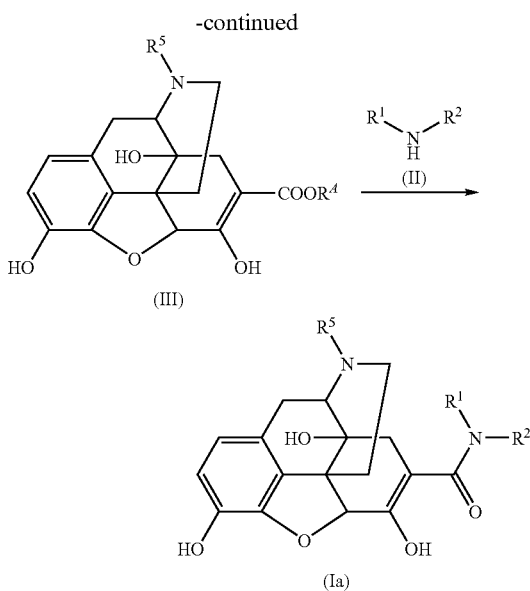

wherein $R^A$ is an ester residue, $R^B$ is hydrogen or hydroxy protecting group, and other symbols are as defined above.

Herein, the ester residue includes lower alkyl such as methyl, ethyl and the like, aryl lower alkyl such as benzyl, phenethyl and the like, acyloxy lower alkyl such as acetyloxymethyl and the like, etc.

The hydroxy protecting group is not limited to, but includes lower alkyl (methyl, tert-butyl etc.), aryl lower alkyl (triphenylmethyl, benzyl etc.), tri lower alkylsilyl(trimethylsilyl, tert-butyldimethylsilyl, triethylsilyl, triisopropylsilyl etc.), lower alkyldiarylsilyl(tert-butyldiphenylsilyl etc.), triaryl lower alkylsilyl(tribenzylsilyl etc.), lower alkoxy lower alkyl (methoxymethyl, 1-ethoxyethyl, 1-methyl-1-methoxyethyl etc.), lower alkoxy lower alkoxy lower alkyl(methoxyethoxymethyl etc.), lower alkylthio lower alkyl(methylthiomethyl etc.), optionally substituted tetrahydropyranyl (tetrahydropyran-2-yl, 4-methoxytetrahydropyran-4-yl etc.), tetrahydrothiopyranyl(tetrahydrothiopyran-2-yl etc.), tetrahydrofuranyl (tetrahydrofuran-2-yl etc.), tetrahydrothiofuranyl(tetrahydrothiofuran-2-yl etc.), aryl lower alkyloxy lower alkyl(benzyloxymethyl etc.), lower alkylsulfonyl (methanesulfonyl, ethanesulfonyl etc.), acyl(acetyl etc.) and arylsulfonyl(p-toluenesulfonyl etc.).

(First Step)

First, the known compound or compound (IV) derived therefrom is deprotected by a conventional method.

For example, when a protecting group is benzyl, the compound is dissolved or suspended in a suitable solvent (ethyl acetate, methanol, ethanol, tetrahydrofuran, dioxane, dimethylformamide, acetic acid, dilute hydrochloric acid, or a mixture thereof), and a hydrogenation reaction using a palladium catalyst (palladium hydroxide, palladium-carbon, palladium-barium sulfate, palladium-aluminum oxide, palladium black etc.) affords compound (III). A reaction may be performed at about 0° C. to about 100° C., preferably about 20° C. to about 50° C. for about 15 minutes to about 24 hours, preferably about 1 hour to about 5 hours.

(Second Step)

Then, the resulting compound (III) is directly amidated to obtain compound (Ia).

For example, compound (III) and compound (II) may be reacted by heating in a suitable solvent (methanol, ethanol, tetrahydrofuran, dimethylformamide, diethyl ether, dichloromethane, dichloroethane, toluene, xylene, chlorobenzene, orthodichlorobenzene, 2-methoxyethanol or diethylene glycol dimethyl ether or a mixture thereof) or without a solvent at about 0° C. to about 250° C., preferably about 80° C. to about 200° C. for about 30 minutes to about 24 hours, preferably about 1 to 12 hours in the presence or the absence of an amine compound (ammonia, dimethylamine, triethylamine, pyridine, dimethylaniline, dimethylaminopyridine, lutidine etc.).

In order to effectively carry a reaction forward, the reaction may be performed by microwave irradiation. A reaction temperature, and an irradiation time are not particularly limited, but are about 100° C. to about 200° C. and about 5 minutes to about 5 hours, preferably about 10 minutes to about 1 hour. It is preferable to use, as a solvent, a polar solvent such as methanol, ethanol, 1-propanol, ethylene glycol, glycerin, 2-methoxyethanol, 2-ethoxyethanol, N,N-dimethylformamide, diethylene glycol dimethyl ether and the like.

When $R^4$ of objective compound (I) is lower alkyl, an objective compound can be obtained by the conventional etherization reaction at an arbitrary stage.

(B Process)

[Chemical formula 9]

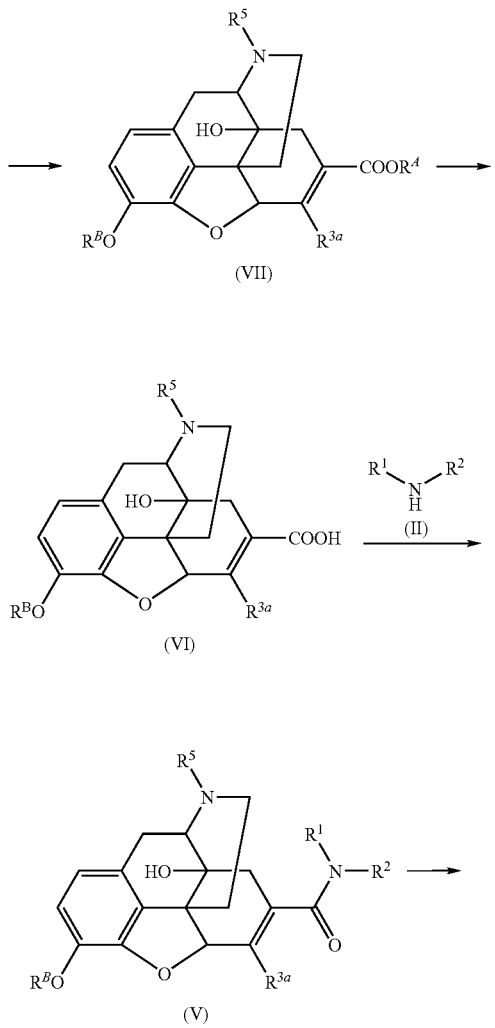

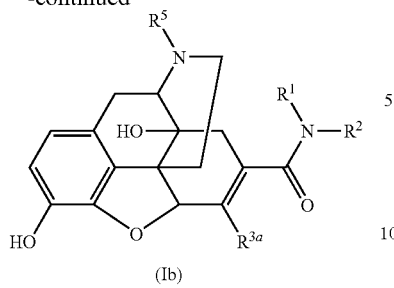

wherein $R^{3a}$ is hydroxy, or optionally substituted lower alkoxy, and other symbols are as defined above.

(First Step)

When $R^3$ of objective compound (I) is optionally substituted lower alkoxy, first, the known compound (IV) is etherized by a conventional method.

For example, the compound is reacted with an alkylating agent or an alcohol having a $R^{3a}$ group corresponding to an objective compound in the presence of a base (sodium hydride, potassium hydride, sodium hydroxide, potassium hydroxide, calcium hydroxide, barium hydroxide, sodium carbonate, potassium carbonate, calcium carbonate, cesium carbonate, sodium methoxide, sodium ethoxide, potassium tert-butoxide, sodium bicarbonate or metal sodium), or under the condition of Mitsunobu reaction in a suitable solvent (N,N-dimethylformamide, dimethyl sulfoxide, toluene, benzene, xylene, a mixture thereof, or the like) cyclohexane, hexane, dichloromethane, 1,2-dichloroethane, tetrahydrofuran, dioxane, acetone, methyl ethyl ketone, acetonitrile, water or a mixture thereof) to obtain compound (VII). The reaction may be performed at −70 to 180° C., preferably about 0 to 150° C. for about 15 minutes to about 24 hours, preferably about 1 hour to about 5 hours.

(Second Step)

Then, compound (VII) is hydrolyzed to obtain compound (VI). The reaction may be performed under ice-cooling to at a reflux temperature of a solvent for about 15 minutes to about 24 hours, preferably, 1 hour to about 5 hours using an inorganic base (sodium hydroxide, lithium hydroxide or potassium hydroxide) in a suitable solvent (methanol, ethanol, tetrahydrofuran, dioxane, dimethylformamide or a mixture thereof).

(Third Step and Fourth Step)

Then, compound (VI) is amidated, and the resulting compound (V) is deprotected to obtain objective compound (Ib). These reactions may be performed by the same methods as those of the second step and the first step in A process, respectively. In an amidation step, the reaction may be performed, if necessary, in the presence of a condensing agent (N,N'-dicyclohexylcarbodiimide, N-dimethylaminopropyl-N'-ethylcarbodiimide, diethyl phosphoryl cyanide, diphenyl phosphoryl azide etc.).

In addition, when $R^4$ of objective compound (I) is lower alkyl, an etherization reaction may be performed at an arbitrary stage as described above.

(C Process)

[Chemical formula 10]

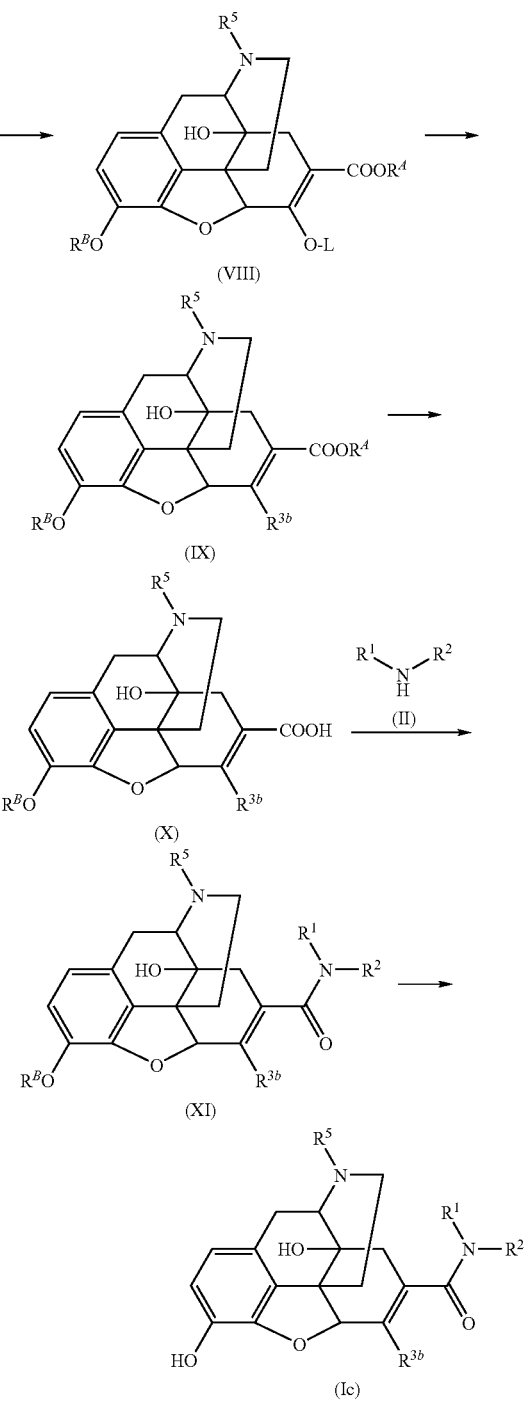

wherein L is a leaving group, $R^{3b}$ is hydrogen, optionally substituted lower alkyl, optionally substituted lower alkenyl, optionally substituted lower alkynyl, optionally substituted lower alkoxy, mercapto, optionally substituted lower alkylthio, optionally substituted amino, optionally substituted carbamoyl, optionally substituted aryl, or optionally substituted heterocyclic group, and other symbols are as defined above.

(First Step)

When $R^3$ of objective compound (I) is the $R^{3b}$, a leaving group L (e.g. trifluoromethanesulfonyl, methanesulfonyl, phosphoric acid ester etc.) is introduced into the known compound (IV). For example, the compound is reacted with trifluoromethanesulfonic anhydride, trifluoromethanesulfonyl chloride, methanesulfonyl chloride, methanesulfonic anhydride, p-toluenesulfonyl chloride, N-phenyltrifluoromethanesulfonimide or various phosphoric acid esterifying reagents in the presence of a base (pyridine, triethylamine, ammonia, dimethylamine, dimethylaniline, dimethylaminopyridine, 2,6-lutidine or 2,6-di-tert-butylpyridine) using dichloromethane, chloroform, tetrahydrofuran, benzene, toluene, dimethylformamide, ethyl acetate or a mixture thereof as a solvent.

(Second Step)

The thus obtained compound (VIII) is subjected to the known substituent introducing reaction to obtain compound (IX).

(Third Step, Fourth Step and Fifth Step)

The compound (IX) is hydrolyzed, amidated, and deprotected by the same methods as those of the second step in B process, the second step in A process and the first step in A step, respectively, to obtain objective the compound (Ic).

In addition, when $R^4$ of the objective compound (I) is lower alkyl, an etherization reaction may be performed at an arbitrary stage as described above.

(D Process)

compound (VIII) is obtained by the first step in C process, amidated according to the method of the fourth step in C process, and subjected to introduction of a substituent $R^{3b}$, deprotection, and a hydrolysis reaction according to the methods of the second step, third step and fifth step in C process, respectively, thereby, objective compound (I) may be also obtained.

All of thus obtained present compounds have the opioid receptor antagonistic activity, and are useful as a drug, and among compounds represented by the formula (I), the following compounds are particularly preferable.

a) a compound in which $R^1$ is hydrogen or lower alkyl,
b) a compound in which $R^1$ is hydrogen or C1-C3 alkyl,
c) a compound in which $R^2$ is:
(c-i) lower alkyl optionally substituted with one or more groups selected from Substituent group β (herein, Substituent group β is cycloalkyl optionally substituted with hydroxy, halogen, hydroxy, lower alkoxy, halogeno lower alkoxy, lower alkylthio, amino, lower alkylamino, carboxy, lower alkoxycarbonyl, cyano, lower alkylsulfonyl, aryl, aryloxy and lower alkylenedioxy),
(c-ii) phenyl optionally substituted with one or more groups selected from group consisting of Substituent group, lower alkyl and halogeno lower alkyl,
(c-iii) aryl lower alkyl optionally substituted with one or more groups selected from Substituent group β,
(c-iv) cycloalkyl optionally substituted with one or more groups selected from Substituent group β,
(c-v) heterocyclic group optionally substituted with one or more groups selected from Substituent group β, or
(c-vi) heterocyclic lower alkyl optionally substituted with one or more groups selected from Substituent group β,
d) a compound in which $R^2$ is:
(d-i) lower alkyl optionally substituted with hydroxy, cycloalkyl optionally substituted with hydroxy, lower alkoxy, lower alkylthio, lower alkylamino or aryloxy,
(d-ii) phenyl optionally substituted with halogen, lower alkyl, halogeno lower alkyl, lower alkoxy, halogeno lower alkoxy, lower alkylthio, amino, lower alkylamino, cyano, lower alkylsulfonyl or lower alkylenedioxy,
(d-iii) aryl lower alkyl optionally substituted with lower alkoxy or lower alkylthio,
(d-iv) cycloalkyl optionally substituted with lower alkyl, carboxy or lower alkoxycarbonyl,
(d-v) a heterocyclic group optionally substituted with lower alkyl, lower alkoxy or phenyl, or
(d-vi) heterocyclic lower alkyl optionally substituted with lower alkyl or aryl,
e) a compound in which $R^1$ and $R^2$ are taken together with a N atom to which they bind to form a 5-membered or 6-membered saturated heterocycle,
f) a compound in which $R^3$ is hydroxy or lower alkoxy,
g) a compound in which $R^3$ is hydroxy,
h) a compound in which $R^3$ is amino optionally substituted with one or more groups selected from Substituent group α,
i) a compound in which $R^3$ is halogen, lower alkyl, or amino substituted with arylsulfonyl optionally substituted with lower alkoxy,
j) a compound in which $R^4$ is hydrogen or methoxy,
k) a compound in which $R^5$ is cycloalkyl lower alkyl or lower alkenyl,
l) a compound in which $R^5$ is cyclopropylmethyl or allyl,
m) a compound in which $R^5$ is cyclopropylmethyl,
n) a compound in which $R^1$ is hydrogen or lower alkyl, $R^2$ is the (d-i), $R^3$ is hydroxy or lower alkoxy, $R^4$ is hydrogen, and $R^5$ is cycloalkyl lower alkyl or lower alkenyl,
o) a compound in which $R^1$ is hydrogen or lower alkyl, $R^2$ is the (d-i), $R^3$ is hydroxy or lower alkoxy, $R^4$ is hydrogen, and $R^5$ is cyclopropylmethyl,
p) a compound in which $R^1$ is hydrogen or lower alkyl, $R^2$ is the (d-i), $R^3$ is halogen, lower alkyl, or amino substituted with arylsulfonyl optionally substituted with lower alkoxy, $R^4$ is hydrogen, and $R^5$ is cycloalkyl lower alkyl or lower alkenyl,
q) a compound in which $R^1$ is hydrogen or lower alkyl, $R^2$ is the (d-i), $R^3$ is halogen, lower alkyl, or amino substituted with arylsulfonyl optionally substituted with lower alkoxy, $R^4$ is hydrogen, and $R^5$ is cyclopropylmethyl,
r) a compound in which $R^1$ is hydrogen or lower alkyl, $R^2$ is the (d-ii), $R^3$ is hydroxy or lower alkoxy, $R^4$ is hydrogen, and $R^5$ is cycloalkyl lower alkyl or lower alkenyl,
s) a compound in which $R^1$ is hydrogen or lower alkyl, $R^2$ is the (d-ii), $R^3$ is hydroxy or lower alkoxy, $R^4$ is hydrogen, and $R^5$ is cyclopropylmethyl,
t) a compound in which $R^1$ is hydrogen or lower alkyl, $R^2$ is the (d-iii), $R^3$ is hydroxy or lower alkoxy, $R^4$ is hydrogen, and $R^5$ is cycloalkyl lower alkyl or lower alkenyl,
u) a compound in which $R^1$ is hydrogen or lower alkyl, $R^2$ is the (d-iii), $R^3$ is hydroxy or lower alkoxy, $R^4$ is hydrogen, and $R^5$ is cyclopropylmethyl,
v) a compound in which $R^1$ is hydrogen or lower alkyl, $R^2$ is the (d-iv), $R^3$ is hydroxy or lower alkoxy, $R^4$ is hydrogen, and $R^5$ is cycloalkyl lower alkyl or lower alkenyl,
w) a compound in which $R^1$ is hydrogen or lower alkyl, $R^2$ is the (d-iv), $R^3$ is hydroxy or lower alkoxy, $R^4$ is hydrogen, and $R^5$ is cyclopropylmethyl,
x) a compound in which $R^1$ is hydrogen or lower alkyl, $R^2$ is the (d-v), $R^3$ is hydroxy or lower alkoxy, $R^4$ is hydrogen, and $R^5$ is cycloalkyl lower alkyl or lower alkenyl,
y) a compound in which $R^1$ is hydrogen or lower alkyl, $R^2$ is the (d-v), $R^3$ is hydroxy or lower alkoxy, $R^4$ is hydrogen, and $R^5$ is cyclopropylmethyl, z) a compound in which $R^1$ is hydrogen or lower alkyl, $R^2$ is the (d-yl), $R^3$ is hydroxy or lower alkoxy, $R^4$ is hydrogen, and $R^5$ is cycloalkyl lower alkyl or lower alkenyl, aa) a compound in which $R^1$ is hydrogen or lower alkyl, $R^2$ is the (d-yl), $R^3$ is hydroxy or lower alkoxy, $R^4$ is hydrogen, and $R^5$ is cyclopropylmethyl, ab) a compound in which $R^1$ and $R^2$ are taken together with a N atom to which they bind to form a 5-membered or 6-membered saturated heterocycle, $R^3$ is hydroxy or lower alkoxy, $R^4$ is hydrogen, and $R^5$ is cycloalkyl lower alkyl group or lower alkenyl, ac) a compound in which $R^1$ and $R^2$ are taken together with a N atom to which they bind to form a 5-membered or 6-membered saturated heterocycle, $R^3$ is hydroxy or lower alkoxy, $R^4$ is hydrogen, and $R^5$ is cyclopropylmethyl, or a pharmaceutically acceptable salt or a solvate thereof.

In a compound represented by the formula (I), a compound in which $R^4$ is hydrogen, $R^5$ is cyclopropylmethyl, and a combination of $NR^1R^2$ and $R^3$ ($NR^1R^2$, $R^3$) is the following.

TABLE 1

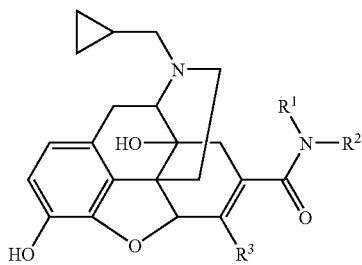

| | NR1R2 | CR9R10 |
|---|---|---|
| AA | —NHiPr | — |
| AB | —NH-phenyl | — |
| AC | —NH-biphenyl | — |
| AD | —NH-pyridyl | — |
| AE | —NH-(2-COOH-phenyl) | — |
| AF | —NH-(4-F-2-COOH-phenyl) | — |
| AG | —NHCR9R10CONH2 | Ra |
| AH | —NHCR9R10CONH2 | Rb |
| AI | —NHCR9R10CONH2 | Rc |
| AJ | —NHCR9R10CONH2 | Rd |
| AK | —NHCR9R10CONH2 | Re |
| AL | —NHCR9R10CONH2 | Rf |
| AM | —NHCR9R10CONH2 | Rg |
| AN | —NHCR9R10CONH2 | Rh |

TABLE 1-continued

| | NR1R2 | CR9R10 |
|---|---|---|
| AO | —NHCR9R10CONH2 | Ri |
| AP | —NHCR9R10CONH2 | Rj |
| AQ | —NHCR9R10CONH2 | Rk |
| AR | —NHCR9R10CONH2 | Rl |
| AS | —NHCR9R10CONH2 | Rm |
| AT | —NHCR9R10CONH2 | Rn |
| AU | —NHCR9R10CONH2 | Ro |
| AV | —NHCR9R10CONH2 | Rp |
| AW | —NHCR9R10CONH2 | Rq |
| AX | —NHCR9R10CONH2 | Rr |
| AY | —NHCR9R10CONH2 | Rs |
| AZ | —NHCR9R10CONH2 | Rt |
| BA | —NHCR9R10CONMe2 | Ra |
| BB | —NHCR9R10CONMe2 | Rb |
| BC | —NHCR9R10CONMe2 | Rc |
| BD | —NHCR9R10CONMe2 | Rd |
| BE | —NHCR9R10CONMe2 | Re |
| BF | —NHCR9R10CONMe2 | Rf |
| BG | —NHCR9R10CONMe2 | Rg |
| BH | —NHCR9R10CONMe2 | Rh |
| BI | —NHCR9R10CONMe2 | Ri |
| BJ | —NHCR9R10CONMe2 | Rj |
| BK | —NHCR9R10CONMe2 | Rk |
| BL | —NHCR9R10CONMe2 | Rl |
| BM | —NHCR9R10CONMe2 | Rm |
| BN | —NHCR9R10CONMe2 | Rn |
| BO | —NHCR9R10CONMe2 | Ro |
| BP | —NHCR9R10CONMe2 | Rp |
| BQ | —NHCR9R10CONMe2 | Rq |
| BR | —NHCR9R10CONMe2 | Rr |
| BS | —NHCR9R10CONMe2 | Rs |
| BT | —NHCR9R10CONMe2 | Rt |
| BU | —NHCR9R10COOH | Ra |
| BV | —NHCR9R10COOH | Rb |
| BW | —NHCR9R10COOH | Rc |
| BX | —NHCR9R10COOH | Rd |
| BY | —NHCR9R10COOH | Re |
| BZ | —NHCR9R10COOH | Rf |
| CA | —NHCR9R10COOH | Rg |
| CB | —NHCR9R10COOH | Rh |
| CC | —NHCR9R10COOH | Ri |
| CD | —NHCR9R10COOH | Rj |
| CE | —NHCR9R10COOH | Rk |
| CF | —NHCR9R10COOH | Rl |
| CG | —NHCR9R10COOH | Rm |
| CH | —NHCR9R10COOH | Rn |
| CI | —NHCR9R10COOH | Ro |
| CJ | —NHCR9R10COOH | Rp |
| CK | —NHCR9R10COOH | Rq |
| CL | —NHCR9R10COOH | Rr |
| CM | —NHCR9R10COOH | Rs |
| CN | —NHCR9R10COOH | Rt |
| CO | —NHCR9R10COOMe | Ra |
| CP | —NHCR9R10COOMe | Rb |
| CQ | —NHCR9R10COOMe | Rc |
| CR | —NHCR9R10COOMe | Rd |

TABLE 2

| | NR1R2 | CR9R10 |
|---|---|---|
| CS | —NHCR9R10COOMe | Re |
| CT | —NHCR9R10COOMe | Rf |
| CU | —NHCR9R10COOMe | Rg |
| CV | —NHCR9R10COOMe | Rh |
| CW | —NHCR9R10COOMe | Ri |
| CX | —NHCR9R10COOMe | Rj |
| CY | —NHCR9R10COOMe | Rk |
| CZ | —NHCR9R10COOMe | Rl |
| DA | —NHCR9R10COOMe | Rm |
| DB | —NHCR9R10COOMe | Rn |
| DC | —NHCR9R10COOMe | Ro |
| DD | —NHCR9R10COOMe | Rp |
| DE | —NHCR9R10COOMe | Rq |
| DF | —NHCR9R10COOMe | Rr |
| DG | —NHCR9R10COOMe | Rs |
| DH | —NHCR9R10COOMe | Rt |
| DI | —NHCR9R10COOEt | Ra |
| DJ | —NHCR9R10COOEt | Rb |
| DK | —NHCR9R10COOEt | Rc |
| DL | —NHCR9R10COOEt | Rd |
| DM | —NHCR9R10COOEt | Re |
| DN | —NHCR9R10COOEt | Rf |
| DO | —NHCR9R10COOEt | Rg |
| DP | —NHCR9R10COOEt | Rh |
| DQ | —NHCR9R10COOEt | Ri |
| DR | —NHCR9R10COOEt | Rj |
| DS | —NHCR9R10COOEt | Rk |
| DT | —NHCR9R10COOEt | Rl |
| DU | —NHCR9R10COOEt | Rm |
| DV | —NHCR9R10COOEt | Rn |
| DW | —NHCR9R10COOEt | Ro |
| DX | —NHCR9R10COOEt | Rp |
| DY | —NHCR9R10COOEt | Rq |
| DZ | —NHCR9R10COOEt | Rr |
| EA | —NHCR9R10COOEt | Rs |
| EB | —NHCR9R10COOEt | Rt |
| EC | —NHCR9R10COOiPr | Ra |
| ED | —NHCR9R10COOiPr | Rb |
| EE | —NHCR9R10COOiPr | Rc |
| EF | —NHCR9R10COOiPr | Rd |
| EG | —NHCR9R10COOiPr | Re |
| EH | —NHCR9R10COOiPr | Rf |
| EI | —NHCR9R10COOiPr | Rg |
| EJ | —NHCR9R10COOiPr | Rh |
| EK | —NHCR9R10COOiPr | Ri |
| EL | —NHCR9R10COOiPr | Rj |
| EM | —NHCR9R10COOiPr | Rk |
| EN | —NHCR9R10COOiPr | Rl |
| EO | —NHCR9R10COOiPr | Rm |
| EP | —NHCR9R10COOiPr | Rn |
| EQ | —NHCR9R10COOiPr | Ro |
| ER | —NHCR9R10COOiPr | Rp |
| ES | —NHCR9R10COOiPr | Rq |
| ET | —NHCR9R10COOiPr | Rr |
| EU | —NHCR9R10COOiPr | Rs |
| EV | —NHCR9R10COOiPr | Rt |
| EW | —NHCR9R10CONHMe | Ra |
| EX | —NHCR9R10CONHMe | Rb |
| EY | —NHCR9R10CONHMe | Rc |
| EZ | —NHCR9R10CONHMe | Rd |
| FA | —NHCR9R10CONHMe | Re |
| FB | —NHCR9R10CONHMe | Rf |
| FC | —NHCR9R10CONHMe | Rg |
| FD | —NHCR9R10CONHMe | Rh |
| FE | —NHCR9R10CONHMe | Ri |
| FF | —NHCR9R10CONHMe | Rj |
| FG | —NHCR9R10CONHMe | Rk |
| FH | —NHCR9R10CONHMe | Rl |
| FI | —NHCR9R10CONHMe | Rm |
| FJ | —NHCR9R10CONHMe | Rn |
| FK | —NHCR9R10CONHMe | Ro |
| FL | —NHCR9R10CONHMe | Rp |
| FM | —NHCR9R10CONHMe | Rq |
| FN | —NHCR9R10CONHMe | Rr |
| FO | —NHCR9R10CONHMe | Rs |
| FP | —NHCR9R10CONHMe | Rt |
| FQ | —NHCR9R10CONHiPr | Ra |
| FR | —NHCR9R10CONHiPr | Rb |
| FS | —NHCR9R10CONHiPr | Rc |
| FT | —NHCR9R10CONHiPr | Rd |
| FU | —NHCR9R10CONHiPr | Re |
| FV | —NHCR9R10CONHiPr | Rf |
| FW | —NHCR9R10CONHiPr | Rg |
| FX | —NHCR9R10CONHiPr | Rh |
| FY | —NHCR9R10CONHiPr | Ri |
| FZ | —NHCR9R10CONHiPr | Rj |
| GA | —NHCR9R10CONHiPr | Rk |
| GB | —NHCR9R10CONHiPr | Rl |
| GC | —NHCR9R10CONHiPr | Rm |
| GD | —NHCR9R10CONHiPr | Rn |
| GE | —NHCR9R10CONHiPr | Ro |
| GF | —NHCR9R10CONHiPr | Rp |
| GG | —NHCR9R10CONHiPr | Rq |
| GH | —NHCR9R10CONHiPr | Rr |
| GI | —NHCR9R10CONHiPr | Rs |
| GJ | —NHCR9R10CONHiPr | Rt |
| GK | —NHCR9R10CONHPh | Ra |
| GL | —NHCR9R10CONHPh | Rb |
| GM | —NHCR9R10CONHPh | Rc |
| GN | —NHCR9R10CONHPh | Rd |
| GO | —NHCR9R10CONHPh | Re |
| GP | —NHCR9R10CONHPh | Rf |
| GQ | —NHCR9R10CONHPh | Rg |
| GR | —NHCR9R10CONHPh | Rh |
| GS | —NHCR9R10CONHPh | Ri |
| GT | —NHCR9R10CONHPh | Rj |
| GU | —NHCR9R10CONHPh | Rk |
| GV | —NHCR9R10CONHPh | Rl |
| GW | —NHCR9R10CONHPh | Rm |
| GX | —NHCR9R10CONHPh | Rn |
| GY | —NHCR9R10CONHPh | Ro |
| GZ | —NHCR9R10CONHPh | Rp |
| HA | —NHCR9R10CONHPh | Rq |
| HB | —NHCR9R10CONHPh | Rr |
| HC | —NHCR9R10CONHPh | Rs |
| HD | —NHCR9R10CONHPh | Rt |

TABLE 3

| | NR1R2 | CR9R10 |
|---|---|---|
| HE | —NHCR9R10CONHCN | Ra |
| HF | —NHCR9R10CONHCN | Rb |
| HG | —NHCR9R10CONHCN | Rc |
| HH | —NHCR9R10CONHCN | Rd |
| HI | —NHCR9R10CONHCN | Re |
| HJ | —NHCR9R10CONHCN | Rf |
| HK | —NHCR9R10CONHCN | Rg |
| HL | —NHCR9R10CONHCN | Rh |
| HM | —NHCR9R10CONHCN | Ri |
| HN | —NHCR9R10CONHCN | Rj |
| HO | —NHCR9R10CONHCN | Rk |
| HP | —NHCR9R10CONHCN | Rl |
| HQ | —NHCR9R10CONHCN | Rm |
| HR | —NHCR9R10CONHCN | Rn |
| HS | —NHCR9R10CONHCN | Ro |
| HT | —NHCR9R10CONHCN | Rp |
| HU | —NHCR9R10CONHCN | Rq |
| HV | —NHCR9R10CONHCN | Rr |
| HW | —NHCR9R10CONHCN | Rs |
| HX | —NHCR9R10CONHCN | Rt |
| HY | —NHCR9R10CONHSO2Me | Ra |
| HZ | —NHCR9R10CONHSO2Me | Rb |
| IA | —NHCR9R10CONHSO2Me | Rc |
| IB | —NHCR9R10CONHSO2Me | Rd |
| IC | —NHCR9R10CONHSO2Me | Re |
| ID | —NHCR9R10CONHSO2Me | Rf |
| IE | —NHCR9R10CONHSO2Me | Rg |
| IF | —NHCR9R10CONHSO2Me | Rh |
| IG | —NHCR9R10CONHSO2Me | Ri |
| IH | —NHCR9R10CONHSO2Me | Rj |
| II | —NHCR9R10CONHSO2Me | Rk |
| IJ | —NHCR9R10CONHSO2Me | Rl |

TABLE 3-continued

| | NR1R2 | CR9R10 |
|---|---|---|
| IK | —NHCR9R10CONHSO2Me | Rm |
| IL | —NHCR9R10CONHSO2Me | Rn |
| IM | —NHCR9R10CONHSO2Me | Ro |
| IN | —NHCR9R10CONHSO2Me | Rp |
| IO | —NHCR9R10CONHSO2Me | Rq |
| IP | —NHCR9R10CONHSO2Me | Rr |
| IQ | —NHCR9R10CONHSO2Me | Rs |
| IR | —NHCR9R10CONHSO2Me | Rt |
| IS | —NHCR9R10CH2OMe | Ra |
| IT | —NHCR9R10CH2OMe | Rb |
| IU | —NHCR9R10CH2OMe | Rc |
| IV | —NHCR9R10CH2OMe | Rd |
| IW | —NHCR9R10CH2OMe | Re |
| IX | —NHCR9R10CH2OMe | Rf |
| IY | —NHCR9R10CH2OMe | Rg |
| IZ | —NHCR9R10CH2OMe | Rh |
| JA | —NHCR9R10CH2OMe | Ri |
| JB | —NHCR9R10CH2OMe | Rj |
| JC | —NHCR9R10CH2OMe | Rk |
| JD | —NHCR9R10CH2OMe | Rl |
| JE | —NHCR9R10CH2OMe | Rm |
| JF | —NHCR9R10CH2OMe | Rn |
| JG | —NHCR9R10CH2OMe | Ro |
| JH | —NHCR9R10CH2OMe | Rp |
| JI | —NHCR9R10CH2OMe | Rq |
| JJ | —NHCR9R10CH2OMe | Rr |
| JK | —NHCR9R10CH2OMe | Rs |
| JL | —NHCR9R10CH2OMe | Rt |
| JM | 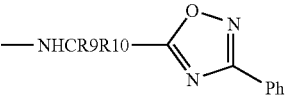 | Ra |
| JN | 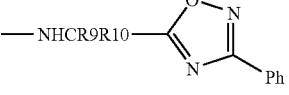 | Rb |
| JO | 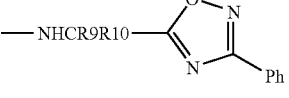 | Rc |
| JP | 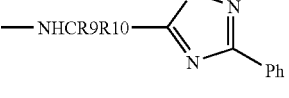 | Rd |
| JQ | 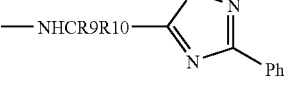 | Re |
| JR | 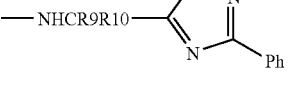 | Rf |
| JS | 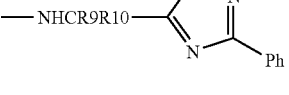 | Rg |
| JT | 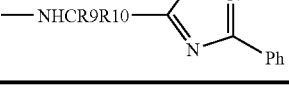 | Rh |

TABLE 4

| | NR1R2 | CR9R10 |
|---|---|---|
| JU | 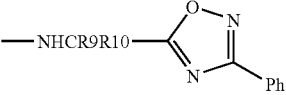 | Ri |
| JV | 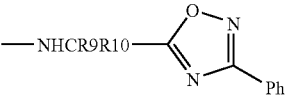 | Rj |
| JW | 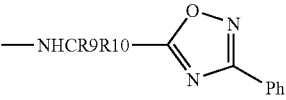 | Rk |
| JX | 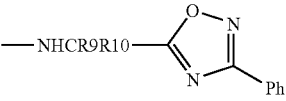 | Rl |
| JY | 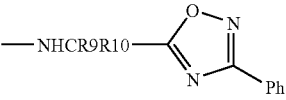 | Rm |
| JZ | 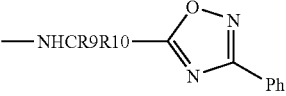 | Rn |
| KA | 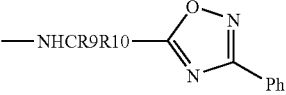 | Ro |
| KB | 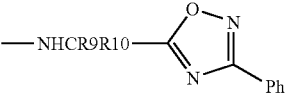 | Rp |
| KC | 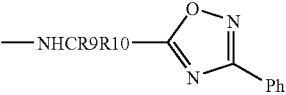 | Rq |
| KD | 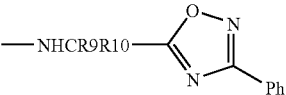 | Rr |
| KE | 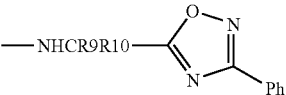 | Rs |
| KF | 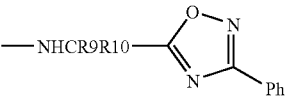 | Rt |
| KG | 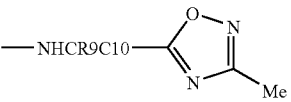 | Ra |

TABLE 4-continued

| | NR1R2 | CR9R10 |
|---|---|---|
| KH | —NHCR9C10—[3-Me-1,2,4-oxadiazol-5-yl] | Rb |
| KI | —NHCR9C10—[3-Me-1,2,4-oxadiazol-5-yl] | Rc |
| KJ | —NHCR9C10—[3-Me-1,2,4-oxadiazol-5-yl] | Rd |
| KK | —NHCR9C10—[3-Me-1,2,4-oxadiazol-5-yl] | Re |
| KL | —NHCR9C10—[3-Me-1,2,4-oxadiazol-5-yl] | Rf |
| KM | —NHCR9C10—[3-Me-1,2,4-oxadiazol-5-yl] | Rg |
| KN | —NHCR9C10—[3-Me-1,2,4-oxadiazol-5-yl] | Rh |
| KO | —NHCR9C10—[3-Me-1,2,4-oxadiazol-5-yl] | Ri |
| KP | —NHCR9C10—[3-Me-1,2,4-oxadiazol-5-yl] | Rj |
| KQ | —NHCR9C10—[3-Me-1,2,4-oxadiazol-5-yl] | Rk |
| KR | —NHCR9C10—[3-Me-1,2,4-oxadiazol-5-yl] | Rl |
| KS | —NHCR9C10—[3-Me-1,2,4-oxadiazol-5-yl] | Rm |
| KT | —NHCR9C10—[3-Me-1,2,4-oxadiazol-5-yl] | Rn |
| KU | —NHCR9C10—[3-Me-1,2,4-oxadiazol-5-yl] | Ro |
| KV | —NHCR9C10—[3-Me-1,2,4-oxadiazol-5-yl] | Rp |
| KW | —NHCR9C10—[3-Me-1,2,4-oxadiazol-5-yl] | Rq |
| KX | —NHCR9C10—[3-Me-1,2,4-oxadiazol-5-yl] | Rr |
| KY | —NHCR9C10—[3-Me-1,2,4-oxadiazol-5-yl] | Rs |
| KZ | —NHCR9C10—[3-Me-1,2,4-oxadiazol-5-yl] | Rt |

TABLE 5

| | NR1R2 | CR9R10 |
|---|---|---|
| LA | —NHCR9C10—[4-Ph-oxazol-2-yl] | Ra |
| LB | —NHCR9C10—[4-Ph-oxazol-2-yl] | Rb |
| LC | —NHCR9C10—[4-Ph-oxazol-2-yl] | Rc |
| LD | —NHCR9C10—[4-Ph-oxazol-2-yl] | Rd |
| LE | —NHCR9C10—[4-Ph-oxazol-2-yl] | Re |
| LF | —NHCR9C10—[4-Ph-oxazol-2-yl] | Rf |

TABLE 5-continued

| | NR1R2 | CR9R10 |
|---|---|---|
| LG | —NHCR9C10-[oxazole-4-Ph] | Rg |
| LH | —NHCR9C10-[oxazole-4-Ph] | Rh |
| LI | —NHCR9C10-[oxazole-4-Ph] | Ri |
| LJ | —NHCR9C10-[oxazole-4-Ph] | Rj |
| LK | —NHCR9C10-[oxazole-4-Ph] | Rk |
| LL | —NHCR9C10-[oxazole-4-Ph] | Rl |
| LM | —NHCR9C10-[oxazole-4-Ph] | Rm |
| LN | —NHCR9C10-[oxazole-4-Ph] | Rn |
| LO | —NHCR9C10-[oxazole-4-Ph] | Ro |
| LP | —NHCR9C10-[oxazole-4-Ph] | Rp |
| LQ | —NHCR9C10-[oxazole-4-Ph] | Rq |
| LR | —NHCR9C10-[oxazole-4-Ph] | Rr |
| LS | —NHCR9C10-[oxazole-4-Ph] | Rs |
| LT | —NHCR9C10-[oxazole-4-Ph] | Rt |
| LU | —NHCR9C10-[oxazole-4-Me] | Ra |
| LV | —NHCR9C10-[oxazole-4-Me] | Rb |
| LW | —NHCR9C10-[oxazole-4-Me] | Rc |
| LX | —NHCR9C10-[oxazole-4-Me] | Rd |
| LY | —NHCR9C10-[oxazole-4-Me] | Re |
| LZ | —NHCR9C10-[oxazole-4-Me] | Rf |
| MA | —NHCR9C10-[oxazole-4-Me] | Rg |
| MB | —NHCR9C10-[oxazole-4-Me] | Rh |
| MC | —NHCR9C10-[oxazole-4-Me] | Ri |
| MD | —NHCR9C10-[oxazole-4-Me] | Rj |
| ME | —NHCR9C10-[oxazole-4-Me] | Rk |
| MF | —NHCR9C10-[oxazole-4-Me] | Rl |

TABLE 6
| | NR1R2 | CR9R10 |
|---|---|---|
| MG | —NHCR9C10— 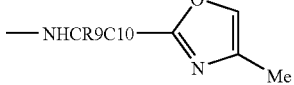 | Rm |
| MH | —NHCR9C10— 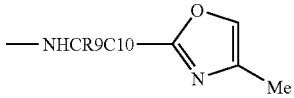 | Rn |
| MI | —NHCR9C10— 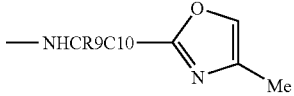 | Ro |
| MJ | —NHCR9C10— 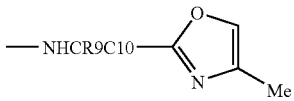 | Rp |
| MK | —NHCR9C10— 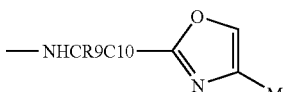 | Rq |
| ML | —NHCR9C10— 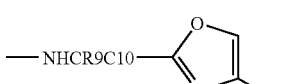 | Rr |
| MM | —NHCR9C10— 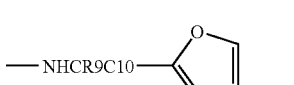 | Rs |
| MN | —NHCR9C10— 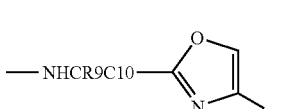 | Rt |
In the above Tables, $CR^9CR^{10}$ is represented by the following symbol.
TABLE 7
| | CR9R10 |
|---|---|
| Ra | 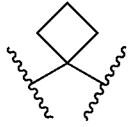 |
| RB | 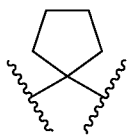 |
| Rc | 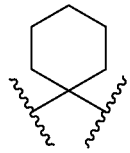 |
TABLE 7-continued
| | CR9R10 |
|---|---|
| Rd | 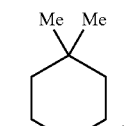 |
| Re | 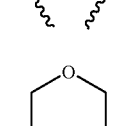 |
| Rf | 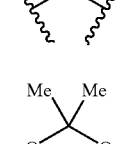 |
| Rg | 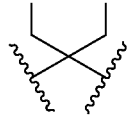 |
| Rh | 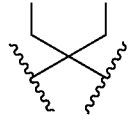 |
| Ri | 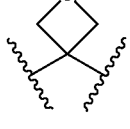 |
| Rj | 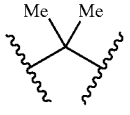 |
| Rk | 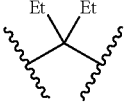 |
| Rl | 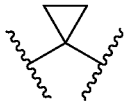 |

TABLE 7-continued

| | CR9R10 |
|---|---|
| Rm | 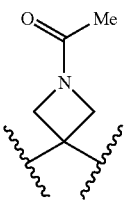 |
| Rn | 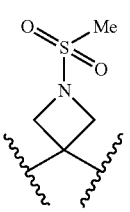 |
| Ro | 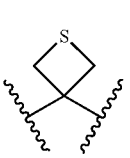 |
| Rp | 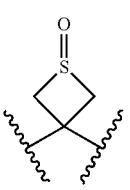 |
| Rq | 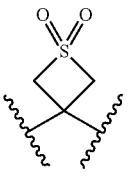 |
| Rr |  |
| Rs |  |
| Rt | 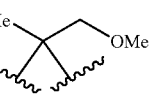 |

TABLE 8

| | R3 |
|---|---|
| VA | H |
| VB | Me |
| VC | OH |
| VD | OMe |
| VE | CONH2 |
| VF | CONHiPr |
| VG | NH2 |
| VH | NHAc |
| VI | NHSO2Me |
| VJ | Ph |

TABLE 8-continued

| | R3 |
|---|---|
| VK | 5-methyl-1,3-benzodioxole |
| VL | 3-methylpyridine |
| VM | acetyl-piperidine |
| VN | acetyl-morpholine |
| VO | NHSO2-C6H4-Me |
| VP | NHSO2-C6H4-CF3 |
| VQ | NHSO2-C6H4-OMe |
| VR | NHSO2-C6H4-Cl |
| VS | NHSO2Ph |
| VT | NHCOPh |
| VU | CONHMe |
| VV | CONMe2 |
| VW | NHMe |
| VX | NHiPr |
| VY | NHPh |
| VZ | 2-methylpyridine |
| WA | 4-methylpyridine |
| WB | NH-2-pyridine |
| WC | NH-(6-methoxy-pyridin-3-yl) |

(AA,VA), (AA,VB), (AA,VC), (AA,VD), (AA,VE), (AA,VF), (AA,VG), (AA,VH), (AA,VI), (AA,VJ), (AA,VK), (AA,VL), (AA,VM), (AA,VN), (AA,VO), (AA,VP), (AA,VQ), (AA,VR), (AA,VS), (AA,VT), (AA,VU), (AA,VV), (AA,VW), (AA,VX), (AA,VY), (AA,VZ), (AA,WA), (AA,WB), (AA,WC), (AB,VA), (AB,VB), (AB,VC), (AB,VD), (AB,VE), (AB,VF), (AB,VG), (AB,VH), (AB,VI), (AB,VJ), (AB,VK), (AB,VL), (AB,VM), (AB,VN), (AB,VO), (AB,VP), (AB,VQ), (AB,VR), (AB,VS), (AB,VT), (AB,VU), (AB,VV), (AB,VW), (AB,VX), (AB,VY), (AB,VZ), (AB,WA), (AB,WB), (AB,WC), (AC,VA), (AC,VB), (AC,VC), (AC,VD), (AC,VE), (AC,VF), (AC,VG), (AC,VH), (AC,VI), (AC,VJ), (AC,VK), (AC,VL), (AC,VM), (AC,VN), (AC,VO), (AC,VP), (AC,VQ), (AC,VR), (AC,VS), (AC,VT), (AC,VU), (AC,VV), (AC,VW), (AC,VX), (AC,VY), (AC,VZ), (AC,WA), (AC,WB), (AC,WC), (AD,VA), (AD,VB), (AD,VC), (AD,VD), (AD,VE), (AD,VF), (AD,VG), (AD,VH), (AD,VI), (AD,VJ), (AD,VK), (AD,VL), (AD,VM), (AD,VN), (AD,VO), (AD,VP), (AD,VQ), (AD,VR), (AD,VS), (AD,VT), (AD,VU), (AD,VW), (AD,VX), (AD,VY), (AD,VZ), (AD,WA), (AD,WB), (AD,WC), (AE,VA), (AE,VB), (AE,VC), (AE,VD), (AE,VE), (AE,VF), (AE,VG), (AE,VH), (AE,VI), (AE,VJ), (AE,VK), (AE,VL), (AE,VM), (AE,VN), (AE,VO), (AE,VP), (AE,VQ), (AE,VR), (AE,VS), (AE,VT), (AE,VU), (AE,VV), (AE,VW), (AE,VX), (AE,VY), (AE,VZ), (AE,WA), (AE,WB), (AE,WC), (AF,VA), (AF,VB), (AF,VC), (AF,VD), (AF,VE), (AF,VF), (AF,VG), (AF,VH), (AF,VI), (AF,VJ), (AF,VK), (AF,VL), (AF,VM), (AF,VN), (AF,VO), (AF,VP), (AF,VQ), (AF,VR), (AF,VS), (AF,VT), (AF,VU), (AF,VV), (AF,VW), (AF,VX), (AF,VY), (AF,VZ), (AF,WA), (AF,WB), (AF,WC), (AG,VA), (AG,VB), (AG,VC), (AG,VD), (AG,VE), (AG,VF), (AG,VG), (AG,VH), (AG,VI), (AG,VJ), (AG,VK), (AG,VL), (AG,VM), (AG,VN), (AG,VO), (AG,VP), (AG,VQ), (AG,VR), (AG,VS), (AG,VT), (AG,VU), (AG,VV), (AG,VW), (AG,VX), (AG,VY), (AG,VZ), (AG,WA), (AG,WB), (AG,WC), (AH,VA), (AH,VB), (AH,VC), (AH,VD), (AH,VE), (AH,VF), (AH,VG), (AH,VH), (AH,VI), (AH,VJ), (AH,VK), (AH,VL), (AH,VM), (AH,VN), (AH,VO), (AH,VP), (AH,VQ), (AH,VR), (AH,VS), (AH,VT), (AH,VU), (AH,VV), (AH,VW), (AH,VX), (AH,VY), (AH,VZ), (AH,WA), (AH,WB), (AH,WC), (AI,VA), (AI,VB), (AI,VC), (AI,VD), (AI,VE), (AI,VF), (AI,VG), (AI,VH), (AI,VI), (AI,VJ), (AI,VK), (AI,VL), (AI,VM), (AI,VN), (AI,VO), (AI,VP), (AI,VQ), (AI,VR), (AI,VS), (AI,VT), (AI,VU), (AI,VV), (AI,VW), (AI,VX), (AI,VY), (AI,VZ), (AI,WA), (AI,WB), (AI,WC), (AJ,VA), (AJ,VB), (AJ,VC), (AJ,VD), (AJ,VE), (AJ,VF), (AJ,VG), (AJ,VH), (AJ,VI), (AJ,VJ), (AJ,VK), (AJ,VL), (AJ,VM), (AJ,VN), (AJ,VO), (AJ,VP), (AJ,VQ), (AJ,VR), (AJ,VS), (AJ,VT), (AJ,VU), (AJ,VV), (AJ,VW), (AJ,VX), (AJ,VY), (AJ,VZ), (AJ,WA), (AJ,WB), (AJ,WC), (AK,VA), (AK,VB), (AK,VC), (AK,VD), (AK,VE), (AK,VF), (AK,VG), (AK,VH), (AK,VI), (AK,VJ), (AK,VK), (AK,VL), (AK,VM), (AK,VN), (AK,VO), (AK,VP), (AK,VQ), (AK,VR), (AK,VS), (AK,VT), (AK,VU), (AK,VV), (AK,VW), (AK,VX), (AK,VY), (AK,VZ), (AK,WA), (AK,WB), (AK,WC), (AL,VA), (AL,VB), (AL,VC), (AL,VD), (AL,VE), (AL,VF), (AL,VG), (AL,VH), (AL,VI), (AL,VJ), (AL,VK), (AL,VL), (AL,VM), (AL,VN), (AL,VO), (AL,VP), (AL,VQ), (AL,VR), (AL,VS), (AL,VT), (AL,VU), (AL,VV), (AL,VW), (AL,VX), (AL,VY), (AL,VZ), (AL,WA), (AL,WB), (AL,WC), (AM,VA), (AM,VB), (AM,VC), (AM,VD), (AM,VE), (AM,VF), (AM,VG), (AM,VH), (AM,VI), (AM,VJ), (AM,VK), (AM,VL), (AM,VM), (AM,VN), (AM,VO), (AM,VP), (AM,VQ), (AM,VR), (AM,VS), (AM,VT), (AM,VU), (AM,VV), (AM,VW), (AM,VX), (AM,VY), (AM,VZ), (AM,WA), (AM,WB), (AM,WC), (AN,VA), (AN,VB), (AN,VC), (AN,VD), (AN,VE), (AN,VF), (AN,VG), (AN,VH), (AN,VI), (AN,VJ), (AN,VK), (AN,VL), (AN,VM), (AN,VN), (AN,VO), (AN,VP), (AN,VQ), (AN,VR), (AN,VS), (AN,VT), (AN,VU), (AN,VV), (AN,VW), (AN,VX), (AN,VY), (AN,VZ), (AN,WA), (AN,WB), (AN,WC), (AO,VA), (AO,VB), (AO,VC), (AO,VD), (AO,VE), (AO,VF), (AO,VG), (AO,VH), (AO,VI), (AO,VJ), (AO,VK), (AO,VL), (AO,VM), (AO,VN), (AO,VO), (AO,VP), (AO,VQ), (AO,VR), (AO,VS), (AO,VT), (AO,VU), (AO,VV), (AO,VW), (AO,VX), (AO,VY), (AO,VZ), (AO,WA), (AO,WB), (AO,WC), (AP,VA), (AP,VB), (AP,VC), (AP,VD), (AP,VE), (AP,VF), (AP,VG), (AP,VH), (AP,VI), (AP,VJ), (AP,VK), (AP,VL), (AP,VM), (AP,VN), (AP,VO), (AP,VP), (AP,VQ), (AP,VR), (AP,VS), (AP,VT), (AP,VU), (AP,VV), (AP,VW), (AP,VX), (AP,VY), (AP,VZ), (AP,WA), (AP,WB), (AP,WC), (AQ,VA), (AQ,VB), (AQ,VC), (AQ,VD), (AQ,VE), (AQ,VF), (AQ,VG), (AQ,VH), (AQ,VI), (AQ,VJ), (AQ,YK), (AQ,VL), (AQ,VM), (AQ,VN), (AQ,VO), (AQ,VP), (AQ,VQ), (AQ,VR), (AQ,VS), (AQ,VT), (AQ,VU), (AQ,VV), (AQ,VW), (AQ,VX), (AQ,VY), (AQ,VZ), (AQ,WA), (AQ,WB), (AQ,WC), (AR,VA), (AR,VB), (AR,VC), (AR,VD), (AR,VE), (AR,VF), (AR,VG), (AR,VH), (AR,VI), (AR,VJ), (AR,VK), (AR,VL), (AR,VM), (AR,VN), (AR,VO), (AR,VP), (AR,VQ), (AR,VR), (AR,VS), (AR,VT), (AR,VU), (AR,VV), (AR,VW), (AR,VX), (AR,VY), (AR,VZ), (AR,WA), (AR,WB), (AR,WC), (AS,VA), (AS,VB), (AS,VC), (AS,VD), (AS,VE), (AS,VF), (AS,VG), (AS,VH), (AS,VI), (AS,VJ), (AS,VK), (AS,VL), (AS,VM), (AS,VN), (AS,VO), (AS,VP), (AS,VQ), (AS,VR), (AS,VS), (AS,VT), (AS,VU), (AS,VV), (AS,VW), (AS,VX), (AS,VY), (AS,VZ), (AS,WA), (AS,WB), (AS,WC), (AT,VA), (AT,VB), (AT,VC), (AT,VD), (AT,VE), (AT,VF), (AT,VG), (AT,VH), (AT,VI), (AT,VJ), (AT,VK), (AT,VL), (AT,VM), (AT,VN), (AT,VO), (AT,VP), (AT,VQ), (AT,VR), (AT,VS), (AT,VT), (AT,VU), (AT,VV), (AT,VW), (AT,VX), (AT,VY), (AT,VZ), (AT,WA), (AT,WB), (AT,WC), (AU,VA), (AU,VB), (AU,VC), (AU,VD), (AU,VE), (AU,VF), (AU,VG), (AU,VH), (AU,VI), (AU,VJ), (AU,VK), (AU,VL), (AU,VM), (AU,VN), (AU,VO), (AU,VP), (AU,VQ), (AU,VR), (AU,VS), (AU,VT), (AU,VU), (AU,VV), (AU,VW), (AU,VX), (AU,VY), (AU,VZ), (AU,WA), (AU,WB), (AU,WC), (AV,VA), (AV,VB), (AV,VC), (AV,VD), (AV,VE), (AV,VF), (AV,VG), (AV,VH), (AV,VI), (AV,VJ), (AV,VK), (AV,VL), (AV,VM), (AV,VN), (AV,VO), (AV,VP), (AV,VQ), (AV,VR), (AV,VS), (AV,VT), (AV,VU), (AV,VV), (AV,VW), (AV,VX), (AV,VY), (AV,VZ), (AV,WA), (AV,WB), (AV,WC), (AW,VA), (AW,VB), (AW,VC), (AW,VD), (AW,VE), (AW,VF), (AW,VG), (AW,VH), (AW,VI), (AW,VJ), (AW,VK), (AW,VL), (AW,VM), (AW,VN), (AW,VO), (AW,VP), (AW,VQ), (AW,VR), (AW,VS), (AW,VT), (AW,VU), (AW,VV), (AW,VW), (AW,VX), (AW,VY), (AW,VZ), (AW,WA), (AW,WB), (AW,WC), (AX,VA), (AX,VB), (AX,VC), (AX,VD), (AX,VE), (AX,VF), (AX,VG), (AX,VH), (AX,VI), (AX,VJ), (AX,VK), (AX,VL), (AX,VM), (AX,VN), (AX,VO), (AX,VP), (AX,VQ), (AX,VR), (AX,VS), (AX,VT), (AX,VU), (AX,VV), (AX,VW), (AX,VX), (AX,VY), (AX,VZ), (AX,WA), (AX,WB), (AX,WC), (AY,VA), (AY,VB), (AY,VC), (AY,VD), (AY,VE), (AY,VF), (AY,VG), (AY,VH), (AY,VI), (AY,VJ), (AY,VK), (AY,VL), (AY,VM), (AY,VN), (AY,VO), (AY,VP), (AY,VQ), (AY,VR), (AY,VS), (AY,VT), (AY,VU), (AY,VV), (AY,VW), (AY,VX), (AY,VY), (AY,VZ), (AY,WA), (AY,WB), (AY,WC), (AZ,VA), (AZ,VB), (AZ,VC), (AZ,VD), (AZ,VE), (AZ,VF), (AZ,VG), (AZ,VH), (AZ,VI), (AZ,VJ), (AZ,VK), (AZ,VL), (AZ,VM), (AZ,VN), (AZ,VO), (AZ,VP), (AZ,VQ), (AZ,

VR), (AZ,VS), (AZ,VT), (AZ,VU), (AZ,VV), (AZ,VW), (AZ,VX), (AZ,VY), (AZ,VZ), (AZ,WA), (AZ,WB), (AZ,WC),
(BA,VA), (BA,VB), (BA,VC), (BA,VD), (BA,VE), (BA,VF), (BA,VG), (BA,VH), (BA,VI), (BA,VJ), (BA,VK), (BA,VL), (BA,VM), (BA,VN), (BA,VO), (BA,VP), (BA,VQ), (BA,VR), (BA,VS), (BA,VT), (BA,VU), (BA,VV), (BA,VW), (BA,VX), (BA,VY), (BA,VZ), (BA,WA), (BA,WB), (BA,WC), (BB,VA), (BB,VB), (BB,VC), (BB,VD), (BB,VE), (BB,VF), (BB,VG), (BB,VH), (BB,VI), (BB,VJ), (BB,VK), (BB,VL), (BB,VM), (BB,VN), (BB,VO), (BB,VP), (BB,VQ), (BB,VR), (BB,VS), (BB,VT), (BB,VU), (BB,VV), (BB,VW), (BB,VX), (BB,VY), (BB,VZ), (BB,WA), (BB,WB), (BB,WC), (BC,VA), (BC,VB), (BC,VC), (BC,VD), (BC,VE), (BC,VF), (BC,VG), (BC,VH), (BC,VI), (BC,VJ), (BC,VK), (BC,VL), (BC,VM), (BC,VN), (BC,VO), (BC,VP), (BC,VQ), (BC,VR), (BC,VS), (BC,VT), (BC,VU), (BC,UV), (BC,VW), (BC,VX), (BC,VY), (BC,VZ), (BC,WA), (BC,WB), (BC,WC), (BD,VA), (BD,VB), (BD,VC), (BD,VD), (BD,VE), (BD,VF), (BD,VG), (BD,VH), (BD,VI), (BD,VJ), (BD,VK), (BD,VL), (BD,VM), (BD,VN), (BD,VO), (BD,VP), (BD,VQ), (BD,VR), (BD,VS), (BD,VT), (BD,VU), (BD,VV), (BD,VW), (BD,VX), (BD,VY), (BD,VZ), (BD,WA), (BD,WB), (BD,WC), (BE,VA), (BE,VB), (BE,VC), (BE,VD), (BE,VE), (BE,VF), (BE,VG), (BE,VH), (BE,VI), (BE,VJ), (BE,VK), (BE,VL), (BE,VM), (BE,VN), (BE,VO), (BE,VP), (BE,VQ), (BE,VR), (BE,VS), (BE,VT), (BE,VU), (BE,VV), (BE,VW), (BE,VX), (BE,VY), (BE,VZ), (BE,WA), (BE,WB), (BE,WC), (BF,VA), (BF,VB), (BF,VC), (BF,VD), (BF,VE), (BF,VF), (BF,VG), (BF,VH), (BF,VI), (BF,VJ), (BF,VK), (BF,VL), (BF,VM), (BF,VN), (BF,VO), (BF,VP), (BF,VQ), (BF,VR), (BF,VS), (BF,VT), (BF,VU), (BF,VV), (BF,VW), (BF,VX), (BF,VY), (BF,VZ), (BF,WA), (BF,WB), (BF,WC), (BG,VA), (BG,VB), (BG,VC), (BG,VD), (BG,VE), (BG,VF), (BG,VG), (BG,VH), (BG,VI), (BG,VJ), (BG,VK), (BG,VL), (BG,VM), (BG,VN), (BG,VO), (BG,VP), (BG,VQ), (BG,VR), (BG,VS), (BG,VT), (BG,VU), (BG,VV), (BG,VW), (BG,VX), (BG,VY), (BG,VZ), (BG,WA), (BG,WB), (BG,WC), (BH,VA), (BH,VB), (BH,VC), (BH,VD), (BH,VE), (BH,VF), (BH,VG), (BH,VH), (BH,VI), (BH,VJ), (BH,VK), (BH,VL), (BH,VM), (BH,VN), (BH,VO), (BH,VP), (BH,VQ), (BH,VR), (BH,VS), (BH,VT), (BH,VU), (BH,VV), (BH,VW), (BH,VX), (BH,VY), (BH,VZ), (BH,WA), (BH,WB), (BH,WC), (BI,VA), (BI,VB), (BI,VC), (BI,VD), (BI,VE), (BI,VF), (BI,VG), (BI,VH), (BI,VI), (BI,VJ), (BI,VK), (BI,VL), (BI,VM), (BI,VN), (BI,VO), (BI,VP), (BI,VQ), (BI,VR), (BI,VS), (BI,VT), (BI,VU), (BI,VV), (BI,VW), (BI,VX), (BI,VY), (BI,VZ), (BI,WA), (BI,WB), (BI,WC), (BJ,VA), (BJ,VB), (BJ,VC), (BJ,VD), (BJ,VE), (BJ,VF), (BJ,VG), (BJ,VH), (BJ,VI), (BJ,VJ), (BJ,VK), (BJ,VL), (BJ,VM), (BJ,VN), (BJ,VO), (BJ,VP), (BJ,VQ), (BJ,VR), (BJ,VS), (BJ,VT), (BJ,VU), (BJ,VV), (BJ,VW), (BJ,VX), (BJ,VY), (BJ,VZ), (BJ,WA), (BJ,WB), (BJ,WC), (BK,VA), (BK,VB), (BK,VC), (BK,VD), (BK,VE), (BK,VF), (BK,VG), (BK,VH), (BK,VI), (BK,VJ), (BK,VK), (BK,VL), (BK,VM), (BK,VN), (BK,VO), (BK,VP), (BK,VQ), (BK,VR), (BK,VS), (BK,VT), (BK,WU), (BK,VV), (BK,VW), (BK,VX), (BK,VY), (BK,VZ), (BK,WA), (BK,WB), (BK,WC), (BL,VA), (BL,VB), (BL,VC), (BL,VD), (BL,VE), (BL,VF), (BL,VG), (BL,VH), (BL,VI), (BL,VJ), (BL,VK), (BL,VL), (BL,VM), (BL,VN), (BL,VO), (BL,VP), (BL,VQ), (BL,VR), (BL,VS), (BL,VT), (BL,VU), (BL,VV), (BL,VW), (BL,VX), (BL,VY), (BL,VZ), (BL,WA), (BL,WB), (BL,WC), (BM,VA), (BM,VB), (BM,VC), (BM,VD), (BM,VE), (BM,VF), (BM,VG), (BM,VH), (BM,VI), (BM,VJ), (BM,VK), (BM,VL), (BM,VM), (BM,VN), (BM,VO), (BM,VP), (BM,VQ), (BM,VR), (BM,VS), (BM,VT), (BM,VU), (BM,VV), (BM,VW), (BM,VX), (BM,VY), (BM,VZ), (BM,WA), (BM,WB), (BM,WC), (BN,VA), (BN,VB), (BN,VC), (BN,VD), (BN,VE), (BN,VF), (BN,VG), (BN,VH), (BN,VI), (BN,VJ), (BN,VK), (BN,VL), (BN,VM), (BN,VN), (BN,VO), (BN,VP), (BN,VQ), (BN,VR), (BN,VS), (BN,VT), (BN,VU), (BN,VV), (BN,VW), (BN,VX), (BN,VY), (BN,VZ), (BN,WA), (BN,WB), (BN,WC), (BO,VA), (BO,VB), (BO,VC), (BO,VD), (BO,VE), (BO,VF), (BO,VG), (BO,VH), (BO,VI), (BO,VJ), (BO,VK), (BO,VL), (BO,VM), (BO,VN), (BO,VO), (BO,VP), (BO,VQ), (BO,VR), (BO,VS), (BO,VT), (BO,VU), (BO,VV), (BO,VW), (BO,VX), (BO,VY), (BO,VZ), (BO,WA), (BO,WB), (BO,WC), (BP,VA), (BP,VB), (BP,VC), (BP,VD), (BP,VE), (BP,VF), (BP,VG), (BP,VH), (BP,VI), (BP,VJ), (BP,VK), (BP,VL), (BP,VM), (BP,VN), (BP,VO), (BP,VP), (BP,VQ), (BP,VR), (BP,VS), (BP,VT), (BP,VU), (BP,VV), (BP,VW), (BP,VX), (BP,VY), (BP,VZ), (BP,WA), (BP,WB), (BP,WC), (BQ,VA), (BQ,VB), (BQ,VC), (BQ,VD), (BQ,VE), (BQ,VF), (BQ,VG), (BQ,VH), (BQ,VI), (BQ,VJ), (BQ,VK), (BQ,VL), (BQ,VM), (BQ,VN), (BQ,VO), (BQ,VP), (BQ,VQ), (BQ,VR), (BQ,VS), (BQ,VT), (BQ,WU), (BQ,VV), (BQ,VW), (BQ,VX), (BQ,VY), (BQ,VZ), (BQ,WA), (BQ,WB), (BQ,WC), (BR,VA), (BR,VB), (BR,VC), (BR,VD), (BR,VE), (BR,VF), (BR,VG), (BR,VH), (BR,VI), (BR,VJ), (BR,VK), (BR,VL), (BR,VM), (BR,VN), (BR,VO), (BR,VP), (BR,VQ), (BR,VR), (BR,VS), (BR,VT), (BR,VU), (BR,VV), (BR,VW), (BR,VX), (BR,VY), (BR,VZ), (BR,WA), (BR,WB), (BR,WC), (BS,VA), (BS,VB), (BS,VC), (BS,VD), (BS,VE), (BS,VF), (BS,VG), (BS,VH), (BS,VI), (BS,VJ), (BS,VK), (BS,VL), (BS,VM), (BS,VN), (BS,VO), (BS,VP), (BS,VQ), (BS,VR), (BS,VS), (BS,VT), (BS,VU), (BS,VV), (BS,VW), (BS,VX), (BS,VY), (BS,VZ), (BS,WA), (BS,WB), (BS,WC), (BT,VA), (BT,VB), (BT,VC), (BT,VD), (BT,VE), (BT,VF), (BT,VG), (BT,VH), (BT,VI), (BT,VJ), (BT,VK), (BT,VL), (BT,VM), (BT,VN), (BT,VO), (BT,VP), (BT,VQ), (BT,VR), (BT,VS), (BT,VT), (BT,VU), (BT,VV), (BT,VW), (BT,VX), (BT,VY), (BT,VZ), (BT,WA), (BT,WB), (BT,WC), (BU,VA), (BU,VB), (BU,VC), (BU,VD), (BU,VE), (BU,VF), (BU,VG), (BU,VH), (BU,VI), (BU,VJ), (BU,VK), (BU,VL), (BU,VM), (BU,VN), (BU,VO), (BU,VP), (BU,VQ), (BU,VR), (BU,VS), (BU,VT), (BU,VU), (BU,VV), (BU,VW), (BU,VX), (BU,VY), (BU,VZ), (BU,WA), (BU,WB), (BU,WC), (BV,VA), (BV,VB), (BV,VC), (BV,VD), (BV,VE), (BV,VF), (BV,VG), (BV,VH), (BV,VI), (BV,VJ), (BV,VK), (BV,VL), (BV,VM), (BV,VN), (BV,VO), (BV,VP), (BV,VQ), (BV,VR), (BV,VS), (BV,VT), (BV,VU), (BV,VV), (BV,VW), (BV,VX), (BV,VY), (BV,VZ), (BV,WA), (BV,WB), (BV,WC), (BW,VA), (BW,VB), (BW,VC), (BW,VD), (BW,VE), (BW,VF), (BW,VG), (BW,VH), (BW,VI), (BW,VJ), (BW,VK), (BW,VL), (BW,VM), (BW,VN), (BW,VO), (BW,VP), (BW,VQ), (BW,VR), (BW,VS), (BW,VT), (BW,VU), (BW,VV), (BW,VW), (BW,VX), (BW,VY), (BW,VZ), (BW,WA), (BW,WB), (BW,WC), (BX,VA), (BX,VB), (BX,VC), (BX,VD), (BX,VE), (BX,VF), (BX,VG), (BX,VH), (BX,VI), (BX,VJ), (BX,VK), (BX,VL), (BX,VM), (BX,VN), (BX,VO), (BX,VP), (BX,VQ), (BX,VR), (BX,VS), (BX,VT), (BX,VU), (BX,Vv), (BX,VW), (BX,VX), (BX,VY), (BX,VZ), (BX,WA), (BX,WB), (BX,WC), (BY,VA), (BY,VB), (BY,VC), (BY,VD), (BY,VE), (BY,VF), (BY,VG), (BY,VH), (BY,VI), (BY,VJ), (BY,VK), (BY,VL), (BY,VM), (BY,VN), (BY,VO), (BY,VP), (BY,VQ), (BY,

VR), (BY,VS), (BY,VT), (BY,VU), (BY,VV), (BY,VW), (BY,VX), (BY,VY), (BY,VZ), (BY,WA), (BY,WB), (BY,WC), (BZ,VA), (BZ,VB), (BZ,VC), (BZ,VD), (BZ,VE), (BZ,VF), (BZ,VG), (BZ,VH), (BZ,VI), (BZ,VJ), (BZ,VK), (BZ,VL), (BZ,VM), (BZ,VN), (BZ,VO), (BZ,VP), (BZ,VQ), (BZ,VR), (BZ,VS), (BZ,VT), (BZ,VU), (BZ,VW), (BZ,VW), (BZ,VX), (BZ,VY), (BZ,VZ), (BZ,WA), (BZ,WB), (BZ,WC),
(CA,VA), (CA,VB), (CA,VC), (CA,VD), (CA,VE), (CA,VF), (CA,VG), (CA,VH), (CA,VI), (CA,VJ), (CA,VK), (CA,VL), (CA,VM), (CA,VN), (CA,VO), (CA,VP), (CA,VQ), (CA,VR), (CA,VS), (CA,VT), (CA,VU), (CA,VV), (CA,VW), (CA,VX), (CA,VY), (CA,VZ), (CA,WA), (CA,WB), (CA,WC), (CB,VA), (CB,VB), (CB,VC), (CB,VD), (CB,VE), (CB,VF), (CB,VG), (CB,VH), (CB,VI), (CB,VJ), (CB,VK), (CB,VL), (CB,VM), (CB,VN), (CB,VO), (CB,VP), (CB,VQ), (CB,VR), (CB,VS), (CB,VT), (CB,VU), (CB,VV), (CB,VW), (CB,VX), (CB,VY), (CB,VZ), (CB,WA), (CB,WB), (CB,WC), (CC,VA), (CC,VB), (CC,VC), (CC,VD), (CC,VE), (CC,VF), (CC,VG), (CC,VH), (CC,VI), (CC,VJ), (CC,VK), (CC,VL), (CC,VM), (CC,VN), (CC,VO), (CC,VP), (CC,VQ), (CC,VR), (CC,VS), (CC,VT), (CC,VU), (CC,VV), (CC,VW), (CC,VX), (CC,VY), (CC,VZ), (CC,WA), (CC,WB), (CC,WC), (CD,VA), (CD,VB), (CD,VC), (CD,VD), (CD,VE), (CD,VF), (CD,VG), (CD,VH), (CD,VI), (CD,VJ), (CD,VK), (CD,VL), (CD,VM), (CD,VN), (CD,VO), (CD,VP), (CD,VQ), (CD,VR), (CD,VS), (CD,VT), (CD,VW), (CD,VV), (CD,VW), (CD,VX), (CD,VY), (CD,VZ), (CD,WA), (CD,WB), (CD,WC), (CE,VA), (CE,VB), (CE,VC), (CE,VD), (CE,VE), (CE,VF), (CE,VG), (CE,VH), (CE,VI), (CE,VJ), (CE,VK), (CE,VL), (CE,VM), (CE,VN), (CE,VO), (CE,VP), (CE,VQ), (CE,VR), (CE,VS), (CE,VT), (CE,VU), (CE,VV), (CE,VW), (CE,VX), (CE,VY), (CE,VZ), (CE,WA), (CE,WB), (CE,WC), (CF,VA), (CF,VB), (CF,VC), (CF,VD), (CF,VE), (CF,VF), (CF,VG), (CF,VH), (CF,VI), (CF,VJ), (CF,VK), (CF,VL), (CF,VM), (CF,VN), (CF,VO), (CF,VP), (CF,VQ), (CF,VR), (CF,VS), (CF,VT), (CF,VU), (CF,VV), (CF,VW), (CF,VX), (CF,VY), (CF,VZ), (CF,WA), (CF,WB), (CF,WC), (CG,VA), (CG,VB), (CG,VC), (CG,VD), (CG,VE), (CG,VF), (CG,VG), (CG,VH), (CG,VI), (CG,VJ), (CG,VK), (CG,VL), (CG,VM), (CG,VN), (CG,VO), (CG,VP), (CG,VQ), (CG,VR), (CG,VS), (CG,VT), (CG,VU), (CG,VV), (CG,VW), (CG,VX), (CG,VY), (CG,VZ), (CG,WA), (CG,WB), (CG,WC), (CH,VA), (CH,VB), (CH,VC), (CH,VD), (CH,VE), (CH,VF), (CH,VG), (CH,VH), (CH,VI), (CH,VJ), (CH,VK), (CH,VL), (CH,VM), (CH,VN), (CH,VO), (CH,VP), (CH,VQ), (CH,VR), (CH,VS), (CH,VT), (CH,VU), (CH,VV), (CH,VW), (CH,VX), (CH,VY), (CH,VZ), (CH,WA), (CH,WB), (CH,WC), (CI,VA), (CI,VB), (CI,VC), (CI,VD), (CI,VE), (CI,VF), (CI,VG), (CI,VH), (CI,VI), (CI,VJ), (CI,VK), (CI,VL), (CI,VM), (CI,VN), (CI,VO), (CI,VP), (CI,VQ), (CI,VR), (CI,VS), (CI,VT), (CI,WU), (CI,VV), (CI,VW), (CI,VX), (CI,VY), (CI,VZ), (CI,WA), (CI,WB), (CI,WC), (CJ,VA), (CJ,VB), (CJ,VC), (CJ,VD), (CJ,VE), (CJ,VF), (CJ,VG), (CJ,VH), (CJ,VI), (CJ,VJ), (CJ,VK), (CJ,VL), (CJ,VM), (CJ,VN), (CJ,VO), (CJ,VP), (CJ,VQ), (CJ,VR), (CJ,VS), (CJ,VT), (CJ,VU), (CJ,VV), (CJ,VW), (CJ,VX), (CJ,VY), (CJ,VZ), (CJ,WA), (CJ,WB), (CJ,WC), (CK,VA), (CK,VB), (CK,VC), (CK,VD), (CK,VE), (CK,VF), (CK,VG), (CK,VH), (CK,VI), (CK,VJ), (CK,VK), (CK,VL), (CK,VM), (CK,VN), (CK,VO), (CK,VP), (CK,VQ), (CK,VR), (CK,VS), (CK,VT), (CK,VU), (CK,VV), (CK,VW), (CK,VX), (CK,VY), (CK,VZ), (CK,WA), (CK,WB), (CK,WC), (CL,VA), (CL,VB), (CL,VC), (CL,VD), (CL,VE), (CL,VF), (CL,VG), (CL,VH), (CL,VI), (CL,VJ), (CL,VK), (CL,VL), (CL,VM), (CL,VN), (CL,VO), (CL,VP), (CL,VQ), (CL,VR), (CL,VS), (CL,VT), (CL,VU), (CL,UV), (CL,VW), (CL,VX), (CL,VY), (CL,VZ), (CL,WA), (CL,WB), (CL,WC), (CM,VA), (CM,VB), (CM,VC), (CM,VD), (CM,VE), (CM,VF), (CM,VG), (CM,VH), (CM,VI), (CM,VJ), (CM,VK), (CM,VL), (CM,VM), (CM,VN), (CM,VO), (CM,VP), (CM,VQ), (CM,VR), (CM,VS), (CM,VT), (CM,VU), (CM,VV), (CM,VW), (CM,VX), (CM,VY), (CM,VZ), (CM,WA), (CM,WB), (CM,WC), (CN,VA), (CN,VB), (CN,VC), (CN,VD), (CN,VE), (CN,VF), (CN,VG), (CN,VH), (CN,VI), (CN,VJ), (CN,VK), (CN,VL), (CN,VM), (CN,VN), (CN,VO), (CN,VP), (CN,VQ), (CN,VR), (CN,VS), (CN,VT), (CN,VU), (CN,VV), (CN,VW), (CN,VX), (CN,VY), (CN,VZ), (CN,WA), (CN,WB), (CN,WC), (CO,VA), (CO,VB), (CO,VC), (CO,VD), (CO,VE), (CO,VF), (CO,VG), (CO,VH), (CO,VI), (CO,VJ), (CO,VK), (CO,VL), (CO,VM), (CO,VN), (CO,VO), (CO,VP), (CO,VQ), (CO,VR), (CO,VS), (CO,VT), (CO,VU), (CO,VV), (CO,VW), (CO,VX), (CO,VY), (CO,VZ), (CO,WA), (CO,WB), (CO,WC), (CP,VA), (CP,VB), (CP,VC), (CP,VD), (CP,VE), (CP,VF), (CP,VG), (CP,VH), (CP,VI), (CP,VJ), (CP,VK), (CP,VL), (CP,VM), (CP,VN), (CP,VO), (CP,VP), (CP,VQ), (CP,VR), (CP,VS), (CP,VT), (CP,VU), (CP,VV), (CP,VW), (CP,VX), (CP,VY), (CP,VZ), (CP,WA), (CP,WB), (CP,WC), (CQ,VA), (CQ,VB), (CQ,VC), (CQ,VD), (CQ,VE), (CQ,VF), (CQ,VG), (CQ,VH), (CQ,VI), (CQ,VJ), (CQ,VK), (CQ,VL), (CQ,VM), (CQ,VN), (CQ,VO), (CQ,VP), (CQ,VQ), (CQ,VR), (CQ,VS), (CQ,VT), (CQ,VU), (CQ,VV), (CQ,VW), (CQ,VX), (CQ,VY), (CQ,VZ), (CQ,WA), (CQ,WB), (CQ,WC), (CR,VA), (CR,VB), (CR,VC), (CR,VD), (CR,VE), (CR,VF), (CR,VG), (CR,VH), (CR,VI), (CR,VJ), (CR,VK), (CR,VL), (CR,VM), (CR,VN), (CR,VO), (CR,VP), (CR,VQ), (CR,VR), (CR,VS), (CR,VT), (CR,VU), (CR,VV), (CR,VW), (CR,VX), (CR,VY), (CR,VZ), (CR,WA), (CR,WB), (CR,WC), (CS,VA), (CS,VB), (CS,VC), (CS,VD), (CS,VE), (CS,VF), (CS,VG), (CS,VH), (CS,VI), (CS,VJ), (CS,VK), (CS,VL), (CS,VM), (CS,VN), (CS,VO), (CS,VP), (CS,VQ), (CS,VR), (CS,VS), (CS,VT), (CS,VU), (CS,VV), (CS,VW), (CS,VX), (CS,VY), (CS,VZ), (CS,WA), (CS,WB), (CS,WC), (CT,VA), (CT,VB), (CT,VC), (CT,VD), (CT,VE), (CT,VF), (CT,VG), (CT,VH), (CT,VI), (CT,VJ), (CT,VK), (CT,VL), (CT,VM), (CT,VN), (CT,VO), (CT,VP), (CT,VQ), (CT,VR), (CT,VS), (CT,VT), (CT,VU), (CT,Vv), (CT,VW), (CT,VX), (CT,VY), (CT,VZ), (CT,WA), (CT,WB), (CT,WC), (CU,VA), (CU,VB), (CU,VC), (CU,VD), (CU,VE), (CU,VF), (CU,VG), (CU,VH), (CU,VI), (CU,VJ), (CU,VK), (CU,VL), (CU,VM), (CU,VN), (CU,VO), (CU,VP), (CU,VQ), (CU,VR), (CU,VS), (CU,VT), (CU,VU), (CU,VV), (CU,VW), (CU,VX), (CU,VY), (CU,VZ), (CU,WA), (CU,WB), (CU,WC), (CV,VA), (CV,VB), (CV,VC), (CV,VD), (CV,VE), (CV,VF), (CV,VG), (CV,VH), (CV,VI), (CV,VJ), (CV,VK), (CV,VL), (CV,VM), (CV,VN), (CV,VO), (CV,VP), (CV,VQ), (CV,VR), (CV,VT), (CV,VU), (CV,VV), (CV,VW), (CV,VX), (CV,VY), (CV,VZ), (CV,WA), (CV,WB), (CV,WC), (CW,VA), (CW,VB), (CW,VC), (CW,VD), (CW,VE), (CW,VF), (CW,VG), (CW,VH), (CW,VI), (CW,VJ), (CW,VK), (CW,VL), (CW,VM), (CW,VN), (CW,VO), (CW,VP), (CW,VQ), (CW,VR), (CW,VS), (CW,VT), (CW,VU), (CW,VV), (CW,VW), (CW,VX), (CW,VY), (CW,VZ), (CW,WA), (CW,WB), (CW,WC), (CX,VA), (CX,VB), (CX,VC), (CX,VD), (CX,VE), (CX,VF), (CX,VG), (CX,VH), (CX,VI), (CX,VJ), (CX,VK), (CX,VL), (CX,VM), (CX,VN), (CX,VO), (CX,VP), (CX,VQ), (CX,VR), (CX,VS), (CX,VT), (CX,VU), (CX,VV), (CX,VW), (CX,VX), (CX,VY), (CX,VZ), (CX,WA), (CX,WB), (CX,WC), (CY, VA), (CY,VB), (CY,VC), (CY,VD), (CY,VE), (CY,VF), (CY,VG), (CY,VH), (CY,VI), (CY,VJ), (CY,VK), (CY,VL), (CY,VM), (CY,VN), (CY,VO), (CY,VP), (CY,VQ), (CY,VR), (CY,VS), (CY,VT), (CY,VU), (CY,VV), (CY,VW), (CY,VX), (CY,VY), (CY,VZ), (CY,WA), (CY,WB), (CY,WC), (CZ,VA), (CZ,VB), (CZ,VC), (CZ,VD), (CZ,VE), (CZ,VF), (CZ,VG), (CZ,VH), (CZ,VI), (CZ,VJ), (CZ,VK), (CZ,VL), (CZ,VM), (CZ,VN), (CZ,VO), (CZ,VP), (CZ,VQ), (CZ,VR), (CZ,VS), (CZ,VT), (CZ,VU), (CZ,VV), (CZ,VW), (CZ,VX), (CZ,VY), (CZ,VZ), (CZ,WA), (CZ,WB), (CZ,WC), (DA,VA), (DA,VB), (DA,VC), (DA,VD), (DA,VE), (DA,VF), (DA,VG), (DA,VH), (DA,VI), (DA,VJ), (DA,VK), (DA,VL), (DA,VM), (DA,VN), (DA,VO), (DA,VP), (DA,VQ), (DA,VR), (DA,VS), (DA,VT), (DA,WU), (DA,VV), (DA,VW), (DA,VX), (DA,VY), (DA,VZ), (DA,WA), (DA,WB), (DA,WC), (DB,VA), (DB,VB), (DB,VC), (DB,VD), (DB,VE), (DB,VF), (DB,VG), (DB,VH), (DB,VI), (DB,VJ), (DB,VK), (DB,VL), (DB,VM), (DB,VN), (DB,VO), (DB,VP), (DB,VQ), (DB,VR), (DB,VS), (DB,VT), (DB,VU), (DB,VV), (DB,VW), (DB,VX), (DB,VY), (DB,VZ), (DB,WA), (DB,WB), (DB,WC), (DC,VA), (DC,VA), (DC,VB), (DC,VB), (DC,VC), (DC,VD), (DC,VE), (DC,VF), (DC,VG), (DC,VH), (DC,VI), (DC,VJ), (DC,VK), (DC,VL), (DC,VM), (DC,VN), (DC,VO), (DC,VP), (DC,VQ), (DC,VR), (DC,VS), (DC,VT), (DC,VU), (DC,VV), (DC,VW), (DC,VX), (DC,VY), (DC,VZ), (DC,WA), (DC,WB), (DC,WC), (DD,VC), (DD,VD), (DD,VE), (DD,VF), (DD,VG), (DD,VH), (DD,VI), (DD,VJ), (DD,VK), (DD,VL), (DD,VM), (DD,VN), (DD,VO), (DD,VP), (DD,VQ), (DD,VR), (DD,VS), (DD,VT), (DD,VU), (DD,VV), (DD,VW), (DD,VX), (DD,VY), (DD,VZ), (DD,WA), (DD,WB), (DD,WC), (DE,VA), (DE,VB), (DE,VC), (DE,VD), (DE,VE), (DE,VF), (DE,VG), (DE,VH), (DE,VI), (DE,VJ), (DE,VK), (DE,VL), (DE,VM), (DE,VN), (DE,VO), (DE,VP), (DE,VQ), (DE,VR), (DE,VS), (DE,VT), (DE,VU), (DE,VV), (DE,VW), (DE,VX), (DE,VY), (DE,VZ), (DE,WA), (DE,WB), (DE,WC), (DF,VA), (DF,VB), (DF,VC), (DF,VD), (DF,VE), (DF,VF), (DF,VG), (DF,VH), (DF,VI), (DF,VJ), (DF,VK), (DF,VL), (DF,VM), (DF,VN), (DF,VO), (DF,VP), (DF,VQ), (DF,VR), (DF,VS), (DF,VT), (DF,VU), (DF,VV), (DF,VW), (DF,VX), (DF,VY), (DF,VZ), (DF,WA), (DF,WB), (DF,WC), (DG,VA), (DG,VB), (DG,VC), (DG,VD), (DG,VE), (DG,VF), (DG,VG), (DG,VH), (DG,VI), (DG,VJ), (DG,VK), (DG,VL), (DG,VM), (DG,VN), (DG,VO), (DG,VP), (DG,VQ), (DG,VR), (DG,VS), (DG,VT), (DG,VU), (DG,VV), (DG,VW), (DG,VX), (DG,VY), (DG,VZ), (DG,WA), (DG,WB), (DG,WC), (DH,VA), (DH,VB), (DH,VC), (DH,VD), (DH,VE), (DH,VF), (DH,VG), (DH,VH), (DH,VI), (DH,VJ), (DH,VK), (DH,VL), (DH,VM), (DH,VN), (DH,VO), (DH,VP), (DH,VQ), (DH,VR), (DH,VS), (DH,VT), (DH,VU), (DH,VV), (DH,VW), (DH,VX), (DH,VY), (DH,VZ), (DH,WA), (DH,WB), (DH,WC), (DI,VA), (DI,VB), (DI,VC), (DI,VD), (DI,VE), (DI,VF), (DI,VG), (DI,VH), (DI,VI), (DI,VJ), (DI,VK), (DI,VL), (DI,VM), (DI,VN), (DI,VO), (DI,VP), (DI,VQ), (DI,VR), (DI,VS), (DI,VT), (DI,VU), (DI,VV), (DI,VW), (DI,VX), (DI,VY), (DI,VZ), (DI,WA), (DI,WB), (DI,WC), (DJ,VA), (DJ,VB), (DJ,VC), (DJ,VD), (DJ,VE), (DJ,VF), (DJ,VG), (DJ,VH), (DJ,VI), (DJ,VJ), (DJ,VK), (DJ,VL), (DJ,VM), (DJ,VN), (DJ,VO), (DJ,VP), (DJ,VQ), (DJ,VR), (DJ,VS), (DJ,VT), (DJ,VU), (DJ,VV), (DJ,VW), (DJ,VX), (DJ,VY), (DJ,VZ), (DJ,WA), (DJ,WB), (DJ,WC), (DK,VA), (DK,VB), (DK,VC), (DK,VD), (DK,VE), (DK,VF), (DK,VG), (DK,VH), (DK,VI), (DK,VJ), (DK,VK), (DK,VL), (DK,VM), (DK,VN), (DK,VO), (DK,VP), (DK,VQ), (DK,VR), (DK,VS), (DK,VT), (DK,VU), (DK,VV), (DK,VW), (DK,VX), (DK,VY), (DK,VZ), (DK,WA), (DK,WB), (DK,WC), (DL,VA), (DL,VB), (DL,VC), (DL,VD), (DL,VE), (DL,VF), (DL,VG), (DL,VH), (DL,VI), (DL,VJ), (DL,VK), (DL,VL), (DL,VM), (DL,VN), (DL,VO), (DL,VP), (DL,VQ), (DL,VR), (DL,VS), (DL,VT), (DL,VU), (DL,VV), (DL,VW), (DL,VX), (DL,VY), (DL,VZ), (DL,WA), (DL,WB), (DL,WC), (DM,VA), (DM,VB), (DM,VC), (DM,VD), (DM,VE), (DM,VF), (DM,VG), (DM,VH), (DM,VI), (DM,VJ), (DM,VK), (DM,VL), (DM,VM), (DM,VN), (DM,VO), (DM,VP), (DM,VQ), (DM,VR), (DM,VS), (DM,VT), (DM,VU), (DM,VV), (DM,VW), (DM,VX), (DM,VY), (DM,VZ), (DM,WA), (DM,WB), (DM,WC), (DN,VA), (DN,VB), (DN,VC), (DN,VD), (DN,VE), (DN,VF), (DN,VG), (DN,VH), (DN,VI), (DN,VJ), (DN,VK), (DN,VL), (DN,VM), (DN,VN), (DN,VO), (DN,VP), (DN,VQ), (DN,VR), (DN,VS), (DN,VT), (DN,VU), (DN,VV), (DN,VW), (DN,VX), (DN,VY), (DN,VZ), (DN,WA), (DN,WB), (DN,WC), (DO,VA), (DO,VB), (DO,VC), (DO,VD), (DO,VE), (DO,VF), (DO,VG), (DO,VH), (DO,VI), (DO,VJ), (DO,VK), (DO,VL), (DO,VM), (DO,VN), (DO,VO), (DO,VP), (DO,VQ), (DO,VR), (DO,VS), (DO,VT), (DO,VU), (DO,VV), (DO,VW), (DO,VX), (DO,VY), (DO,VZ), (DO,WA), (DO,WB), (DO,WC), (DP,VA), (DP,VB), (DP,VC), (DP,VD), (DP,VE), (DP,VF), (DP,VG), (DP,VH), (DP,VI), (DP,VJ), (DP,VK), (DP,VL), (DP,VM), (DP,VN), (DP,VO), (DP,VP), (DP,VQ), (DP,VR), (DP,VS), (DP,VT), (DP,VU), (DP,VV), (DP,VW), (DP,VX), (DP,VY), (DP,VZ), (DP,WA), (DP,WB), (DP,WC), (DQ,VA), (DQ,VB), (DQ,VC), (DQ,VD), (DQ,VE), (DQ,VF), (DQ,VG), (DQ,VH), (DQ,VI), (DQ,VJ), (DQ,VK), (DQ,VL), (DQ,VM), (DQ,VN), (DQ,VO), (DQ,VP), (DQ,VQ), (DQ,VR), (DQ,VS), (DQ,VT), (DQ,VU), (DQ,VV), (DQ,VW), (DQ,VX), (DQ,VY), (DQ,VZ), (DQ,WA), (DQ,WB), (DQ,WC), (DR,VA), (DR,VB), (DR,VC), (DR,VD), (DR,VE), (DR,VF), (DR,VG), (DR,VH), (DR,VI), (DR,VJ), (DR,VK), (DR,VL), (DR,VM), (DR,VN), (DR,VO), (DR,VP), (DR,VQ), (DR,VR), (DR,VS), (DR,VT), (DR,VU), (DR,VV), (DR,VW), (DR,VX), (DR,VY), (DR,VZ), (DR,WA), (DR,WB), (DR,WC), (DS,VA), (DS,VB), (DS,VC), (DS,VD), (DS,VE), (DS,VF), (DS,VG), (DS,VH), (DS,VI), (DS,VJ), (DS,VK), (DS,VL), (DS,VM), (DS,VN), (DS,VO), (DS,VP), (DS,VQ), (DS,VR), (DS,VS), (DS,VT), (DS,VU), (DS,VV), (DS,VW), (DS,VX), (DS,VY), (DS,VZ), (DS,WA), (DS,WB), (DS,WC), (DT,VA), (DT,VB), (DT,VC), (DT,VD), (DT,VE), (DT,VF), (DT,VG), (DT,VH), (DT,VI), (DT,VJ), (DT,VK), (DT,VL), (DT,VM), (DT,VN), (DT,VO), (DT,VP), (DT,VQ), (DT,VR), (DT,VS), (DT,VT), (DT,VU), (DT,VV), (DT,VW), (DT,VX), (DT,VY), (DT,VZ), (DT,WA), (DT,WB), (DT,WC), (DU,VA), (DU,VB), (DU,VC), (DU,VD), (DU,VE), (DU,VF), (DU,VG), (DU,VH), (DU,VI), (DU,VJ), (DU,VK), (DU,VL), (DU,VM), (DU,VN), (DU,VO), (DU,VP), (DU,VQ), (DU,VR), (DU,VS), (DU,VT), (DU,VU), (DU,VV), (DU,VW), (DU,VX), (DU,VY), (DU,VZ), (DU,WA), (DU,WB), (DU,WC), (DV,VA), (DV,VB), (DV,VC), (DV,VD), (DV,VE), (DV,VF), (DV,VG), (DV,VH), (DV,VI), (DV,VJ), (DV,VK), (DV,VL), (DV,VM), (DV,VN), (DV,VO), (DV,VP), (DV,VQ), (DV,VR), (DV,VS), (DV,VT), (DV,VU), (DV,VV), (DV,VW), (DV,VX), (DV,VY), (DV,VZ), (DV,WA), (DV,WB), (DV,WC), (DW,VA), (DW,VB), (DW,VC), (DW,VD), (DW,VE), (DW,VF), (DW,VG), (DW,VH), (DW,VI), (DW,VJ), (DW,VK), (DW,VL), (DW,VM), (DW,VN), (DW,VO), (DW,VP), (DW,VQ), (DW,VR), (DW,VS), (DW,VT), (DW,VU), (DW,VV), (DW,VW), (DW,VX), (DW,VY), (DW,VZ), (DW,WA), (DW,WB), (DW,WC), (DX,VA), (DX,VB), (DX,VC), (DX,VD), (DX,VE), (DX,VF), (DX,VG), (DX,VH), (DX,VI), (DX,VJ), (DX,VK), (DX,VL), (DX,VM), (DX,VN), (DX,VO), (DX,VP), (DX,VQ), (DX,VR), (DX,VS), (DX,VT), (DX,VU), (DX,VV), (DX,VW), (DX,VX), (DX,VY), (DX,VZ), (DX,WA), (DX,WB), (DX,WC), (DY,VA), (DY,VB), (DY,VC), (DY,VD), (DY,VE), (DY,VF), (DY,VG), (DY,VH), (DY,VI), (DY,VJ), (DY,VK), (DY,VL), (DY,VM), (DY,VN), (DY,VO), (DY,VP), (DY,VQ), (DY,VR), (DY,VS), (DY,VT), (DY,VU), (DY,VV), (DY,VW), (DY,VX), (DY,VY), (DY,VZ), (DY,WA), (DY,WB), (DY,WC), (DZ,VA), (DZ,VB), (DZ,VC), (DZ,VD), (DZ,VE), (DZ,VF), (DZ,VG), (DZ,VH), (DZ,VI), (DZ,VJ), (DZ,VK), (DZ,VL), (DZ,VM), (DZ,VN), (DZ,VO), (DZ,VP), (DZ,VQ), (DZ,VR), (DZ,VS), (DZ,VT), (DZ,VU), (DZ,VV), (DZ,VW), (DZ,VX), (DZ,VY), (DZ,VZ), (DZ,WA), (DZ,WB), (DZ,WC), (EA,VA), (EA,VB), (EA,VC), (EA,VD), (EA,VE), (EA,VF), (EA,VG), (EA,VH), (EA,VI), (EA,VJ), (EA,VK), (EA,VL), (EA,VM), (EA,VN), (EA,VO), (EA,VP), (EA,VQ), (EA,VR), (EA,VS), (EA,VT), (EA,VU), (EA,VV), (EA,VW), (EA,VX), (EA,VY), (EA,VZ), (EA,WA), (EA,WB), (EA,WC), (EB,VA), (EB,VB), (EB,VC), (EB,VD), (EB,VE), (EB,VF), (EB,VG), (EB,VH), (EB,VI), (EB,VJ), (EB,VK), (EB,VL), (EB,VM), (EB,VN), (EB,VO), (EB,VP), (EB,VQ), (EB,VR), (EB,VS), (EB,VT), (EB,VU), (EB,VV), (EB,VW), (EB,VX), (EB,VY), (EB,VZ), (EB,WA), (EB,WB), (EB,WC), (EC,VA), (EC,VA), (EC,VB), (EC,VB), (EC,VC), (EC,VD), (EC,VE), (EC,VF), (EC,VG), (EC,VH), (EC,VI), (EC,VJ), (EC,VK), (EC,VL), (EC,VM), (EC,VN), (EC,VO), (EC,VP), (EC,VQ), (EC,VR), (EC,VS), (EC,VT), (EC,VU), (EC,VV), (EC,VW), (EC,VX), (EC,VY), (EC,VZ), (EC,WA), (EC,WB), (EC,WC), (ED,VC), (ED,VD), (ED,VE), (ED,VF), (ED,VG), (ED,VH), (ED,VI), (ED,VJ), (ED,VK), (ED,VL), (ED,VM), (ED,VN), (ED,VO), (ED,VP), (ED,VQ), (ED,VR), (ED,VS), (ED,VT), (ED,VU), (ED,VV), (ED,VW), (ED,VX), (ED,VY), (ED,VZ), (ED,WA), (ED,WB), (ED,WC), (EE,VA), (EE,VB), (EE,VC), (EE,VD), (EE,VE), (EE,VF), (EE,VG), (EE,VH), (EE,VI), (EE,VJ), (EE,VK), (EE,VL), (EE,VM), (EE,VN), (EE,VO), (EE,VP), (EE,VQ), (EE,VR), (EE,VS), (EE,VT), (EE,VU), (EE,VV), (EE,VW), (EE,VX), (EE,VY), (EE,VZ), (EE,WA), (EE,WB), (EE,WC), (EF,VA), (EF,VB), (EF,VC), (EF,VD), (EF,VE), (EF,VF), (EF,VG), (EF,VH), (EF,VI), (EF,VJ), (EF,VK), (EF,VL), (EF,VM), (EF,VN), (EF,VO), (EF,VP), (EF,VQ), (EF,VR), (EF,VS), (EF,VT), (EF,VU), (EF,VV), (EF,VW), (EF,VX), (EF,VY), (EF,VZ), (EF,WA), (EF,WB), (EF,WC), (EG,VA), (EG,VB), (EG,VC), (EG,VD), (EG,VE), (EG,VF), (EG,VG), (EG,VH), (EG,VI), (EG,VJ), (EG,VK), (EG,VL), (EG,VM), (EG,VN), (EG,VO), (EG,VP), (EG,VQ), (EG,VR), (EG,VS), (EG,VT), (EG,VU), (EG,VV), (EG,VW), (EG,VX), (EG,VY), (EG,VZ), (EG,WA), (EG,WB), (EG,WC), (EH,VA), (EH,VB), (EH,VC), (EH,VD), (EH,VE), (EH,VF), (EH,VG), (EH,VH), (EH,VI), (EH,VJ), (EH,VK), (EH,VL), (EH,VM), (EH,VN), (EH,VO), (EH,VP), (EH,VQ), (EH,VR), (EH,VS), (EH,VT), (EH,VU), (EH,VV), (EH,VW), (EH,VX), (EH,VY), (EH,VZ), (EH,WA), (EH,WB), (EH,WC), (EI,VA), (EI,VB), (EI,VC), (EI,VD), (EI,VE), (EI,VF), (EI,VG), (EI,VH), (EI,VI), (EI,VJ), (EI,VK), (EI,VL), (EI,VM), (EI,VN), (EI,VO), (EI,VP), (EI,VQ), (EI,VR), (EI,VS), (EI,VT), (EI,VU), (EI,VV), (EI,VW), (EI,VX), (EI,VY), (EI,VZ), (EI,WA), (EI,WB), (EI,WC), (EJ,VA), (EJ,VB), (EJ,VC), (EJ,VD), (EJ,VE), (EJ,VF), (EJ,VG), (EJ,VH), (EJ,VI), (EJ,VJ), (EJ,VK), (EJ,VL), (EJ,VM), (EJ,VN), (EJ,VO), (EJ,VP), (EJ,VQ), (EJ,VR), (EJ,VS), (EJ,VT), (EJ,VU), (EJ,VV), (EJ,VW), (EJ,VX), (EJ,VY), (EJ,VZ), (EJ,WA), (EJ,WB), (EJ,WC), (EK,VA), (EK,VB), (EK,VC), (EK,VD), (EK,VE), (EK,VF), (EK,VG), (EK,VH), (EK,VI), (EK,VJ), (EK,VK), (EK,VL), (EK,VM), (EK,VN), (EK,VO), (EK,VP), (EK,VQ), (EK,VR), (EK,VS), (EK,VT), (EK,VU), (EK,VW), (EK,VW), (EK,VX), (EK,VY), (EK,VZ), (EK,WA), (EK,WB), (EK,WC), (EL,VA), (EL,VB), (EL,VC), (EL,VD), (EL,VE), (EL,VF), (EL,VG), (EL,VH), (EL,VI), (EL,VJ), (EL,VK), (EL,VL), (EL,VM), (EL,VN), (EL,VO), (EL,VP), (EL,VQ), (EL,VR), (EL,VS), (EL,VT), (EL,VU), (EL,VV), (EL,VW), (EL,VX), (EL,VY), (EL,VZ), (EL,WA), (EL,WB), (EL,WC), (EM,VA), (EM,VB), (EM,VC), (EM,VD), (EM,VE), (EM,VF), (EM,VG), (EM,VH), (EM,VI), (EM,VJ), (EM,VK), (EM,VL), (EM,VM), (EM,VN), (EM,VO), (EM,VP), (EM,VQ), (EM,VR), (EM,VS), (EM,VT), (EM,VU), (EM,VV), (EM,VW), (EM,VX), (EM,VY), (EM,VZ), (EM,WA), (EM,WB), (EM,WC), (EN,VA), (EN,VB), (EN,VC), (EN,VD), (EN,VE), (EN,VF), (EN,VG), (EN,VH), (EN,VI), (EN,VJ), (EN,VK), (EN,VL), (EN,VM), (EN,VN), (EN,VO), (EN,VP), (EN,VQ), (EN,VR), (EN,VS), (EN,VT), (EN,VU), (EN,VV), (EN,VW), (EN,VX), (EN,VY), (EN,VZ), (EN,WA), (EN,WB), (EN,WC), (EO,VA), (EO,VB), (EO,VC), (EO,VD), (EO,VE), (EO,VF), (EO,VG), (EO,VH), (EO,VI), (EO,VJ), (EO,VK), (EO,VL), (EO,VM), (EO,VN), (EO,VO), (EO,VP), (EO,VQ), (EO,VR), (EO,VS), (EO,VT), (EO,VU), (EO,VV), (EO,VW), (EO,VX), (EO,VY), (EO,VZ), (EO,WA), (EO,WB), (EO,WC), (EP,VA), (EP,VB), (EP,VC), (EP,VD), (EP,VE), (EP,VF), (EP,VG), (EP,VH), (EP,VI), (EP,VJ), (EP,VK), (EP,VL), (EP,VM), (EP,VN), (EP,VO), (EP,VP), (EP,VQ), (EP,VR), (EP,VS), (EP,VT), (EP,VU), (EP,VV), (EP,VW), (EP,VX), (EP,VY), (EP,VZ), (EP,WA), (EP,WB), (EP,WC), (EQ,VA), (EQ,VB), (EQ,VC), (EQ,VD), (EQ,VE), (EQ,VF), (EQ,VG), (EQ,VH), (EQ,VI), (EQ,VJ), (EQ,VK), (EQ,VL), (EQ,VM), (EQ,VN), (EQ,VO), (EQ,VP), (EQ,VQ), (EQ,VR), (EQ,VS), (EQ,VT), (EQ,VU), (EQ,VV), (EQ,VW), (EQ,VX), (EQ,VY), (EQ,VZ), (EQ,WA), (EQ,WB), (EQ,WC), (ER,VA), (ER,VB), (ER,VC), (ER,VD), (ER,VE), (ER,VF), (ER,VG), (ER,VH), (ER,VI), (ER,VJ), (ER,VK), (ER,VL), (ER,VM), (ER,VN), (ER,VO), (ER,VP), (ER,VQ), (ER,VR), (ER,VS), (ER,VT), (ER,VU), (ER,VV), (ER,VW), (ER,VX), (ER,VY), (ER,VZ), (ER,WA), (ER,WB), (ER,WC), (ES,VA), (ES,VB), (ES,VC), (ES,VD), (ES,VE), (ES,VF), (ES,VG), (ES,VH), (ES,VI), (ES,VJ), (ES,VK), (ES,VL), (ES,VM), (ES,VN), (ES,VO), (ES,VP), (ES,VQ), (ES,VR), (ES,VS), (ES,VT), (ES,VU), (ES,VV), (ES,VW), (ES,VX), (ES,VY), (ES,VZ), (ES,WA), (ES,WB), (ES,WC), (ET,VA), (ET,VB), (ET,VC), (ET,VD), (ET,VE), (ET,VF), (ET,VG), (ET,VH), (ET,VI), (ET,VJ), (ET,VK), (ET,VL), (ET,VM), (ET,VN), (ET,VO), (ET,VP), (ET,VQ), (ET,VR), (ET,VS), (ET,VT), (ET,VU), (ET,VV), (ET,VW), (ET,VX), (ET,VY), (ET,VZ), (ET,WA), (ET,WB), (ET,WC), (EU,VA), (EU,VB), (EU,VC), (EU,VD), (EU,VE), (EU,VF), (EU,VG), (EU,VH), (EU,VI), (EU,VJ), (EU,VK), (EU,VL), (EU,VM), (EU,VN), (EU,VO), (EU,VP), (EU,VQ), (EU,VR), (EU,VS), (EU,VT), (EU,VU), (EU,VV), (EU,VW), (EU,VX), (EU,VY), (EU,VZ), (EU,WA), (EU,WB), (EU,WC), (EV,VA), (EV,VB), (EV,VC), (EV,VD), (EV,VE), (EV,VF), (EV,VG), (EV,VH), (EV,VI), (EV,VJ), (EV,VK), (EV,VL), (EV,VM), (EV,VN), (EV,VO), (EV,VP), (EV,VQ), (EV,VR), (EV,VS), (EV,VT), (EV,VU), (EV,VV), (EV,VW), (EV,VX), (EV,VY), (EV,VZ), (EV,

WA), (EV,WB), (EV,WC), (EW,VA), (EW,VB), (EW,VC), (EW,VD), (EW,VE), (EW,VF), (EW,VG), (EW,VH), (EW, VI), (EW,VJ), (EW,VK), (EW,VL), (EW,VM), (EW,VN), (EW,VO), (EW,VP), (EW,VQ), (EW,VR), (EW,VS), (EW, VT), (EW,VU), (EW,VV), (EW,VW), (EW,VX), (EW,VY), (EW,VZ), (EW,WA), (EW,WB), (EW,WC), (EX,VA), (EX,VB), (EX,VC), (EX,VD), (EX,VE), (EX, VF), (EX,VG), (EX,VH), (EX,VI), (EX,VJ), (EX,VK), (EX,VL), (EX,VM), (EX,VN), (EX,VO), (EX,VP), (EX, VQ), (EX,VR), (EX,VS), (EX,VT), (EX,VU), (EX,VV), (EX,VW), (EX,VX), (EX,VY), (EX,VZ), (EX,WA), (EX, WB), (EX,WC), (EY,VA), (EY,VB), (EY,VC), (EY,VD), (EY,VE), (EY,VF), (EY,VG), (EY,VH), (EY,VI), (EY,VJ), (EY,VK), (EY,VL), (EY,VM), (EY,VN), (EY,VO), (EY, VP), (EY,VQ), (EY,VR), (EY,VS), (EY,VT), (EY,VU), (EY,VV), (EY,VW), (EY,VX), (EY,VY), (EY,VZ), (EY, WA), (EY,WB), (EY,WC), (EZ,VA), (EZ,VB), (EZ,VC), (EZ,VD), (EZ,VE), (EZ,VF), (EZ,VG), (EZ,VH), (EZ,VI), (EZ,VJ), (EZ,VK), (EZ,VL), (EZ,VM), (EZ,VN), (EZ,VO), (EZ,VP), (EZ,VQ), (EZ,VR), (EZ,VS), (EZ,VT), (EZ,VU), (EZ,VV), (EZ,VW), (EZ, VX), (EZ,VY), (EZ,VZ), (EZ,WA), (EZ,WB), (EZ,WC), (FA,VA), (FA,VB), (FA,VC), (FA,VD), (FA,VE), (FA,VF), (FA,VG), (FA,VH), (FA,VI), (FA,VJ), (FA,VK), (FA,VL), (FA,VM), (FA,VN), (FA,VO), (FA,VP), (FA,VQ), (FA, VR), (FA,VS), (FA,VT), (FA,VU), (FA,VV), (FA,VW), (FA,VX), (FA,VY), (FA,VZ), (FA,WA), (FA,WB), (FA, WC), (FB,VA), (FB,VB), (FB,VC), (FB,VD), (FB,VE), (FB,VF), (FB,VG), (FB,VH), (FB,VI), (FB,VJ), (FB,VK), (FB,VL), (FB,VM), (FB,VN), (FB,VO), (FB,VP), (FB, VQ), (FB,VR), (FB,VS), (FB,VT), (FB,VU), (FB,VV), (FB,VW), (FB,VX), (FB,VY), (FB,VZ), (FB,WA), (FB, WB), (FB,WC), (FC,VA), (FC,VA), (FC,VB), (FC,VB), (FC,VC), (FC,VD), (FC,VE), (FC,VF), (FC,VG), (FC,VH), (FC,VI), (FC,VJ), (FC,VK), (FC,VL), (FC,VM), (FC,VN), (FC,VO), (FC,VP), (FC,VQ), (FC, VR), (FC,VS), (FC,VT), (FC,VU), (FC,VV), (FC,VW), (FC,VX), (FC,VY), (FC,VZ), (FC,WA), (FC,WB), (FC, WC), (FD,VC), (FD,VD), (FD,VE), (FD,VF), (FD,VG), (FD,VH), (FD,VI), (FD,VJ), (FD,VK), (FD,VL), (FD,VM), (FD,VN), (FD,VO), (FD,VP), (FD,VQ), (FD, VR), (FD,VS), (FD,VT), (FD,WU), (FD,VV), (FD,VW), (FD,VX), (FD,VY), (FD,VZ), (FD,WA), (FD,WB), (FD, WC), (FE,VA), (FE,VB), (FE,VC), (FE,VD), (FE,VE), (FE,VF), (FE,VG), (FE,VH), (FE,VI), (FE,VJ), (FE,VK), (FE,VL), (FE,VM), (FE,VN), (FE,VO), (FE,VP), (FE,VQ), (FE,VR), (FE,VS), (FE,VT), (FE,VU), (FE,VV), (FE,VW), (FE,VX), (FE,VY), (FE,VZ), (FE,WA), (FE,WB), (FE,WC), (FF,VA), (FF,VB), (FF,VC), (FF,VD), (FF,VE), (FF,VF), (FF,VG), (FF,VH), (FF,VI), (FF,VJ), (FF,VK), (FF,VL), (FF,VM), (FF,VN), (FF,VO), (FF,VP), (FF,VQ), (FF,VR), (FF,VS), (FF,VT), (FF,VU), (FF,VV), (FF,VW), (FF,VX), (FF,VY), (FF,VZ), (FF,WA), (FF,WB), (FF,WC), (FG,VA), (FG,VB), (FG, VC), (FG,VD), (FG,VE), (FG,VF), (FG,VG), (FG,VH), (FG,VI), (FG,VJ), (FG,VK), (FG,VL), (FG,VM), (FG,VN), (FG,VO), (FG,VP), (FG,VQ), (FG,VR), (FG, VS), (FG,VT), (FG,VU), (FG,VV), (FG,VW), (FG,VX), (FG,VY), (FG,VZ), (FG,WA), (FG,WB), (FG,WC), (FH, VA), (FH,VB), (FH,VC), (FH,VD), (FH,VE), (FH,VF), (FH,VG), (FH,VH), (FH,VI), (FH,VJ), (FH,VK), (FH,VL), (FH,VM), (FH,VN), (FH,VO), (FH,VP), (FH, VQ), (FH,VR), (FH,VS), (FH,VT), (FH,VU), (FH,VV), (FH,VW), (FH,VX), (FH,VY), (FH,VZ), (FH,WA), (FH, WB), (FH,WC), (FI,VA), (FI,VB), (FI,VC), (FI,VD), (FI, VE), (FI,VF), (FI,VG), (FI,VH), (FI,VI), (FI,VJ), (FI,VK), (FI,VL), (FI,VM), (FI,VN), (FI,VO), (FI,VP), (FI,VQ), (FI,VR), (FI,VS), (FI,VT), (FI,VU), (FI,VV), (FI,VW), (FI,VX), (FI,VY), (FI,VZ), (FI,WA), (FI,WB), (FI,WC), (FJ,VA), (FJ,VB), (FJ,VC), (FJ,VD), (FJ,VE), (FJ,VF), (FJ,VG), (FJ,VH), (FJ,VI), (FJ,VJ), (FJ,VK), (FJ,VL), (FJ, VM), (FJ,VN), (FJ,VO), (FJ,VP), (FJ,VQ), (FJ,VR), (FJ, VS), (FJ,VT), (FJ,VU), (FJ,VV), (FJ,VW), (FJ,VX), (FJ, VY), (FJ,VZ), (FJ,WA), (FJ,WB), (FJ,WC), (FK,VA), (FK,VB), (FK,VC), (FK,VD), (FK,VE), (FK,VF), (FK, VG), (FK,VH), (FK,VI), (FK,VJ), (FK,VK), (FK,VL), (FK,VM), (FK,VN), (FK,VO), (FK,VP), (FK,VQ), (FK, VR), (FK,VS), (FK,VT), (FK,VU), (FK,VV), (FK,VW), (FK,VX), (FK,VY), (FK,VZ), (FK,WA), (FK,WB), (FK, WC), (FL,VA), (FL,VB), (FL,VC), (FL,VD), (FL,VE), (FL,VF), (FL,VG), (FL,VH), (FL,VI), (FL,VJ), (FL,VK), (FL,VL), (FL,VM), (FL,VN), (FL,VO), (FL,VP), (FL,VQ), (FL,VR), (FL,VS), (FL,VT), (FL,VU), (FL,VV), (FL,VW), (FL,VX), (FL,VY), (FL,VZ), (FL,WA), (FL,WB), (FL,WC), (FM,VA), (FM,VB), (FM, VC), (FM,VD), (FM,VE), (FM,VF), (FM,VG), (FM,VH), (FM,VI), (FM,VJ), (FM,VK), (FM,VL), (FM,VM), (FM, VN), (FM,VO), (FM,VP), (FM,VQ), (FM,VR), (FM,VS), (FM,VT), (FM,VU), (FM,VV), (FM,VW), (FM,VX), (FM,VY), (FM,VZ), (FM,WA), (FM,WB), (FM,WC), (FN,VA), (FN,VB), (FN,VC), (FN,VD), (FN,VE), (FN, VF), (FN,VG), (FN,VH), (FN,VI), (FN,VJ), (FN,VK), (FN,VL), (FN,VM), (FN,VN), (FN,VO), (FN,VP), (FN, VQ), (FN,VR), (FN,VS), (FN,VT), (FN,VU), (FN,VV), (FN,VW), (FN,VX), (FN,VY), (FN,VZ), (FN,WA), (FN, WB), (FN,WC), (FO,VA), (FO,VB), (FO,VC), (FO,VD), (FO,VE), (FO,VF), (FO,VG), (FO,VH), (FO,VI), (FO,VJ), (FO,VK), (FO,VL), (FO,VM), (FO,VN), (FO, VO), (FO,VP), (FO,VQ), (FO,VR), (FO,VS), (FO,VT), (FO,VU), (FO,VV), (FO,VW), (FO,VX), (FO,VY), (FO, VZ), (FO,WA), (FO,WB), (FO,WC), (FP,VA), (FP,VB), (FP,VC), (FP,VD), (FP,VE), (FP,VF), (FP,VG), (FP,VH), (FP,VI), (FP,VJ), (FP,VK), (FP,VL), (FP,VM), (FP,VN), (FP,VO), (FP,VP), (FP,VQ), (FP,VR), (FP,VS), (FP,VT), (FP,VU), (FP,VV), (FP,Vw), (FP,VX), (FP,VY), (FP,VZ), (FP,WA), (FP,WB), (FP,WC), (FQ,VA), (FQ,VB), (FQ,VC), (FQ,VD), (FQ,VE), (FQ,VF), (FQ,VG), (FQ, VH), (FQ,VI), (FQ,VJ), (FQ,VK), (FQ,VL), (FQ,VM), (FQ,VN), (FQ,VO), (FQ,VP), (FQ,VQ), (FQ,VR), (FQ, VS), (FQ,VT), (FQ,VU), (FQ,VV), (FQ,VW), (FQ,VX), (FQ,VY), (FQ,VZ), (FQ,WA), (FQ,WB), (FQ,WC), (FR, VA), (FR,VB), (FR,VC), (FR,VD), (FR,VE), (FR,VF), (FR,VG), (FR,VH), (FR,VI), (FR,VJ), (FR,VK), (FR,VL), (FR,VM), (FR,VN), (FR,VO), (FR,VP), (FR,VQ), (FR, VR), (FR,VS), (FR,VT), (FR,VU), (FR,VV), (FR,VW), (FR,VX), (FR,VY), (FR,VZ), (FR,WA), (FR,WB), (FR, WC), (FS,VA), (FS,VB), (FS,VC), (FS,VD), (FS,VE), (FS,VF), (FS,VG), (FS,VH), (FS,VI), (FS,VJ), (FS,VK), (FS,VL), (FS,VM), (FS,VN), (FS,VO), (FS,VP), (FS,VQ), (FS,VR), (FS,VS), (FS,VT), (FS,VU), (FS,VV), (FS,VW), (FS,VX), (FS,VY), (FS,VZ), (FS,WA), (FS,WB), (FS,WC), (FT,VA), (FT,VB), (FT,VC), (FT,VD), (FT,VE), (FT,VF), (FT,VG), (FT,VH), (FT,VI), (FT,VJ), (FT,VK), (FT,VL), (FT,VM), (FT,VN), (FT,VO), (FT,VP), (FT,VQ), (FT,VR), (FT,VS), (FT,VT), (FT,VU), (FT,VV), (FT,VW), (FT,VX), (FT,VY), (FT,VZ), (FT,WA), (FT,WB), (FT,WC), (FU,VA), (FU,VB), (FU,VC), (FU,VD), (FU, VE), (FU,VF), (FU,VG), (FU,VH), (FU,VI), (FU,VJ), (FU,VK), (FU,VL), (FU,VM), (FU,VN), (FU,VO), (FU, VP), (FU,VQ), (FU,VR), (FU,VS), (FU,VT), (FU,VU), (FU,VV), (FU,VW), (FU,VX), (FU,VY), (FU,VZ), (FU, WA), (FU,WB), (FU,WC), (FV,VA), (FV,VB), (FV,VC), (FV,VD), (FV,VE), (FV,VF), (FV,VG), (FV,VH), (FV,VI), (FV,VJ), (FV,VK), (FV,VL), (FV,VM), (FV,VN), (FV,VO), (FV,VP), (FV,VQ), (FV,VR), (FV,VS), (FV,VT), (FV,VU), (FV,VV), (FV,VW), (FV,VX), (FV,VY), (FV,VZ), (FV,WA), (FV,WB), (FV,WC), (FW,VA), (FW,VB), (FW,VC), (FW,VD), (FW,VE), (FW,VF), (FW,VG), (FW,VH), (FW,VI), (FW,VJ), (FW,VK), (FW,VL), (FW,VM), (FW,VN), (FW,VO), (FW,VP), (FW,VQ), (FW,VR), (FW,VS), (FW,VT), (FW,VU), (FW,VV), (FW,VW), (FW,VX), (FW,VY), (FW,VZ), (FW,WA), (FW,WB), (FW,WC), (FX,VA), (FX,VB), (FX,VC), (FX,VD), (FX,VE), (FX,VF), (FX,VG), (FX,VH), (FX,VI), (FX,VJ), (FX,VK), (FX,VL), (FX,VM), (FX,VN), (FX,VO), (FX,VP), (FX,VQ), (FX,VR), (FX,VS), (FX,VT), (FX,WU), (FX,VV), (FX,VW), (FX,VX), (FX,VY), (FX,VZ), (FX,WA), (FX,WB), (FX,WC), (FY,VA), (FY,VB), (FY,VC), (FY,VD), (FY,VE), (FY,VF), (FY,VG), (FY,VH), (FY,VI), (FY,VJ), (FY,VK), (FY,VL), (FY,VM), (FY,VN), (FY,VO), (FY,VP), (FY,VQ), (FY,VR), (FY,VS), (FY,VT), (FY,VU), (FY,VV), (FY,VW), (FY,VX), (FY,VY), (FY,VZ), (FY,WA), (FY,WB), (FY,WC), (FZ,VA), (FZ,VB), (FZ,VC), (FZ,VD), (FZ,VE), (FZ,VF), (FZ,VG), (FZ,VH), (FZ,VI), (FZ,VJ), (FZ,VK), (FZ,VL), (FZ,VM), (FZ,VN), (FZ,VO), (FZ,VP), (FZ,VQ), (FZ,VR), (FZ,VS), (FZ,VT), (FZ,VU), (FZ,VV), (FZ,VW), (FZ,VX), (FZ,VY), (FZ,VZ), (FZ,WA), (FZ,WB), (FZ,WC), (GA,VA), (GA,VB), (GA,VC), (GA,VD), (GA,VE), (GA,VF), (GA,VG), (GA,VH), (GA,VI), (GA,VJ), (GA,VK), (GA,VL), (GA,VM), (GA,VN), (GA,VO), (GA,VP), (GA,VQ), (GA,VR), (GA,VS), (GA,VT), (GA,VU), (GA,VV), (GA,VW), (GA,VX), (GA,VY), (GA,VZ), (GA,WA), (GA,WB), (GA,WC), (GB,VA), (GB,VB), (GB,VC), (GB,VD), (GB,VE), (GB,VF), (GB,VG), (GB,VH), (GB,VI), (GB,VJ), (GB,VK), (GB,VL), (GB,VM), (GB,VN), (GB,VO), (GB,VP), (GB,VQ), (GB,VR), (GB,VS), (GB,VT), (GB,VU), (GB,VV), (GB,VW), (GB,VX), (GB,VY), (GB,VZ), (GB,WA), (GB,WB), (GB,WC), (GC,VA), (GC,VA), (GC,VB), (GC,VB), (GC,VC), (GC,VD), (GC,VE), (GC,VF), (GC,VG), (GC,VH), (GC,VI), (GC,VJ), (GC,VI), (GC,VL), (GC,VM), (GC,VN), (GC,VO), (GC,VP), (GC,VQ), (GC,VR), (GC,VS), (GC,VT), (GC,VU), (GC,VW), (GC,VW), (GC,VX), (GC,VY), (GC,VZ), (GC,WA), (GC,WB), (GC,WC), (GD,VC), (GD,VD), (GD,VE), (GD,VF), (GD,VG), (GD,VH), (GD,VI), (GD,VJ), (GD,VK), (GD,VL), (GD,VM), (GD,VN), (GD,VO), (GD,VP), (GD,VQ), (GD,VR), (GD,VS), (GD,VT), (GD,VU), (GD,VV), (GD,VW), (GD,VX), (GD,VY), (GD,VZ), (GD,WA), (GD,WB), (GD,WC), (GE,VA), (GE,VB), (GE,VC), (GE,VD), (GE,VE), (GE,VF), (GE,VG), (GE,VH), (GE,VI), (GE,VJ), (GE,VK), (GE,VL), (GE,VM), (GE,VN), (GE,VO), (GE,VP), (GE,VQ), (GE,VR), (GE,VS), (GE,VT), (GE,VU), (GE,VV), (GE,VW), (GE,VX), (GE,VY), (GE,VZ), (GE,WA), (GE,WB), (GE,WC), (GF,VA), (GF,VB), (GF,VC), (GF,VD), (GF,VE), (GF,VF), (GF,VG), (GF,VH), (GF,VI), (GF,VJ), (GF,VK), (GF,VL), (GF,VM), (GF,VN), (GF,VO), (GF,VP), (GF,VQ), (GF,VR), (GF,VS), (GF,VT), (GF,VU), (GF,VV), (GF,VW), (GF,VX), (GF,VY), (GF,VZ), (GF,WA), (GF,WB), (GF,WC), (GG,VA), (GG,VB), (GG,VC), (GG,VD), (GG,VE), (GG,VF), (GG,VG), (GG,VH), (GG,VI), (GG,VJ), (GG,VK), (GG,VL), (GG,VM), (GG,VN), (GG,VO), (GG,VP), (GG,VQ), (GG,VR), (GG,VS), (GG,VT), (GG,VU), (GG,VV), (GG,VW), (GG,VX), (GG,VY), (GG,VZ), (GG,WA), (GG,WB), (GG,WC), (GH,VA), (GH,VB), (GH,VC), (GH,VD), (GH,VE), (GH,VF), (GH,VG), (GH,VH), (GH,VI), (GH,VJ), (GH,VK), (GH,VL), (GH,VM), (GH,VN), (GH,VO), (GH,VP), (GH,VQ), (GH,VR), (GH,VS), (GH,VT), (GH,VU), (GH,VW), (GH,VW), (GH,VX), (GH,VY), (GH,VZ), (GH,WA), (GH,WB), (GH,WC), (GI,VA), (GI,VB), (GI,VC), (GI,VD), (GI,VE), (GI,VF), (GI,VG), (GI,VH), (GI,VI), (GI,VJ), (GI,VK), (GI,VL), (GI,VM), (GI,VN), (GI,VO), (GI,VP), (GI,VQ), (GI,VR), (GI,VS), (GI,VT), (GI,VU), (GI,VV), (GI,VW), (GI,VX), (GI,VY), (GI,VZ), (GI,WA), (GI,WB), (GI,WC), (GJ,VA), (GJ,VB), (GJ,VC), (GJ,VD), (GJ,VE), (GJ,VF), (GJ,VG), (GJ,VH), (GJ,VI), (GJ,VJ), (GJ,VK), (GJ,VL), (GJ,VM), (GJ,VN), (GJ,VO), (GJ,VP), (GJ,VQ), (GJ,VR), (GJ,VS), (GJ,VT), (GJ,VU), (GJ,VV), (GJ,VW), (GJ,VX), (GJ,VY), (GJ,VZ), (GJ,WA), (GJ,WB), (GJ,WC), (GK,VA), (GK,VB), (GK,VC), (GK,VD), (GK,VE), (GK,VF), (GK,VG), (GK,VH), (GK,VI), (GK,VJ), (GK,VK), (GK,VL), (GK,VM), (GK,VN), (GK,VO), (GK,VP), (GK,VQ), (GK,VR), (GK,VS), (GK,VT), (GK,VU), (GK,VV), (GK,VW), (GK,VX), (GK,VY), (GK,VZ), (GK,WA), (GK,WB), (GK,WC), (GL,VA), (GL,VB), (GL,VC), (GL,VD), (GL,VE), (GL,VF), (GL,VG), (GL,VH), (GL,VI), (GL,VJ), (GL,VK), (GL,VL), (GL,VM), (GL,VN), (GL,VO), (GL,VP), (GL,VQ), (GL,VR), (GL,VS), (GL,VT), (GL,VU), (GL,VV), (GL,VW), (GL,VX), (GL,VY), (GL,VZ), (GL,WA), (GL,WB), (GL,WC), (GM,VA), (GM,VB), (GM,VC), (GM,VD), (GM,VE), (GM,VF), (GM,VG), (GM,VH), (GM,VI), (GM,VJ), (GM,VK), (GM,VL), (GM,VM), (GM,VN), (GM,VO), (GM,VP), (GM,VQ), (GM,VR), (GM,VS), (GM,VT), (GM,VU), (GM,VV), (GM,VW), (GM,VX), (GM,VY), (GM,VZ), (GM,WA), (GM,WB), (GM,WC), (GN,VA), (GN,VB), (GN,VC), (GN,VD), (GN,VE), (GN,VF), (GN,VG), (GN,VH), (GN,VI), (GN,VJ), (GN,VK), (GN,VL), (GN,VM), (GN,VN), (GN,VO), (GN,VP), (GN,VQ), (GN,VR), (GN,VS), (GN,VT), (GN,VU), (GN,VV), (GN,VW), (GN,VX), (GN,VY), (GN,VZ), (GN,WA), (GN,WB), (GN,WC), (GO,VA), (GO,VB), (GO,VC), (GO,VD), (GO,VE), (GO,VF), (GO,VG), (GO,VH), (GO,VI), (GO,VJ), (GO,VK), (GO,VL), (GO,VM), (GO,VN), (GO,VO), (GO,VP), (GO,VQ), (GO,VR), (GO,VS), (GO,VT), (GO,VU), (GO,VV), (GO,VW), (GO,VX), (GO,VY), (GO,VZ), (GO,WA), (GO,WB), (GO,WC), (GP,VA), (GP,VB), (GP,VC), (GP,VD), (GP,VE), (GP,VF), (GP,VG), (GP,VH), (GP,VI), (GP,VJ), (GP,VK), (GP,VL), (GP,VM), (GP,VN), (GP,VO), (GP,VP), (GP,VQ), (GP,VR), (GP,VS), (GP,VT), (GP,VU), (GP,UV), (GP,VW), (GP,VX), (GP,VY), (GP,VZ), (GP,WA), (GP,WB), (GP,WC), (GQ,VA), (GQ,VB), (GQ,VC), (GQ,VD), (GQ,VE), (GQ,VF), (GQ,VG), (GQ,VH), (GQ,VI), (GQ,VJ), (GQ,VK), (GQ,VL), (GQ,VM), (GQ,VN), (GQ,VO), (GQ,VP), (GQ,VQ), (GQ,VR), (GQ,VS), (GQ,VT), (GQ,VU), (GQ,VV), (GQ,VW), (GQ,VX), (GQ,VY), (GQ,VZ), (GQ,WA), (GQ,WB), (GQ,WC), (GR,VA), (GR,VB), (GR,VC), (GR,VD), (GR,VE), (GR,VF), (GR,VG), (GR,VH), (GR,VI), (GR,VJ), (GR,VK), (GR,VL), (GR,VM), (GR,VN), (GR,VO), (GR,VP), (GR,VQ), (GR,VR), (GR,VS), (GR,VT), (GR,VU), (GR,VV), (GR,VW), (GR,VX), (GR,VY), (GR,VZ), (GR,WA), (GR,WB), (GR,WC), (GS,VA), (GS,VB), (GS,VC), (GS,VD), (GS,VE), (GS,VF), (GS,VG), (GS,VH), (GS,VI), (GS,VJ), (GS,VK), (GS,VL), (GS,VM), (GS,VN), (GS,VO), (GS,VP), (GS,VQ), (GS,VR), (GS,VS), (GS,VT), (GS,VU), (GS,VV), (GS,VW), (GS,VX), (GS,VY), (GS,VZ), (GS,WA), (GS,WB), (GS,WC), (GT,VA), (GT,VB), (GT,VC), (GT,VD), (GT,VE), (GT,VF), (GT,VG), (GT,VH), (GT,VI), (GT,VJ), (GT,VK), (GT,VL), (GT,VM), (GT,VN), (GT,VO), (GT,VP), (GT,VQ), (GT,VR), (GT,VS), (GT,VT), (GT,VU), (GT,VV), (GT,VW), (GT,VX), (GT,VY), (GT,VZ), (GT,WA), (GT,WB), (GT,WC), (GU,VA), (GU,VB), (GU,VC), (GU,VD), (GU,VE), (GU,VF), (GU,VG), (GU,VH), (GU,VI), (GU,VJ), (GU,VK), (GU,VL), (GU,VM), (GU,VN), (GU,VO), (GU,VP), (GU,VQ), (GU,VR), (GU,VS), (GU,VT), (GU,VU), (GU,VV), (GU,VW), (GU,VX), (GU,VY), (GU,VZ), (GU,WA), (GU,WB), (GU,WC), (GV,VA), (GV,VB), (GV,VC), (GV,VD), (GV,VE), (GV,VF), (GV,VG), (GV,VH), (GV,VI), (GV,VJ), (GV,VK), (GV,VL), (GV,VM), (GV,VN), (GV,VO), (GV,VP), (GV,VQ), (GV,VR), (GV,VS), (GV,VT), (GV,VU), (GV,VV), (GV,VW), (GV,VX), (GV,VY), (GV,VZ), (GV,WA), (GV,WB), (GV,WC), (GW,VA), (GW,VB), (GW,VC), (GW,VD), (GW,VE), (GW,VF), (GW,VG), (GW,VH), (GW,VI), (GW,VJ), (GW,VK), (GW,VL), (GW,VM), (GW,VN), (GW,VO), (GW,VP), (GW,VQ), (GW,VR), (GW,VS), (GW,VT), (GW,VU), (GW,VV), (GW,VW), (GW,VX), (GW,VY), (GW,VZ), (GW,WA), (GW,WB), (GW,WC), (GX,VA), (GX,VB), (GX,VC), (GX,VD), (GX,VE), (GX,VF), (GX,VG), (GX,VH), (GX,VI), (GX,VJ), (GX,VK), (GX,VL), (GX,VM), (GX,VN), (GX,VO), (GX,VP), (GX,VQ), (GX,VR), (GX,VS), (GX,VT), (GX,VU), (GX,VV), (GX,VW), (GX,VX), (GX,VY), (GX,VZ), (GX,WA), (GX,WB), (GX,WC), (GY,VA), (GY,VB), (GY,VC), (GY,VD), (GY,VE), (GY,VF), (GY,VG), (GY,VH), (GY,VI), (GY,VJ), (GY,VK), (GY,VL), (GY,VM), (GY,VN), (GY,VO), (GY,VP), (GY,VQ), (GY,VR), (GY,VS), (GY,VT), (GY,VU), (GY,VV), (GY,VW), (GY,VX), (GY,VY), (GY,VZ), (GY,WA), (GY,WB), (GY,WC), (GZ,VA), (GZ,VB), (GZ,VC), (GZ,VD), (GZ,VE), (GZ,VF), (GZ,VG), (GZ,VH), (GZ,VI), (GZ,VJ), (GZ,VK), (GZ,VL), (GZ,VM), (GZ,VN), (GZ,VO), (GZ,VP), (GZ,VQ), (GZ,VR), (GZ,VS), (GZ,VT), (GZ,VU), (GZ,VV), (GZ,VW), (GZ,VX), (GZ,VY), (GZ,VZ), (GZ,WA), (GZ,WB), (GZ,WC), (HA,VA), (HA,VB), (HA,VC), (HA,VD), (HA,VE), (HA,VF), (HA,VG), (HA,VH), (HA,VI), (HA,VJ), (HA,VK), (HA,VL), (HA,VM), (HA,VN), (HA,VO), (HA,VP), (HA,VQ), (HA,VR), (HA,VS), (HA,VT), (HA,VU), (HA,VV), (HA,VW), (HA,VX), (HA,VY), (HA,VZ), (HA,WA), (HA,WB), (HA,WC), (HB,VA), (HB,VB), (HB,VC), (HB,VD), (HB,VE), (HB,VF), (HB,VG), (HB,VH), (HB,VI), (HB,VJ), (HB,VK), (HB,VL), (HB,VM), (HB,VN), (HB,VO), (HB,VP), (HB,VQ), (HB,VR), (HB,VS), (HB,VT), (HB,VU), (HB,VV), (HB,VW), (HB,VX), (HB,VY), (HB,VZ), (HB,WA), (HB,WB), (HB,WC), (HC,VA), (HC,VA), (HC,VB), (HC,VB), (HC,VC), (HC,VD), (HC,VE), (HC,VF), (HC,VG), (HC,VH), (HC,VI), (HC,VJ), (HC,VK), (HC,VL), (HC,VM), (HC,VN), (HC,VO), (HC,VP), (HC,VQ), (HC,VR), (HC,VS), (HC,VT), (HC,WU), (HC,VV), (HC,VW), (HC,VX), (HC,VY), (HC,VZ), (HC,WA), (HC,WB), (HC,WC), (HD,VC), (HD,VD), (HD,VE), (HD,VF), (HD,VG), (HD,VH), (HD,VI), (HD,VJ), (HD,VK), (HD,VL), (HD,VM), (HD,VN), (HD,VO), (HD,VP), (HD,VQ), (HD,VR), (HD,VS), (HD,VT), (HD,VU), (HD,VV), (HD,VW), (HD,VX), (HD,VY), (HD,VZ), (HD,WA), (HD,WB), (HD,WC), (HE,VA), (HE,VB), (HE,VC), (HE,VD), (HE,VE), (HE,VF), (HE,VG), (HE,VH), (HE,VI), (HE,VJ), (HE,VK), (HE,VL), (HE,VM), (HE,VN), (HE,VO), (HE,VP), (HE,VQ), (HE,VR), (HE,VS), (HE,VT), (HE,VU), (HE,VV), (HE,VW), (HE,VX), (HE,VY), (HE,VZ), (HE,WA), (HE,WB), (HE,WC), (HF,VA), (HF,VB), (HF,VC), (HF,VD), (HF,VE), (HF,VF), (HF,VG), (HF,VH), (HF,VI), (HF,VJ), (HF,VK), (HF,VL), (HF,VM), (HF,VN), (HF,VO), (HF,VP), (HF,VQ), (HF,VR), (HF,VS), (HF,VT), (HF,VU), (HF,VV), (HF,VW), (HF,VX), (HF,VY), (HF,VZ), (HF,WA), (HF,WB), (HF,WC), (HG,VA), (HG,VB), (HG,VC), (HG,VD), (HG,VE), (HG,VF), (HG,VG), (HG,VH), (HG,VI), (HG,VJ), (HG,VK), (HG,VL), (HG,VM), (HG,VN), (HG,VO), (HG,VP), (HG,VQ), (HG,VR), (HG,VS), (HG,VT), (HG,VU), (HG,VV), (HG,VW), (HG,VX), (HG,VY), (HG,VZ), (HG,WA), (HG,WB), (HG,WC), (HH,VA), (HH,VB), (HH,VC), (HH,VD), (HH,VE), (HH,VF), (HH,VG), (HH,VH), (HH,VI), (HH,VJ), (HH,VK), (HH,VL), (HH,VM), (HH,VN), (HH,VO), (HH,VP), (HH,VQ), (HH,VR), (HH,VS), (HH,VT), (HH,VU), (HH,VV), (HH,VW), (HH,VX), (HH,VY), (HH,VZ), (HH,WA), (HH,WB), (HH,WC), (HI,VA), (HI,VB), (HI,VC), (HI,VD), (HI,VE), (HI,VF), (HI,VG), (HI,VH), (HI,VI), (HI,VJ), (HI,VK), (HI,VL), (HI,VM), (HI,VN), (HI,VO), (HI,VP), (HI,VQ), (HI,VR), (HI,VS), (HI,VT), (HI,VU), (HI,VV), (HI,VW), (HI,VX), (HI,VY), (HI,VZ), (HI,WA), (HI,WB), (HI,WC), (HJ,VA), (HJ,VB), (HJ,VC), (HJ,VD), (HJ,VE), (HJ,VF), (HJ,VG), (HJ,VH), (HJ,VI), (HJ,VJ), (HJ,VK), (HJ,VL), (HJ,VM), (HJ,VN), (HJ,VO), (HJ,VP), (HJ,VQ), (HJ,VR), (HJ,VS), (HJ,VT), (HJ,VU), (HJ,VV), (HJ,VW), (HJ,VX), (HJ,VY), (HJ,VZ), (HJ,WA), (HJ,WB), (HJ,WC), (HK,VA), (HK,VB), (HK,VC), (HK,VD), (HK,VE), (HK,VF), (HK,VG), (HK,VH), (HK,VI), (HK,VJ), (HK,VK), (HK,VL), (HK,VM), (HK,VN), (HK,VO), (HK,VP), (HK,VQ), (HK,VR), (HK,VS), (HK,VT), (HK,VU), (HK,VV), (HK,VW), (HK,VX), (HK,VY), (HK,VZ), (HK,WA), (HK,WB), (HK,WC), (HL,VA), (HL,VB), (HL,VC), (HL,VD), (HL,VE), (HL,VF), (HL,VG), (HL,VH), (HL,VI), (HL,VJ), (HL,VK), (HL,VL), (HL,VM), (HL,VN), (HL,VO), (HL,VP), (HL,VQ), (HL,VR), (HL,VS), (HL,VT), (HL,VU), (HL,VV), (HL,VW), (HL,VX), (HL,VY), (HL,VZ), (HL,WA), (HL,WB), (HL,WC), (HM,VA), (HM,VB), (HM,VC), (HM,VD), (HM,VE), (HM,VF), (HM,VG), (HM,VH), (HM,VI), (HM,VJ), (HM,VK), (HM,VL), (HM,VM), (HM,VN), (HM,VO), (HM,VP), (HM,VQ), (HM,VR), (HM,VS), (HM,VT), (HM,VU), (HM,VV), (HM,VW), (HM,VX), (HM,VY), (HM,VZ), (HM,WA), (HM,WB), (HM,WC), (HN,VA), (HN,VB), (HN,VC), (HN,VD), (HN,VE), (HN,VF), (HN,VG), (HN,VH), (HN,VI), (HN,VJ), (HN,VK), (HN,VL), (HN,VM), (HN,VN), (HN,VO), (HN,VP), (HN,VQ), (HN,VR), (HN,VS), (HN,VT), (HN,VU), (HN,VV), (HN,VW), (HN,VX), (HN,VY), (HN,VZ), (HN,WA), (HN,WB), (HN,WC), (HO,VA), (HO,VB), (HO,VC), (HO,VD), (HO,VE), (HO,VF), (HO,VG), (HO,VH), (HO,VI), (HO,VJ), (HO,VK), (HO,VL), (HO,VM), (HO,VN), (HO,VO), (HO,VP), (HO,VQ), (HO,VR), (HO,VS), (HO,VT), (HO,VU), (HO,VV), (HO,VW), (HO,VX), (HO,VY), (HO,VZ), (HO,WA), (HO,WB), (HO,WC), (HP,VA), (HP,VB), (HP,VC), (HP,VD), (HP,VE), (HP,VF), (HP,VG), (HP,VH), (HP,VI), (HP,VJ), (HP,VK), (HP,VL), (HP,VM), (HP,VN), (HP,VO), (HP,VP), (HP,VQ), (HP,VR), (HP,VS), (HP,VT), (HP,VU), (HP,VV), (HP,VW), (HP,VX), (HP,VY), (HP,VZ), (HP,WA), (HP,WB), (HP,WC), (HQ,VA), (HQ,VB), (HQ,VC), (HQ,VD), (HQ,VE), (HQ,VF), (HQ,VG), (HQ,VH), (HQ,VI), (HQ,VJ), (HQ,VK), (HQ,VL), (HQ,VM), (HQ,VN), (HQ,VO), (HQ,VP), (HQ,VQ), (HQ,VR), (HQ,VS), (HQ,VT), (HQ,VU), (HQ,VV), (HQ,VW), (HQ,VX), (HQ,VY), (HQ,VZ), (HQ,WA), (HQ,WB), (HQ,WC), (HR,VA), (HR,VB), (HR,VC), (HR,VD), (HR,VE), (HR,VF), (HR,VG), (HR,VH), (HR,VI), (HR,VJ), (HR,VK), (HR,VL), (HR,VM), (HR,VN), (HR,VO), (HR,VP), (HR,VQ), (HR,VR), (HR,VS), (HR,VT), (HR,VU), (HR,VV), (HR,VW), (HR,VX), (HR,VY), (HR,VZ), (HR,WA), (HR,WB), (HR,WC), (HS,VA), (HS,VB), (HS,VC), (HS,VD), (HS,VE), (HS,VF), (HS,VG), (HS,VH), (HS,VI), (HS,VJ), (HS,VK), (HS,VL), (HS,VM), (HS,VN), (HS,VO), (HS,VP), (HS,VQ), (HS,VR), (HS,VS), (HS,VT), (HS,VU), (HS,VV), (HS,VW), (HS,VX), (HS,VY), (HS,VZ), (HS,WA), (HS,WB), (HS,WC), (HT,VA), (HT,VB), (HT,VC), (HT,VD), (HT,VE), (HT,VF), (HT,VG), (HT,VH), (HT,VI), (HT,VJ), (HT,VK), (HT,VL), (HT,VM), (HT,VN), (HT,VO), (HT,VP), (HT,VQ), (HT,VR), (HT,VS), (HT,VT), (HT,VU), (HT,VV), (HT,VW), (HT,VX), (HT,VY), (HT,VZ), (HT,WA), (HT,WB), (HT,WC), (HU,VA), (HU,VB), (HU,VC), (HU,VD), (HU,VE), (HU,VF), (HU,VG), (HU,VH), (HU,VI), (HU,VJ), (HU,VK), (HU,VL), (HU,VM), (HU,VN), (HU,VO), (HU,VP), (HU,VQ), (HU,VR), (HU,VS), (HU,VT), (HU,VU), (HU,VV), (HU,VW), (HU,VX), (HU,VY), (HU,VZ), (HU,WA), (HU,WB), (HU,WC), (HV,VA), (HV,VB), (HV,VC), (HV,VD), (HV,VE), (HV,VF), (HV,VG), (HV,VH), (HV,VI), (HV,VJ), (HV,VK), (HV,VL), (HV,VM), (HV,VN), (HV,VO), (HV,VP), (HV,VQ), (HV,VR), (HV,VS), (HV,VT), (HV,VU), (HV,VV), (HV,VW), (HV,VX), (HV,VY), (HV,VZ), (HV,WA), (HV,WB), (HV,WC), (HW,VA), (HW,VB), (HW,VC), (HW,VD), (HW,VE), (HW,VF), (HW,VG), (HW,VH), (HW,VI), (HW,VJ), (HW,VK), (HW,VL), (HW,VM), (HW,VN), (HW,VO), (HW,VP), (HW,VQ), (HW,VR), (HW,VS), (HW,VT), (HW,VU), (HW,VV), (HW,VW), (HW,VX), (HW,VY), (HW,VZ), (HW,WA), (HW,WB), (HW,WC), (HX,VA), (HX,VB), (HX,VC), (HX,VD), (HX,VE), (HX,VF), (HX,VG), (HX,VH), (HX,VI), (HX,VJ), (HX,VK), (HX,VL), (HX,VM), (HX,VN), (HX,VO), (HX,VP), (HX,VQ), (HX,VR), (HX,VS), (HX,VT), (HX,VU), (HX,VV), (HX,VW), (HX,VX), (HX,VY), (HX,VZ), (HX,WA), (HX,WB), (HX,WC), (HY,VA), (HY,VB), (HY,VC), (HY,VD), (HY,VE), (HY,VF), (HY,VG), (HY,VH), (HY,VI), (HY,VJ), (HY,VK), (HY,VL), (HY,VM), (HY,VN), (HY,VO), (HY,VP), (HY,VQ), (HY,VR), (HY,VS), (HY,VT), (HY,VU), (HY,VV), (HY,VW), (HY,VX), (HY,VY), (HY,VZ), (HY,WA), (HY,WB), (HY,WC), (HZ,VA), (HZ,VB), (HZ,VC), (HZ,VD), (HZ,VE), (HZ,VF), (HZ,VG), (HZ,VH), (HZ,VI), (HZ,VJ), (HZ,VK), (HZ,VL), (HZ,VM), (HZ,VN), (HZ,VO), (HZ,VP), (HZ,VQ), (HZ,VR), (HZ,VS), (HZ,VT), (HZ,VU), (HZ,VV), (HZ,VW), (HZ,VX), (HZ,VY), (HZ,VZ), (HZ,WA), (HZ,WB), (HZ,WC), (IA,VA), (IA,VB), (IA,VC), (IA,VD), (IA,VE), (IA,VF), (IA,VG), (IA,VH), (IA,VI), (IA,VJ), (IA,VK), (IA,VL), (IA,VM), (IA,VN), (IA,VO), (IA,VP), (IA,VQ), (IA,VR), (IA,VS), (IA,VT), (IA,VU), (IA,VV), (IA,VW), (IA,VX), (IA,VY), (IA,VZ), (IA,WA), (IA,WB), (IA,WC), (IB,VA), (IB,VB), (IB,VC), (IB,VD), (IB,VE), (IB,VF), (IB,VG), (IB,VH), (IB,VI), (IB,VJ), (IB,VK), (IB,VL), (IB,VM), (IB,VN), (IB,VO), (IB,VP), (IB,VQ), (IB,VR), (IB,VS), (IB,VT), (IB,VU), (IB,VV), (IB,VW), (IB,VX), (IB,VY), (IB,VZ), (IB,WA), (IB,WB), (IB,WC), (IC,VA), (IC,VA), (IC,VB), (IC,VB), (IC,VC), (IC,VD), (IC,VE), (IC,VF), (IC,VG), (IC,VH), (IC,VI), (IC,VJ), (IC,VK), (IC,VL), (IC,VM), (IC,VN), (IC,VO), (IC,VP), (IC,VQ), (IC,VR), (IC,VS), (IC,VT), (IC,VU), (IC,VV), (IC,VW), (IC,VX), (IC,VY), (IC,VZ), (IC,WA), (IC,WB), (IC,WC), (ID,VC), (ID,VD), (ID,VE), (ID,VF), (ID,VG), (ID,VH), (ID,VI), (ID,VJ), (ID,VK), (ID,VL), (ID,VM), (ID,VN), (ID,VO), (ID,VP), (ID,VQ), (ID,VR), (ID,VS), (ID,VT), (ID,VU), (ID,VV), (ID,VW), (ID,VX), (ID,VY), (ID,VZ), (ID,WA), (ID,WB), (ID,WC), (IE,VA), (IE,VB), (IE,VC), (IE,VD), (IE,VE), (IE,VF), (IE,VG), (IE,VH), (IE,VI), (IE,VJ), (IE,VK), (IE,VL), (IE,VM), (IE,VN), (IE,VO), (IE,VP), (IE,VQ), (IE,VR), (IE,VS), (IE,VT), (IE,VU), (IE,VV), (IE,VW), (IE,VX), (IE,VY), (IE,VZ), (IE,WA), (IE,WB), (IE,WC), (IF,VA), (IF,VB), (IF,VC), (IF,VD), (IF,VE), (IF,VF), (IF,VG), (IF,VH), (IF,VI), (IF,VJ), (IF,VK), (IF,VL), (IF,VM), (IF,VN), (IF,VO), (IF,VP), (IF,VQ), (IF,VR), (IF,VS), (IF,VT), (IF,VU), (IF,VV), (IF,VW), (IF,VX), (IF,VY), (IF,VZ), (IF,WA), (IF,WB), (IF,WC), (IG,VA), (IG,VB), (IG,VC), (IG,VD), (IG,VE), (IG,VF), (IG,VG), (IG,VH), (IG,VI), (IG,VJ), (IG,VK), (IG,VL), (IG,VM), (IG,VN), (IG,VO), (IG,VP), (IG,VQ), (IG,VR), (IG,VS), (IG,VT), (IG,VU), (IG,VV), (IG,VW), (IG,VX), (IG,VY), (IG,VZ), (IG,WA), (IG,WB), (IG,WC), (IH,VA), (IH,VB), (IH,VC), (IH,VD), (IH,VE), (IH,VF), (IH,VG), (IH,VH), (IH,VI), (IH,VJ), (IH,VK), (IH,VL), (IH,VM), (IH,VN), (IH,VO), (IH,VP), (IH,VQ), (IH,VR), (IH,VS), (IH,VT), (IH,VU), (IH,VV), (IH,VW), (IH,VX), (IH,VY), (IH,VZ), (IH,WA), (IH,WB), (IH,WC), (II,VA), (II,VB), (II,VC), (II,VD), (II,VE), (II,VF), (II,VG), (II,VH), (II,VI), (II,VJ), (II,VK), (II,VL), (II,VM), (II,VN), (II,VO), (II,VP), (II,VQ), (II,VR), (II,VS), (II,VT), (II,VU), (II,VV), (II,VW), (II,VX), (II,VY), (II,VZ), (II,WA), (II,WB), (II,WC), (IJ,VA), (IJ,VB), (IJ,VC), (IJ,VD), (IJ,VE), (IJ,VF), (IJ,VG), (IJ,VH), (IJ,VI), (IJ,VJ), (IJ,VK), (IJ,VL), (IJ,VM), (IJ,VN), (IJ,VO), (IJ,VP), (IJ,VQ), (IJ,VR), (IJ,VS), (IJ,VT), (IJ,VU), (IJ,VV), (IJ,VW), (IJ,VX), (IJ,VY), (IJ,VZ), (IJ,WA), (IJ,WB), (IJ,WC), (IK,VA), (IK,VB), (IK,VC), (IK,VD), (IK,VE), (IK,VF), (IK,VG), (IK,VH), (IK,VI), (IK,VJ), (IK,VK), (IK,VL), (IK,VM), (IK,VN), (IK,VO), (IK,VP), (IK,VQ), (IK,VR), (IK,VS), (IK,VT), (IK,VU), (IK,VV), (IK,VW), (IK,VX), (IK,VY), (IK,VZ), (IK,WA), (IK,WB), (IK,WC), (IL,VA), (IL,VB), (IL,VC), (IL,VD), (IL,VE), (IL,VF), (IL,VG), (IL,VH), (IL,VI), (IL,VJ), (IL,VK), (IL,VL), (IL,VM), (IL,VN), (IL,VO), (IL,VP), (IL,VQ), (IL,VR), (IL,VS), (IL,VT), (IL,VU), (IL,VV), (IL,VW), (IL,VX), (IL,VY), (IL,VZ), (IL,WA), (IL,WB), (IL,WC), (IM,VA), (IM,VB), (IM,VC), (IM,VD), (IM,VE), (IM,VF), (IM,VG), (IM,VH), (IM,VI), (IM,VJ), (IM,VK), (IM,VL), (IM,VM), (IM,VN), (IM,VO), (IM,VP), (IM,VQ), (IM,VR), (IM,VS), (IM,VT), (IM,VU), (IM,VV), (IM,VW), (IM,VX), (IM,VY), (IM,VZ), (IM,WA), (IM,WB), (IM,WC), (IN,VA), (IN,VB), (IN,VC), (IN,VD), (IN,VE), (IN,VF), (IN,VG), (IN,VH), (IN,VI), (IN,VJ), (IN,VK), (IN,VL), (IN,VM), (IN,VN), (IN,VO), (IN,VP), (IN,VQ), (IN,VR), (IN,VS), (IN,VT), (IN,VU), (IN,VV), (IN,VW), (IN,VX), (IN,VY), (IN,VZ), (IN,WA), (IN,WB), (IN,WC), (IO,VA), (IO,VB), (IO,VC), (IO,VD), (IO,VE), (IO,VF), (IO,VG), (IO,VH), (IO,VI), (IO,VJ), (IO,VK), (IO,VL), (IO,VM), (IO,VN), (IO,VO), (IO,VP), (IO,VQ), (IO,VR), (IO,VS), (IO,VT), (IO,VU), (IO,VV), (IO,VW), (IO,VX), (IO,VY), (IO,VZ), (IO,WA), (IO,WB), (IO,WC), (IP,VA), (IP,VB), (IP,VC), (IP,VD), (IP,VE), (IP,VF), (IP,VG), (IP,VH), (IP,VI), (IP,VJ), (IP,VK), (IP,VL), (IP,VM), (IP,VN), (IP,VO), (IP,VP), (IP,VQ), (IP,VR), (IP,VS), (IP,VT), (IP,VU), (IP,VV), (IP,VW), (IP,VX), (IP,VY), (IP,VZ), (IP,WA), (IP,WB), (IP,WC), (IQ,VA), (IQ,VB), (IQ,VC), (IQ,VD), (IQ,VE), (IQ,VF), (IQ,VG), (IQ,VH), (IQ,VI), (IQ,VJ), (IQ,VK), (IQ,VL), (IQ,VM), (IQ,VN), (IQ,VO), (IQ,VP), (IQ,VQ), (IQ,VR), (IQ,VS), (IQ,VT), (IQ,VU), (IQ,VV), (IQ,VW), (IQ,VX), (IQ,VY), (IQ,VZ), (IQ,WA), (IQ,WB), (IQ,WC), (IR,VA), (IR,VB), (IR,VC), (IR,VD), (IR,VE), (IR,VF), (IR,VG), (IR,VH), (IR,VI), (IR,VJ), (IR,VK), (IR,VL), (IR,VM), (IR,VN), (IR,VO), (IR,VP), (IR,VQ), (IR,VR), (IR,VS), (IR,VT), (IR,VU), (IR,VV), (IR,VW), (IR,VX), (IR,VY), (IR,VZ), (IR,WA), (IR,WB), (IR,WC), (IS,VA), (IS,VB), (IS,VC), (IS,VD), (IS,VE), (IS,VF), (IS,VG), (IS,VH), (IS,VI), (IS,VJ), (IS,VK), (IS,VL), (IS,VM), (IS,VN), (IS,VO), (IS,VP), (IS,VQ), (IS,VR), (IS,VS), (IS,VT), (IS,VU), (IS,VW), (IS,VW), (IS,VX), (IS,VY), (IS,VZ), (IS,WA), (IS,WB), (IS,WC), (IT,VA), (IT,VB), (IT,VC), (IT,VD), (IT,VE), (IT,VF), (IT,VG), (IT,VH), (IT,VI), (IT,VJ), (IT,VK), (IT,VL), (IT,VM), (IT,VN), (IT,VO), (IT,VP), (IT,VQ), (IT,VR), (IT,VS), (IT,VT), (IT,VU), (IT,VV), (IT,VW), (IT,VX), (IT,VY), (IT,VZ), (IT,WA), (IT,WB), (IT,WC), (IU,VA), (IU,VB), (IU,VC), (IU,VD), (IU,VE), (IU,VF), (IU,VG), (IU,VH), (IU,VI), (IU,

VJ), (IU,VK), (IU,VL), (IU,VM), (IU,VN), (IU,VO), (IU,VP), (IU,VQ), (IU,VR), (IU,VS), (IU,VT), (IU,VU), (IU,VV), (IU,VW), (IU,VX), (IU,VY), (IU,VZ), (IU,WA), (IU,WB), (IU,WC), (IV,VA), (IV,VB), (IV,VC), (IV,VD), (IV,VE), (IV,VF), (IV,VG), (IV,VH), (IV,VI), (IV,VJ), (IV,VK), (IV,VL), (IV,VM), (IV,VN), (IV,VO), (IV,VP), (IV,VQ), (IV,VR), (IV,VS), (IV,VT), (IV,VU), (IV,VV), (IV,VW), (IV,VX), (IV,VY), (IV,VZ), (IV,WA), (IV,WB), (IV,WC), (IW,VA), (IW,VB), (IW,VC), (IW,VD), (IW,VE), (IW,VF), (IW,VG), (IW,VH), (IW,VI), (IW,VJ), (IW,VK), (IW,VL), (IW,VM), (IW,VN), (IW,VO), (IW,VP), (IW,VQ), (IW,VR), (IW,VS), (IW,VT), (IW,VU), (IW,VV), (IW,VW), (IW,VX), (IW,VY), (IW,VZ), (IW,WA), (IW,WB), (IW,WC), (IX,VA), (IX,VB), (IX,VC), (IX,VD), (IX,VE), (IX,VF), (IX,VG), (IX,VH), (IX,VI), (IX,VJ), (IX,VK), (IX,VL), (IX,VM), (IX,VN), (IX,VO), (IX,VP), (IX,VQ), (IX,VR), (IX,VS), (IX,VT), (IX,VU), (IX,VV), (IX,VW), (IX,VX), (IX,VY), (IX,VZ), (IX,WA), (IX,WB), (IX,WC), (IY,VA), (IY,VB), (IY,VC), (IY,VD), (IY,VE), (IY,VF), (IY,VG), (IY,VH), (IY,VI), (IY,VJ), (IY,VK), (IY,VL), (IY,VM), (IY,VN), (IY,VO), (IY,VP), (IY,VQ), (IY,VR), (IY,VS), (IY,VT), (IY,VU), (IY,VV), (IY,VW), (IY,VX), (IY,VY), (IY,VZ), (IY,WA), (IY,WB), (IY,WC), (IZ,VA), (IZ,VB), (IZ,VC), (IZ,VD), (IZ,VE), (IZ,VF), (IZ,VG), (IZ,VH), (IZ,VI), (IZ,VJ), (IZ,VK), (IZ,VL), (IZ,VM), (IZ,VN), (IZ,VO), (IZ,VP), (IZ,VQ), (IZ,VR), (IZ,VS), (IZ,VT), (IZ,VU), (IZ,VV), (IZ,VW), (IZ,VX), (IZ,VY), (IZ,VZ), (IZ,WA), (IZ,WB), (IZ,WC), (JA,VA), (JA,VB), (JA,VC), (JA,VD), (JA,VE), (JA,VF), (JA,VG), (JA,VH), (JA,VI), (JA,VJ), (JA,VK), (JA,VL), (JA,VM), (JA,VN), (JA,VO), (JA,VP), (JA,VQ), (JA,VR), (JA,VS), (JA,VT), (JA,VU), (JA,VV), (JA,VW), (JA,VX), (JA,VY), (JA,VZ), (JA,WA), (JA,WB), (JA,WC), (JB,VA), (JB,VB), (JB,VC), (JB,VD), (JB,VE), (JB,VF), (JB,VG), (JB,VH), (JB,VI), (JB,VJ), (JB,VK), (JB,VL), (JB,VM), (JB,VN), (JB,VO), (JB,VP), (JB,VQ), (JB,VR), (JB,VS), (JB,VT), (JB,VU), (JB,VV), (JB,VW), (JB,VX), (JB,VY), (JB,VZ), (JB,WA), (JB,WB), (JB,WC), (JC,VA), (JC,VA), (JC,VB), (JC,VB), (JC,VC), (JC,VD), (JC,VE), (JC,VF), (JC,VG), (JC,VH), (JC,VI), (JC,VJ), (JC,VK), (JC,VL), (JC,VM), (JC,VN), (JC,VO), (JC,VP), (JC,VQ), (JC,VR), (JC,VS), (JC,VT), (JC,VU), (JC,VV), (JC,VW), (JC,VX), (JC,VY), (JC,VZ), (JC,WA), (JC,WB), (JC,WC), (JD,VC), (JD,VD), (JD,VE), (JD,VF), (JD,VG), (JD,VH), (JD,VI), (JD,VJ), (JD,VK), (JD,VL), (JD,VM), (JD,VN), (JD,VO), (JD,VP), (JD,VQ), (JD,VR), (JD,VS), (JD,VT), (JD,VU), (JD,VV), (JD,VW), (JD,VX), (JD,VY), (JD,VZ), (JD,WA), (JD,WB), (JD,WC), (JE,VA), (JE,VB), (JE,VC), (JE,VD), (JE,VE), (JE,VF), (JE,VG), (JE,VH), (JE,VI), (JE,VJ), (JE,VK), (JE,VL), (JE,VM), (JE,VN), (JE,VO), (JE,VP), (JE,VQ), (JE,VR), (JE,VS), (JE,VT), (JE,VU), (JE,VV), (JE,VW), (JE,VX), (JE,VY), (JE,VZ), (JE,WA), (JE,WB), (JE,WC), (JF,VA), (JF,VB), (JF,VC), (JF,VD), (JF,VE), (JF,VF), (JF,VG), (JF,VH), (JF,VI), (JF,VJ), (JF,VK), (JF,VL), (JF,VM), (JF,VN), (JF,VO), (JF,VP), (JF,VQ), (JF,VR), (JF,VS), (JF,VT), (JF,VU), (JF,VV), (JF,VW), (JF,VX), (JF,VY), (JF,VZ), (JF,WA), (JF,WB), (JF,WC), (JG,VA), (JG,VB), (JG,VC), (JG,VD), (JG,VE), (JG,VF), (JG,VG), (JG,VH), (JG,VI), (JG,VJ), (JG,VK), (JG,VL), (JG,VM), (JG,VN), (JG,VO), (JG,VP), (JG,VQ), (JG,VR), (JG,VS), (JG,VT), (JG,VU), (JG,VV), (JG,VW), (JG,VX), (JG,VY), (JG,VZ), (JG,WA), (JG,WB), (JG,WC), (JH,VA), (JH,VB), (JH,VC), (JH,VD), (JH,VE), (JH,VF), (JH,VG), (JH,VH), (JH,VI), (JH,VJ), (JH,VK), (JH,VL), (JH,VM), (JH,VN), (JH,VO), (JH,VP), (JH,VQ), (JH,VR), (JH,VS), (JH,VT), (JH,VU), (JH,VV), (JH,VW), (JH,VX), (JH,VY), (JH,VZ), (JH,WA), (JH,WB), (JH,WC), (JI,VA), (JI,VB), (JI,VC), (JI,VD), (JI,VE), (JI,VF), (JI,VG), (JI,VH), (JI,VI), (JI,VJ), (JI,VK), (JI,VL), (JI,VM), (JI,VN), (JI,VO), (JI,VP), (JI,VQ), (JI,VR), (JI,VS), (JI,VT), (JI,VU), (JI,VM), (JI,VW), (JI,VX), (JI,VY), (JI,VZ), (JI,WA), (JI,WB), (JI,WC), (JJ,VA), (JJ,VB), (JJ,VC), (JJ,VD), (JJ,VE), (JJ,VF), (JJ,VG), (JJ,VW), (JJ,VW), (JJ,VJ), (JJ,VB), (JJ,VL), (JJ,VM), (JJ,VN), (JJ,VO), (JJ,VP), (JJ,VQ), (JJ,VR), (JJ,VS), (JJ,VT), (JJ,VU), (JJ,VV), (JJ,VW), (JJ,VX), (JJ,VY), (JJ,VZ), (JJ,WA), (JJ,WB), (JJ,WC), (JK,VA), (JK,VB), (JK,VC), (JK,VD), (JK,VZ), (JK,VF), (JK,VG), (JK,VH), (JK,VI), (JK,VJ), (JK,VK), (JK,VL), (JK,VM), (JK,VN), (JK,VO), (JK,VP), (JK,VQ), (JK,VR), (JK,VS), (JK,VT), (JK,VU), (JK,VV), (JK,Vw), (JK,VX), (JK,VY), (JK,VZ), (JK,WA), (JK,WB), (JK,WC), (JL,VA), (JL,VB), (JL,VC), (JL,VD), (JL,VE), (JL,VF), (JL,VG), (JL,VH), (JL,VI), (JL,VJ), (JL,VK), (JL,VL), (JL,VM), (JL,VN), (JL,VO), (JL,VP), (JL,VQ), (JL,VR), (JL,VS), (JL,VT), (JL,VU), (JL,VV), (JL,VW), (JL,VX), (JL,VY), (JL,VZ), (JL,WA), (JL,WB), (JL,WC), (JM,VA), (JM,VB), (JM,VC), (JM,VD), (JM,VE), (JM,VF), (JM,VG), (JM,VH), (JM,VI), (JM,VJ), (JM,VK), (JM,VL), (JM,VM), (JM,VN), (JM,VO), (JM,VP), (JM,VQ), (JM,VR), (JM,VS), (JM,VT), (JM,VU), (JM,VV), (JM,VW), (JM,VX), (JM,VY), (JM,VZ), (JM,WA), (JM,WB), (JM,WC), (JN,VA), (JN,VB), (JN,VC), (JN,VD), (JN,VE), (JN,VF), (JN,VG), (JN,VH), (JN,VI), (JN,VJ), (JN,VK), (JN,VL), (JN,VM), (JN,VN), (JN,VO), (JN,VP), (JN,VQ), (JN,VR), (JN,VS), (JN,VT), (JN,VU), (JN,VV), (JN,VW), (JN,VX), (JN,VY), (JN,VZ), (JN,WA), (JN,WB), (JN,WC), (JO,VA), (JO,VB), (JO,VC), (JO,VD), (JO,VE), (JO,VF), (JO,VG), (JO,VH), (JO,VI), (JO,VJ), (JO,VK), (JO,VL), (JO,VM), (JO,VN), (JO,VO), (JO,VP), (JO,VQ), (JO,VR), (JO,VS), (JO,VT), (JO,VU), (JO,VV), (JO,VW), (JO,VX), (JO,VY), (JO,VZ), (JO,WA), (JO,WB), (JO,WC), (JP,VA), (JP,VB), (JP,VC), (JP,VD), (JP,VE), (JP,VF), (JP,VG), (JP,VH), (JP,VI), (JP,VJ), (JP,VK), (JP,VL), (JP,VM), (JP,VN), (JP,VO), (JP,VP), (JP,VQ), (JP,VR), (JP,VS), (JP,VT), (JP,VU), (JP,VV), (JP,VW), (JP,VX), (JP,VY), (JP,VZ), (JP,WA), (JP,WB), (JP,WC), (JQ,VA), (JQ,VB), (JQ,VC), (JQ,VD), (JQ,VE), (JQ,VF), (JQ,VG), (JQ,VH), (JQ,VI), (JQ,VJ), (JQ,VK), (JQ,VL), (JQ,VM), (JQ,VN), (JQ,VO), (JQ,VP), (JQ,VQ), (JQ,VR), (JQ,VS), (JQ,VT), (JQ,VU), (JQ,VV), (JQ,VW), (JQ,VX), (JQ,VY), (JQ,VZ), (JQ,WA), (JQ,WB), (JQ,WC), (JR,VA), (JR,VB), (JR,VC), (JR,VD), (JR,VE), (JR,VF), (JR,VG), (JR,VH), (JR,VI), (JR,VJ), (JR,VK), (JR,VL), (JR,VM), (JR,VN), (JR,VO), (JR,VP), (JR,VQ), (JR,VR), (JR,VS), (JR,VT), (JR,WU), (JR,VV), (JR,VW), (JR,VX), (JR,VY), (JR,VZ), (JR,WA), (JR,WB), (JR,WC), (JS,VA), (JS,VB), (JS,VC), (JS,VD), (JS,VE), (JS,VF), (JS,VG), (JS,VH), (JS,VI), (JS,VJ), (JS,VK), (JS,VL), (JS,VM), (JS,VN), (JS,VO), (JS,VP), (JS,VQ), (JS,VR), (JS,VS), (JS,VT), (JS,VU), (JS,Vv), (JS,VW), (JS,VX), (JS,VY), (JS,VZ), (JS,WA), (JS,WB), (JS,WC), (JT,VA), (JT,VB), (JT,VC), (JT,VD), (JT,VE), (JT,VF), (JT,VG), (JT,VH), (JT,VI), (JT,VJ), (JT,VK), (JT,VL), (JT,VM), (JT,VN), (JT,VO), (JT,VP), (JT,VQ), (JT,VR), (JT,VS), (JT,VT), (JT,VU), (JT,VV), (JT,VW), (JT,VX), (JT,VY), (JT,VZ), (JT,WA), (JT,WB), (JT,WC), (JU,VA), (JU,VB), (JU,VC), (JU,VD), (JU,VE), (JU,VF), (JU,VG), (JU,VH), (JU,VI), (JU,VJ), (JU,VK), (JU,VL), (JU,VM), (JU,VN), (JU,VO), (JU,VP), (JU,VQ), (JU,VR), (JU,VS), (JU,VT), (JU,VU), (JU,VV), (JU,VW), (JU,VX), (JU,VY), (JU,VZ), (JU,WA), (JU,WB), (JU,WC), (JV,VA), (JV,VB), (JV,VC), (JV,VD), (JV,VE), (JV,VF), (JV,VG), (JV,VH), (JV,VI), (JV,VJ), (JV,VK), (JV,VL), (JV,VM), (JV,VN), (JV,VO), (JV,VP), (JV,VQ), (JV,VR), (JV,VS), (JV,VT), (JV,VU), (JV,VV), (JV,VW), (JV,VX), (JV,VY), (JV,VZ), (JV,WA), (JV,WB), (JV,WC), (JW,VA), (JW,VB), (JW,VC), (JW,VD), (JW,VE), (JW,VF), (JW,VG), (JW,VH), (JW,VI), (JW,VJ), (JW,VK), (JW,VL), (JW,VM), (JW,VN), (JW,VO), (JW,VP), (JW,VQ), (JW,VR), (JW,VS), (JW,VT), (JW,VU), (JW,VV), (JW,VW), (JW,VX), (JW,VY), (JW,VZ), (JW,WA), (JW,WB), (JW,WC), (JX,VA), (JX,VB), (JX,VC), (JX,VD), (JX,VE), (JX,VF), (JX,VG), (JX,VH), (JX,VI), (JX,VJ), (JX,VK), (JX,VL), (JX,VM), (JX,VN), (JX,VO), (JX,VP), (JX,VQ), (JX,VR), (JX,VS), (JX,VT), (JX,VU), (JX,VV), (JX,VW), (JX,VX), (JX,VY), (JX,VZ), (JX,WA), (JX,WB), (JX,WC), (JY,VA), (JY,VB), (JY,VC), (JY,VD), (JY,VE), (JY,VF), (JY,VG), (JY,VH), (JY,VI), (JY,VJ), (JY,VK), (JY,VL), (JY,VM), (JY,VN), (JY,VO), (JY,VP), (JY,VQ), (JY,VR), (JY,VS), (JY,VT), (JY,VU), (JY,VV), (JY,VW), (JY,VX), (JY,VY), (JY,VZ), (JY,WA), (JY,WB), (JY,WC), (JZ,VA), (JZ,VB), (JZ,VC), (JZ,VD), (JZ,VE), (JZ,VF), (JZ,VG), (JZ,VH), (JZ,VI), (JZ,VJ), (JZ,VK), (JZ,VL), (JZ,VM), (JZ,VN), (JZ,VO), (JZ,VP), (JZ,VQ), (JZ,VR), (JZ,VS), (JZ,VT), (JZ,VU), (JZ,VV), (JZ,VW), (JZ,VX), (JZ,VY), (JZ,VZ), (JZ,WA), (JZ,WB), (JZ,WC), (KA,VA), (KA,VB), (KA,VC), (KA,VD), (KA,VE), (KA,VF), (KA,VG), (KA,VH), (KA,VI), (KA,VJ), (KA,VK), (KA,VL), (KA,VM), (KA,VN), (KA,VO), (KA,VP), (KA,VQ), (KA,VR), (KA,VS), (KA,VT), (KA,VU), (KA,VW), (KA,VW), (KA,VX), (KA,VY), (KA,VZ), (KA,WA), (KA,WB), (KA,WC), (KB,VA), (KB,VB), (KB,VC), (KB,VD), (KB,VE), (KB,VF), (KB,VG), (KB,VH), (KB,VI), (KB,VJ), (KB,VK), (KB,VL), (KB,VM), (KB,VN), (KB,VO), (KB,VP), (KB,VQ), (KB,VR), (KB,VS), (KB,VT), (KB,VU), (KB,VV), (KB,VW), (KB,VX), (KB,VY), (KB,VZ), (KB,WA), (KB,WB), (KB,WC), (KC,VA), (KC,VA), (KC,VB), (KC,VB), (KC,VC), (KC,VD), (KC,VE), (KC,VF), (KC,VG), (KC,VH), (KC,VI), (KC,VJ), (KC,VK), (KC,VL), (KC,VM), (KC,VN), (KC,VO), (KC,VP), (KC,VQ), (KC,VR), (KC,VS), (KC,VT), (KC,VU), (KC,VV), (KC,VW), (KC,VX), (KC,VY), (KC,VZ), (KC,WA), (KC,WB), (KC,WC), (KD,VC), (KD,VD), (KD,VE), (KD,VF), (KD,VG), (KD,VH), (KD,VI), (KD,VJ), (KD,VK), (KD,VL), (KD,VM), (KD,VN), (KD,VO), (KD,VP), (KD,VQ), (KD,VR), (KD,VS), (KD,VT), (KD,VU), (KD,VV), (KD,VW), (KD,VX), (KD,VY), (KD,VZ), (KD,WA), (KD,WB), (KD,WC), (KE,VA), (KE,VB), (KE,VC), (KE,VD), (KE,VE), (KE,VF), (KE,VG), (KE,VH), (KE,VI), (KE,VJ), (KE,VK), (KE,VL), (KE,VM), (KE,VN), (KE,VO), (KE,VP), (KE,VQ), (KE,VR), (KE,VS), (KE,VT), (KE,VU), (KE,VV), (KE,VW), (KE,VX), (KE,VY), (KE,VZ), (KE,WA), (KE,WB), (KE,WC), (KF,VA), (KF,VB), (KF,VC), (KF,VD), (KF,VE), (KF,VF), (KF,VG), (KF,VH), (KF,VI), (KF,VJ), (KF,VK), (KF,VL), (KF,VM), (KF,VN), (KF,VO), (KF,VP), (KF,VQ), (KF,VR), (KF,VS), (KF,VT), (KF,VU), (KF,VV), (KF,VW), (KF,VX), (KF,VY), (KF,VZ), (KF,WA), (KF,WB), (KF,WC), (KG,VA), (KG,VB), (KG,VC), (KG,VD), (KG,VE), (KG,VF), (KG,VG), (KG,VH), (KG,VI), (KG,VJ), (KG,VK), (KG,VL), (KG,VM), (KG,VN), (KG,VO), (KG,VP), (KG,VQ), (KG,VR), (KG,VS), (KG,VT), (KG,VU), (KG,VV), (KG,VW), (KG,VX), (KG,VY), (KG,VZ), (KG,WA), (KG,WB), (KG,WC), (KH,VA), (KH,VB), (KH,VC), (KH,VD), (KH,VE), (KH,VF), (KH,VG), (KH,VH), (KH,VI), (KH,VJ), (KH,VK), (KH,VL), (KH,VM), (KH,VN), (KH,VO), (KH,VP), (KH,VQ), (KH,VR), (KH,VS), (KH,VT), (KH,VU), (KH,VV), (KH,VW), (KH,VX), (KH,VY), (KH,VZ), (KH,WA), (KH,WB), (KH,WC), (KI,VA), (KI,VB), (KI,VC), (KI,VD), (KI,VE), (KI,VF), (KI,VG), (KI,VH), (KI,VI), (KI,VJ), (KI,VK), (KI,VL), (KI,VM), (KI,VN), (KI,VO), (KI,VP), (KI,VQ), (KI,VR), (KI,VS), (KI,VT), (KI,VU), (KI,VV), (KI,VW), (KI,VX), (KI,VY), (KI,VZ), (KI,WA), (KI,WB), (KI,WC), (KJ,VA), (KJ,VB), (KJ,VC), (KJ,VD), (KJ,VE), (KJ,VF), (KJ,VG), (KJ,VH), (KJ,VI), (KJ,VJ), (KJ,VK), (KJ,VL), (KJ,VM), (KJ,VN), (KJ,VO), (KJ,VP), (KJ,VQ), (KJ,VR), (KJ,VS), (KJ,VT), (KJ,VU), (KJ,VV), (KJ,VW), (KJ,VX), (KJ,VY), (KJ,VZ), (KJ,WA), (KJ,WB), (KJ,WC), (KK,VA), (KK,VB), (KK,VC), (KK,VD), (KK,VE), (KK,VF), (KK,VG), (KK,VH), (KK,VI), (KK,VJ), (KK,VK), (KK,VL), (KK,VM), (KK,VN), (KK,VO), (KK,VP), (KK,VQ), (KK,VR), (KK,VS), (KK,VT), (KK,VU), (KK,VV), (KK,VW), (KK,VX), (KK,VY), (KK,VZ), (KK,WA), (KK,WB), (KK,WC), (KL,VA), (KL,VB), (KL,VC), (KL,VD), (KL,VE), (KL,VF), (KL,VG), (KL,VH), (KL,VI), (KL,VJ), (KL,VK), (KL,VL), (KL,VM), (KL,VN), (KL,VO), (KL,VP), (KL,VQ), (KL,VR), (KL,VS), (KL,VT), (KL,VU), (KL,VV), (KL,VW), (KL,VX), (KL,VY), (KL,VZ), (KL,WA), (KL,WB), (KL,WC), (KM,VA), (KM,VB), (KM,VC), (KM,VD), (KM,VE), (KM,VF), (KM,VG), (KM,VH), (KM,VI), (KM,VJ), (KM,VK), (KM,VL), (KM,VM), (KM,VN), (KM,VO), (KM,VP), (KM,VQ), (KM,VR), (KM,VS), (KM,VT), (KM,VU), (KM,VV), (KM,VW), (KM,VX), (KM,VY), (KM,VZ), (KM,WA), (KM,WB), (KM,WC), (KN,VA), (KN,VB), (KN,VC), (KN,VD), (KN,VE), (KN,VF), (KN,VG), (KN,VH), (KN,VI), (KN,VJ), (KN,VK), (KN,VL), (KN,VM), (KN,VN), (KN,VO), (KN,VP), (KN,VQ), (KN,VR), (KN,VS), (KN,VT), (KN,VU), (KN,VV), (KN,VW), (KN,VX), (KN,VY), (KN,VZ), (KN,WA), (KN,WB), (KN,WC), (KO,VA), (KO,VB), (KO,VC), (KO,VD), (KO,VE), (KO,VF), (KO,VG), (KO,VH), (KO,VI), (KO,VJ), (KO,VK), (KO,VL), (KO,VM), (KO,VN), (KO,VO), (KO,VP), (KO,VQ), (KO,VR), (KO,VS), (KO,VT), (KO,VU), (KO,VV), (KO,VW), (KO,VX), (KO,VY), (KO,VZ), (KO,WA), (KO,WB), (KO,WC), (KP,VA), (KP,VB), (KP,VC), (KP,VD), (KP,VE), (KP,VF), (KP,VG), (KP,VH), (KP,VI), (KP,VJ), (KP,VK), (KP,VL), (KP,VM), (KP,VN), (KP,VO), (KP,VP), (KP,VQ), (KP,VR), (KP,VS), (KP,VT), (KP,VU), (KP,VV), (KP,VW), (KP,VX), (KP,VY), (KP,VZ), (KP,WA), (KP,WB), (KP,WC), (KQ,VA), (KQ,VB), (KQ,VC), (KQ,VD), (KQ,VE), (KQ,VF), (KQ,VG), (KQ,VH), (KQ,VI), (KQ,VJ), (KQ,VK), (KQ,VL), (KQ,VM), (KQ,VN), (KQ,VO), (KQ,VP), (KQ,VQ), (KQ,VR), (KQ,VS), (KQ,VT), (KQ,VU), (KQ,VV), (KQ,VW), (KQ,VX), (KQ,VY), (KQ,VZ), (KQ,WA), (KQ,WB), (KQ,WC), (KR,VA), (KR,VB), (KR,VC), (KR,VD), (KR,VE), (KR,VF), (KR,VG), (KR,VH), (KR,VI), (KR,VJ), (KR,VK), (KR,VL), (KR,VM), (KR,VN), (KR,VO), (KR,VP), (KR,VQ), (KR,VR), (KR,VS), (KR,VT), (KR,VU), (KR,VV), (KR,VW), (KR,VX), (KR,VY), (KR,VZ), (KR,WA), (KR,WB), (KR,WC), (KS,VA), (KS,VB), (KS,VC), (KS,VD), (KS,VE), (KS,VF), (KS,VG), (KS,VH), (KS,VI), (KS,VJ), (KS,VK), (KS,VL), (KS,VM), (KS,VN), (KS,VO), (KS,VP), (KS,VQ), (KS,VR), (KS,VS), (KS,VT), (KS,VU), (KS,UV), (KS,VW), (KS,VX), (KS,VY), (KS,VZ), (KS,WA), (KS,WB), (KS,WC), (KT,VA), (KT,VB), (KT,VC), (KT,VD), (KT,VE), (KT,VF), (KT,VG), (KT,VH), (KT,VI), (KT,VJ), (KT,VK), (KT,VL), (KT,VM), (KT,VN), (KT,VO), (KT,VP), (KT,VQ), (KT,VR), (KT,VS), (KT,VT), (KT,VU), (KT,VV), (KT,VW), (KT,VX), (KT,VY), (KT,VZ), (KT,WA), (KT,WB), (KT,WC), (KU,VA), (KU,VB), (KU,VC), (KU,VD), (KU,VE), (KU,VF), (KU,VG), (KU,VH), (KU,VI), (KU,VJ), (KU,VK), (KU,VL), (KU,VM), (KU,VN), (KU,VO), (KU,VP), (KU,VQ), (KU,VR), (KU,VS), (KU,VT), (KU,VU), (KU,VV), (KU,VW), (KU,VX), (KU,VY), (KU,VZ), (KU,WA), (KU,WB), (KU,WC), (KV,VA), (KV,VB), (KV,VC), (KV,VD), (KV,VE), (KV,VF), (KV,VG), (KV,VH), (KV,VI), (KV,VJ), (KV,VK), (KV,VL), (KV,VM), (KV,VN), (KV,VO), (KV,VP), (KV,VQ), (KV,VR), (KV,VS), (KV,VT), (KV,VU), (KV,VV), (KV,VW), (KV,VX), (KV,VY), (KV,VZ), (KV,WA), (KV,WB), (KV,WC), (KW,VA), (KW,VB), (KW,VC), (KW,VD), (KW,VE), (KW,VF), (KW,VG), (KW,VH), (KW,VI), (KW,VJ), (KW,VK), (KW,VL), (KW,VM), (KW,VN), (KW,VO), (KW,VP), (KW,VQ), (KW,VR), (KW,VS), (KW,VT), (KW,VU), (KW,VV), (KW,VW), (KW,VX), (KW,VY), (KW,VZ), (KW,WA), (KW,WB), (KW,WC), (KX,VA), (KX,VB), (KX,VC), (KX,VD), (KX,VE), (KX,VF), (KX,VG), (KX,VH), (KX,VI), (KX,VJ), (KX,VK), (KX,VL), (KX,VM), (KX,VN), (KX,VO), (KX,VP), (KX,VQ), (KX,VR), (KX,VS), (KX,VT), (KX,VU), (KX,VV), (KX,VW), (KX,VX), (KX,VY), (KX,VZ), (KX,WA), (KX,WB), (KX,WC), (KY,VA), (KY,VB), (KY,VC), (KY,VD), (KY,VE), (KY,VF), (KY,VG), (KY,VH), (KY,VI), (KY,VJ), (KY,VK), (KY,VL), (KY,VM), (KY,VN), (KY,VO), (KY,VP), (KY,VQ), (KY,VR), (KY,VS), (KY,VT), (KY,VU), (KY,VV), (KY,VW), (KY,VX), (KY,VY), (KY,VZ), (KY,WA), (KY,WB), (KY,WC), (KZ,VA), (KZ,VB), (KZ,VC), (KZ,VD), (KZ,VE), (KZ,VF), (KZ,VG), (KZ,VH), (KZ,VI), (KZ,VJ), (KZ,VK), (KZ,VL), (KZ,VM), (KZ,VN), (KZ,VO), (KZ,VP), (KZ,VQ), (KZ,VR), (KZ,VS), (KZ,VT), (KZ,VU), (KZ,VV), (KZ,VW), (KZ,VX), (KZ,VY), (KZ,VZ), (KZ,WA), (KZ,WB), (KZ,WC), (LA,VA), (LA,VB), (LA,VC), (LA,VD), (LA,VE), (LA,VF), (LA,VG), (LA,VH), (LA,VI), (LA,VJ), (LA,VK), (LA,VL), (LA,VM), (LA,VN), (LA,VO), (LA,VP), (LA,VQ), (LA,VR), (LA,VS), (LA,VT), (LA,VU), (LA,VV), (LA,VW), (LA,VX), (LA,VY), (LA,VZ), (LA,WA), (LA,WB), (LA,WC), (LB,VA), (LB,VB), (LB,VC), (LB,VD), (LB,VE), (LB,VF), (LB,VG), (LB,VH), (LB,VI), (LB,VJ), (LB,VK), (LB,VL), (LB,VM), (LB,VN), (LB,VO), (LB,VP), (LB,VQ), (LB,VR), (LB,VS), (LB,VT), (LB,VU), (LB,VV), (LB,VW), (LB,VX), (LB,VY), (LB,VZ), (LB,WA), (LB,WB), (LB,WC), (LC,VA), (LC,VA), (LC,VB), (LC,VB), (LC,VC), (LC,VD), (LC,VE), (LC,VF), (LC,VG), (LC,VH), (LC,VI), (LC,VJ), (LC,VK), (LC,VL), (LC,VM), (LC,VN), (LC,VO), (LC,VP), (LC,VQ), (LC,VR), (LC,VS), (LC,VT), (LC,VU), (LC,VV), (LC,VW), (LC,VX), (LC,VY), (LC,VZ), (LC,WA), (LC,WB), (LC,WC), (LD,VC), (LD,VD), (LD,VE), (LD,VF), (LD,VG), (LD,VH), (LD,VI), (LD,VJ), (LD,VK), (LD,VL), (LD,VM), (LD,VN), (LD,VO), (LD,VP), (LD,VQ), (LD,VR), (LD,VS), (LD,VT), (LD,VU), (LD,VV), (LD,VW), (LD,VX), (LD,VY), (LD,VZ), (LD,WA), (LD,WB), (LD,WC), (LE,VA), (LE,VB), (LE,VC), (LE,VD), (LE,VE), (LE,VF), (LE,VG), (LE,VH), (LE,VI), (LE,VJ), (LE,VK), (LE,VL), (LE,VM), (LE,VN), (LE,VO), (LE,VP), (LE,VQ), (LE,VR), (LE,VS), (LE,VT), (LE,VU), (LE,VV), (LE,VW), (LE,VX), (LE,VY), (LE,VZ), (LE,WA), (LE,WB), (LE,WC), (LF,VA), (LF,VB), (LF,VC), (LF,VD), (LF,VE), (LF,VF), (LF,VG), (LF,VH), (LF,VI), (LF,VJ), (LF,VK), (LF,VL), (LF,VM), (LF,VN), (LF,VO), (LF,VP), (LF,VQ), (LF,VR), (LF,VS), (LF,VT), (LF,VU), (LF,VV), (LF,VW), (LF,VX), (LF,VY), (LF,VZ), (LF,WA), (LF,WB), (LF,WC), (LG,VA), (LG,VB), (LG,VC), (LG,VD), (LG,VE), (LG,VF), (LG,VG), (LG,VH), (LG,VI), (LG,VJ), (LG,VK), (LG,VL), (LG,VM), (LG,VN), (LG,VO), (LG,VP), (LG,VQ), (LG,VR), (LG,VS), (LG,VT), (LG,VU), (LG,VV), (LG,VW), (LG,VX), (LG,VY), (LG,VZ), (LG,WA), (LG,WB), (LG,WC), (LH,VA), (LH,VB), (LH,VC), (LH,VD), (LH,VE), (LH,VF), (LH,VG), (LH,VH), (LH,VI), (LH,VJ), (LH,VK), (LH,VL), (LH,VM), (LH,VN), (LH,VO), (LH,VP), (LH,VQ), (LH,VR), (LH,VS), (LH,VT), (LH,VU), (LH,VV), (LH,VW), (LH,VX), (LH,VY), (LH,VZ), (LH,WA), (LH,WB), (LH,WC), (LI,VA), (LI,VB), (LI,VC), (LI,VD), (LI,VE), (LI,VF), (LI,VG), (LI,VH), (LI,VI), (LI,VJ), (LI,VK), (LI,VL), (LI,VM), (LI,VN), (LI,VO), (LI,VP), (LI,VQ), (LI,VR), (LI,VS), (LI,VT), (LI,VU), (LI,VV), (LI,VW), (LI,VX), (LI,VY), (LI,VZ), (LI,WA), (LI,WB), (LI,WC), (LJ,VA), (LJ,VB), (LJ,VC), (LJ,VD), (LJ,VE), (LJ,VF), (LJ,VG), (LJ,VH), (LJ,VI), (LJ,VJ), (LJ,VK), (LJ,VL), (LJ,VM), (LJ,VN), (LJ,VO), (LJ,VP), (LJ,VQ), (LJ,VR), (LJ,VS), (LJ,VT), (LJ,VU), (LJ,VV), (LJ,VW), (LJ,VX), (LJ,VY), (LJ,VZ), (LJ,WA), (LJ,WB), (LJ,WC), (LK,VA), (LK,VB), (LK,VC), (LK,VD), (LK,VE), (LK,VF), (LK,VG), (LK,VH), (LK,VI), (LK,VJ), (LK,VK), (LK,VL), (LK,VM), (LK,VN), (LK,VO), (LK,VP), (LK,VQ), (LK,VR), (LK,VS), (LK,VT), (LK,VU), (LK,VV), (LK,VW), (LK,VX), (LK,VY), (LK,VZ), (LK,WA), (LK,WB), (LK,WC), (LL,VA), (LL,VB), (LL,VC), (LL,VD), (LL,VE), (LL,VF), (LL,VG), (LL,VH), (LL,VI), (LL,VJ), (LL,VK), (LL,VL), (LL,VM), (LL,VN), (LL,VO), (LL,VP), (LL,VQ), (LL,VR), (LL,VS), (LL,VT), (LL,VU), (LL,VV), (LL,VW), (LL,VX), (LL,VY), (LL,VZ), (LL,WA), (LL,WB), (LL,WC), (LM,VA), (LM,VB), (LM,VC), (LM,VD), (LM,VE), (LM,VF), (LM,VG), (LM,VH), (LM,VI), (LM,VJ), (LM,VK), (LM,VL), (LM,VM), (LM,VN), (LM,VO), (LM,VP), (LM,VQ), (LM,VR), (LM,VS), (LM,VT), (LM,VU), (LM,VV), (LM,VW), (LM,VX), (LM,VY), (LM,VZ), (LM,WA), (LM,WB), (LM,WC), (LN,VA), (LN,VB), (LN,VC), (LN,VD), (LN,VE), (LN,VF), (LN,VG), (LN,VH), (LN,VI), (LN,VJ), (LN,VK), (LN,VL), (LN,VM), (LN,VN), (LN,VO), (LN,VP), (LN,VQ), (LN,VR), (LN,VS), (LN,VT), (LN,VU), (LN,VV), (LN,VW), (LN,VX), (LN,VY), (LN,VZ), (LN,WA), (LN,WB), (LN,WC), (LO,VA), (LO,VB), (LO,VC), (LO,VD), (LO,VE), (LO,VF), (LO,VG), (LO,VH), (LO,VI), (LO,VJ), (LO,VK), (LO,VL), (LO,VM), (LO,VN), (LO,VO), (LO,VP), (LO,VQ), (LO,VR), (LO,VS), (LO,VT), (LO,VU), (LO,VV), (LO,VW), (LO,VX), (LO,VY), (LO,VZ), (LO,WA), (LO,WB), (LO,WC), (LP,VA), (LP,VB), (LP,VC), (LP,VD), (LP,VE), (LP,VF), (LP,VG), (LP,VH), (LP,VI), (LP,VJ), (LP,VK), (LP,VL), (LP,VM), (LP,VN), (LP,VO), (LP,VP), (LP,VQ), (LP,VR), (LP,VS), (LP,VT), (LP,VU), (LP,VV), (LP,VW), (LP,VX), (LP,VY), (LP,VZ), (LP,WA), (LP,WB), (LP,WC), (LQ,VA), (LQ,VB), (LQ,VC), (LQ,VD), (LQ,VE), (LQ,VF), (LQ,VG), (LQ,VH), (LQ,VI), (LQ,VJ), (LQ,VK), (LQ,VL), (LQ,VM), (LQ,VN), (LQ,VO), (LQ,VP), (LQ,VQ), (LQ,VR), (LQ,VS), (LQ,VT), (LQ,VU), (LQ,VV), (LQ,VW), (LQ,VX), (LQ,VY), (LQ,VZ), (LQ,WA), (LQ,WB), (LQ,WC), (LR,VA), (LR,VB), (LR,VC), (LR,VD), (LR,VE), (LR,VF), (LR,VG), (LR,VH), (LR,VI), (LR,VJ), (LR,VK), (LR,VL), (LR,VM), (LR,VN), (LR,VO), (LR,VP), (LR,VQ), (LR,VR), (LR,VS), (LR,VT), (LR,VU), (LR,VV), (LR,VW), (LR,VX), (LR,VY), (LR,VZ), (LR,WA), (LR,WB), (LR,WC), (LS,VA), (LS,VB), (LS,VC), (LS,VD), (LS,VE), (LS,VF), (LS,VG), (LS,VH), (LS,VI), (LS,VJ), (LS,VK), (LS,VL), (LS,VM), (LS,VN), (LS,VO), (LS,VP), (LS,VQ), (LS,VR), (LS,VS), (LS,VT), (LS,VU), (LS,VV), (LS,VW), (LS,VX), (LS,VY), (LS,VZ), (LS,WA), (LS,WB), (LS,WC), (LT,VA), (LT,VB), (LT,VC), (LT,VD), (LT,VE), (LT,VF), (LT,VG), (LT,VH), (LT,VI), (LT,VJ), (LT,VK), (LT,VL), (LT,VM), (LT,VN), (LT,VO), (LT,VP), (LT,VQ), (LT,VR), (LT,VS), (LT,VT), (LT,VU), (LT,VV), (LT,VW), (LT,VX), (LT,VY), (LT,VZ), (LT,WA), (LT,WB), (LT,WC), (LU,VA), (LU,VB), (LU,VC), (LU,VD), (LU,VE), (LU,VF), (LU,VG), (LU,VH), (LU,VI), (LU,VJ), (LU,VK), (LU,VL), (LU,VM), (LU,VN), (LU,VO), (LU,VP), (LU,VQ), (LU,VR), (LU,VS), (LU,VT), (LU,VU), (LU,VV), (LU,VW), (LU,VX), (LU,VY), (LU,VZ), (LU,WA), (LU,WB), (LU,WC), (LV,VA), (LV,VB), (LV,VC), (LV,VD), (LV,VE), (LV,VF), (LV,VG), (LV,VH), (LV,VI), (LV,VJ), (LV,VK), (LV,VL), (LV,VM), (LV,VN), (LV,VO), (LV,VP), (LV,VQ), (LV,VR), (LV,VS), (LV,VT), (LV,VU), (LV,VV), (LV,VW), (LV,VX), (LV,VY), (LV,VZ), (LV,WA), (LV,WB), (LV,WC), (LW,VA), (LW,VB), (LW,VC), (LW,VD), (LW,VE), (LW,VF), (LW,VG), (LW,VH), (LW,VI), (LW,VJ), (LW,VK), (LW,VL), (LW,VM), (LW,VN), (LW,VO), (LW,VP), (LW,VQ), (LW,VR), (LW,VS), (LW,VT), (LW,VU), (LW,VV), (LW,VW), (LW,VX), (LW,VY), (LW,VZ), (LW,WA), (LW,WB), (LW,WC), (LX,VA), (LX,VB), (LX,VC), (LX,VD), (LX,VE), (LX,VF), (LX,VG), (LX,VH), (LX,VI), (LX,VJ), (LX,VK), (LX,VL), (LX,VM), (LX,VN), (LX,VO), (LX,VP), (LX,VQ), (LX,VR), (LX,VS), (LX,VT), (LX,VU), (LX,VV), (LX,VW), (LX,VX), (LX,VY), (LX,VZ), (LX,WA), (LX,WB), (LX,WC), (LY,VA), (LY,VB), (LY,VC), (LY,VD), (LY,VE), (LY,VF), (LY,VG), (LY,VH), (LY,VI), (LY,VJ), (LY,VK), (LY,VL), (LY,VM), (LY,VN), (LY,VO), (LY,VP), (LY,VQ), (LY,VR), (LY,VS), (LY,VT), (LY,VU), (LY,VV), (LY,VW), (LY,VX), (LY,VY), (LY,VZ), (LY,WA), (LY,WB), (LY,WC), (LZ,VA), (LZ,VB), (LZ,VC), (LZ,VD), (LZ,VE), (LZ,VF), (LZ,VG), (LZ,VH), (LZ,VI), (LZ,VJ), (LZ,VK), (LZ,VL), (LZ,VM), (LZ,VN), (LZ,VO), (LZ,VP), (LZ,VQ), (LZ,VR), (LZ,VS), (LZ,VT), (LZ,VU), (LZ,VV), (LZ,VW), (LZ,VX), (LZ,VY), (LZ,VZ), (LZ,WA), (LZ,WB), (LZ,WC), (MA,VA), (MA,VB), (MA,VC), (MA,VD), (MA,VE), (MA,VF), (MA,VG), (MA,VH), (MA,VI), (MA,VJ), (MA,VK), (MA,VL), (MA,VM), (MA,VN), (MA,VO), (MA,VP), (MA,VQ), (MA,VR), (MA,VS), (MA,VT), (MA,VU), (MA,UV), (MA,VW), (MA,VX), (MA,VY), (MA,VZ), (MA,WA), (MA,WB), (MA,WC), (MB,VA), (MB,VB), (MB,VC), (MB,VD), (MB,VE), (MB,VF), (MB,VG), (MB,VH), (MB,VI), (MB,VJ), (MB,VK), (MB,VL), (MB,VM), (MB,VN), (MB,VO), (MB,VP), (MB,VQ), (MB,VR), (MB,VS), (MB,VT), (MB,VU), (MB,VV), (MB,VW), (MB,VX), (MB,VY), (MB,VZ), (MB,WA), (MB,WB), (MB,WC), (MC,VA), (MC,VA), (MC,VB), (MC,VB), (MC,VC), (MC,VD), (MC,VE), (MC,VF), (MC,VG), (MC,VH), (MC,VI), (MC,VJ), (MC,VK), (MC,VL), (MC,VM), (MC,VN), (MC,VO), (MC,VP), (MC,VQ), (MC,VR), (MC,VS), (MC,VT), (MC,VU), (MC,VW), (MC,VW), (MC,VX), (MC,VY), (MC,VZ), (MC,WA), (MC,WB), (MC,WC), (MD,VC), (MD,VD), (MD,VE), (MD,VF), (MD,VG), (MD,VH), (MD,VI), (MD,VJ), (MD,VK), (MD,VL), (MD,VM), (MD,VN), (MD,VO), (MD,VP), (MD,VQ), (MD,VR), (MD,VS), (MD,VT), (MD,VU), (MD,VV), (MD,VW), (MD,VX), (MD,VY), (MD,VZ), (MD,WA), (MD,WB), (MD,WC), (ME,VA), (ME,VB), (ME,VC), (ME,VD), (ME,VE), (ME,VF), (ME,VG), (ME,VH), (ME,VI), (ME,VJ), (ME,VK), (ME,VL), (ME,VM), (ME,VN), (ME,VO), (ME,VP), (ME,VQ), (ME,VR), (ME,VS), (ME,VT), (ME,VU), (ME,VV), (ME,VW), (ME,VX), (ME,VY), (ME,VZ), (ME,WA), (ME,WB), (ME,WC), (MF,VA), (MF,VB), (MF,VC), (MF,VD), (MF,VE), (MF,VF), (MF,VG), (MF,VH), (MF,VI), (MF,VJ), (MF,VK), (MF,VL), (MF,VM), (MF,VN), (MF,VO), (MF,VP), (MF,VQ), (MF,VR), (MF,VS), (MF,VT), (MF,VU), (MF,VV), (MF,VW), (MF,VX), (MF,VY), (MF,VZ), (MF,WA), (MF,WB), (MF,WC), (MG,VA), (MG,VB), (MG,VC), (MG,VD), (MG,VE), (MG,VF), (MG,VG), (MG,VH), (MG,VI), (MG,VJ), (MG,VK), (MG,VL), (MG,VM), (MG,VN), (MG,VO), (MG,VP), (MG,VQ), (MG,VR), (MG,VS), (MG,VT), (MG,VU), (MG,VV), (MG,VW), (MG,VX), (MG,VY), (MG,VZ), (MG,WA), (MG,WB), (MG,WC), (MH,VA), (MH,VB), (MH,VC), (MH,VD), (MH,VE), (MH,VF), (MH,VG), (MH,VH), (MH,VI), (MH,VJ), (MH,VK), (MH,VL), (MH,VM), (MH,VN), (MH,VO), (MH,VP), (MH,VQ), (MH,VR), (MH,VS), (MH,VT), (MH,VU), (MH,VV), (MH,VW), (MH,VX), (MH,VY), (MH,VZ), (MH,WA), (MH,WB), (MH,WC), (MI,VA), (MI,VB), (MI,VC), (MI,VD), (MI,VE), (MI,VF), (MI,VG), (MI,VH), (MI,VI), (MI,VJ), (MI,VK), (MI,VL), (MI,VM), (MI,VN), (MI,VO), (MI,VP), (MI,VQ), (MI,VR), (MI,VS), (MI,VT), (MI,VU), (MI,VV), (MI,VW), (MI,VX), (MI,VY), (MI,VZ), (MI,WA), (MI,WB), (MI,WC), (MJ,VA), (MJ,VB), (MJ,VC), (MJ,VD), (MJ,VE), (MJ,VF), (MJ,VG), (MJ,VH), (MJ,VI), (MJ,VJ), (MJ,VK), (MJ,VL), (MJ,VM), (MJ,VN), (MJ,VO), (MJ,VP), (MJ,VQ), (MJ,VR), (MJ,VS), (MJ,VT), (MJ,VU), (MJ,VV), (MJ,VW), (MJ,VX), (MJ,VY), (MJ,Vz), (MJ,WA), (MJ,WB), (MJ,WC), (MK,VA), (MK,VB), (MK,VC), (MK,VD), (MK,VE), (MK,VF), (MK,VG), (MK,VH), (MK,VI), (MK,VJ), (MK,VK), (MK,VL), (MK,VM), (MK,VN), (MK,VO), (MK,VP), (MK,VQ), (MK,VR), (MK,VS), (MK,VT), (MK,VU), (MK,VV), (MK,VW), (MK,VX), (MK,VY), (MK,VZ), (MK,WA), (MK,WB), (MK,WC), (ML,VA), (ML,VB), (ML,VC), (ML,VD), (ML,VE), (ML,VF), (ML,VG), (ML,VH), (ML,VI), (ML,VJ), (ML,VK), (ML,VL), (ML,VM), (ML,VN), (ML,VO), (ML,VP), (ML,VQ), (ML,VR), (ML,VS), (ML,VT), (ML,VU), (ML,VV), (ML,VW), (ML,VX), (ML,VY), (ML,VZ), (ML,WA), (ML,WB), (ML,WC), (MM,VA), (MM,VB), (MM,VC), (MM,VD), (MM,VE), (MM,VF), (MM,VG), (MM,VH), (MM,VI), (MM,VJ), (MM,VK), (MM,VL), (MM,VM), (MM,VN), (MM,VO), (MM,VP), (MM,VQ), (MM,VR), (MM,VS), (MM,VT), (MM,VU), (MM,VV), (MM,VW), (MM,VX), (MM,VY), (MM,VZ), (MM,WA), (MM,WB), (MM,WC), (MN,VA), (MN,VB), (MN,VC), (MN,VD), (MN,VE), (MN,VF), (MN,VG), (MN,VH), (MN,VI), (MN,VJ), (MN,VK), (MN,VL), (MN,VM), (MN,VN), (MN,VO), (MN,VP), (MN,VQ), (MN,VR), (MN,VS), (MN,VT), (MN,VU), (MN,VV), (MN,VW), (MN,VX), (MN,VY), (MN,VZ), (MN,WA), (MN,WB), (MN,WC)

As used herein, the "emesis, vomiting and/or constipation" includes nausea, emesis, vomiting and/or constipation which are induced by ingestion of a compound having the opioid receptor (particularly, opioid receptor) agonistic activity. Specifically, examples of the "compound having the opioid receptor agonistic activity" include morphine, oxycodone, fentanyl, methadone, codeine, dihydrocodeine, hydromorphone, levorphanol, meperidine, propoxyphene, dextropropoxyphen, tramadol, and a pharmaceutically acceptable salt, or a solvate thereof. Particularly, when the compound is morphine, oxycodone, or a pharmaceutically acceptable salt, or a solvate thereof, the present compound is particularly effective.

Influence of the present compound on emesis or vomiting can be confirmed, for example, by the following test.

At thirty minutes after ingestion of a diet, each test substance is administered to a ferret. The test compound is dissolved in 5% xylitol, and is administered at 5 mg/kg. At thirty minutes after administration of the test compound, 0.6 mg/kg of morphine was subcutaneously administered, and the vomiting symptom is observed visually until 30 minutes after administration of morphine.

For each of emesis (rhythmic constriction movement at an abdominal part) and vomiting (vomiting conduct of excreting a vomiting substance or a similar conduct), an appearance time, a latent time (time from morphine administration to initial appearance of vomiting symptom) and a sustaining time (time from initial vomiting to final vomiting) are collected.

In addition, influence of the present compound on constipation can be confirmed, for example, by the following test.

1) Preparation of Test Diet (Dye)

Using a 0.5 w/v % Evans Blue aqueous solution, a 2.5 w/v % carboxymethylcellulose salt solution is prepared, and this is used as a test diet.

2) Animal

For example, a Wistar male rat (6 to 7 week old) may be used. The animal is fasted from about 20 or more hours before test initiation, and water is given ad lib.

3) Test Compound and Medium

The test compound is dissolved in a solvent (DMAA/Solutol/5% meglumine=15/15/70).

DMAA: N,N-dimethylacetamide

Solutol (registered trademark) HS15

Meglumine: D (-)-N-methylglucamine

Morphine hydrochloride is dissolved in a physiological saline.

The test compound, the solvent and morphine are all administered at a liquid amount of 2 mL/kg.

4) Method

The test compound 0.03, 0.1, 0.3, 1 or 3 mg/kg (test compound administration group) or the solvent (solvent administration group) is subcutaneously administered, and amount of 3 mg/kg of morphine is subcutaneously administered to all groups after 75 minutes. As a control group, the solvent is subcutaneously administered, and a physiological saline is administered after 75 minutes.

The test diet 2 mL/rat is orally administered at 30 minutes after administration of morphine. At fifteen minutes after the test diet (at 120 minutes after administration of the test substance), the rats are isolated from esophagus to an ileocecal part near a stomach cardia part. A distance from pyloric part of the stomach to an ileocecal part (full length of small intestine) and a distance until a dye reaching front part (dye movement distance) are measured.

5) Data Processing

Transport rate (%)=(dye movement distance (cm))/full length of small intestine (cm))×100

M.P.E. (%)={(small intestine transport rate (%) of each individual of test compound administration group−average small intestine transport rate (%) of solvent administration group)/(average small intestine transport rate (%) of control group−average small intestine transport rate (%) of solvent administration group)}×100

An $ED_{50}$ value is calculated by reverse estimation of regression a SAS program using % MPE and letting a value of a control group to be 100%.

The present compound has the opioid receptor (particularly, opioid δ and μ receptors) antagonistic activity. Therefore, the present compound is effective in treating and/or preventing digestive tract passage disorder which occurs by a cause such as acute dyspepsia, acute alcoholism, food poisoning, cold, stomach ulcer, duodenum ulcer, stomach cancer, ileus, appendicitis, peritonitis, cholelithiasis, hepatitis, liver inflammation, encephalitis, meningitis, increased brain pressure, head trauma, motion sickness, vomiting of pregnancy, side effect due to chemotherapy, side effect due to radiation therapy, side effect due to anti-cancer agent, pressure•stenosis of digestive tract, and intestinal tract coalescence after operation, treating and/or preventing emesis and vomiting which occurs by a cause such as increase in brain pressure due to brain tumor•brain bleeding•meningitis•irradiation of brain with radiation, and treating and/or preventing acute constipation derived from a cause such as ileus, duodenum ulcer or appendicitis, relaxing constipation derived from a cause such as nervous disorder, low nutrient, general prostration, vitamin deficiency, anemia, sensitivity reduction or mechanical stimulation insufficiency, or convulsive constipation derived from a cause such as stress, in addition to emesis•vomiting•constipation induced by a compound having the opioid receptor agonistic activity.

Since the present compound has low brain transition, it exhibits the high alleviating effect on a side effect such as emesis, vomiting, constipation and the like induced by an opioid receptor agonistic activity almost without inhibiting the analgesic activity of a compound having the opioid receptor agonistic activity which is administered to the patient with a decease accompanying pain (e.g. cancerous pain (pain due to bone transition, nervous pressure, increased intracranial pressure, soft tissue infiltration, pain due to constipation or spasm of muscle, pain of internal organ, muscle, fascia, waist or shoulder joint periphery, chronic pain after operation), AIDS etc.). In addition, the present compound has pure antagonistic activity on an opioid receptor, and also has an advantage in safety point that the hERG channel inhibitory activity is low, there is no cardiac toxicity, and so on. Further, the present compound also has an advantageous characteristic in dynamics in a body such as high oral absorbability, high stability in human plasma, high bioavailability and the like, and is very effective as a medicament.

When the present compound is administered against emesis, vomiting, or constipation induced by a compound having the opioid receptor agonistic activity, the administration may be any of before, after or at the same time with administration of the compound having the opioid receptor agonistic activity. An administration interval between these two kinds of drugs is not particularly limited. For example, when the present compound is administered after administration of the compound having the opioid receptor agonistic activity, if the administration is immediately after to in about 3 days, preferably immediately after to in about 1 day from administration of the compound having the opioid receptor agonistic activity, the present compound works more effectively. In addition, when the present invention is administered before administration of the compound having the opioid receptor agonistic activity, if the administration is immediately before to before about 1 day, preferably immediately before to before about 12 hours from administration of the compound having the opioid receptor agonistic activity, the present compound works more effectively.

When the present compound is administered as an agent for treating and/or preventing emesis, vomiting and/or constipation, it may be used jointly with other agent for treating and/or preventing emesis, vomiting and/or constipation. For example, it is possible to administer the agent jointly with ondansetrone hydrochloride, adrenal cortical steroid (methylprednisolone, prednisolone, dexamethasone etc.), prochlorperazine, haloperidol, thymiperone, perphenazine, metoclopramide, domperidone, scopolamine, chlorpromazine hydrochloride, droperidol, stimulating laxative (sennoside, picosulfate sodium etc.), osmotic laxative (lactulose etc.), or salt laxative (magnesium oxide etc.).

Alternatively, a combination agent between the present compound and a compound having the opioid receptor agonistic activity, or a combination agent between the present compound and other agent for treating and/or preventing emesis, vomiting and/or constipation can be administered.

When the present compound is administered to a human, it can be administered orally as powders, granules, tablets, capsules, pills, solutions, or the like, or parenterally as injectables, suppositories, transdermal absorbable agents, absorbable agents, or the like. Oral agents are preferable.

In addition, the present compound can be formulated into pharmaceutical preparations by adding pharmaceutical additives such as excipients, binders, wetting agents, disintegrating agents, lubricants and the like, which are suitable for formulations and, an effective amount of the present compound.

The present compound may be formulated into medical mixtures in which a compound having the opioid receptor agonistic activity and/or other agent for treating and/or preventing emesis, vomiting and/or constipation and, if necessary, various pharmaceutical additives.

A dose is different depending on state of a disease, an administration route, and an age and a weight of a patient, and is usually 0.1 μg to 1 g/day, preferably 0.01 to 200 mg/day when orally administered to an adult, and is usually 0.1 μg to 10 g/day, preferably 0.1 to 2 g/day when parenterally administered.

Following Examples and Test Examples illustrate the present invention in more detail, but the present invention is not limited by these Examples.

EXAMPLE 1

Production of Compound (I-4)

[Chemical formula 11]

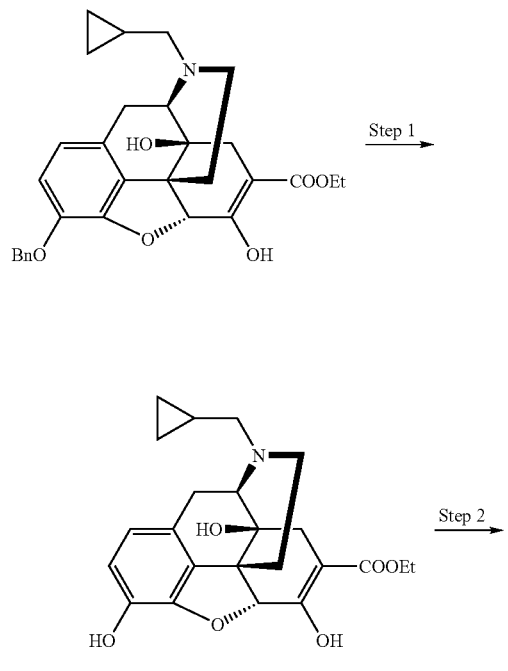

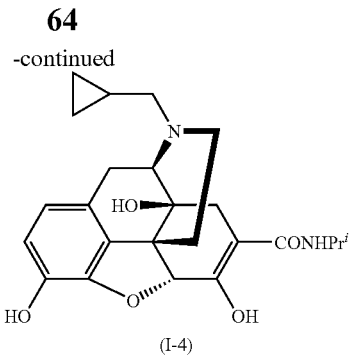

wherein Bn indicates benzyl, Et indicates ethyl, and Pr$^i$ indicates isopropyl.

(First Step) 7-ethoxycarbonylnaltrexone

To a suspension of 3-O-benzyl-7-ethoxycarbonylnaltrexone described in Non-Patent Literature 2 (11.16 g, 22.15 mmol) in ethyl acetate (50 mL) and methanol (50 mL) was added palladium hydroxide (Perlman's catalyst) (1.2 g), and the mixture was vigorously stirred for 2 hours under a hydrogen atmosphere. After filtration of the catalyst, the filtrate was concentrated, and the residue was crystallized from ethyl acetate and hexane to obtain 8.96 g (92%) of the title compound as colorless crystals.

NMR (300 MHz, CDCl$_3$) δ 0.14-0.17 (m, 2H), 0.55-0.58 (m, 2H), 0.86 (m, 1H), 1.23-1.29 (m, 3H), 1.67 (d, 1H, J=9.6 Hz), 2.02 (dd, 1H, J=1.2, 16.2 Hz), 2.20-2.79 (m, 8H), 3.08 (d, 1H, J =18.6 Hz), 3.24 (br, 1H), 4.12-4.20 (m, 2H), 4.96 (s, 1H), 5.17 (br, 1H), 6.59 (d, 1H, J=8.1 Hz), 6.72 (d, 1H, J=8.1 Hz), 12.12 (s, 1H).

Elemental analysis (C23H27NO6.0.2H2O) (Calculated value) C, 66.24; H, 6.62; N, 3.36. (Found value) C, 66.29; H, 6.50; N, 3.45.

(Second Step) 7-isopropylaminocarbonylnaltrexone

A solution of 7-ethoxycarbonylnaltrexone obtained in the first step (200 mg, 0.484 mmol), isopropylamine (0.412 mL, 4.84 mmol) and triethylamine (0.202 mL, 1.45 mmol) in 2-methoxyethanol (1.5 mL) was stirred at 180° C. for 45 minutes under microwave irradiation. After cooled to room temperature, 7 mL of 5 mol/L hydrochloric acid was added to the reaction mixture, and stirring was continued at 70° C. for 20 minutes. After the reaction solution was cooled, pH value was adjusted to 8.5 with aqueous ammonia, followed by extraction with ethyl acetate. The organic layer was washed with water, and dried, and the solvent was evaporated. The residue was purified by silica gel column chromatography (chloroform:methanol=99:1 to 94:6) to obtain 140 mg of the title compound at a yield of 68%.

NMR (300 MHz, d6-DMSO) δ 0.12-0.15 (m, 2H), 0.44-0.53 (m, 2H), 0.83 (m, 1H), 1.02 (d, 3H, J=6.6 Hz), 1.08 (d, 3H, J=6.6 Hz), 1.41 (d, 1H, J=11.4 Hz), 1.85 (d, 1H, J=15.6 Hz), 2.04-2.62 (m, 8H), 3.04 (d, 1H, J=18.6 Hz), 3.24 (m, 1H), 3.96 (m, 1H), 4.71 (s, 1H), 4.74 (s, 1H), 6.51 (d, 1H, J=8.4 Hz), 6.56 (d, 1H, J=8.4 Hz), 7.40 (br d, 1H, J=7.2 Hz), 9.16 (s, 1H), 14.50 (s, 1H).

Elemental analysis (C24H30N2O5.0.2H2O) (Calculated value) C, 67.02; H, 7.12; N, 6.51. (Found value) C, 67.02; H, 7.20; N, 6.49.

EXAMPLE 2

Preparation of Compound (I-44)

[Chemical formula 12]

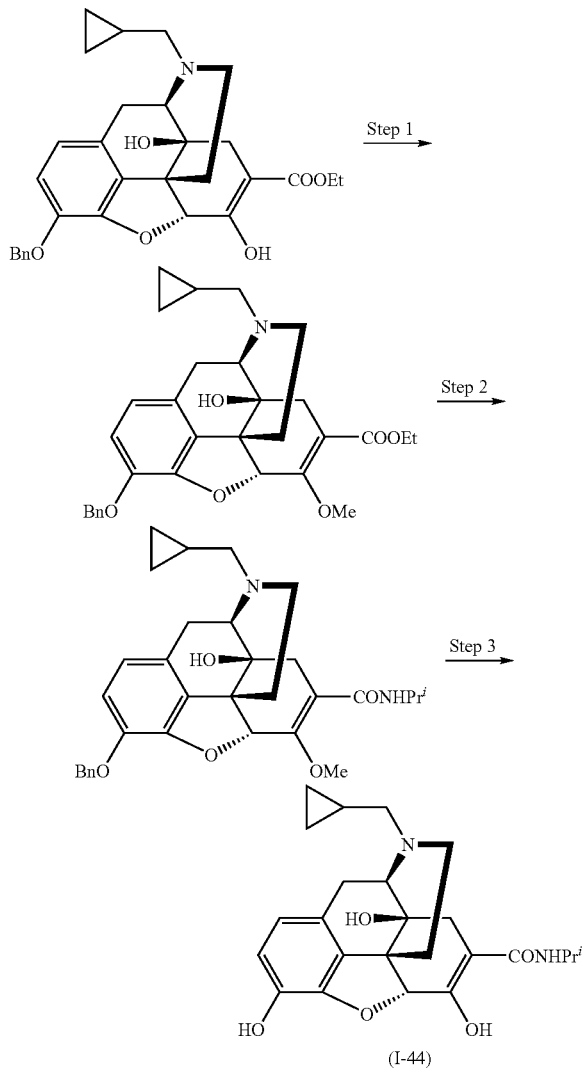

(I-44)

wherein Bn indicates benzyl, Me indicates methyl, Et indicates ethyl, and Pr$^i$ indicates isopropyl.

(First Step) 3-O-benzyl-7-ethoxycarbonyl-6-O-methylnaltrexone

To a solution of 3-O-benzyl-7-ethoxycarbonylnaltrexone described in Non-Patent Literature 2 (504 mg, 1 mmol) in tetrahydrofuran (10 mL) were successively added 1,1'-azodicarbonylpiperidine (379 mg, 1.5 mmol), tri-n-butylphosphine (370 μL, 1.5 mmol) and methanol (41 μl, 1 mmol), and the mixture was stirred at room temperature for 7 hours. The reaction solution was concentrated under reduced pressure, and the residue was purified by silica gel column chromatography (hexane/ethyl acetate) to obtain the title compound (421 mg, 81%) as colorless oil.

$^1$H NMR (CDCl$_3$, δ $_{ppm}$): 0.10-0.20 (m, 2H), 0.50-0.65 (m, 2H), 0.88 (m, 1H), 1.26 (t, J=6.6 Hz, 3H), 1.67 (d, J=11.4 Hz, 1H), 2.15-2.80 (m, 8H), 3.00-3.30 (m, 2H), 3.93 (s, 3H), 4.05-4.20 (m, 2H), 4.86 (br s, 1H), 5.15 (s, 2H), 5.18 (br s, 1H), 6.57 (d, J=8.1 Hz, 1H), 6.72 (d, J=8.1 Hz, 1H), 7.28-7.45 (m, 5H)

(Second Step) 3-O-benzyl-7-isopropylaminocarbonyl-6-O-methylnaltrexone

To a mixed solution of 3-O-benzyl-7-ethoxycarbonyl-6-O-methylnaltrexone obtained in the first step (145 mg, 0.28 mmol) in methanol (6 mL) and dioxane (2 mL) was added a 50% potassium hydroxide aqueous solution (2 mL), and the mixture was stirred at 50° C. for 30 minutes. The reaction solution was cooled to room temperature, and adjusted to pH=4 with 0.5M an aqueous citric acid solution, followed by extraction with ethyl acetate. The organic layer was successively washed with water, brinebrine, dried with anhydrous sodium sulfate, and concentrated under reduced pressure. The resulting crystalline residue, 3-O-benzyl-7-carboxy-6-O-methylnaltrexone was used in the next reaction without purification. To a solution of the above residue in dimethylformamide (3 mL) were successively added 1-ethyl-3-(3-dimethylaminopropyl) carbodiimide hydrochloride (40 mg, 0.2 mmol), 1-hydroxybenzotriazole (27 mg, 0.2 mmol) and isopropylamine (16 μL, 0.182 mmol), and the mixture was stirred at room temperature for 15 hours. The reaction solution was poured into water and this was extracted with ethyl acetate, and the organic layer was washed with water, dried with anhydrous sodium sulfate, and concentrated under reduced pressure. The residue was purified by silica gel column chromatography (chloroform/methanol=9/1) to obtain the title compound (39 mg, 44%) as a colorless foam.

$^1$H NMR (CDCl$_3$, δ ppm): 0.10-0.20 (m, 2H), 0.50-0.65 (m, 2H), 0.88 (m, 1H), 1.13 (d, J=2.1 Hz, 3H), 1.15 (d, J=1.8 Hz, 3H), 1.58 (d, J=11.4 Hz, 1H), 2.08-2.80 (m, 8H), 2.99-3.30 (m, 2H), 3.94 (s, 3H), 4.06 (m, 1H), 4.83 (br s, 1H), 5.14 (d, J=2.4 Hz, 2H), 5.23 (br s, 1H), 6.56 (d, J=8.4 Hz, 1H), 6.72 (d, J=8.4 Hz, 1H), 7.28-7.45 (m, 6H)

(Third Step) 7-isopropylaminocarbonyl-6-O-methylnaltrexone

To a solution of 3-O-benzyl-7-isopropylaminocarbonyl-6-O-methylnaltrexone obtained in the second step (33 mg, 0.073 mmol) in tetrahydrofuran (5 mL) was added palladium hydroxide (33 mg), and the mixture was stirred for 1 hour under a hydrogen atmosphere. The reaction solution was filtered with Celite, and the filtrate was concentrated under reduced pressure. The residue was purified by silica gel column chromatography (chloroform/methanol=9/1) to obtain the title compound (13 mg, 41%) as a colorless foam.

$^1$H NMR (CDCl$_3$, δ ppm): 0.10-0.15 (m, 2H), 0.50-0.70 (m, 2H), 0.85 (m, 1H), 1.12 (d, J=0.9 Hz, 3H), 1.14 (d, J=0.9 Hz, 3H), 1.66 (d, J=11.4 Hz, 1H), 2.06-2.80 (m, 8H), 3.00-

3.30 (m, 2H), 3.92 (s, 3H), 4.05 (m, 1H), 4.80 (br s, 1H), 5.26 (br s, 1H), 6.56 (d, J=8.1 Hz, 1H), 6.69 (d, J=8.1 Hz, 1H), 7.36 (d, J=7.8 Hz, 1H)

EXAMPLE 3

[Chemical formula 13]

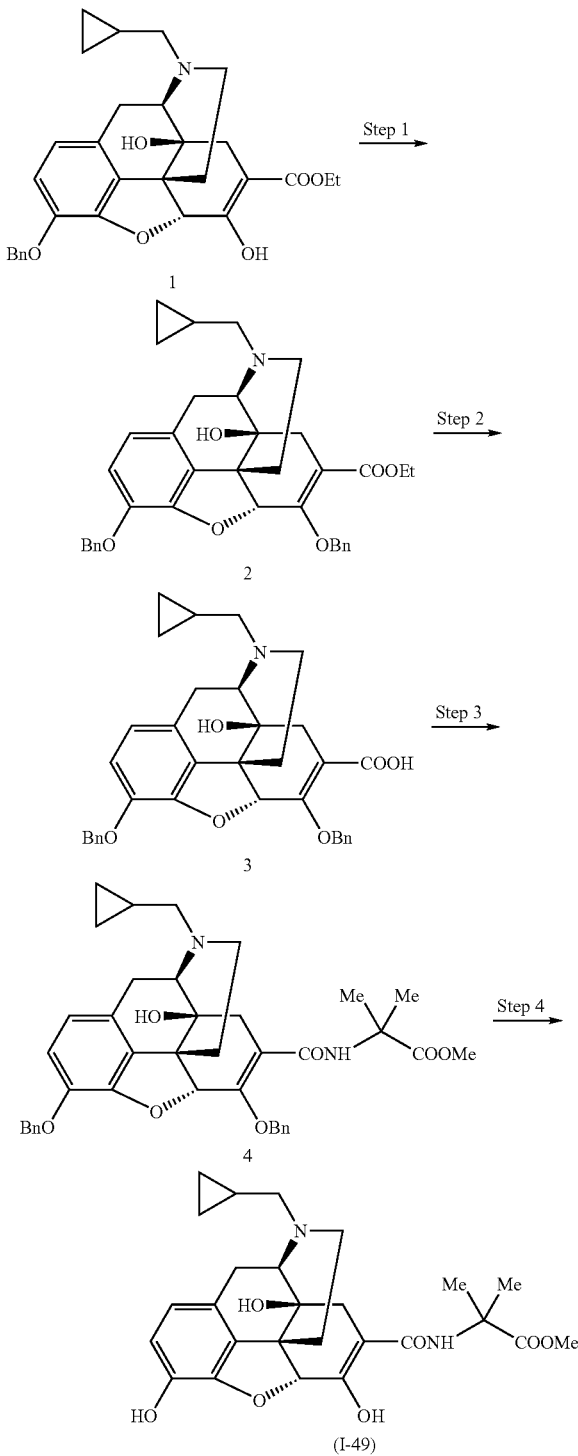

wherein Bn indicates benzyl, Me indicates methyl, and Et indicates ethyl.

(First Step)

A solution of compound (1) (28.7 g, 57.0 mmol) in tetrahydrofuran (250 mL) was cooled to −10° C. and to the solution were 1,1'-azodicarbonylpiperidine (21.6 g, 85.5 mol), tri-n-butylphosphine (21.4 mL, 85.5 mmol) and benzyl alcohol (6.50 mL, 62.7 mmol) successively added, and the mixture was stirred at room temperature for 6 hours and 45 minutes. The reaction solution was filtered and the filtrate was concentrated under reduced pressure, and the residue was purified by silica gel column chromatography (chloroform→chloroform/methanol=50/1) to obtain quantitatively the objective compound (2) (33.8 g) as a pale yellow oil.

$^1$H NMR (CDCl$_3$, δ ppm): 0.10-0.20 (m, 2H), 0.50-0.65 (m, 2H), 0.88 (m, 1H), 0.94 (t, J=7.2 Hz, 3H), 1.20-3.60 (m, 11H), 4.14 (q, J=7.2 Hz, 2H), 5.10-5.35 (m, 5H), 6.58 (d, J=8.1 Hz, 1H), 6.74 (d, J=8.1 Hz, 1H), 7.15-7.50 (m, 10H)

(Second Step)

To a mixed solution of compound (2) obtained in the first step (33.8 g, 57.0 mmol) in methanol (130 mL) and dioxane (43 mL) was added a 4N-potassium hydroxide aqueous solution (43 mL), and the mixture was stirred at 50° C. for 14 hours and 35 minutes. The reaction solution was cooled to room temperature, and concentrated under reduced pressure, and the residue was adjusted to pH=3 to 4 with ice-water and 2N-hydrochloric acid, followed by extraction with a mixed solution of ethyl acetate and tetrahydrofuran. The organic layer was successively washed with water, and brine, dried with anhydrous sodium sulfate, and concentrated under reduced pressure. The residue was converted into a powder with ether to obtain the objective compound (3) (24.8 g, 77%) as a colorless powder.

$^1$H NMR (DMSO-d$_6$, δ ppm): 0.20-0.40 (m, 2H), 0.50-0.65 (m, 2H), 0.95 (m, 1H), 1.30-3.60 (m, 11H), 5.00-5.25 (m, 5H), 5.39 (s, 1H), 6.68 (d, J=8.1 Hz, 1H), 6.88 (d, J=8.1 Hz, 1H), 7.27-7.52 (m, 10H)

(Third Step)

To a solution of compound (3) obtained in the second step (350 mg, 0.619 mmol) in tetrahydrofuran (4 mL) were successively added 1-ethyl-3-(3-dimethylaminopropyl)carbodiimide hydrochloride (142 mg, 0.743 mmol), 1-hydroxybenzotriazole (100 mg, 0.743 mmol.), dimethylglycine methyl ester hydrochloride (114 mg, 0.743 mmol) and N-methylmorpholine (82 μL, 0.743 mmol), and the mixture was stirred at room temperature overnight. The reaction solution was poured into ice-water and a saturated sodium bicarbonate aqueous solution, followed by extracted with ethyl acetate, and the organic layer was washed with brine, dried with anhydrous sodium sulfate, and concentrated under the reduced pressure. The residue was purified by silica gel column chromatography (chloroform/methanol=50/1) to obtain the objective compound (4) (300 mg, 73%) as a pale yellow foam.

$^1$H NMR (CDCl$_3$, δ ppm): 0.08-0.20 (m, 2H), 0.50-0.60 (m, 2H), 0.87 (m, 1H), 1.13 (s, 3H), 1.22 (s, 3H), 1.55-2.80 (m, 11H), 3.62 (s, 3H), 4.85 (br s, 1H), 5.13-5.40 (m, 5H), 6.58 (d, J=8.4 Hz, 1H), 6.76 (d, J=8.4 Hz, 1H), 7.26-7.48 (m, 10H), 7.94 (s, 1H)

(Fourth Step)

To a solution of compound (4) obtained in the third step (290 mg, 0.436 mmol) in methanol (4 mL) was added palladium hydroxide (60 mg), followed by stirring for 3 hours under a hydrogen atmosphere. The reaction solution was filtered with Celite, and the filtrate was concentrated under reduced pressure. The residue was crystallized with hexane/ethyl acetate to obtain the objective compound (I-49) (181 mg, 86%) as colorless crystals.

1H NMR (DMSO-d6, δ ppm): 0.10-0.20 (m, 2H), 0.40-0.57 (m, 2H), 0.84 (m, 1H), 1.33 (s, 3H), 1.37 (s, 3H), 1.40-3.40 (m, 11H), 3.55 (s, 3H), 4.72 (s, 1H), 4.77 (br s, 1H), 6.52 (d, J=8.1 Hz, 1H), 6.57 (d, J=8.1 Hz, 1H), 7.68 (br s, 1H), 9.18 (br s, 1H), 13.78 (br s, 1H)

According to the same procedure, other compounds (I) can be synthesized. Structural formulas and physical constants are shown below.

In Tables, Me indicates methyl, Et indicates ethyl, Pr$^j$ indicates isopropyl, and Ph indicates phenyl.

In addition, in Tables,

[Chemical formula 14]

indicates

TABLE 9

| Compound No. | Chemical structure | | NMR (1H-NMR (d6-DMSO) δ) |
|---|---|---|---|
| I-1 | (structure) | Chiral | 0.10-0.25 (m, 2H), 0.50-0.60 (m, 2H), 1.87 (m, 1H), 1.13 (t, J = 7.2 Hz, 3H), 1.68 (d, J = 11.4 Hz, 1H), 2.20-2.80 (m, 7H), 3.00-3.35 (m, 5H), 4.94 (s, 1H), 5.40 (m, 1H), 6.57 (d, J = 8.1 Hz, 1H), 6.72 (d, J = 8.1 Hz, 1H), 14.20 8br s, 1H) |
| I-2 | (structure) | Chiral | 0.10-0.20 (m, 2H), 0.40-0.60 (m, 2H), 0.85 (m, 1H), 1.41 (d, J = 11.4 Hz, 1H), 1.90-3.40 (m, 14H), 4.71 (s, 1H), 4.73 (br s, 1H), 6.50 (d, J = 8.1 Hz, 1H), 6.55 (d, J = 8.1 Hz, 1H), 7.77 (br s, 1H) |
| I-3 | (structure) | Chiral | (CDCl3) 0.10-0.25 (m, 2H), 0.50-0.62 (m, 2H), 0.81-0.98 (m, 4H), 1.24-1.74 (m, 6H), 2.21-2.77 (m, 7H), 3.05-3.30 (m, 5H), 4.93 (s, 1H), 5.40 (br t, 1H), 6.57 (d, J = 8.7 Hz, 1H), 6.72 (d, J = 8.7 Hz, 1H), 14.21 (s, 1H). |
| I-4 | (structure) | Chiral | 0.12-0.15 (m, 2H), 0.44-0.53 (m, 2H), 0.83 (m, 1H), 1.02 (d, 3H, J = 6.6 Hz), 1.08 (d, 3H, J = 6.6 Hz), 1.41 (d, 1H, J = 11.4 Hz), 1.85 (d, 1H, J = 15.6 Hz), 2.04-2.62 (m, 8H), 3.04 (d, 1H, J = 18.6 Hz), 3.24 (m, 1H), 3.96 (m, 1H), 4.71 (s, 1H), 4.74 (s, 1H), 6.51 (d, 1H, J = 8.4 Hz), 6.56 (d, 1H, J = 8.4 Hz), 7.40 (br d, 1H, J = 7.2 Hz), 9.16 (s, 1H), 14.50 (s, 1H) |

TABLE 9-continued

| Compound No. | Chemical structure | NMR (1H-NMR (d6-DMSO) δ) |
| --- | --- | --- |
| I-5 | 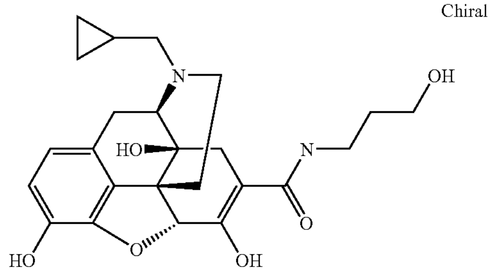 | Chiral 0.10-0.25 (m, 2H), 0.50-0.62 (m, 2H), 0.85 (m, 1H), 1.40-1.60 (m, 4H), 1.83-3.20 (m, 11H), 4.41 (br s, 1H), 4.72 (s, 1H), 4.74 (s, 1H), 6.51 (d, J = 8.7 Hz), 6.56 (d, J = 8.7 Hz, 1H), 7.70 (s, 1H). 9.15 (br s, 1H), 14.42 (s, 1H). |
| I-6 | 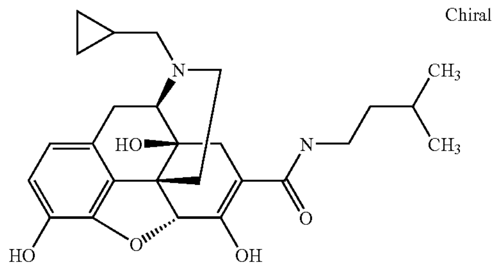 | Chiral 0.10-0.25 (m, 2H), 0.50-0.62 (m, 2H), 0.85 (m, 1H), 1.42 (d, J = 11.7 Hz, 1H), 1.83-2.64 (m, 10H), 2.10 (s, 6H), 3.00-3.18 (m, 3H), 4.72 (s, 1H), 4.74 (s, 1H), 6.51 (d, J = 8.7 Hz), 6.56 (d, J = 8.7 Hz, 1H), 7.65 (s, 1H), 9.10 (br s, 1H). |
| I-7 | 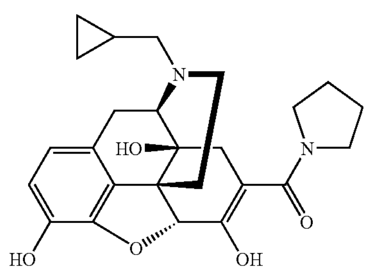 | 0.10-0.25 (m, 2H), 0.50-0.60 (m, 2H), 1.90 (m, 1H), 1.57 (dd, J = 2.4, 12.6 Hz, 2H), 1.85-2.80 (m, 10H), 3.00-3.25 (m, 3H), 3.35-3.60 (m, 3H), 4.20 (m, 1H), 4.76 (br s, 1H), 5.85 (br s, 1H), 6.58 (d, J = 8.1 Hz, 1H), 6.70 (d, J = 8.1 Hz, 1H) |

TABLE 10

| Compound No. | Chemical structure | NMR (1H-NMR (d6-DMSO) δ) |
| --- | --- | --- |
| I-8 | Chiral | 0.10-0.20 (m, 2H), 0.45-0.68 (m, 2H), 1.88 (m, 1H), 1.35 (d, J = 11.4 Hz, 1H), 1.65-2.20 (m, 4H), 2.30-3.60 (m, 13H), 4.29 (dd, J = 4.8, 12.6 Hz, 1H), 5.08 (s, 1H), 5.23 (br s, 1H), 6.53 (d, J = 8.1 Hz, 1H), 6.57 (d, J = 8.1 Hz, 1H), 9.25 (br s, 1H) |
| I-9 | Chiral | (CDCl3) 0.10-0.25 (m, 2H), 0.50-0.62 (m, 2H), 0.85 (m, 1H), 1.62-2.77 (m, 6H), 3.07 (d, J = 18.6 Hz, 1H), 3.23 (d, J = 7.2 Hz, 1H), 4.42 (d, J = 5.4 Hz, 2H), 4.93 (s, 1H), 5.66 (br s, 1H), 6.55 (d, J = 8.7 Hz), 6.72 (d, J = 8.7 Hz, 1H), 7.22-7.39 (m, 5H), 14.15 (s, 1H). |

TABLE 10-continued

| Compound No. | Chemical structure | NMR (1H-NMR (d6-DMSO) δ) |
|---|---|---|
| I-10 | Chiral | 0.10-0.24 (m, 2H), 0.45-0.60 (m, 2H), 0.89 (m, 1H), 1.45 (d, J = 11.1 Hz, 1H), 1.70-3.40 (m, 10H), 4.78 (s, 1H), 4.82 (s, 1H), 6.54 (d, J = 8.4 Hz, 1H), 6.58 (d, J = 8.4 Hz, 1H), 7.05 (m, 1H), 7.29 (t, J = 7.8 Hz, 2H), 7.51 (d, J = 8.7 Hz, 2H), 9.14 (s, 1H), 9.24 (br s, 1H), 13.90 (br s, 1H) |
| I-11 | Chiral | 0.10-0.22 (m, 2H), 0.44-0.58 (m, 2H), 0.89 (m, 1H), 1.45 (d, J = 10.8 Hz, 1H), 1.75-3.40 (m, 10H), 4.78 (s, 1H), 4.83 (s, 1H), 6.53 (d, J = 8.1 Hz, 1H), 6.58 (d, J = 8.1 Hz, 1H), 7.13 (t, J = 8.7 Hz, 2H), 7.48-7.56 (m, 2H), 9.17 (s, 1H), 9.27 (br s, 1H), 13.90 (br s, 1H) |
| I-12 | Chiral | 0.10-0.18 (m, 2H), 0.52-0.60 (m, 2H), 0.80-0.98 (m, 2H), 0.98-3.21 (m, 26H), 4.41 (br, 1H), 4.70 (d, J = 12.3 Hz, 1H), 6.55 (d, J = 8.1 Hz, 1H), 6.65 (d, J = 8.1 Hz, 1H) |
| I-13 | Chiral | 0.10-0.25 (m, 2H), 0.50-0.60 (m, 2H), 0.87 (m, 1H), 1.58 (d, J = 111.7 Hz, 1H), 2.05-2.50 (m, 6H), 2.55-2.90 (m, 5H), 3.00-3.30 (m, 2H), 4.42 (s, 1H), 4.81-4.87 (m, 2H), 5.55 (br s, 1H), 6.60 (d, J = 8.1 Hz, 1H), 6.72 (d, J = 8.1 Hz, 1H), 7.20-7.40 (m, 5H) |
| I-14 | Chiral | 0.10-0.22 (m, 2H), 0.45-0.60 (m, 2H), 0.90 (m, 1H), 1.45 (d, J = 10.8 Hz, 1H), 2.10-3.40 (m, 10H), 3.78 (s, 3H), 4.96 (s, 1H), 6.36 (br s, 1H), 6.59 (d, J = 8.1 Hz, 1H), 6.73 (d, J = 8.1 Hz, 1H), 6.84 (d, J = 9.0 Hz, 2H), 6.98 (br s, 1H), 7.29 (d, J = 9.0 Hz, 2H), 14.00 (br s, 1H) |

TABLE 11
| Compound No. | Chemical structure | NMR (1H-NMR (d6-DMSO) δ) |
|---|---|---|
| I-15 | 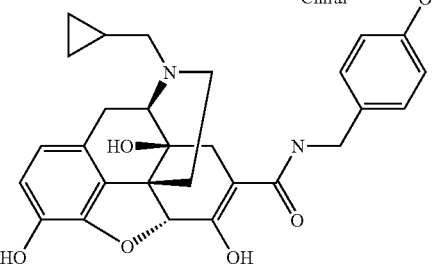 | 0.05-0.20 (m, 2H), 0.45-0.60 (m, 2H), 0.88 (m, 1H), 1.45 (d, J = 10.8 Hz, 1H), 2.00-3.35 (m, 10H), 3.78 (s, 3H), 4.34 (d, J = 5.1 Hz, 2H), 4.91 (s, 1H), 5.61 (br s, 1H), 6.55 (d, J = 8.1 Hz, 1H), 6.71 (d, J = 8.1 Hz, 1H), 6.85 (d, J = 8.4 Hz, 2H), 7.19 (d, J = 8.4 Hz, 2H), 14.13 (br s, 1H) |
| I-16 | 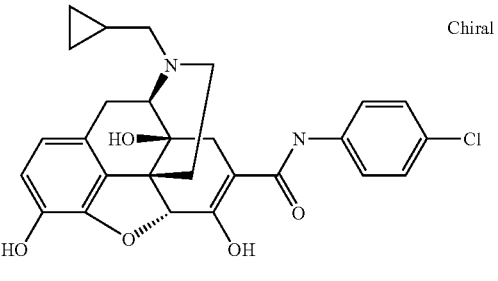 | 0.10-0.25 (m, 2H), 0.40-0.60 (m, 2H), 0.90 (m, 1H), 1.45 (d, J = 10.8 Hz, 1H), 1.70-3.40 (m, 10H), 4.77 (s, 1H), 4.84 (s, 1H), 6.53 (d, J = 8.1 Hz, 1H), 6.58 (d, J = 8.1 Hz, 1H), 7.30-7.38 (m, 2H), 7.53-7.60 (m, 2H), 9.17 (s, 1H), 9.28 (br s, 1H), 13.80 (br s, 1H) |
| I-17 | 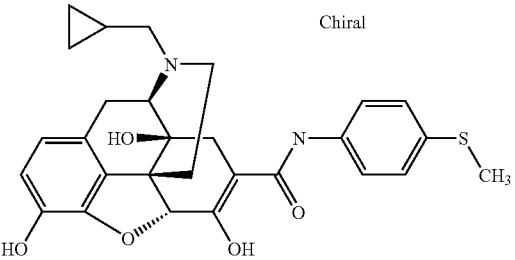 | 0.10-0.25 (m, 2H), 0.40-0.60 (m, 2H), 0.89 (m, 1H), 1.45 (d, J = 10.8 Hz, 1H), 1.70-3.40 (m, 13H), 4.77 (s, 1H), 4.82 (s, 1H), 6.53 (d, J = 8.1 Hz, 1H), 6.58 (d, J = 8.1 Hz, 1H), 7.20 (d, J = 8.7 Hz, 2H), 7.48 (d, J = 8.7 Hz, 2H), 9.17 (s, 1H), 9.27 (br s, 1H), 13.90 (br s, 1H) |
| I-18 | 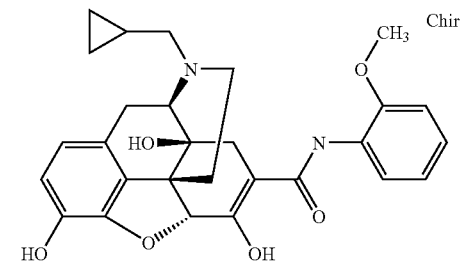 | 0.10-0.25 (m, 2H), 0.40-0.60 (m, 2H), 0.89 (m, 1H), 1.45 (d, J = 10.8 Hz, 1H), 1.65-3.40 (m, 10H), 3.80 (s, 3H), 4.81 (br s, 2H), 6.52 (d, J = 8.1 Hz, 1H), 6.58 (d, J = 8.1 Hz, 1H), 6.87 (m, 1H), 6.98-7.10 (m, 2H), 7.82 (m, 1H), 9.19 (s, 1H), 9.70 (br s, 1H), 12.90 (br s, 1H) |
| I-19 | 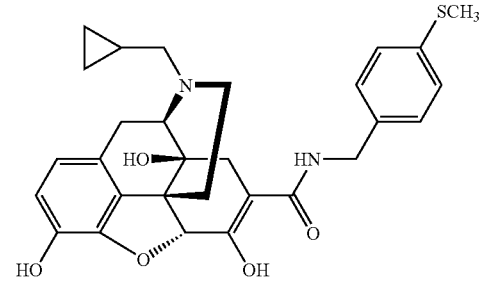 | |

TABLE 11-continued

| Compound No. | Chemical structure | NMR (1H-NMR (d6-DMSO) δ) |
| --- | --- | --- |
| I-20 | Chiral | 0.12-0.14 (d, J = 4.5 Hz, 2H), 0.46-0.52 (t, J = 8.3 Hz, 2H), 0.71-0.85 (m, 4H), 0.98-1.06 (dd, J = 6.8, 17.3 Hz, 4H), 1.35-1.45 (m, 4H), 1.82-1.92 (m, 2H), 2.44-2.61 (m), 3.04 (d, J = 18.9 Hz, 1H), 3.19-3.24 (m, 1H), 3.71-3.82 (m, 1H), 4.71-4.76 (m, 2H), 6.50-6.57 (dd, J = 8.1, 14.4 Hz, 2H), 7.31-7.38 (m, 1H), 9.15 (br s, 1H), 14.52 (br s, 1H) |
| I-21 | Chiral | 0.12-0.14 (d, J = 4.2 Hz, 2H), 0.49 (t, J = 8.1 Hz, 2H), 0.69-0.86 (m, 6H), 1.32-1.47 (m, 5H), 1.88 (d, J = 15.3 Hz, 1H), 2.06-2.30 (m, 4H), 2.45-2.61 (m), 3.04 (d, J = 18.0 Hz, 1H), 3.19-3.24 (m, 1H), 4.71-4.75 (m, 2H), 6.05-6.58 (dd, J = 8.8, 14.4 Hz, 2H), 7.24 (d, J = 7.8 Hz, 1H), 9.15 (br s, 1H), 14.55 (br s, 1H) |

TABLE 12

| Compound No. | Chemical structure | NMR (1H-NMR (d6-DMSO) δ) |
| --- | --- | --- |
| I-22 | Chiral | 0.12-0.14 (d, J = 4.5 Hz, 2H), 0.49 (t, J = 8.1 Hz, 2H), 0.85 (m, 1H), 1.06 (m, 1H), 1.16-1.28 (m, 4H), 1.39-1.43 (d, J = 11.4 Hz, 1H), 1.54-1.70 (m, 6H), 1.84-1.89 (d, J = 15.6 Hz, 1H), 2.08-2.60 (m, 6H), 3.00-3.07 (d, J = 18.6 Hz, 1H), 3.17-3.24 (m, 1H), 3.60 (br s, 1H), 4.71-4.76 (m, 2H), 6.49-6.57 (dd, J = 8.1, 14.7 Hz, 2H), 7.37 (d, J = 9.0 Hz, 1H), 9.13 (br s, 1H), 14.47 (br s, 1H) |
| I-23 | Chiral | 0.12-0.14 (d, J = 4.5 Hz, 2H), 0.49 (t, J = 7.8 Hz, 2H), 0.83-0.92 (m, 4H), 1.19-1.70 (m, 9H), 1.83-1.93 (m, 1H), 2.06-2.61 (m, 9H), 3.01-3.07 (d, J = 18.3 Hz, 1H), 3.18-3.20 (d, J = 4.2 Hz, 1H), 3.67 (m, 1H), 4.71-4.76 (m, 2H), 6.52-6.55 (dd, J = 8.1, 14.4 Hz, 2H), 9.13 (br s, 1H), 14.48 (br s, 1H) |
| I-24 | Chiral | 0.12-0.14 (d, J = 4.5 Hz, 2H), 0.49 (t, J = 8.0 Hz, 2H), 0.83-0.87 (m, 1H), 1.34-1.55 (m, 12H), 1.84-1.89 (d, J = 15.6 Hz, 1H), 2.09-2.60 (m, 9H), 3.00-3.07 (d, J = 18.3 Hz, 1H), 3.17-3.19 (d, J = 6.0 Hz, 1H), 3.78-3.81 (m, 1H), 4.71-4.76 (m, 2H), 6.49-6.57 (dd, J = 8.1, 14.7 Hz, 2H), 7.39 (d, J = 8.1 Hz, 1H), 9.13 (br s, 1H), 14.46 (br s, 1H) |

TABLE 12-continued

| Compound No. | Chemical structure | NMR (1H-NMR (d6-DMSO) δ) |
|---|---|---|
| I-25 | Chiral | 0.13-0.14 (d, J = 4.5 Hz, 2H), 0.49 (t, J = 7.8 Hz, 2H), 0.85 (m, 1H), 1.39-1.43 (d, J = 11.1 Hz, 1H), 1.56-1.64 (m, 2H), 1.85-2.32 (m, 12H), 2.43-2.61 (m), 3.01-3.07 (d, J = 18.3 Hz, 1H), 3.18-3.20 (d, J = 6.0 Hz, 1H), 4.16-4.27 (m, 1H), 4.72-4.73 (m, 2H), 6.50-6.57 (dd; J = 8.1, 18.9 Hz, 2H), 7.77 (d, J = 7.5 Hz, 1H), 9.12 (br s, 1H), 14.41 (br s, 1H) |
| I-26 | Chiral | 0.16-0.19 (m, 2H), 0.48-0.57 (m, 2H), 0.88 (m, 1H), 1.46 (d, J = 11.2 Hz, 1H), 1.92 (d, J = 15.6 Hz, 1H), 2.04-2.66 (m, 6H), 3.08 (d, J = 18.8 Hz, 1H), 3.17-3.40 (m, 6H), 3.24 (s, 3H), 4.77 (s, 1H), 6.55 (d, J = 8.0 Hz, 1H), 6.62 (d, J = 8.0 Hz, 1H), 7.76 (br t, 1H), 9.15 (s, 1H), 14.33 (s, 1H). |
| I-27 | Chiral | 0.16-0.19 (m, 2H), 0.48-0.57 (m, 2H), 0.90 (m, 1H), 1.10 (t, J = 6.8 Hz, 3H), 1.46 (d, J = 11.2 Hz, 1H), 1.92 (d, J = 15.6 Hz, 1H), 2.04-2.66 (m, 6H), 3.08 (d, J = 18.8 Hz, 1H), 3.17-3.46 (m, 8H),, 4.77 (s, 1H), 6.55 (d, J = 8.4 Hz, 1H), 6.62 (d, J = 8.0 Hz, 1H), 7.77 (br, 1H), 9.15 (s, 1H), 14.32 (s, 1H). |
| I-28 | Chiral | 0.16-0.17 (m, 2H), 0.50-0.63 (m, 2H), 0.89 (m, 1H), 1.46 (d, J = 12.0 Hz, 1H), 1.92 (d, J = 15.2 Hz, 1H), 2.06 (s, 3H), 2.06-2.70 (m, 6H), 3.08 (d, J = 18.4 Hz, 1H), 3.20-3.32 (m, 6H), 4.77 (s, 1H), 6.55 (d, J = 8.0 Hz, 1H), 6.62 (d, J = 8.0 Hz, 1H), 7.76 (br s, 1H), 9.16 (s, 1H), 14.31 (s, 1H). |

TABLE 13

| Compound No. | Chemical structure | NMR (1H-NMR (d6-DMSO) δ) |
|---|---|---|
| I-29 | Chiral | 0.17-0.18 (m, 2H), 0.51-0.57 (m, 2H), 0.90 (m, 1H), 1.46 (d, J = 11.6 Hz, 1H), 1.93 (d, J = 16.0 Hz. 1H), 2.11-2.78 (m, 6H), 3.08 (d, J = 18.4 Hz, 1H), 3.21 (d, J = 6.0 Hz, 1H), 3.27-3.32 (m, 5H), 4.77 (s, 1H), 6.56 (d, J = 8.0 Hz, 1H), 6.61 (d, J = 8.0 Hz, 1H), 7.19-7.32 (m, 5H), 7.86 (br s, 1H), 9.16 (s, 1H), 14.38 (s, 1H). |

TABLE 13-continued
| Compound No. | Chemical structure | NMR (1H-NMR (d6-DMSO) δ) |
|---|---|---|
| I-30 | 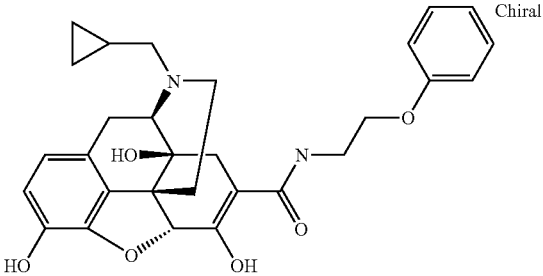 | 0.16-0.19 (m, 2H), 0.48-0.57 (m, 2H), 0.88 (m, 1H), 1.46 (d, J = 11.2 Hz, 1H), 1.94 (d, J = 15.6 Hz, 1H), 2.11-2.71 (m, 6H), 3.08 (d, J = 18.8 Hz, 1H), 3.49-3.51 (m, 2H), 3.96-4.4.05 (m, 2H), 4.79 (s, 1H), 6.56 (d, J = 8.0 Hz, 1H), 6.63 (d, J = 8.0 Hz, 1H), 6.94-6.97 (m, 3H), 7.27-7.34 (m, 2H), 7.94 (br, 1H), 9.17 (s, 1H), 14.28 (s, 1H). |
| I-31 | 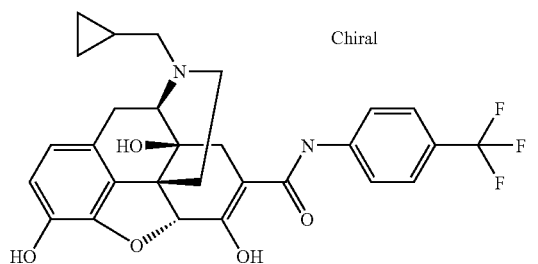 | 0.10-0.28 (m, 2H), 0.44-0.65 (m, 2H), 0.94 (m, 1H), 1.50 (d, J = 10.8 Hz, 1H), 1.70-3.40 (m, 10H), 4.72 (br s, 1H), 4.86 (s, 1H), 6.53 (d, J = 8.1 Hz, 1H), 6.58 (d, J = 8.1 Hz, 1H), 7.54-7.80 (m, 4H), 9.16 (s, 1H), 9.32 (s, 1H), 13.90 (br s, 1H) |
| I-32 | 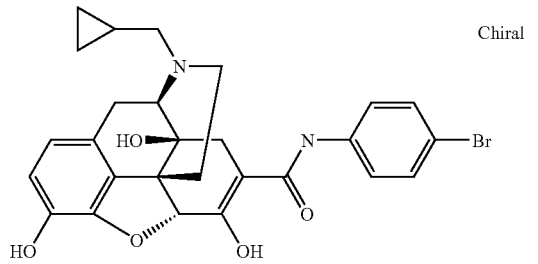 | 0.10-0.25 (m, 2H), 0.42-0.62 (m, 2H), 0.90 (m, 1H), 1.45 (d, J = 10.8 Hz, 1H), 1.70-3.40 (m, 10H), 4.75 (br s, 1H), 4.84 (s, 1H), 6.53 (d, J = 8.1 Hz, 1H), 6.58 (d, J = 8.1 Hz, 1H), 7.41-7.54 (m, 4H), 9.17 (s, 1H), 9.28 (s, 1H), 13.85 (br s, 1H) |
| I-33 | 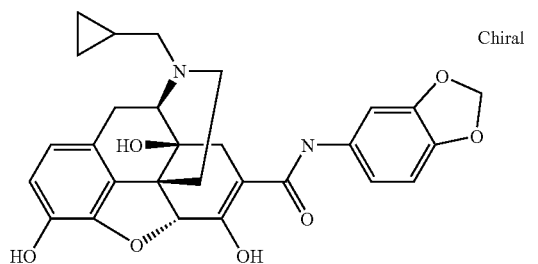 | 0.10-0.25 (m, 2H), 0.40-0.60 (m, 2H), 0.90 (m, 1H), 1.45 (d, J = 10.8 Hz, 1H), 1.70-3.40 (m, 10H), 4.77 (s, 1H), 4.81 (s, 1H), 5.98 (s, 2H), 6.53 (d, J = 8.1 Hz, 1H), 6.58 (d, J = 8.1 Hz, 1H), 6.82-6.95 (m, 2H), 7.15 (d, J = 1.8 Hz, 1H), 9.16 (s, 1H), 9.26 (s, 1H), 13.98 (br s, 1H) |
| I-34 | 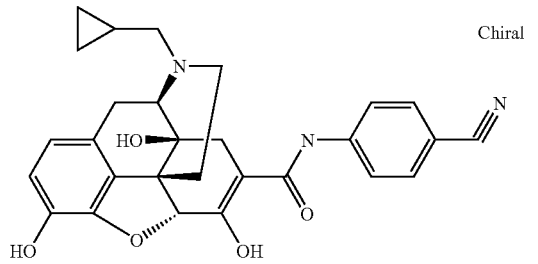 | 0.20-0.40 (m, 2H), 0.45-0.65 (m, 2H), 0.96 (m, 1H), 1.50 (m, 1H), 1.70-3.40 (m, 10H), 4.65 (br s, 1H), 4.88 (s, 1H), 6.53 (d, J = 8.1 Hz, 1H), 6.59 (d, J = 8.1 Hz, 1H), 7.60-7.80 (m, 4H), 9.17 (s, 1H), 9.30 (s, 1H), 14.00 (br s, 1H) |

TABLE 13-continued

| Compound No. | Chemical structure | NMR (1H-NMR (d6-DMSO) δ) |
|---|---|---|
| I-35 | 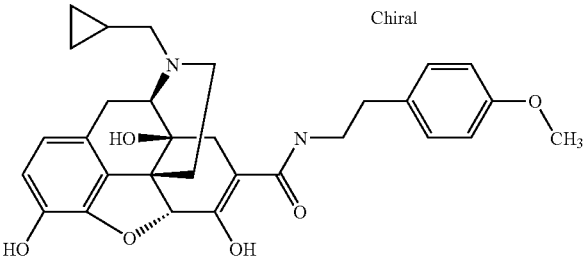 Chiral | 0.10-0.20 (m, 2H), 0.50-0.62 (m, 2H), 0.88 (m, 1H), 1.65 (d, J = 10.8 Hz, 1H), 2.00-3.60 (m, 14H), 3.78 (s, 3H), 4.93 (s, 1H), 5.46 (br s, 1H), 6.57 (d, J = 8.1 Hz, 1H), 6.72 (d, J = 8.1 Hz, 1H), 6.82 (d, J = 8.4 Hz, 2H), 7.06 (d, J = 8.4 Hz, 2H), 14.17 (br s, 1H) |

TABLE 14

| Compound No. | Chemical structure | NMR (1H-NMR (d6-DMSO) δ) |
|---|---|---|
| I-36 | 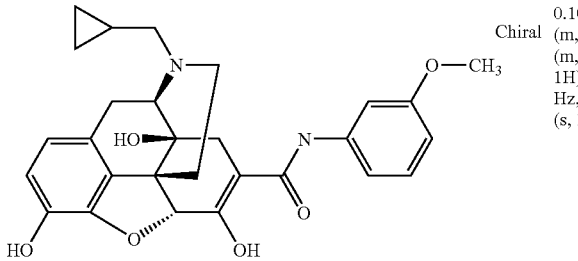 Chiral | 0.10-0.25 (m, 2H), 0.43-0.63 (m, 2H), 0.88 (m, 1H), 1.45 (d, J = 10.8 Hz, 1H), 1.70-3.40 (m, 10H), 3.71 (s, 3H), 4.77 (s, 1H), 4.82 (s, 1H), 6.53 (d, J = 8.1 Hz, 1H), 6.58 (d, J = 8.1 Hz, 1H), 6.64 (m, 1H), 7.00-7.25 (m, 3H), 9.17 (s, 1H), 9.27 (s, 1H), 13.90 (br s, 1H) |
| I-37 | 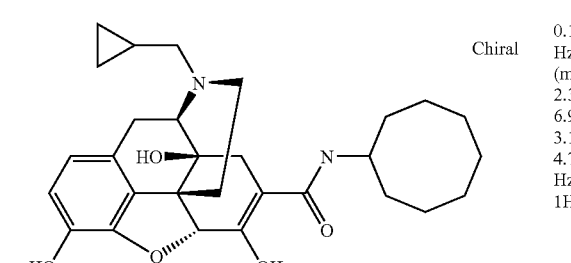 Chiral | 0.12-0.14 (d, J = 4.5 Hz, 2H), 0.49 (t, J = 8.1 Hz, 2H), 0.85 (m, 1H), 1.06 (m, 1H), 1.39-1.62 (m, 18H), 1.84-1.89 (d, J = 15.6 Hz, 1H), 2.08-2.34 (m, 5H), 2.43-2.54 (m), 2.58-2.60 (d, J = 6.9 Hz, 1H), 3.00-3.07 (d, J = 18.6 Hz, 1H), 3.18-3.20 (d, J = 6 Hz, 1H), 3.87 (br s, 1H), 4.71-4.76 (m, 2H), 6.49-6.57 (dd, J = 8.1, 14.7 Hz, 2H), 7.38 (d, J = 7.8 Hz, 1H), 9.13 (br s, 1H), 14.47 (br s, 1H) |
| I-38 | 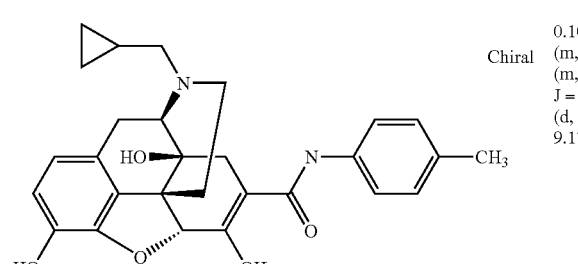 Chiral | 0.10-0.25 (m, 2H), 0.40-0.60 (m, 2H), 0.89 (m, 1H), 1.45 (d, J = 10.8 Hz, 1H), 1.70-3.40 (m, 13H), 4.78 (s, 1H), 4.82 (s, 1H), 6.53 (d, J = 8.1 Hz, 1H), 6.58 (d, J = 8.1 Hz, 1H), 7.09 (d, J = 8.4 Hz, 2H), 7.39 (d, J = 8.4 Hz, 2H), 9.17 (s, 1H), 9.27 (s, 1H), 14.00 (br s, 1H) |
| I-39 | 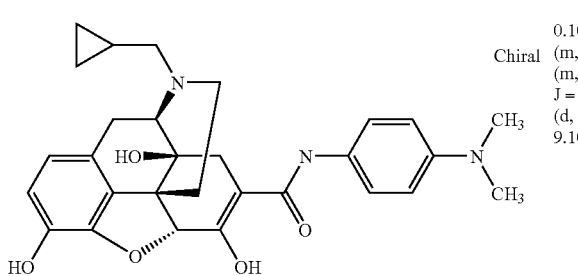 Chiral | 0.10-0.20 (m, 2H), 0.40-0.60 (m, 2H), 0.87 (m, 1H), 1.45 (d, J =10.8 Hz, 1H), 1.70-3.40 (m, 16H), 4.76 (s, 1H), 4.80 (s, 1H), 6.53 (d, J = 8.1 Hz, 1H), 6.57 (d, J = 8.1 Hz, 1H), 6.65 (d, J = 9.0 Hz, 2H), 7.29 (d, J = 9.0 Hz, 2H), 9.10 (br s, 2H), 14.20 (br s, 1H) |

TABLE 14-continued

| Compound No. | Chemical structure | NMR (1H-NMR (d6-DMSO) δ) |
|---|---|---|
| I-40 | 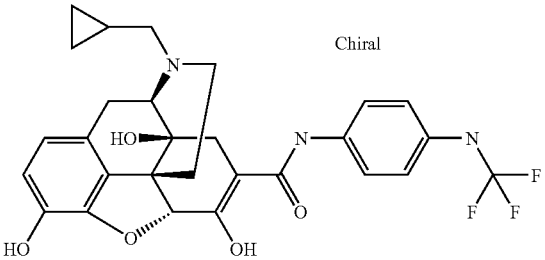 | 0.10-0.30 (m, 2H), 0.45-0.65 (m, 2H), 0.90 (m, 1H), 1.48 (d, J = 10.8 Hz, 1H), 1.70-3.40 (m, 10H), 4.77 (s, 1H), 4.85 (s, 1H), 6.54 (d, J = 8.1 Hz, 1H), 6.58 (d, J = 8.1 Hz, 1H), 7.25-7.35 (m, 2H), 7.64 (d, J = 9.0 Hz, 2H), 9.18 (s, 1H), 9.29 (s, 1H), 13.90 (br s, |

TABLE 15

| Compound No. | Chemical structure | NMR (1H-NMR (d6-DMSO) δ) |
|---|---|---|
| I-41 | 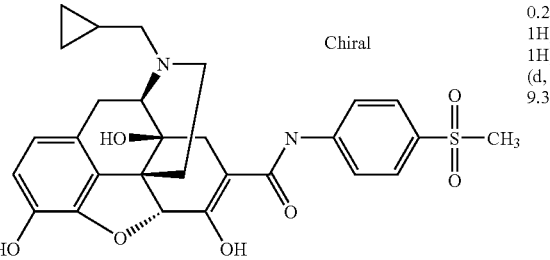 | 0.20-0.40 (m, 2H), 0.45-0.70 (m, 2H), 0.96 (m, 1H), 1.50 (m, 1H), 1.70-3.40 (m, 13H), 4.67 (br s, 1H), 4.88 (s, 1H), 6.53 (d, J = 8.1 Hz, 1H), 6.59 (d, J = 8.1 Hz, 1H), 7.76 (s, 4H), 9.18 (s, 1H), 9.31 (s, 1H), 14.00 (br s, 1H) |
| I-42 | 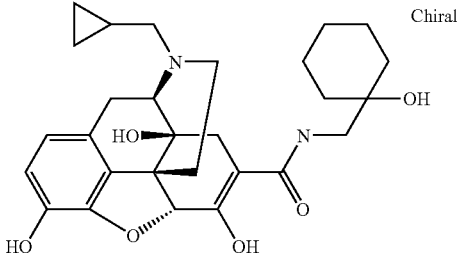 | 0.18 (br, s, 2H), 0.42-0.63 (m, 3H), 0.80-0.97 (m, 2H), 1.20-3.43 (m, 24H), 4.92 (s, 1H), 5.89 (br, s, 1H), 6.58 (d, J = 8.1 Hz, 1H), 6.71 (d, J = 7.8 Hz, 1H), 14.13 (br, s, 1H) |
| I-43 | 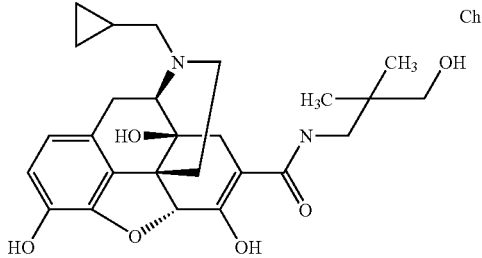 | 0.12-0.19 (m, 2H), 0.41-0.58 (m, 2H), 0.74 (d, J = 3.3 Hz, 6H), 1.43 (m, 1H), 1.88-3.41 (m, 16H), 4.56 (br, s, 1H), 4.65-4.80 (m, 2H), 6.50-6.62 (m, 2H), 7.51 (br, s, 1H), 9.13 (s, 1H), 14.23 (br, s, 1H) |
| I-44 | 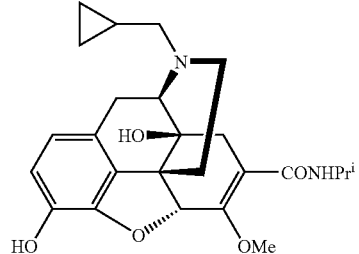 | 0.10-0.15 (m, 2H), 0.50-0.70 (m, 2H), 0.85 (m, 1H), 1.12 (d, J = 0.9 Hz, 3H), 1.14 (d, J = 0.9 Hz, 3H), 1.66 (d, J = 11.4 Hz, 1H), 2.06-2.80 (m, 8H), 3.00-3.30 (m, 2H), 3.92 (s, 3H), 4.05 (m, 1H), 4.80 (br s, 1H), 5.26 (br s, 1H), 6.56 (d, J = 8.1 Hz, 1H), 6.69 (d, J = 8.1 Hz, 1H), 7.36 (d, J = 7.8 Hz, 1H) |

TABLE 15-continued
| Compound No. | Chemical structure | NMR (1H-NMR (d6-DMSO) δ) |
|---|---|---|
| I-45 | 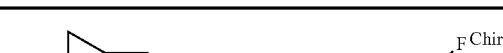 | |
TABLE 16
| Compound No. | Chemical structure | NMR (1H-NMR (d6-DMSO) δ) |
|---|---|---|
| I-46 | 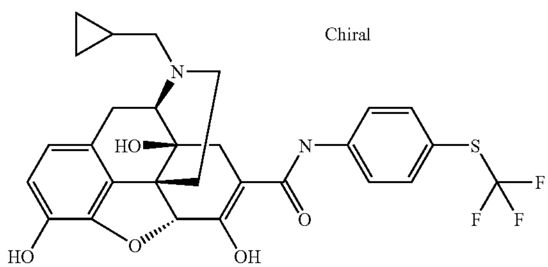 | 0.15-0.35 (m, 2H), 0.45-0.70 (m, 2H), 0.92 (m, 1H), 1.50 (d, J = 10.8 Hz, 1H), 1.70-3.40 (m, 10H), 4.72 (br s, 1H), 4.86 (s, 1H), 6.53 (d, J = 8.1 Hz, 1H), 6.58 (d, J = 8.1 Hz, 1H), 7.54-7.74 (m, 4H), 9.16 (s, 1H), 9.27 (s, 1H), 14.00 (br s, 1H) |
| I-47 | 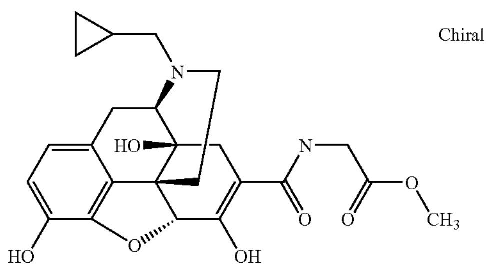 | 0.10-0.20 (m, 2H), 0.40-0.60 (m, 2H), 0.86 (m, 1H), 1.42 (d, J = 10.8 Hz, 1H), 1.70-3.40 (m, 10H), 3.61 (s, 3H), 3.82 (d, J = 5.7 Hz, 2H), 4.77 (s, 2H), 6.53 (d, J = 8.1 Hz, 1H), 6.58 (d, J = 8.1 Hz, 1H), 8.21 (br t, J = 5.7 Hz, 1H), 9.17 (s, 1H), 13.87 (br s, 1H) |
| I-48 | 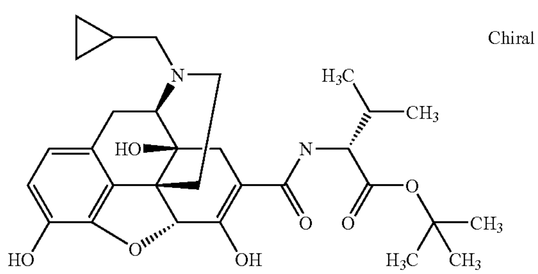 | 0.10-0.20 (m, 2H), 0.50-0.65 (m, 2H), 0.89 (m, 1H), 0.90 (d, J = 4.5 Hz, 3H), 0.94 (d, J = 4.5 Hz, 3H), 1.45 (s, 9H), 1.66 (d, J = 10.8 Hz, 1H), 2.10-3.40 (m, 11H), 4.43 (dd, J = 4.5, 8.1 Hz, 1H), 4.94 (s, 1H), 6.00 (d, J = 8.1 Hz, 1H), 6.58 (d, J = 8.1 Hz, 1H), 6.71 (d, J = 8.1 Hz, 1H), 13.99 (br s, 1H) |
| I-49 | 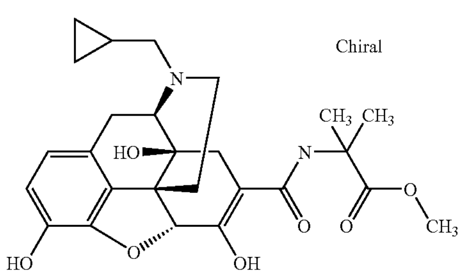 | 0.10-0.30 (m, 2H), 0.45-0.70 (m, 2H), 0.90 (m, 1H), 1.34 (s, 3H), 1.38 (s, 3H), 1.50-3.40 (m, 11H), 3.56 (s, 3H), 4.77 (br s, 2H), 6.58 (br s, 2H), 7.69 (br s, 1H), 9.20 (br s, 1H), 13.76 (br s, 1H) |

TABLE 16-continued

| Compound No. | Chemical structure | NMR (1H-NMR (d6-DMSO) δ) |
|---|---|---|
| I-50 | (Chiral) | 0.10-0.20 (m, 2H), 0.40-0.60 (m, 2H), 0.88 (m, 1H), 1.44 (d, J = 11.7 Hz, 1H), 1.90-3.40 (m, 10H), 3.68 (d, J = 4.5 Hz, 2H), 4.77 (s, 1H), 6.52 (d, J = 8.1 Hz, 1H), 6.58 (d, J = 8.1 Hz, 1H), 8.00 (br t, J = 4.5 hz, 1H), 9.18 (br s, 1H), 14.00 (br s, 1H) |

TABLE 17

| Compound No. | Chemical structure | NMR (1H-NMR (d6-DMSO) δ) |
|---|---|---|
| I-51 | (Chiral) | 0.30-0.50 (m, 2H), 0.55-0.75 (m, 2H), 0.89 (d, J = 3.3 Hz, 3H), 0.91 (d, J = 3.3 Hz, 3H), 1.04 (m, 1H), 1.65 (d, J = 13.5 Hz, 1H), 2.00-3.92 (m, 11H), 4.10 (t, J = 6.6 Hz, 1H), 4.95 (s, 1H), 6.64 (d, J = 8.1 Hz, 1H), 6.69 (d, J = 8.1 Hz, 1H), 7.53 (d, J = 7.8 Hz, 1H), 9.43 (s, 1H), 13.66 (br s, 1H) |
| I-52 | (Chiral) | 0.10-0.25 (m, 2H), 0.45-0.60 (m, 2H), 0.89 (m, 1H), 1.34 (s, 3H), 1.36 (s, 3H), 1.46 (d, J = 9.6 Hz, 1H), 1.90-3.40 (m, 10H), 4.75 (s, 1H), 6.54 (d, J = 8.1 Hz, 1H), 6.59 (d, J = 8.1 Hz, 1H), 7.68 (s, 1H), 9.21 (br s, 1H), 14.11 (br s, 1H) |
| I-53 | (Chiral) | 0.13-0.14 (m, 2H), 0.47-0.49 (m, 2H), 0.88 (m, 1H), 1.30 (m, 1H), 1.63-2.10 (m, 6H), 2.30-2.70 (m, 4H), 2.96-3.58 (m, 6H), 4.06-4.23 (m, 3H), 5.04 (s, 1H), 5.23 (br, 1H), 6.54 (d, J = 8.0 Hz, 1H), 6.58 (d, J = 8.0 Hz, 1H), 8.08 (br, 1H), 9.23 (br, 1H). |
| I-54 | (Chiral) | 0.13-0.14 (m, 2H), 0.47-0.49 (m, 2H), 0.88 (m, 1H), 1.30 (d, J = 12.0 Hz, 1H), 1.63-2.12 (m, 6H), 2.28-2.70 (m, 4H), 2.97-3.53 (m, 6H), 4.06-4.23 (m, 3H), 5.06 (s, 1H), 5.22 (br, 1H), 6.54 (d, J = 8.0 Hz, 1H), 6.58 (d, J = 8.0 Hz, 1H), 8.13 (d, J = 6.4 Hz, 1H), 8.32 (s, 1H), 9.23 (br, 1H), 10.97 (s, 1H). |

TABLE 18

| Compound No. | Chemical structure | NMR (1H-NMR (d6-DMSO) δ) |
|---|---|---|
| I-55 | 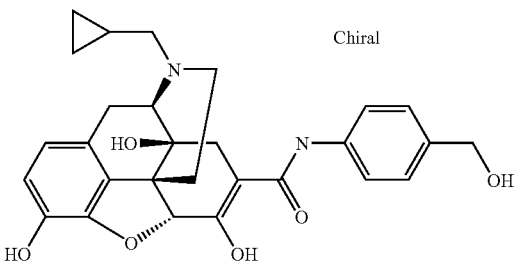 Chiral | 0.10-0.25 (m, 2H), 0.40-0.60 (m, 2H), 0.90 (m, 1H), 1.45 (d, J = 10.8 Hz, 1H), 1.70-3.40 (m, 10H), 4.42 (s, 2H), 4.77 (s, 1H), 5.12 (s, 1H), 6.55 (d, J = 8.1 Hz, 1H), 6.59 (d, J = 8.1 Hz, 1H), 7.23 (d, J = 8.4 Hz, 2H), 7.46 (d, J = 8.4 Hz, 2H), 9.20 (s, 1H), 9.28 (s, 1H), 14.00 (br s, 1H) |
| I-56 | 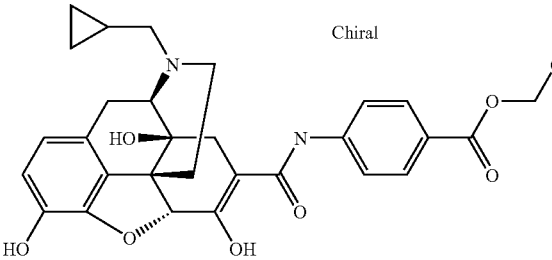 Chiral | 0.10-0.40 (m, 2H), 0.45-0.70 (m, 2H), 0.92 (m, 1H), 1.29 (t, J = 7.2 Hz, 3H), 1.49 (d, J = 9.0 Hz, 1H), 1.70-3.40 (m, 10H), 4.26 (q, J = 7.2 Hz, 2H), 4.72 (br s, 1H), 4.86 (s, 1H), 6.54 (d, J = 8.1 Hz, 1H), 6.59 (d, J = 8.1 Hz, 1H), 7.65 (d, J = 9.0 Hz, 2H), 7.90 (d, J = 9.0 Hz, 2H), 9.18 (s, 1H), 9.29 (s, 1H) |
| I-57 | 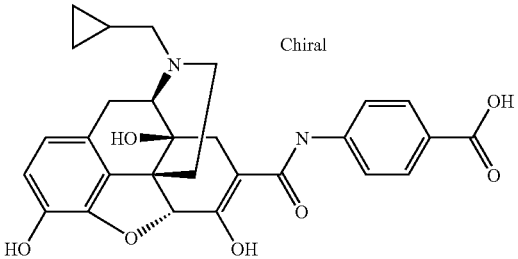 Chiral | 0.25-0.40 (m, 2H), 0.50-0.70 (m, 2H), 1.00 (m, 1H), 1.56 (d, J = 10.8 Hz, 1H), 1.70-3.40 (m, 10H), 4.87 (s, 1H), 4.92 (s, 1H), 6.59 (d, J = 8.1 Hz, 1H), 6.64 (d, J = 8.1 Hz, 1H), 7.68 (d, J = 8.4 Hz, 2H), 7.86 (d, J = 8.4 Hz, 2H), 9.33 (br s, 2H) |
| I-58 | 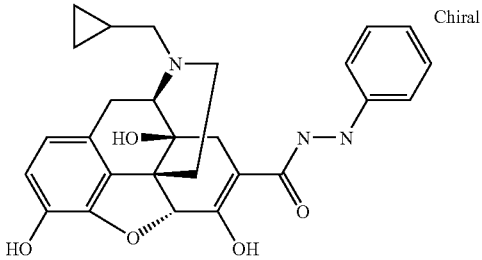 Chiral | 0.08-0.20 (m, 2H), 0.43-0.57 (m, 2H), 0.88 (m, 1H), 1.22-3.40 (m, 11H), 4.76 (s, 1H), 4.84 (s, 1H), 6.54 (d, J = 8.1 Hz, 1H), 6.58 (d, J = 8.1 Hz, 1H), 6.62-6.81 (m, 3H), 7.06-7.16 (m, 2H), 7.73 (s, 1H), 9.16 (s, 1H), 9.61 (s, 1H), 13.80 (br s, 1H) |
| I-59 | 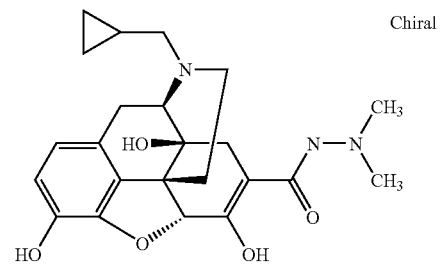 Chiral | 0.08-0.10 (m, 2H), 0.38-0.58 (m, 2H), 0.86 (m, 1H), 1.22-3.40 (m, 17H), 4.71 (s, 2H), 6.51 (d, J = 8.1 Hz, 2H), 6.56 (d, J = 8.1 Hz, 1H), 8.58 (s, 1H), 9.15 (s, 1H), 14.30 (br s, 1H) |

TABLE 19

| Compound No. | Chemical structure | NMR (1H-NMR (d6-DMSO) δ) |
| --- | --- | --- |
| I-60 | Chiral | 0.10-0.20 (m, 2H), 0.45-0.55 (m, 2H), 0.88 (m, 1H), 1.81 (t, J = 7.2 Hz, 3H), 1.20-3.75 (m, 20H), 4.07 (q, J = 7.2 Hz, 2H), 5.13 (s, 1H), 5.21 (br s, 1H), 6.53 (d, J = 8.4 Hz, 1H), 6.57 (d, J = 8.4 Hz, 1H), 9.21b (br s, 1H) |
| I-61 | Chiral | 0.11-0.39 (m, 2H), 0.53-0.70 (m, 2H), 0.95 (m, 1H), 1.10-1.20 (m, 3H), 1.66-1.73 (m, 1H), 1.82-3.99(m, 24H), 4.90 (s, 1H), 6.32 (br, s, 1H), 6.56 (d, J = 8.4 Hz, 1H), 6.68-6.73 (m, 1H), 14.03 (br, s, 1H) |
| I-62 | Chiral | 0.10-0.18 (m, 2H), 0.42-0.56 (m, 2H), 0.85 (m, 1H), 1.03 (d, J = 6.9 Hz, 3H), 1.41 (m, 1H), 1.88 (d, J = 15.6 Hz, 1H), 2.04-2.31 (m, 4H), 2.42-2.62 (m, 6H), 3.04 (d, J = 18.0 Hz, 1H), 3.17-3.35 (m, 7H), 3.87 (m, 1H), 4.64 (t, J = 5.7 Hz, 1H), 4.72 (s, 1H), 6.50-6.57 (m, 2H), 7.27 (d, J = 8.1 Hz, 1H), 9.13 (s, 1H), 14.45 (s, 1H) |
| I-63 | Chiral | 0.13 (d, J = 4.2 Hz, 2H), 0.43-0.55 (m, 2H), 0.85 (m, 1H), 0.98 (d, J = 6.9 Hz, 3H), 1.41 (d, J = 10.8 Hz, 1H), 1.89 (d, J = 15.9 Hz, 1H), 2.04-2.32 (m, 4H), 2.43-2.63 (m, 3H), 3.04 (d, J = 18.3 Hz, 1H), 3.19-3.40 (m, 11H), 3.86 (m, 1H), 4.72 (s, 1H), 6.50-6.58 (m, 2H), 7.24 (m, 1H), 9.14 (s, 1H), 14.41 (br, s, 1H) |

TABLE 20

| Compound No. | Chemical structure | NMR (1H-NMR (d6-DMSO) δ) |
| --- | --- | --- |
| I-64 | Chiral | 0.13 (d, J = 4.8 Hz, 2H), 0.43-0.55 (m, 2H), 0.85 (m, 1H), 1.41 (d, J = 12.3 Hz, 1H), 1.92 (d, J = 16.2 Hz, 1H), 2.06-2.32 (m, 4H), 2.43-2.61 (m, 3H), 3.04 (d, J = 18.3 Hz, 1H), 3.20 (d, J = 6.6 Hz, 1H), 3.33-3.44 (m, 4H), 3.82 (m, 1H), 4.59 (t, J = 5.7 Hz, 1H), 4.68 (t, J = 5.7 Hz, 1H), 4.73 (s, 2H), 6.50-6.59 (m, 2H), 7.14 (br, s, 1H), 9.14 (s, 1H), 14.33 (br, s, 1H) |

TABLE 20-continued
| Compound No. | Chemical structure | NMR (1H-NMR (d6-DMSO) δ) |
|---|---|---|
| I-65 | 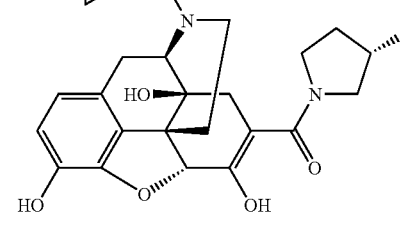 | 0.17-0.18 (m, 2H), 0.51-0.53 (m, 2H), 0.92 (m, 1H), 1.34 (m, 1H), 1.35 (br s, 9H), 1.71-3.49 (m, 14H), 3.95-4.20 (m, 3H), 5.10 (br, 1H), 5.26 (br, 1H), 6.57 (d, J = 8.4 Hz, 1H), 6.61 (d, J = 8.4 Hz, 1H), 7.10 (br, 1H), 8.35 (s, 1H), 9.24 (s, 1H). |
| I-66 | 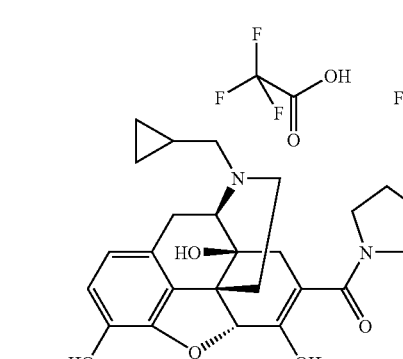 | 0.41 (m, 1H), 0.50 (m, 1H), 0.60 (m, 1H), 0.69 (m, 1H), 1.08 (m, 1H), 1.56 (m, 1H), 1.76-4.29 (m, 17H), 5.19 (s, 1H), 6.66 (d, J = 8.0 Hz, 1H), 6.71 (d, J = 8.0 Hz, 1H), 8.14 (br, 1H), 8.20 (br, 1H), 8.98 (br, 1H). |
| I-67 | 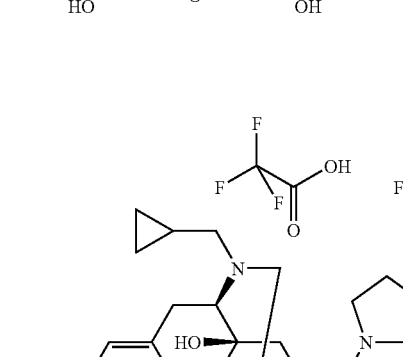 | 0.41 (m, 1H), 0.50 (m, 1H), 0.59 (m, 1H), 0.69 (m, 1H), 1.09 (m, 1H), 1.30-4.29 (m, 18H), 5.19 (s, 1H), 5.75 (br, 1H), 6.66 (d, J = 8.4 Hz, 1H), 6.71 (d, J = 8.4 Hz, 1H), 8.21 (br, 1H), 8.26 (br, 1H), 8.99 (br, 1H). |
TABLE 21
| Compound No. | Chemical structure | NMR (1H-NMR (d6-DMSO) δ) |
|---|---|---|
| I-68 | 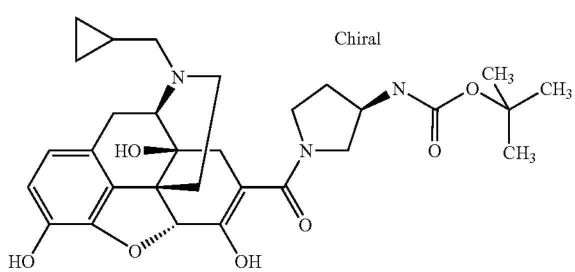 | 0.17-0.18 (m, 2H), 0.51-0.53 (m, 2H), 0.92 (m, 1H), 1.34 (m, 1H), 1.43 (br s, 9H), 1.71-2.03 (m, 5H), 2.18-2.74 (m, 4H), 2.92-3.69 (m, 5H), 3.95-4.20 (m, 2H), 5.07 (s, 1H), 5.26 (br, 1H), 6.57 (d, J = 8.0 Hz, 1H), 6.61 (d, J = 8.0 Hz, 1H), 7.20 (br, 1H), 9.25 (s, 1H). |

TABLE 21-continued

| Compound No. | Chemical structure | NMR (1H-NMR (d6-DMSO) δ) |
|---|---|---|
| I-69 | 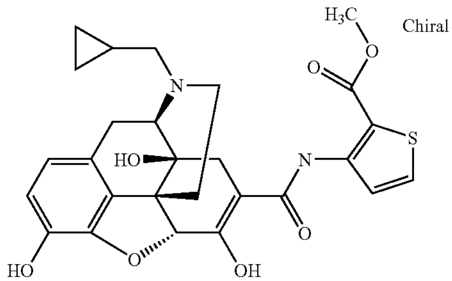 | 0.10-0.26 (m, 2H), 0.42-0.60 (m, 2H), 0.90 (m, 1H), 1.47 (d, J = 10.5 Hz, 1H), 1.90-3.40 (m, 10H), 3.84 (s, 3H), 4.81 (br s, 1H), 6.52 (d, J = 8.1 Hz, 1H), 6.58 (d, J = 8.1 Hz, 1H), 7.80 (br s, 1H), 8.08 (br s, 1H), 9.18 (br s, 1H), 11.60 (br s, 1H) |
| I-70 | 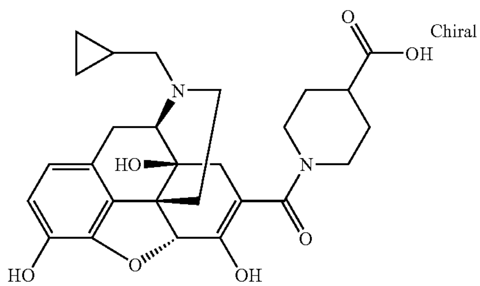 | 0.10-0.20 (m, 2H), 0.40-0.55 (m, 2H), 0.88 (m, 1H), 1.30-4.35 (m, 20H), 5.13 (s, 1H), 6.52 (d, J = 8.1 Hz, 1H), 6.58 (d, J = 8.1 Hz, 1H), 9.20 (br s, 1H) |
| I-71 | 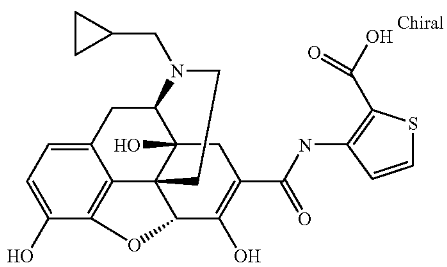 | 0.25-0.45 (m, 2H), 0.45-0.70 (m, 2H), 0.97 (m, 1H), 1.64 (d, J = 11.1 Hz, 1H), 2.00-3.40(m, 10H), 4.07 (br s, 1H), 4.97 (s, 1H), 6.63 (d, J = 8.1 Hz, 1H), 6.68 (d, J = 8.1 Hz, 1H), 7.44 (d, J = 5.4 Hz, 1H), 7.80 (d, J = 5.4 Hz, 1H), 9.44 (br s, 1H), 13.40 (br s, 1H) |
| I-72 | 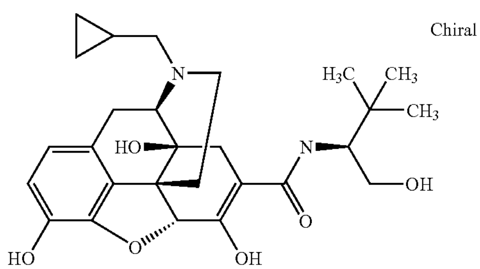 | 0.14 (d, J = 4.5 Hz, 2H), 0.40-0.58 (m, 2H), 0.79-0.92 (m, 13H), 1.25 (br, s, 1H), 1.41 (m, 1H), 1.907 (s, 1H), 2.11-2.64 (m, 8H), 3.03 (m, 1H), 3.21-3.77 (m, 8H), 3.03 (m, 1H) 3.21-3.77 (m, 4H), 4.53 (br, s, 1H), 4.72-4.80 (m, 2H), 6.50-6.58 (m, 2H), 6.95-7.22 (m, 2H), 9.13 (s, 1H), 14.39 (br, s, 1H) |

TABLE 22

| Compound No. | Chemical structure | NMR (1H-NMR (d6-DMSO) δ) |
|---|---|---|
| I-73 | 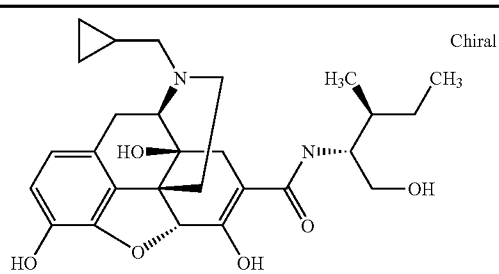 | 0.14 (d, J = 4.5 Hz, 2H), 0.40-0.58 (m, 3H), 0.74-1.01 (m, 10H), 1.25-1.61 (m, 4H), 1.88 (m, 1H), 2.06-2.62 (m, 8H), 3.03 (m, 1H), 3.21 (d, J = 6.0 Hz, 1H), 3.45 (t, J = 5.4 Hz, 1H) 3.68 (m, 1H), 4.57 (m, 1H), 4.72 (s, 1H), 4.76 (br, s, 1H), 6.51-6.58 (m, 2H), 7.14-7.27 (m, 2H), 9.15 (s, 1H), 14.44 (s, 1H) |

TABLE 22-continued

| Compound No. | Chemical structure | NMR (1H-NMR (d6-DMSO) δ) |
|---|---|---|
| I-74 | 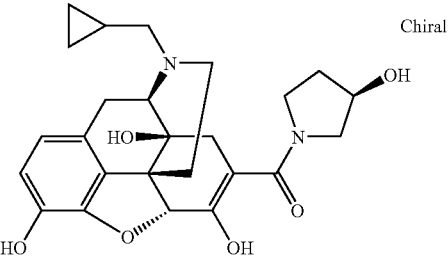 Chiral | 0.16-0.18 (m, 2H), 0.52 (br d, J = 7.6 Hz, 2H), 0.92(m, 1H), 1.35 (d, J = 11.2 Hz, 1H), 1.72-3.48 (m, 16H), 4.11-4.29 (m, 3H), 4.73-5.25 (m, 2H), 6.57 (d, J = 8.0 Hz, 1H), 6.61 (d, J = 8.0 Hz, 1H), 9.23 (s, 1H), 11.16 (s, 1H). |
| I-75 | 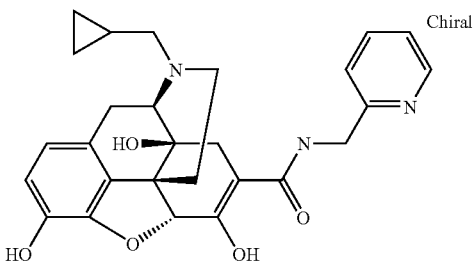 Chiral | 0.14-0.15 (m, 2H), 0.43-0.57 (m, 2H), 0.87 (m, 1H), 1.44 (d, J = 11.2 Hz, 1H), 1.97 (d, J = 15.6 Hz, 1H), 2.08-3.22 (m, 10H), 4.15-4.48 (m, 2H), 4.76 (s, 1H), 6.55 (d, J = 8.0 Hz, 1H), 6.62 (d, J = 8.4 Hz, 1H), 7.23-7.29 (m, 2H), 7.75 (m, 1H), 8.48-8.54 (m, 2H). |
| I-76 | 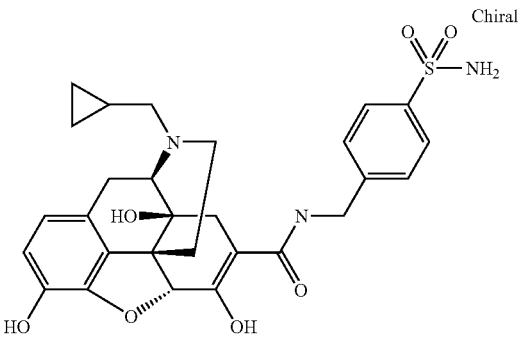 Chiral | 0.16-0.71 (m, 2H), 0.50-0.56 (m, 2H), 0.89 (m, 1H), 1.43 (br d, 1H), 1.97 (d, J = 15.6 Hz, 1H), 2.11-3.21 (m, 10H), 4.30-4.46 (m, 2H), 4.77 (s, 1H), 6.56 (d, J = 8.0 Hz, 1H), 7.29 (s, 2H), 7.44 (d, J = 8.0 Hz, 2H), 7.78 (d, J = 8.0 Hz, 2H), 8.42 (br, 1H), 9.17 (br, 1H), 14.19 (s, 1H). |

TABLE 23

| Compound No. | Chemical structure | NMR (1H-NMR (d6-DMSO) δ) |
|---|---|---|
| I-77 | 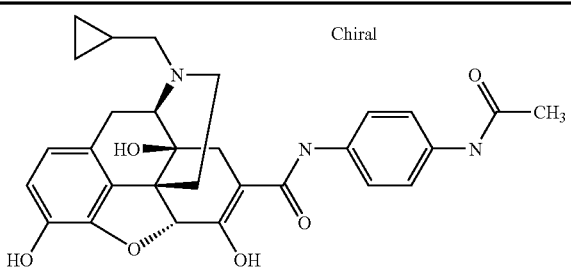 Chiral | 0.10-0.25 (m, 2H), 0.44-0.60 (m, 2H), 0.88 (m, 1H), 1.45 (d, J = 11.1 Hz, 1H), 1.70-3.40 (m, 13H), 4.78 (s, 1H), 4.81 (s, 1H), 6.53 (d, J = 8.1 Hz, 1H), 6.58 (d, J = 8.1 Hz, 1H), 7.46 (d, J = 9.0 Hz, 2H), 7.48 (d, J = 9.0 Hz, 2H), 9.15 (s, 1H), 9.25 (s, 1H), 9.88 (s, 1H), 14.00 (br s, 1H) |
| I-78 | 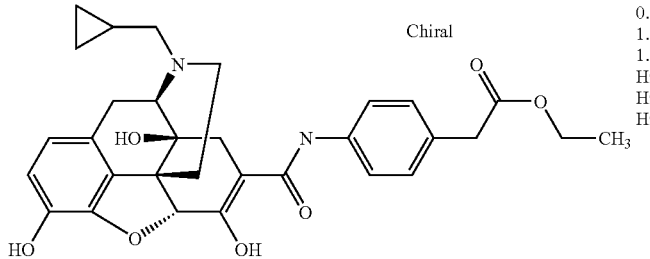 Chiral | 0.10-0.25 (m, 2H), 0.44-0.60 (m, 2H), 0.89 (m, 1H), 1.17 (t, J = 7.2 Hz, 3H), 1.45 (d, J = 11.4 Hz, 1H), 1.70-3.40 (m, 10H), 3.60 (s, 2H), 4.06 (q, J = 7.2 Hz, 2H), 4.78 (s, 1H), 4.83 (s, 1H), 6.58 (d, J = 8.1 Hz, 1H), 7.17 (d, J = 8.7 Hz, 2H), 7.45 (d, J = 8.7 Hz, 2H), 9.16 (s, 1H), 9.26 (s, 1H), 13.95 (br s, 1H) |

TABLE 23-continued

| Compound No. | Chemical structure | NMR (1H-NMR (d6-DMSO) δ) |
|---|---|---|
| I-79 | 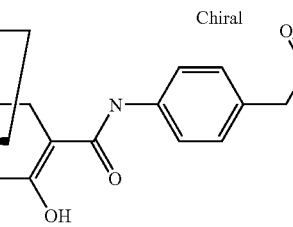 | 0.12-0.30 (m, 2H), 0.44-0.62 (m, 2H), 0.90 (m, 1H), 1.48 (d, J = 11.4 Hz, 1H), 1.70-3.40 (m, 10H), 3.51 (s, 2H), 4.81 (s, 1H), 6.55 (d, J = 8.1 Hz, 1H), 6.60 (d, J = 8.1 Hz, 1H), 7.17 (d, J = 8.4 Hz, 2H), 7.44 (d, J = 8.4 Hz, 2H), 9.20 (s, 1H), 9.40 (br s, 1H), 14.00 (br s, 1H) |
| I-80 | 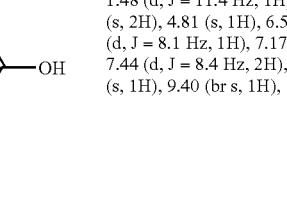 | 0.10-0.17 (m, 2H), 0.46-0.52 (m, 2H), 0.86 (m, 1H), 1.41 (d, J = 13.2 Hz, 1H), 1.87 (m, 1H), 2.09-2.64 (m, 8H), 3.00-3.50 (m, 15H), 4.57 (m, 1H), 4.73 (br, s, 2H), 6.50-6.57 (m, 2H), 7.73 (br, s, 1H), 9.14 (s, 1H), 14.38 (br, s, 1H) |
| I-81 | 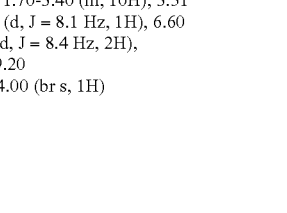 | 0.30-0.50 (m, 2H), 0.50-0.70 (m, 2H) 1.05 (m, 1H), 1.50-3.40 (m, 11H), 4.58 (s, 1H), 5.39 (s, 1H), 6.52 (d, J = 6.0 Hz, 1H), 6.59 (d, J = 6.0 Hz, 1H), 6.84 (br s, 1H), 7.26 (m, 1H), 7.38 (m, 1H), 9.15 (m, 1H) |

TABLE 24

| Compound No. | Chemical structure | NMR (1H-NMR (d6-DMSO) δ) |
|---|---|---|
| I-82 | 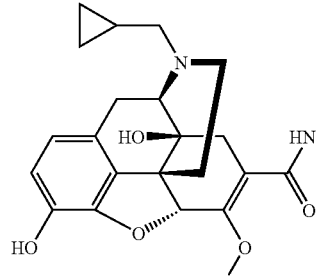 | 1H-NMR (CDCl3 + CD3OD) d: 0.17 (brs, 2 H), 0.59 (brs, 2 H), 0.89 (brs, 1 H), 1.71 (d, J = 10.8 Hz, 1 H), 2.17 (d.d, J = 17.1 & 1.8 Hz, 1 H), 2.22-2.57 (m, 4 H), 2.60-2.84 (m, 3 H), 3.06 (d, J = 15.6 Hz, 1 H), 3.24 (brs, 1 H), 4.07 (s, 3 H), 5.31 (s, 1 H), 6.56 (d, J = 8.4 Hz, 1 H), 6.67 (d, J = 8.4 Hz, 1 H), 7.02-7.10 (m, 1 H), 7.26-7.32 (m, 2 H), 7.39 (d.d, J = 8.4 & 0.9 Hz, 2 H), 9.61 (s, 1 H). |
| I-83 | 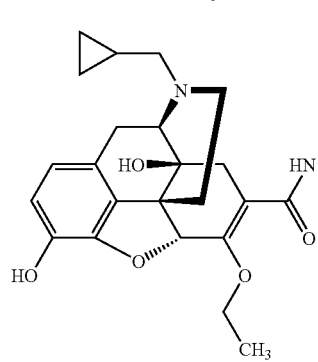 | 1H-NMR (CDCl3 + CD3OD) d: 0.15 (brs, 2 H), 0.58 (brs, 2 H), 0.88 (brs, 1 H), 1.49 (t, J = 6.9 Hz, 3 H), 1.68 (d, J = 9.9 Hz, 1 H). 2.15 (d.d, J = 17.1 & 1.5 Hz, 1 H), 2.28 (brs, 2 H), 2.39 (brs, 2 H). 2.60-2.80 (m, 3 H), 3.06 (d, J = 18.3 Hz, 1 H), 3.26 (brs, 1 H), 4.29 (q, J = 6.9 Hz, 1 H), 4.48 (q, J = 6.9 Hz, 1 H), 5.27 (s, 1 H), 6.56 (d, J = 7.8 Hz, 1 H), 6.66 (d, J =7.8 Hz, 1 H), 7.03-7.09 (m, 1 H), 7.26-7.31 (m, 2 H), 7.50 (d.d, J = 8.7 & 0.9 Hz, 2 H). |

TABLE 24-continued

| Compound No. | Chemical structure | NMR (1H-NMR (d6-DMSO) δ) |
|---|---|---|
| I-84 | 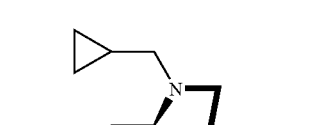 | 1H-NMR (CDCl3 + CD3OD) d: 0.16 (brs, 2 H), 0.57 (brs, 2 H), 0.86 (brs, 1 H), 1.13 (d, J = 6.6 Hz, 3 H), 1.14 (d, J = 6.6 Hz, 3 H), 1.39 (t, J = 6.9 Hz, 3 H), 1.66 (d, J = 9.0 Hz, 1 H), 2.08 (d.d, J = 17.1 & 1.5 Hz, 1 H), 2.21 (brs, 2 H), 2.38 (brs, 2 H), 2.58-2.77 (m, 3 H), 3.03 (d, J = 18.6 Hz, 1 H), 3.21 (brs, 1 H), 4.03 (quint, J = 6.6 Hz, 1 H), 4.20 (q, J = 6.9 Hz, 1 H), 4.40 (q, J = 6.9 Hz, 1 H), 5.19 (s, 1 H), 6.54 (d, J = 8.1 Hz, 1 H), 6.65 (d, J = 8.1 Hz, 1 H), 7.50 (d, J = 7.5 Hz, 1 H). |

TABLE 25

| Compound No. | Chemical structure | NMR (1H-NMR (d6-DMSO) δ) |
|---|---|---|
| I-85 | 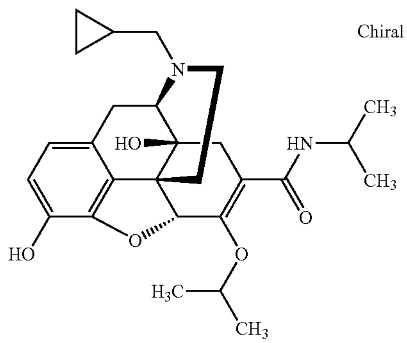 | 1H-NMR (CDCl3 + CD3OD) d: 0.14 (brs, 2 H), 0.56 (brs, 2 H), 0.86 (brs, 1 H), 1.14 (d, J = 6.6 Hz, 3 H), 1.15 (d, J = 6.6 Hz, 3 H), 1.32 (d, J = 4.8 Hz, 1 H), 1.34 (d, J = 4.8 Hz, 3 H), 1.64 (d, J = 9.9 Hz, 1 H), 2.10 (d.d, J = 17.1 & 1.5 Hz, 1 H), 2.27 (brs, 2 H), 2.39 (brs, 2 H), 2.55-2.77 (m, 3 H), 3.04 (d, J = 18.3 Hz, 1 H), 3.22 (brs, 1 H), 4.03 (quint, J = 6.6 Hz, 1 H), 4.81 (quint., J = 6.0 Hz, 1 H), 5.10 (s, 1 H), 6.54 (d, J = 8.4 Hz, 1 H), 6.67 (d, J = 8.4 Hz, 1 H), 7.76 (d, J = 6.9 Hz, 1 H). |
| I-86 | 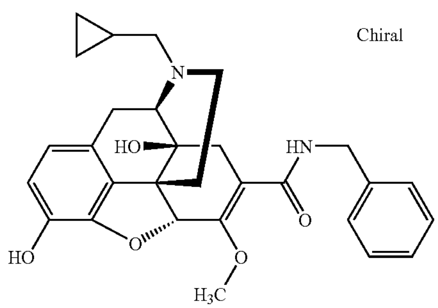 | 1H-NMR (CDCl3 + CD3OD) d: 0.16 (brs, 2 H), 0.568 (brs, 2 H), 0.87 (brs, 1 H), 1.67 (d, J = 9.9 Hz, 1 H), 2.14 (d.d, J = 18.3 & 1.2 Hz, 1 H), 2.27 (brs, 2 H), 2.41 (brs, 2 H), 3.05 (d, J = 18.6 Hz, 1 H), 3.25 (brd, J = 4.5 Hz, 1 H), 3.92 (s, 1 H), 4.46 (d, J = 5.7 Hz, 2 H), 5.23 (s, 1 H), 6.54 (d, J = 8.1 Hz, 1 H), 6.64 (d, J = 8.1 Hz, 1 H), 7.20-7.36 (m, 5 H), 8.03 (brt, J = 5.7 Hz, 1 H). |
| I-87 | 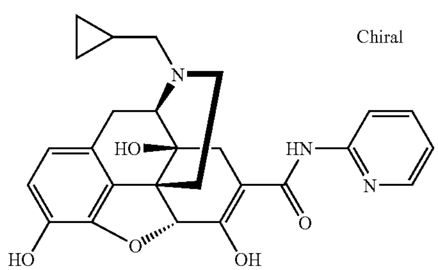 | 1H-NMR (CDCl3 + CD3OD) d: 0.26 (brs, 2 H), 0.63 (brs, 2 H), 0.94 brs, 1 H), 1.72 (brd, J = 9.0 Hz, 1 H), 2.09-2.93 (m, 8 H), 3.15 (d, J = 18.9 Hz, 1 H), 4.97 (s, 1 H), 6.61 (d, J = 8.1 Hz, 1 H), 6.70 (d, J = 8.1 Hz, 1 H), 7.04-7.08 (m, 1 H), 7.69-7.75 (m, 1 H), 8.13 (d, J = 14.0 Hz, 2 H), 8.23 (d, J = 3.9 Hz, 1 H). |

TABLE 26

| Compound No. | Chemical structure | LC/MS*1 | NMR (1H-NMR (d6-DMSO) δ) |
|---|---|---|---|
| I-89 | Chiral | m/z 462 [M + H]+ 0.94 min | |
| I-90 | Chiral | m/z 511 [M + H]+ 0.63 min | |
| I-91 | Chiral | m/z 500 [M + H]+ 0.44 min | |
| I-92 | Chiral | m/z 462 [M + H]+ 0.44 min | |
| I-93 | Chiral | m/z 487 [M + H]+ 0.50 min | |

TABLE 27
| Compound No. | Chemical structure | LC/MS[*1] | NMR (1H-NMR (d6-DMSO) δ) |
|---|---|---|---|
| I-94 | 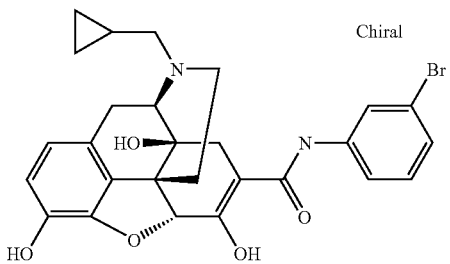 Chiral | m/z 540 [M + H]+ 1.07 min | |
| I-95 | 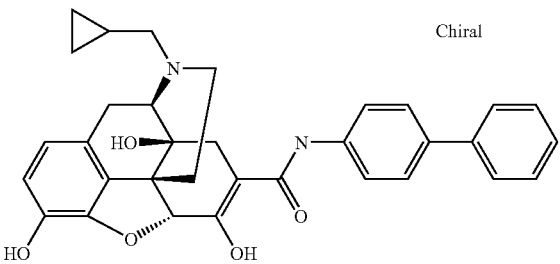 Chiral | m/z 537 [M + H]+ 1.12 min | |
| I-96 | 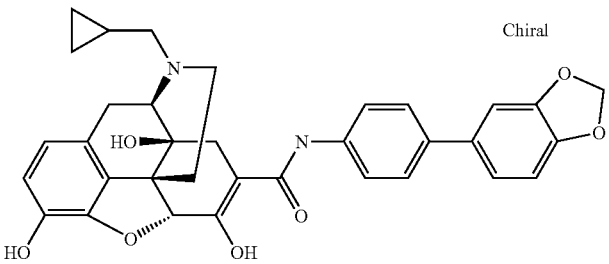 Chiral | m/z 581 [M + H]+ 1.15 min | |
| I-97 | 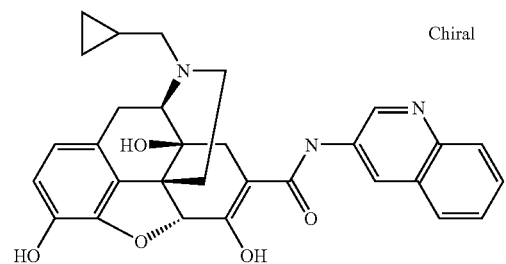 Chiral | m/z 512 [M + H]+ 0.50 min | |
| I-98 | 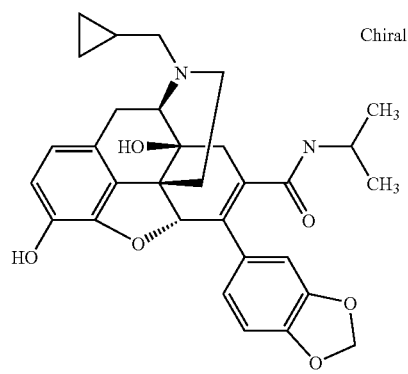 Chiral | m/z 531 [M + H]+ 0.50 min | |

TABLE 28

| Compound No. | Chemical structure | LC/MS*1 | NMR (1H-NMR (d6-DMSO) δ) |
|---|---|---|---|
| I-99 | Chiral | m/z 537 [M + H]+ 1.17 min | |
| I-100 | Chiral | m/z 581 [M + H]+ 1.15 min | |
| I-101 | Chiral | m/z 581 [M + H]+ 1.03 min | |
| I-102 | Chiral | m/z 538 [M + H]+ 0.85 min | |
| I-103 | Chiral | m/z 540 [M + H]+ 1.05 min | |

TABLE 29

| Compound No. | Chemical structure | LC/MS*1 | NMR (1H-NMR (d6-DMSO) δ) |
|---|---|---|---|
| I-104 | 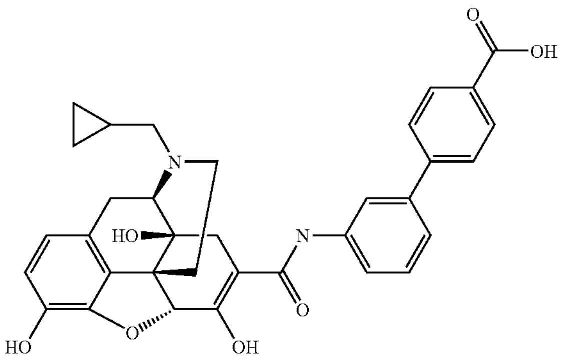 | Chiral | m/z 581 [M + H]+ 1.12 min |
| I-105 | 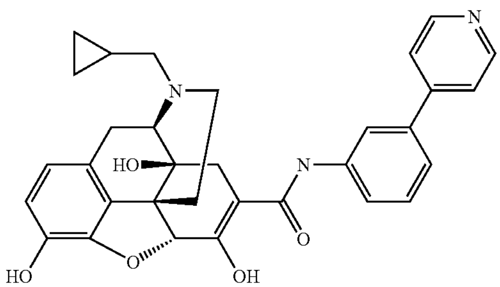 | Chiral | m/z 538 [M + H]+ 0.90 min |
| I-106 | 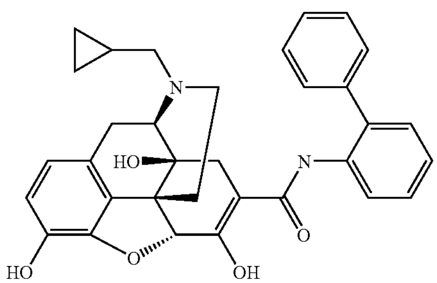 | Chiral | m/z 537 [M + H]+ 1.05 min |
| I-107 | 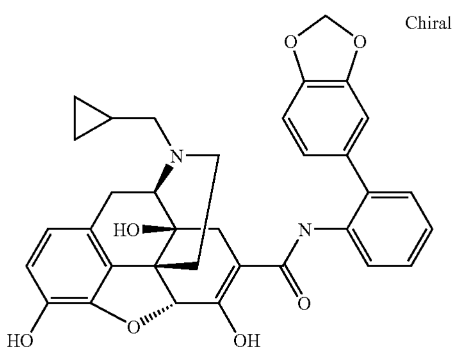 | Chiral | m/z 581 [M + H]+ 1.09 min |

TABLE 30

| Compound No. | Chemical structure | LC/MS*1 | NMR (1H-NMR (d6-DMSO) δ) |
|---|---|---|---|
| I-108 | 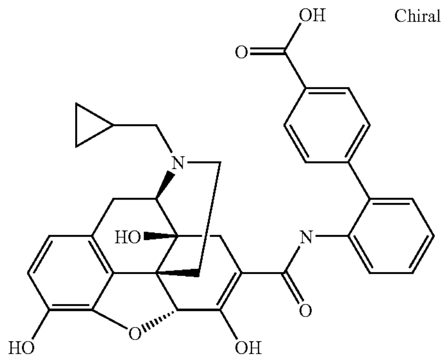 | m/z 581 [M + H]+ 1.03 min | |
| I-109 | 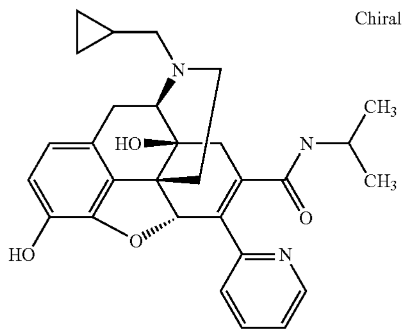 | m/z 488 [M + H]+ 0.50 min | |
| I-110 | 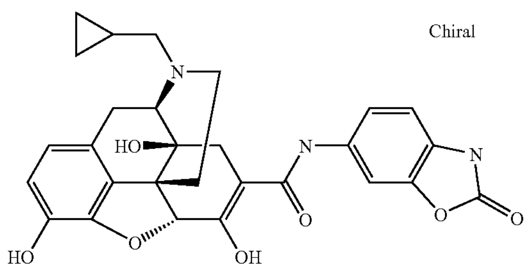 | m/z 518 [M + H]+ 0.50 min | |
| I-111 | 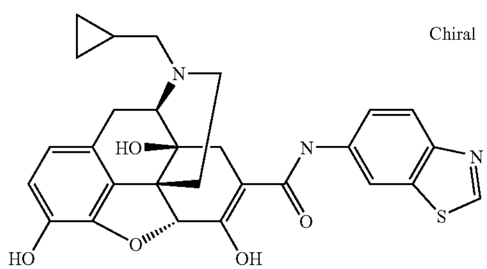 | m/z 518 [M + H]+ 0.56 min | |
| I-112 | 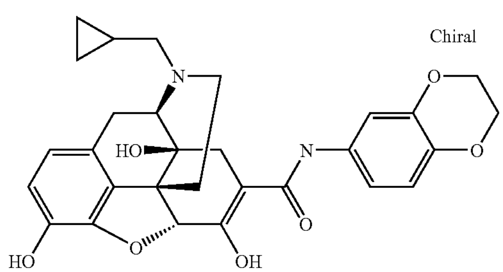 | m/z 519 [M + H]+ 0.50 min | |

TABLE 31

| Compound No. | Chemical structure | LC/MS*1 | NMR (1H-NMR (d6-DMSO) δ) |
|---|---|---|---|
| I-113 | Chiral | m/z 511 [M + H]+ 0.50 min | |
| I-114 | Chiral | m/z 486 [M + H]+ 0.57 min | |
| I-115 | Chiral | m/z 462 [M + H]+ 0.44 min | |
| I-116 | Chiral | m/z 497 [M + H]+ 0.63 min | |
| I-117 | Chiral | m/z 513 [M + H]+ 0.69 min | |

TABLE 32

| Compound No. | Chemical structure | LC/MS*1 | NMR (1H-NMR (d6-DMSO) δ) |
|---|---|---|---|
| I-118 | 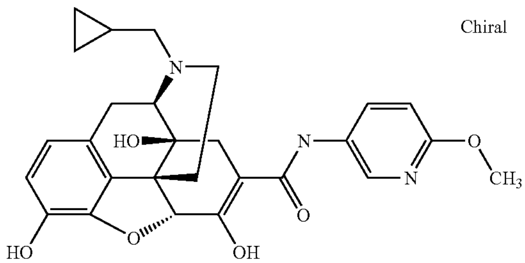 | Chiral | m/z 493 [M + H]+ 1.06 min |
| I-119 | 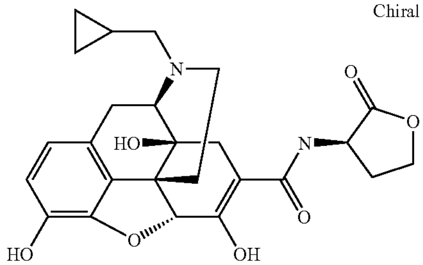 | Chiral | m/z 469 [M + H]+ 0.44 min |
| I-120 | 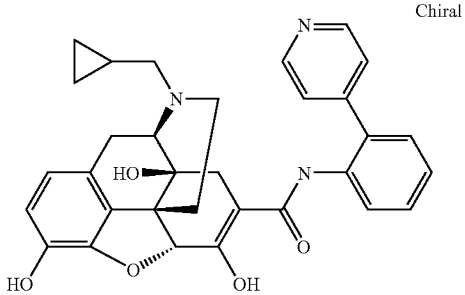 | Chiral | m/z 538 [M + H]+ 0.94 min |
| I-121 | 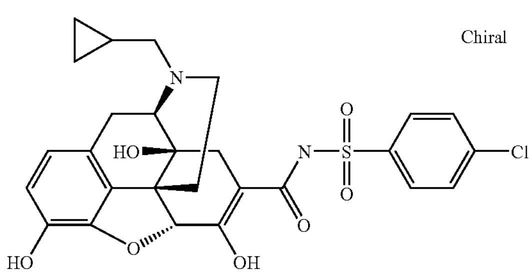 | Chiral | m/z 559 [M + H]+ 0.69 min |
| I-122 | 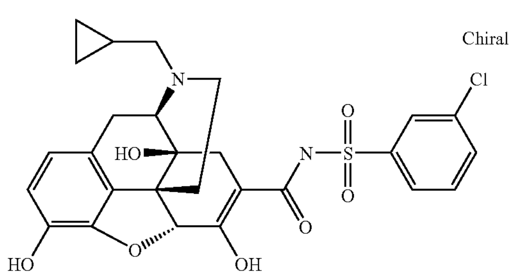 | Chiral | m/z 559 [M + H]+ 0.69 min |

TABLE 33

| Compound No. | Chemical structure | LC/MS[*1] | NMR (1H-NMR (d6-DMSO) δ) |
|---|---|---|---|
| I-123 | Chiral | m/z 555 [M + H]+ 0.56 min | |
| I-124 | Chiral | m/z 543 [M + H]+ 0.63 min | |
| I-125 | Chiral | m/z 425 [M + H]+ 0.50 min | |
| I-126 | Chiral | m/z 525 [M + H]+ 0.56 min | |
| I-127 | Chiral | | (CDCl3 + CD3OD) d: 0.10-0.21 (m, 2 H), 0.48-0.63 (m, 2 H), 0.78-0.94 (m, 1 H), 1.67 (d, J = 9.6 Hz, 1 H), 2.10-2.50 (m, 6 H), 2.57-2.80 (m, 2 H), 3.06 (d, J = 18.6 Hz, 1 H), 3.27 (brs, 1 H), 5.10 (d, J = 1.7 Hz, 1 H), 6.31-6.40 (m, 1 H), 6.53 (d, J = 8.1 Hz, 1 H), 6.65 (d, J = 8.1 Hz, 1 H), 7.02-7.12 (m, 1 H), 7.22-7.34 (m, 2 H), 7.44-7.56 (m, 2 H). |

TABLE 34

| Compound No. | Chemical structure | | LC/MS*1 | NMR (1H-NMR (d6-DMSO) δ) |
|---|---|---|---|---|
| I-128 | 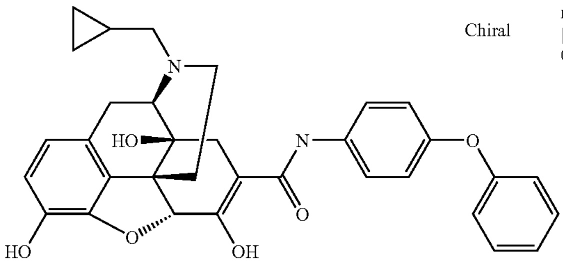 | Chiral | m/z 553 [M + H]+ 0.94 min | |
| I-129 | 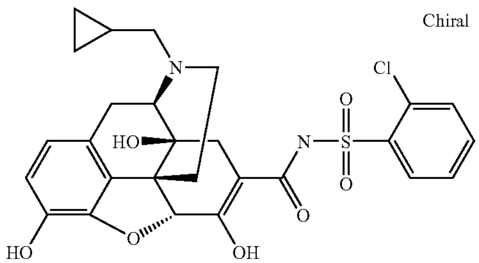 | Chiral | m/z 559 [M + H]+ 0.63 min | |
| I-130 | 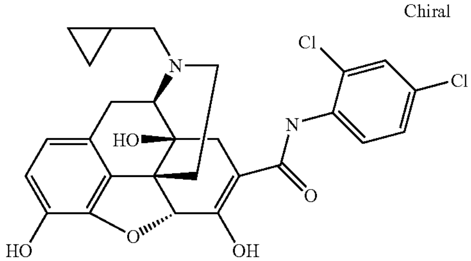 | Chiral | m/z 529 [M + H]+ 0.75 min | |
| I-131 | 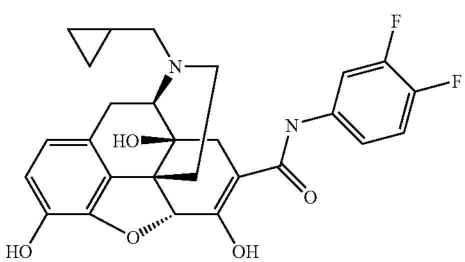 | Chiral | m/z 497 [M + H]+ 0.63 min | |
| I-132 | 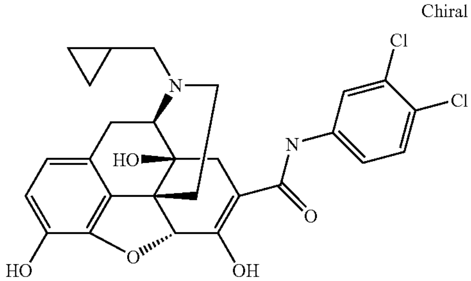 | Chiral | m/z 529 [M + H]+ 0.88 min | |

TABLE 35

| Compound No. | Chemical structure | LC/MS*1 | NMR (1H-NMR (d6-DMSO) δ) |
|---|---|---|---|
| I-133 | 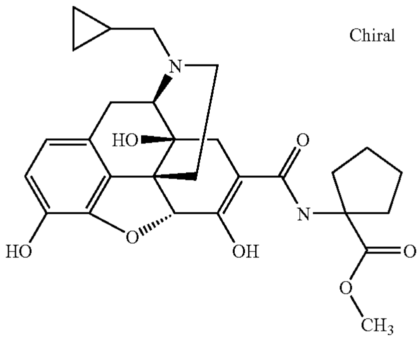 | m/z 511 Chiral [M + H]+ 0.97 min | 0.12-0.16 (m, 2 H), 0.46-0.52 (m, 2 H), 0.86 (m, 1 H), 1.42 (d, J = 10.5 Hz, 1 H), 1.86 (d, J = 15.6 Hz, 1 H), 2.06-2.65 (m, 15 H), 3.05 (d, J = 18.3 Hz, 1 H), 3.26 (d, J = 5.9 Hz, 1 H), 3.55 (s, 3 H), 4.73 (s 1 H), 6.52 (d, J = 8.1 Hz, 1 H), 6.58 (d, J = 8.1 Hz, 1 H), 7.76 (brs, 1 H), 9.31 (brs, 1 H), 13.8 (brs, 1 H) |
| I-134 | 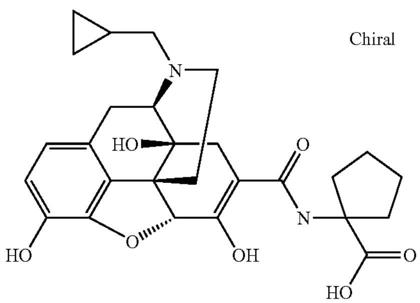 | m/z 498 Chiral [M + H]+ 0.96 min | 0.13-0.16 (m, 2 H), 0.48-0.54 (m, 2 H), 0.87 (m, 1 H), 1.43 (d, J = 10.5 Hz, 1 H), 1.86 (d, J = 15.6 Hz, 1 H), 2.06-2.67 (m, 15 H), 3.06 (d, J = 18.6 Hz, 1 H), 3.27 (d, J = 6.0 Hz, 1 H), 4.73 (s 1 H), 6.53 (d, J = 8.1 Hz, 1 H), 6.58 (d, J = 8.1 Hz, 1 H), 7.72 (brs, 1 H), 9.20 (brs, 1 H), 14.1 (brs, 1 H) |
| I-135 | 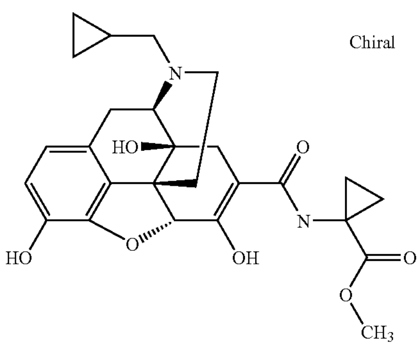 | m/z 483 Chiral [M + H]+ 0.87 min | 0.12-0.14 (m, 2 H), 0.46-0.51 (m, 2 H), 0.85 (m, 1 H), 1.06-1.09 (m, 2 H), 1.35-1.36 (m, 2 H), 1.41 (d, J = 11.7 Hz, 1 H), 1.86 (d, J = 15.6 Hz, 1 H), 2.17-2.61 (m, 7 H), 3.03 (d, J = 18.3 Hz, 1 H), 3.17 (d, J = 6.0 Hz, 1 H), 3.56 (s, 3 H), 4.74 (s, 1 H), 4.77 (brs, 1 H), 6.51 (d, J = 8.1 Hz, 1 H), 6.56 (d, J = 8.1 Hz, 1 H), 9.17 (brs, 1 H), 14.1 (brs, 1 H) |
| I-136 | 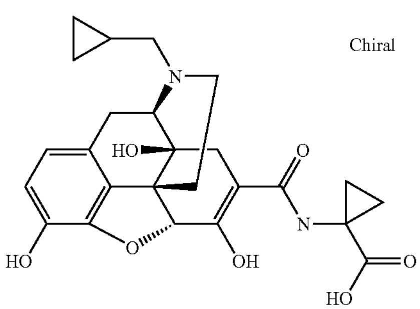 | m/z 469 Chiral [M + H]+ 0.89 min | 0.12-0.16 (m, 2 H), 0.43-0.51 (m, 2 H), 0.85 (m, 1 H), 1.06-1.12 (m, 2 H), 1.35-1.36 (m, 2 H), 1.42 (d, J = 11.7 Hz, 1 H), 1.86 (d, J = 15.6 Hz, 1 H), 2.06-2.63 (m, 7 H), 3.02 (d, J = 18.3 Hz, 1 H), 3.13 (d, J = 5.4 Hz, 1 H), 4.76 (s 1 H), 4.77 (brs, 1 H), 6.52 (d, J = 8.1 Hz, 1 H), 6.56 (d, J = 8.1 Hz, 1 H), 9.18 (brs, 1 H), 14.1 (brs, 1 H) |

TABLE 36

| Compound No. | Chemical structure | LC/MS*1 | NMR (1H-NMR (d6-DMSO) δ) |
|---|---|---|---|
| I-137 | 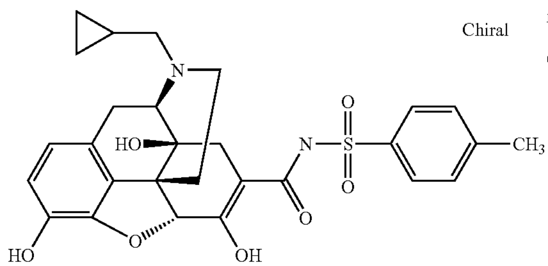 | Chiral | m/z 539 [M + H]+ 0.50 min |
| I-138 | 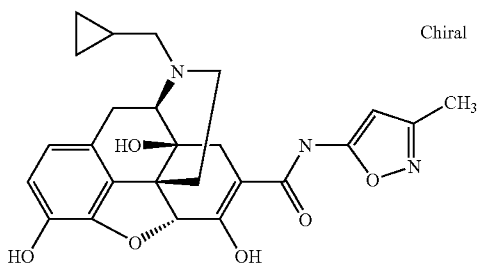 | Chiral | m/z 466 [M + H]+ 0.57 min |
| I-139 | 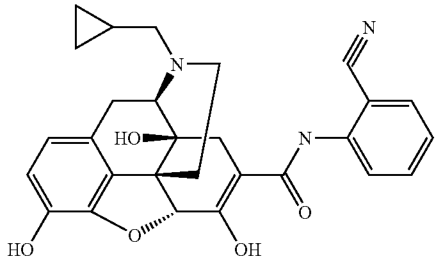 | Chiral | m/z 486 [M + H]+ 0.44 min |
| I-140 | 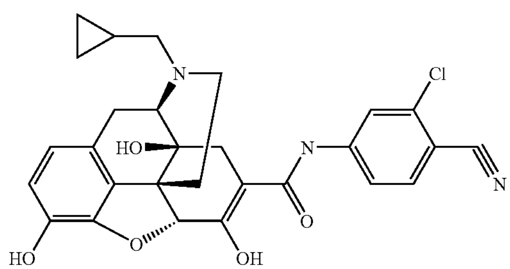 | Chiral | m/z 520 [M + H]+ 0.56 min |
| I-141 | 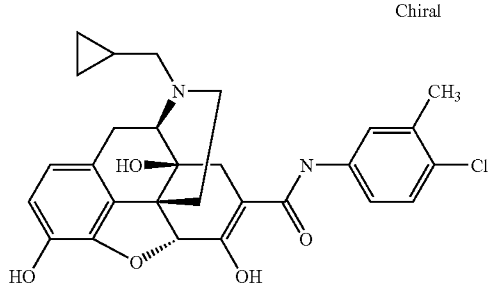 | Chiral | m/z 510 [M + H]+ 0.75 min |

TABLE 37

| Compound No. | Chemical structure | | LC/MS*1 | NMR (1H-NMR (d6-DMSO) δ) |
|---|---|---|---|---|
| I-142 | 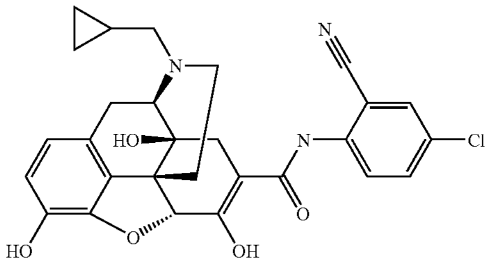 | Chiral | m/z 521 [M + H]+ 0.50 min | |
| I-143 | 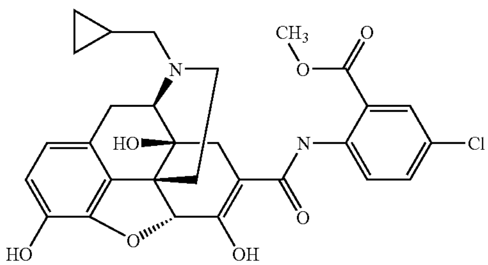 | Chiral | m/z 553 [M + H]+ 0.88 min | |
| I-144 | 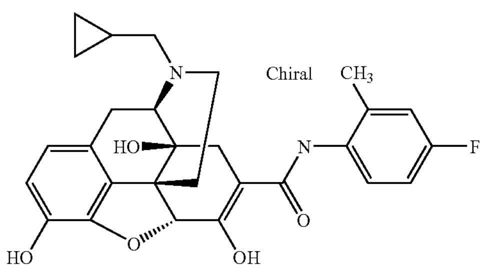 | Chiral | m/z 494 [M + H]+ 0.57 min | |
| I-145 | 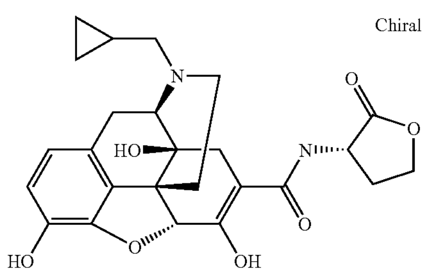 | Chiral | m/z 469 [M + H]+ 0.83 min | |
| I-146 | 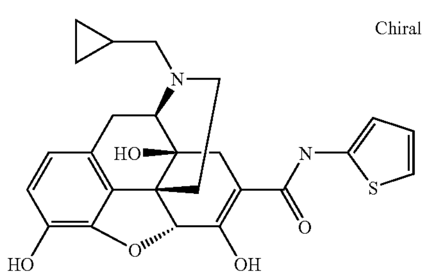 | Chiral | m/z 467 [M + H]+ 1.01 min | |

TABLE 38

| Compound No. | Chemical structure | LC/MS*1 | NMR (1H-NMR (d6-DMSO) δ) |
|---|---|---|---|
| I-147 | 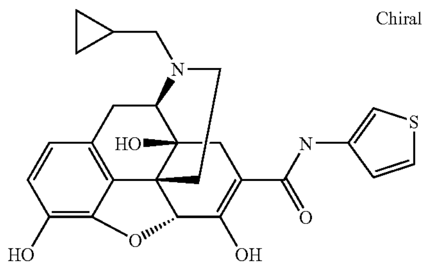 | Chiral | m/z 467 [M + H]+ 1.00 min |
| I-148 | 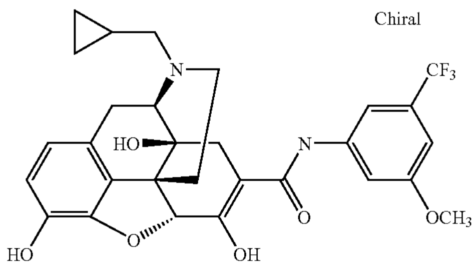 | Chiral | m/z 559 [M + H]+ 1.16 min** |
| I-149 | 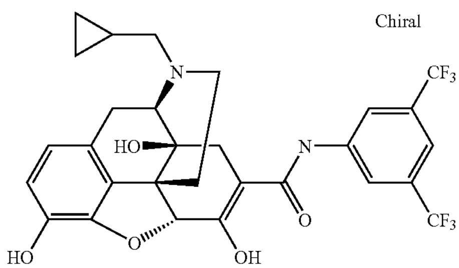 | Chiral | m/z 598 [M + H]+ 1.34 min** |
| I-150 | 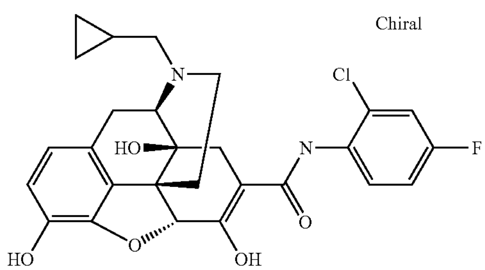 | Chiral | m/z 514 [M + H]+ 0.50 min |
| I-151 | 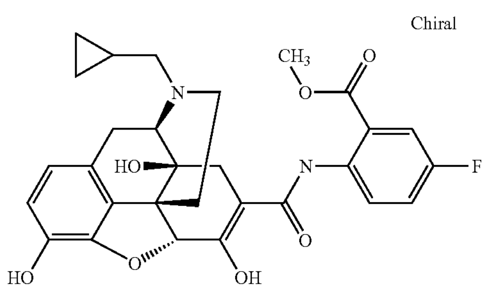 | Chiral | m/z 538 [M + H]+ 0.63 min |

TABLE 39

| Compound No. | Chemical structure | LC/MS*1 | NMR (1H-NMR (d6-DMSO) δ) |
|---|---|---|---|
| I-152 | (structure: cyclopropylmethyl-N morphinan with N-(4-fluoro-3-methylphenyl)carboxamide) | m/z 494 [M + H]+ 0.56 min | |
| I-153 | (structure: cyclopropylmethyl-N morphinan with N-(1-methyl-1H-pyrazol-5-yl)carboxamide) | m/z 465 [M + H]+ 0.90 min | |
| I-154 | (structure: cyclopropylmethyl-N morphinan with N-(1-methyl-1H-pyrazol-3-yl)carboxamide) | m/z 465 [M + H]+ 0.96 min | |
| I-155 | (structure: cyclopropylmethyl-N morphinan with N-(4-morpholinophenyl)carboxamide) | m/z 544 [M + H]+ 1.00 min | |
| I-156 | (structure: cyclopropylmethyl-N morphinan with N-(5-methyl-1,3,4-thiadiazol-2-yl)carboxamide) | m/z 483 [M + H]+ 0.35 min | |

TABLE 40

| Compound No. | Chemical structure | LC/MS[*1] | NMR (1H-NMR (d6-DMSO) δ) |
|---|---|---|---|
| I-157 | Chiral | m/z 510 [M + H]+ 0.96 min | 0.11-0.14 (m, 2 H), 0.46-0.50 (m, 2 H), 0.83 (m, 1 H), 0.87 (t, J = 7.2 Hz, 1 H), 0.99 (d, J = 4.2 Hz, 3 H), 1.01 (d, J = 4.2 Hz, 3 H), 1.08-1.43 (m, 5 H), 1.95 (d, J = 17.1 Hz, 1 H), 2.11-2.65 (m, 7 H), 2.96-3.16 (m, 4 H), 3.78 (q, J = 7.5 Hz, 1 H), 4.78 (brs, 1 H), 5.21 (s, 1 H), 6.49 (d, J = 8.1 Hz, 1 H), 6.55 (d, J = 8.1 Hz, 1 H), 7.41 (t, J = 5.1 Hz, 1 H), 7.50 (d, J = 7.8 Hz, 1 H), 9.02 (brs, 1 H) |
| I-158 | Chiral | m/z 496 [M + H]+ 0.93 min | 0.11-0.13 (m, 2 H), 0.46-0.50 (m, 2 H), 0.85 (m, 1 H), 1.01 (d, J = 4.1 Hz, 3 H), 1.02 (d, J = 4.2 Hz, 3 H), 1.07 (d, J = 4.0 Hz, 3 H), 1.09 (d, J = 4.0 Hz, 3 H), 1.40 (d, J = 11.1 Hz, 1 H), 1.95 (d, J = 17.1 Hz, 1 H), 2.09-2.63 (m, 7 H), 2.98 (d J = 18.1 Hz, 1 H), 3.13 (d, J = 5.4 Hz, 1 H), 3.82 (q, J = 6.6 Hz, 1 H), 3.88 (q, J = 6.9 Hz, 1 H), 5.24 (brs, 1 H), 5.76 (s, 1 H), 6.50 (d, J = 7.5 Hz, 1 H), 6.55 (d, J = 7.5 Hz, 1 H), 7.20 (d, J = 7.2 Hz, 1 H), 7.54 (d, J = 6.9 Hz, 1 H), 9.01 (brs, 1 H) |
| I-159 | Chiral | m/z 536 [M + H]+ 0.95 min | 0.11-0.13 (m, 2 H), 0.46-0.50 (m, 2 H), 0.83 (m, 1 H), 0.99 (d, J = 3.0 Hz, 3 H), 1.01 (d, J = 3.0 Hz, 3 H), 1.15-1.38 (m, 6 H), 1.40 (d, J = 11.1 Hz, 1 H), 1.52-1.80 (m, 4 H), 1.97 (d, J = 17.1 Hz, 1 H), 2.09-2.65 (m, 7 H), 2.98 (d, J = 18.6 Hz, 1 H), 3.13 (d, J = 5.7 Hz, 1 H), 3.58 (m, 1 H), 3.79 (q, J = 6.9 Hz, 1 H), 5.23 (s, 1 H), 6.50 (d, J = 7.8 Hz, 1 H), 6.55 (d, J = 7.8 Hz, 1 H), 7.17 (d, J = 7.8 Hz, 1 H), 7.57 (d, J = 7.8 Hz, 1 H), 9.00 (brs, 1 H) |

TABLE 41

| Compound No. | Chemical structure | LC/MS*1 | NMR (1H-NMR (d6-DMSO) δ) |
|---|---|---|---|
| I-160 | 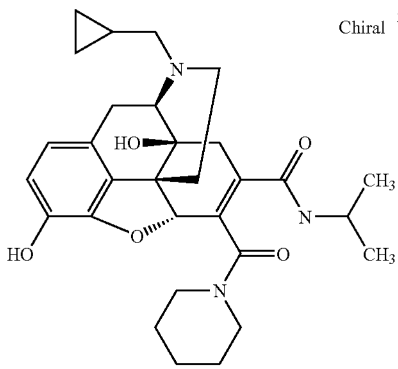 | Chiral m/z 522 [M + H]+ 1.04 min | 0.12-0.13 (m, 2 H), 0.46-0.51 (m, 2 H), 0.85 (m, 1 H), 0.99 (d, J = 3.3 Hz, 3 H), 1.01 (d, J = 3.3 Hz, 3 H), 1.15-1.49 (m, 7 H), 1.91 (d, J = 16.5 Hz, 1 H), 2.08-2.65 (m, 7 H), 2.98 (d, J = 17.5 Hz, 1 H), 3.12 (d, J = 5.7 Hz, 1 H), 3.16-3.34 (m, 4 H), 3.79 (q, J = 6.9 Hz, 1 H), 4.76 (brs, 1 H), 5.01 (s, 1 H), 6.54 (d, J = 7.8 Hz, 1 H), 6.58 (d, J = 7.8 Hz, 1 H), 7.19 (d, J = 7.5 Hz, 1 H), 9.01 (brs, 1 H) |
| I-161 | 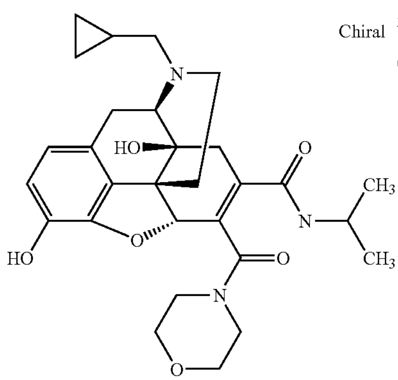 | Chiral m/z 524 [M + H]+ 0.92 min | 0.12-0.14 (m, 2 H), 0.46-0.51 (m, 2 H), 0.86 (m, 1 H), 0.99 (d, J = 3.3 Hz, 3 H), 1.01 (d, J = 3.3 Hz, 3 H), 1.41 (d, J = 11.1 Hz, 1 H), 1.95 (d, J = 17.1 Hz, 1 H), 2.08-2.67 (m, 11 H), 2.98 (d, J = 17.5 Hz, 1 H), 3.12 (d, J = 5.7 Hz, 1 H), 3.49-3.60 (m, 4 H), 3.82 (q, J = 6.9 Hz, 1 H), 4.78 (brs, 1 H), 5.01 (s, 1 H), 6.54 (d, J = 8.1 Hz, 1 H), 6.58 (d, J = 8.1 Hz, 1 H), 7.38 (d, J = 7.8 Hz, 1 H), 9.13 (brs, 1 H) |
| I-162 | 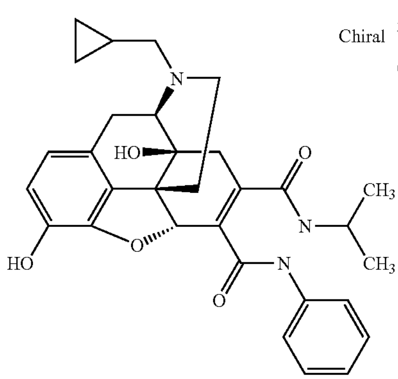 | Chiral m/z 530 [M + H]+ 0.94 min | 0.13-0.14 (m, 2 H), 0.47-0.51 (m, 2 H), 0.83 (m, 1 H), 0.84 (d, J = 6.6 Hz, 3 H), 0.93 (d, J = 6.6 Hz, 3 H), 1.44 (d, J = 10.5 Hz, 1 H), 2.02 (d, J = 16.8 Hz, 1 H), 2.11-2.65 (m, 7 H), 3.03 (d, J = 18.6 Hz, 1 H), 3.17 (d, J = 5.7 Hz, 1 H), 3.58 (m, 1 H), 3.74 (q, J = 6.3 Hz, 1 H), 4.86 (brs, 1 H), 5.39 (s, 1 H), 6.52 (d, J = 8.1 Hz, 1 H), 6.57 (d, J = 8.1 Hz, 1 H), 7.03 (t, J = 7.2 Hz, 1 H), 7.26 (t, J = 7.8 Hz, 2 H), 7.56 (d, J = 7.8 Hz, 1 H), 7.64 (d, J = 8.1 Hz, 2 H), 9.01 (brs, 1 H), 9.70 (brs, 1 H) |

TABLE 42

| Compound No. | Chemical structure | LC/MS*1 | NMR (1H-NMR (d6-DMSO) δ) |
|---|---|---|---|
| I-163 | Chiral | m/z 445 [M + H]+ 0.83 min | |
| I-164 | Chiral | | 0.14-0.22 (m, 2 H), 0.48-0.61 (m, 2 H), 0.91 (m, 1 H), 1.12 (d, J = 6.6 Hz, 6 H), 1.53-1.66 (m, 1 H), 2.15-2.22 (m, 2 H), 2.23-2.30 (m, 2 H), 2.35-2.49 (m, 2 H), 2.70 (d.d, J = 18.9 & 6.6 Hz, 2 H), 3.13 (d, J = 18.9 Hz, 1 H), 3.27 (d, J = 6.6 Hz, 1 H), 3.98 (quintet, J = 6.6 Hz, 1 H), 4.99-5.04 (m, 1 H), 6.32-6.36 (m, 1 H), 6.53 (d, J = 8.4 Hz, 1 H), 6.58 (d, J = 8.4 Hz, 1 H). |
| I-165 | Chiral | m/z 543 [M + H]+ 0.63 min | |
| I-166 | Chiral | m/z 446 [M + H]+ 0.94 min | |

TABLE 43

| Compound No. | Chemical structure | LC/MS*1 | NMR (1H-NMR (d6-DMSO) δ) |
|---|---|---|---|
| I-167 | Chiral | | (CD3OD) d: 0.12-0.22 (m, 2 H), 0.48-0.63 (m, 2 H), 0.82-1.00 (m, 1 H), 1.63 (d, J = 8.1 Hz, 1 H), 2.10-2.50 (m, 7 H), 2.72 (d.d, J = 18.6 & 6.6 Hz, 2 H), 3.15 (d, J = 18.6 Hz, 1 H), 5.10 (brs, 1 H), 6.50-6.65 (m, 3 H), 7.67 (d.d, J = 4.8 & 1.5 Hz, 1 H), 8.36 (d.d, J = 4.8 & 1.5 Hz, 1 H). |

TABLE 43-continued
| Compound No. | Chemical structure | LC/MS*1 | NMR (1H-NMR (d6-DMSO) δ) |
|---|---|---|---|
| I-168 | 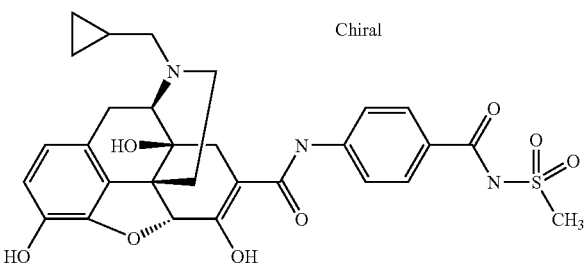 Chiral | m/z 582 [M + H]+ 0.90 min | |
| I-169 | 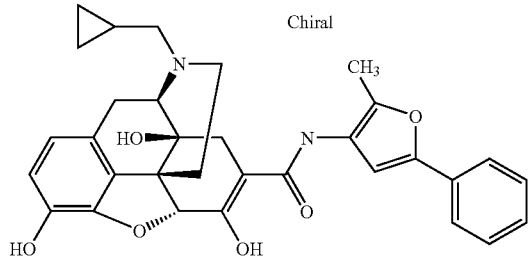 Chiral | m/z 541 [M + H]+ 1.15 min | |
| I-170 | 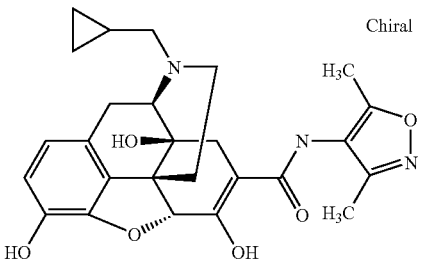 Chiral | m/z 480 [M + H]+ 0.37 min | |
| I-171 | 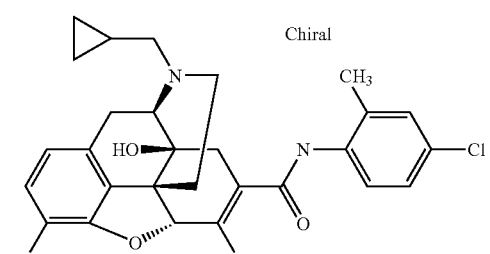 Chiral | m/z 509 [M + H]+ 0.75 min | |

TABLE 44

| Compound No. | Chemical structure | LC/MS*1 | NMR (1H-NMR (d6-DMSO) δ) |
|---|---|---|---|
| I-172 | (Chiral structure shown) | m/z 505 [M + H]+ 0.97 min | 0.11-0.13 (m, 2 H), 0.46-0.50 (m, 2 H), 0.84 (m, 1 H), 0.98 (d, J = 3.1 Hz, 3 H), 1.01 (d, J = 3.1 Hz, 3 H), 1.37 (d, J = 10.8 Hz, 1 H), 2.08 (d, J = 17.4 Hz, 1 H), 2.11-2.24 (m, 2 H), 2.35 (d, J = 6.6 Hz, 1 H), 2.51-2.63 (m, 2 H), 3.01 (d, J = 18.3 Hz, 1 H), 3.13 (d, J = 5.7 Hz, 1 H), 3.54 (s, 3 H), 3.86 (q, J = 7.2 Hz, 1 H), 4.79 (brs, 1 H), 4.98 (brs, 1 H), 5.76 (s, 1 H), 6.54 (d, J = 7.8 Hz, 1 H), 6.59 (d, J = 7.8 Hz, 1 H), 7.35 (d, J = 7.5 Hz, 1 H), 9.16 (brs, 1 H) |
| I-173 | (Chiral structure shown) | m/z 426 [M + H]+ 0.90 min | 0.12-0.14 (m, 2 H), 0.46-0.52 (m, 2 H), 0.85 (m, 1 H), 0.97 (d, J = 6.6 Hz, 3 H), 1.03 (d, J = 6.6 Hz, 3 H), 1.38 (d, J = 10.2 Hz, 1 H), 1.86 (d, J = 15.0 Hz, 1 H), 2.02 (d, J = 15.0 Hz, 1 H), 2.10-2.17 (m, 2 H), 2.28 (dd, J = 6.9, 6.9 Hz, 1 H), 2.43 (dd, J = 6.9, 8.4 Hz, 1 H), 2.54-2.62 (m, 2 H), 3.01 (d, J = 18.3 Hz, 1 H), 3.17 (d, J = 5.7 Hz, 1H), 3.58 (m, 1 H), 3.88 (q, J = 7.2 Hz, 1 H), 4.62 (brs, 1 H), 4.68 (s, 1 H), 6.47 (d, J = 8.1 Hz, 1 H), 6.55 (d, J = 8.1 Hz, 1 H), 6.94 (brs, 1 H), 9.06 (brs, 1 H) |
| I-174 | (Chiral structure shown) | | (CD3OD) d: 0.10-0.25 (m, 2 H), 0.48-0.63 (m, 2 H), 0.83-1.00 (m, 1 H), 1.55 (d, J = 8.1 Hz, 1 H), 2.01 (d, J = 15.6 Hz, 1 H), 2.22-2.57 (m, 6 H), 2.70 (d.d, J = 18.3 & 7.2 Hz, 2 H), 3.12 (d, J = 18.3 Hz, 1 H), 4.67 (s, 1 H), 6.44-6.62 (m, 3 H), 7.54 (d.d, J = 9.6 & 3.6 Hz, 1 H), 8.00 (d, J = 3.6 Hz, 1 H). |

TABLE 45

| Compound No. | Chemical structure | LC/MS*1 | NMR (1H-NMR (d6-DMSO) δ) |
|---|---|---|---|
| I-175 | (Chiral structure shown) | m/z 458 [M + H]+ 0.86 min | |

TABLE 45-continued

| Compound No. | Chemical structure | LC/MS*1 | NMR (1H-NMR (d6-DMSO) δ) |
|---|---|---|---|
| I-176 | 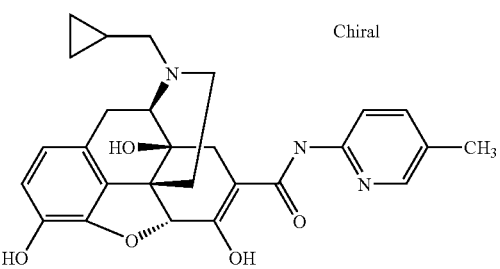 Chiral | ESI: m/z 458 [M + H]+ | |
| I-177 | 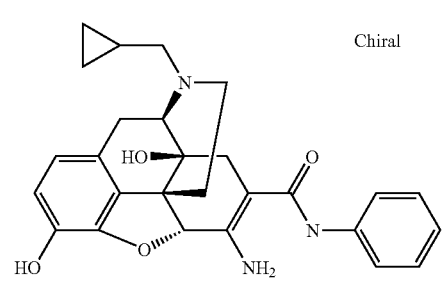 Chiral | m/z 460 [M + H]+ 1.20 min | 0.13-0.17 (m, 2 H), 0.47-0.50 (m, 2 H), 0.87 (m, 1 H), 1.41 (d, J = 10.5 Hz, 1 H), 2.07 (d, J = 15.0 Hz, 1 H), 2.10-2.25 (m, 2 H), 2.32 (dd, J = 5.7, 6.9 Hz, 1 H), 2.45 (dd, J = 5.7, 6.0 Hz, 1 H), 2.63 (dt, J = 6.3, 11.7, 2 H), 3.05 (d, J = 18.3 Hz, 1 H), 3.19 (d, J = 6.0 Hz, 1 H), 4.67 (brs, 1 H), 4.75 (s, 1 H), 6.51 (d, J = 8.1 Hz, 1 H), 6.57 (d, J = 8.1 Hz, 1 H), 6.96 (t, J = 7.5 Hz, 1 H), 7.21 (t, J = 8.4 Hz, 1 H), 7.25 (d, J = 3.6 Hz, 2 H), 7.52 (d, J = 7.5 Hz, 2 H), 8.38 (brs, 1 H), 9.07 (brs, 1 H) |

TABLE 46

| Compound No. | Chemical structure | LC/MS*1 | NMR (1H-NMR (d6-DMSO) δ) |
|---|---|---|---|
| I-178 | 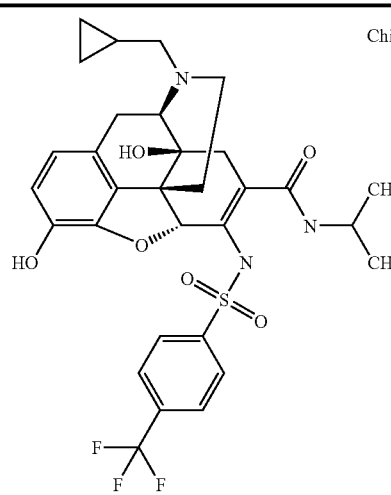 Chiral | m/z 636 [M + H]+ 1.11 min | 0.11-0.13 (m, 2 H), 0.46-0.51 (m, 2 H), 0.86 (m, 1 H), 0.95 (d, J = 6.6 Hz, 6 H), 1.46 (d, J = 11.1 Hz, 1 H), 1.87 (d, J = 18.0 Hz, 1 H), 2.11-2.63 (m, 7 H), 2.25 (s, 3 H), 3.03 (d, J = 17.4 Hz, 1 H), 3.18 (brs, 1 H), 3.84 (q, J = 7.2 Hz, 1 H), 4.71 (brs, 1 H), 5.45 (brs, 1 H), 6.50 (brs, 1 H), 6.57 (brs, 1 H), 7.61-8.19 (m, 4 H), 9.03 (brs, 1 H), 10.7 (brs, 1 H), 12.7 (brs, 1 H) |

TABLE 46-continued

| Compound No. | Chemical structure | LC/MS*1 | NMR (1H-NMR (d6-DMSO) δ) |
|---|---|---|---|
| I-179 | (structure) | Chiral m/z 581 [M + H]+ 1.06 min | 0.11-0.13 (m, 2 H), 0.46-0.51 (m, 2 H), 0.86 (m, 1 H), 0.95 (d, J = 6.6 Hz, 6 H), 1.46 (d, J = 11.1 Hz, 1 H), 1.87 (d, J = 18.0 Hz, 1 H), 2.09 (s, 3 H), 2.11-2.63 (m, 7 H), 3.03 (d, J = 17.4 Hz, 1 H), 3.18 (brs, 1 H), 3.84 (q, J = 7.2 Hz, 1 H), 4.69 (brs, 1 H), 5.45 (brs, 1 H), 6.48 (d, J = 7.2 Hz, 1 H), 6.55 (d, J = 7.2 Hz, 1 H), 7.33 (brd, J = 5.4 Hz, 2 H), 7.54 (brs, 1 H), 7.74 (d, J = 7.5 Hz, 2 H), 9.11 (brs, 1 H), 12.3 (brs, 1 H) |

TABLE 47

| Compound No. | Chemical structure | LC/MS*1 | NMR (1H-NMR (d6-DMSO) δ) |
|---|---|---|---|
| I-180 | (structure) | Chiral m/z 597 [M + H]+ 1.03 min | 0.11-0.13 (m, 2 H), 0.46-0.51 (m, 2 H), 0.85 (m, 1 H), 0.95 (d, J = 6.6 Hz, 6 H), 1.46 (d, J = 9.9 Hz, 1 H), 1.87 (d, J = 17.4 Hz, 1 H), 2.11-2.62 (m, 7 H), 3.01 (d, J = 17.7 Hz, 1 H), 3.15 (d, J = 4.6 Hz, 1 H), 3.82 (s, 3 H), 3.83 (q, J = 5.4 Hz, 1 H), 4.67 (brs, 1 H), 5.44 (s, 1 H), 6.49 (d, J = 8.1 Hz, 1 H), 6.55 (d, J = 8.1 Hz, 1 H), 7.04 (d, J = 8.4 Hz, 2 H), 7.52 (brd, J = 9.3 Hz, 1 H), 7.79 (d, J = 8.4 Hz, 2 H), 9.12 (brs, 1 H), 12.2 (brs, 1 H) |
| I-181 | (structure) | Chiral m/z 502 [M + H]+ 0.35 min | |

TABLE 47-continued

| Compound No. | Chemical structure | LC/MS*1 | NMR (1H-NMR (d6-DMSO) δ) |
|---|---|---|---|
| I-182 | Chiral | m/z 553 [M + H]+ 0.68 min | |
| I-183 | Chiral | m/z 539 [M + H]+ FAB-MS | |

TABLE 48

| Compound No. | Chemical structure | LC/MS*1 | NMR (1H-NMR (d6-DMSO) δ) |
|---|---|---|---|
| I-184 | Chiral | m/z 458 [M + H]+ 0.97 min | |
| I-185 | Chiral | m/z 519 [M + H]+ 0.43 min | |

TABLE 48-continued

| Compound No. | Chemical structure | LC/MS*1 | NMR (1H-NMR (d6-DMSO) δ) |
|---|---|---|---|
| I-186 | (Chiral) | m/z 519 [M + H]+ 1.67 min** | |
| I-187 | (Chiral) | m/z 539 [M + H]+ 0.50 min | |

TABLE 49

| Compound No. | Chemical structure | LC/MS*1 | NMR (1H-NMR (d6-DMSO) δ) |
|---|---|---|---|
| I-188 | (Chiral) | m/z 505 [M + H]+ 0.35 min | |
| I-189 | (Chiral) | m/z 505 [M + H]+ 0.42 min | |

TABLE 49-continued
| Compound No. | Chemical structure | LC/MS*1 | NMR (1H-NMR (d6-DMSO) δ) |
|---|---|---|---|
| I-190 | 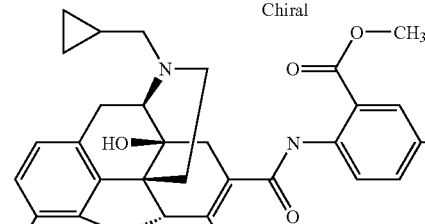 Chiral | m/z 597 [M + H]+ 0.77 min | |
| I-191 | Chiral | m/z 523 [M + H]+ 1.20 min | |
| I-192 | Chiral | m/z 546 [M + H]+ 1.00 min | |
TABLE 50
| Compound No. | Chemical structure | LC/MS*1 | NMR (1H-NMR (d6-DMSO) δ) |
|---|---|---|---|
| I-193 | 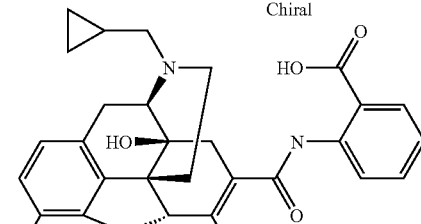 Chiral | m/z 580 [M + H]+ 1.09 min | |
| I-194 | 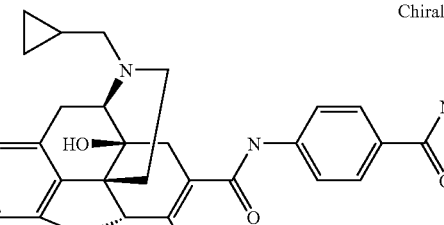 Chiral | m/z 474 [M + H]+ 0.88 min | |

TABLE 50-continued

| Compound No. | Chemical structure | LC/MS*1 | NMR (1H-NMR (d6-DMSO) δ) |
|---|---|---|---|
| I-195 | 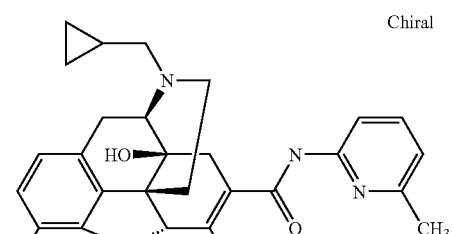 Chiral | m/z 458 [M + H]+ 1.08 min | |
| I-196 | 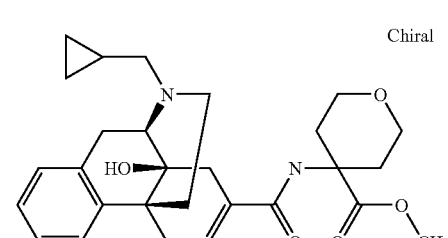 Chiral | | 0.12-0.16 (m, 2 H), 0.46-0.55 (m, 2 H), 0.88 (m, 1 H), 1.43 (d, J = 12.4 Hz, 1 H), 1.65-2.65 (m, 12 H), 2.97-3.70 (m, 6 H), 3.59 (s, 3 H), 4.74 (s 1 H), 6.55 (d, J = 8.0 Hz, 1 H), 6.59 (d, J = 8.0 Hz, 1 H), 7.68 (brs, 1 H), 9.16 (brs, 1 H), 13.5 (brs, 1 H) |

TABLE 51

| Compound No. | Chemical structure | LC/MS*1 | NMR (1H-NMR (d6-DMSO) δ) |
|---|---|---|---|
| I-197 | 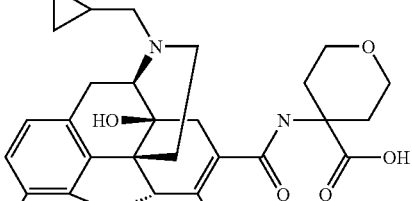 Chiral | | 0.20-0.40 (m, 2 H), 0.46-0.65 (m, 2 H), 0.97 (m, 1 H), 1.54 (d, J = 6.8 Hz, 1 H), 1.80-2.10 (m, 3 H), 2.31-3.69 (m, 15 H), 4.83 (s 1 H), 6.59 (d, J = 8.0 Hz, 1 H), 6.65 (d, J = 8.0 Hz, 1 H), 7.56 (brs, 1 H), 9.29 (brs, 1 H), 13.6 (brs, 1 H) |
| I-198 | 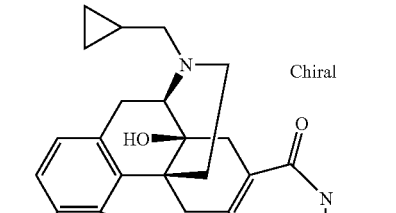 Chiral | m/z 533 [M + H]+ 0.95 min | 0.11-0.13 (m, 2 H), 0.46-0.52 (m, 2 H), 0.86 (m, 1 H), 1.03 (d, J = 6.3 Hz, 3 H), 1.08 (d, J = 6.3 Hz, 3 H), 1.46 (brd, J = 8.4 Hz, 1 H), 1.94 (d, J = 17.7 Hz, 1 H), 2.71-2.60 (m, 7 H), 2.81 (s, 6 H), 3.04 (d, J = 17.1 Hz, 1 H), 3.18 (brs, 1 H), 3.95 (q, J = 5.4 Hz, 1 H), 4.77 (brs, 1 H), 5.45 (s, 1 H), 6.51 (d, J = 7.5 Hz, 1 H), 6.57 (d, J = 7.5 Hz, 1 H), 7.64 (brs, 1 H), 9.14 (brs, 1 H), 12.2 (brs, 1 H) |

TABLE 51-continued

| Compound No. | Chemical structure | LC/MS*1 | NMR (1H-NMR (d6-DMSO) δ) |
|---|---|---|---|
| I-199 | Chiral | m/z 497 [M + H]+ 0.97 min | 0.13-0.15 (m, 2 H), 0.48-0.52 (m, 2 H), 0.86 (m, 1 H), 1.41 (d, J = 11.4 Hz, 1 H), 1.85 (t, J = 7.8 Hz, 2 H), 1.93 (d, J = 16.5 Hz, 1 H), 2.07-2.62 (m, 11 H), 3.05 (d, J = 18.3 Hz, 1 H), 3.21 (d, J = 6.0 Hz, 1 H), 3.59 (s, 3 H), 4.72 (s, 1 H), 4.77 (brs, 1 H), 6.53 (d, J = 8.1 Hz, 1 H), 6.57 (d, J = 8.1 Hz, 1 H), 8.26 (brs, 1 H), 9.15 (brs, 1 H), 14.1 (brs, 1 H) |
| I-200 | Chiral | m/z 553 [M + H]+ 0.47 min | |

TABLE 52

| Compound No. | Chemical structure | LC/MS*1 | NMR (1H-NMR (d6-DMSO) δ) |
|---|---|---|---|
| I-201 | Chiral | m/z 601 [M + H]+ 1.01 min | |
| I-202 | Chiral | m/z 563 [M + H]+ 0.58 min | |

TABLE 52-continued
| Compound No. | Chemical structure | LC/MS*1 | NMR (1H-NMR (d6-DMSO) δ) |
|---|---|---|---|
| I-203 | 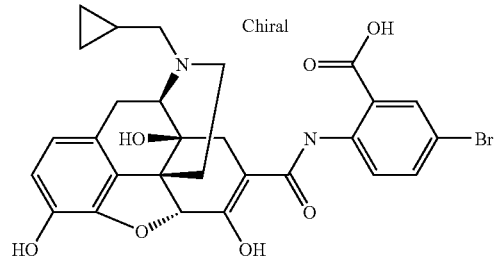 | m/z 583 [M + H]+ 0.54 min | |
| I-204 | 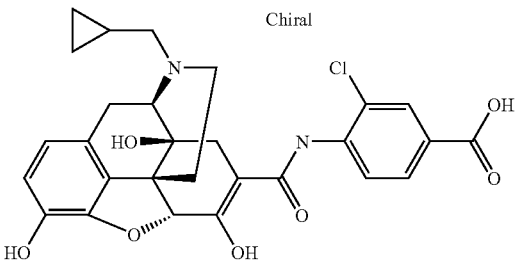 | m/z 539 [M + H]+ 0.33 min | |
| I-205 | 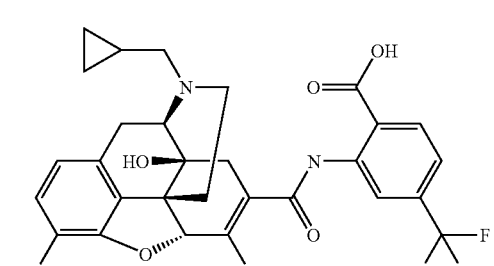 | m/z 573 [M + H]+ 0.62 min | |
TABLE 53
| Compound No. | Chemical structure | LC/MS*1 | NMR (1H-NMR (d6-DMSO) δ) |
|---|---|---|---|
| I-206 | 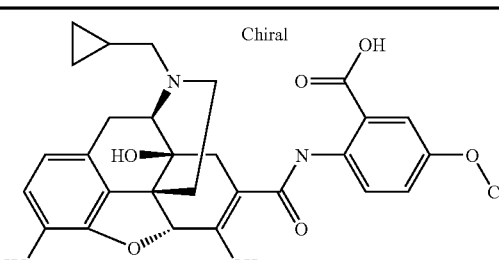 | m/z 535 [M + H]+ 0.41 min | |
| I-207 | 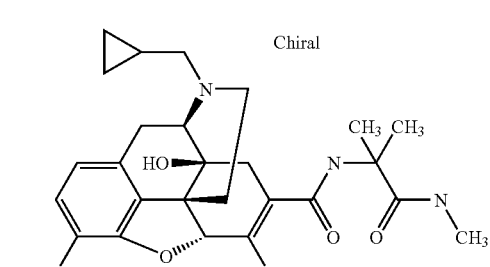 | m/z 484 [M + H]+ 0.32 min | |

TABLE 53-continued

| Compound No. | Chemical structure | LC/MS*1 | NMR (1H-NMR (d6-DMSO) δ) |
|---|---|---|---|
| I-208 | (structure: cyclopropylmethyl-naltrexone core with N-(5-nitropyridin-2-yl) carboxamide) | m/z 507 [M + H]+ 1.05 min | |
| I-209 | (structure: cyclopropylmethyl-naltrexone core with N-(3-acetamidophenyl) carboxamide) | m/z 518 [M + H]+ 1.14 min** | |
| I-210 | (structure: cyclopropylmethyl-naltrexone core with N-(3-chlorophenyl) carboxamide) | m/z 495 [M + H]+ 1.64 min** | |

TABLE 54

| Compound No. | Chemical structure | LC/MS*1 | NMR (1H-NMR (d6-DMSO) δ) |
|---|---|---|---|
| I-211 | (structure: cyclopropylmethyl-naltrexone core with N-(4-acetylphenyl) carboxamide) | m/z 503 [M + H]+ 1.33 min** | |
| I-212 | (structure: cyclopropylmethyl-naltrexone core with N-(quinolin-8-yl) carboxamide) | m/z 512 [M + H]+ 1.67 min** | |

TABLE 54-continued
| Compound No. | Chemical structure | LC/MS*[1] | NMR (1H-NMR (d6-DMSO) δ) |
|---|---|---|---|
| I-213 | 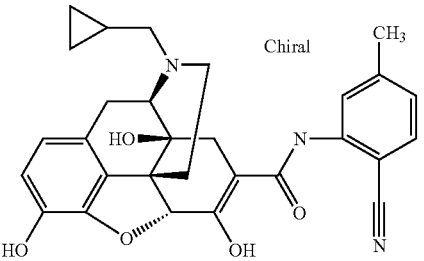 | m/z 500 [M + H]+ 1.41 min** | |
| I-214 | 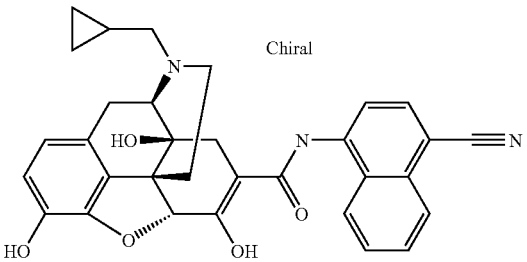 | m/z 536 [M + H]+ 1.69 min** | |
TABLE 55
| Compound No. | Chemical structure | LC/MS*[1] | NMR (1H-NMR (d6-DMSO) δ) |
|---|---|---|---|
| I-215 | 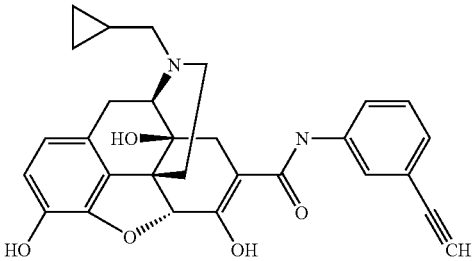 | m/z 485 [M + H]+ 1.60 min** | |
| I-216 | 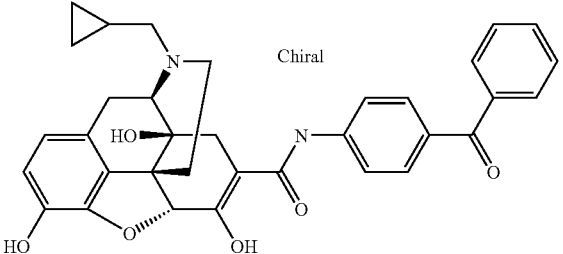 | m/z 565 [M + H]+ 1.82 min** | |
| I-217 | 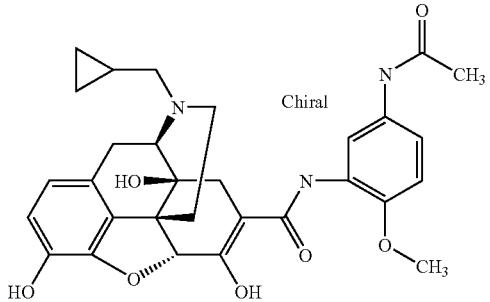 | m/z 548 [M + H]+ 1.17 min** | |

TABLE 55-continued

| Compound No. | Chemical structure | LC/MS*[1] | NMR (1H-NMR (d6-DMSO) δ) |
|---|---|---|---|
| I-218 | 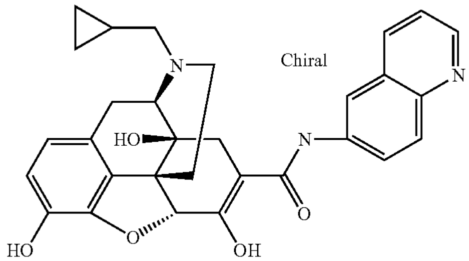 | m/z 512 [M + H]+ 0.95 min** | |
| I-219 | 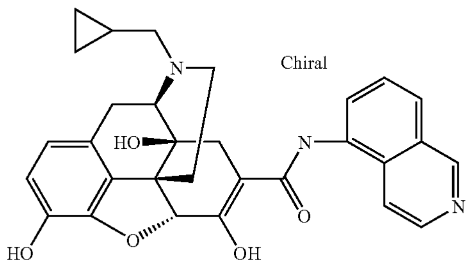 | m/z 512 [M + H]+ 1.66 min** | |
| I-220 | 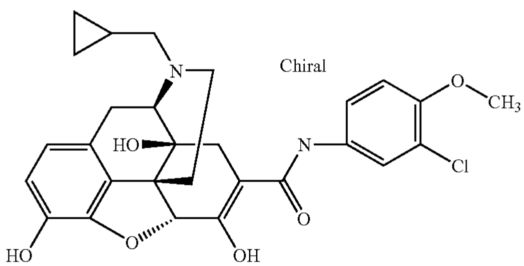 | m/z 525 [M + H]+ 1.60 min** | |
| I-221 | 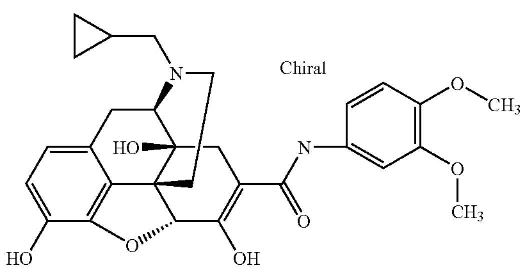 | m/z 521 [M + H]+ 1.35 min** | |

TABLE 56

| Compound No. | Chemical structure | LC/MS*[1] | NMR (1H-NMR (d6-DMSO) δ) |
|---|---|---|---|
| I-222 | 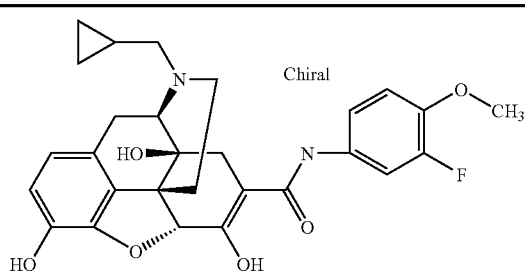 | m/z 509 [M + H]+ 1.57 min** | |

TABLE 56-continued

| Compound No. | Chemical structure | LC/MS*1 | NMR (1H-NMR (d6-DMSO) δ) |
| --- | --- | --- | --- |
| I-223 | 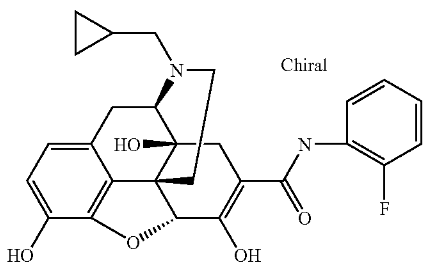 | m/z 479 [M + H]+ 1.50 min** | |
| I-224 | 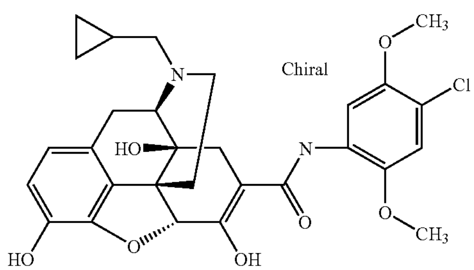 | m/z 555 [M + H]+ 1.76 min** | |
| I-225 | 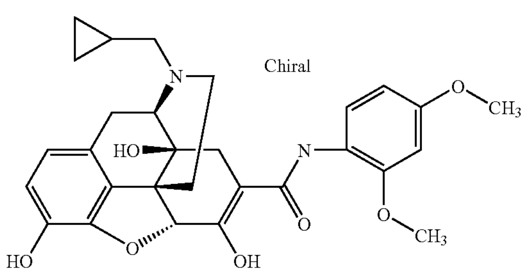 | m/z 519 [M + H]+ 1.67 min** | |
| I-226 | 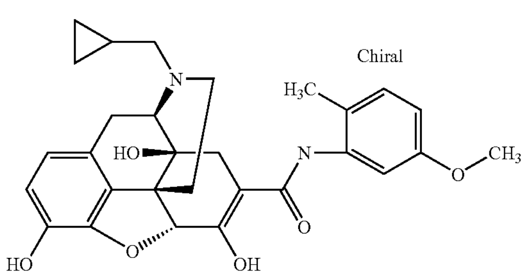 | m/z 505 [M + H]+ 1.53 min** | |
| I-227 | 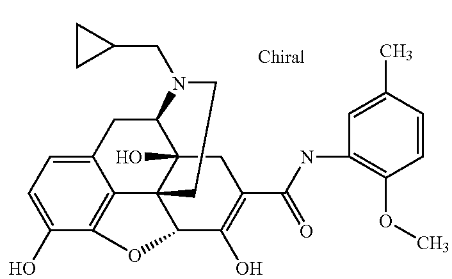 | m/z 505 [M + H]+ 1.64 min** | |

TABLE 56-continued
| Compound No. | Chemical structure | LC/MS*[1] | NMR (1H-NMR (d6-DMSO) δ) |
|---|---|---|---|
| I-228 | 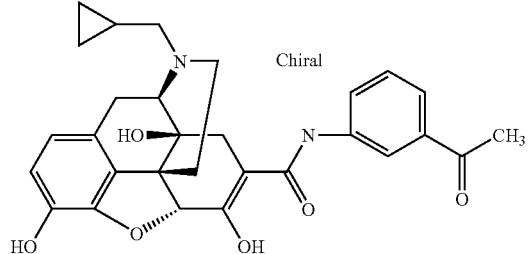 | m/z 503 [M + H]+ 1.38 min** | |
TABLE 57
| Compound No. | Chemical structure | LC/MS*[1] | NMR (1H-NMR (d6-DMSO) δ) |
|---|---|---|---|
| I-229 | 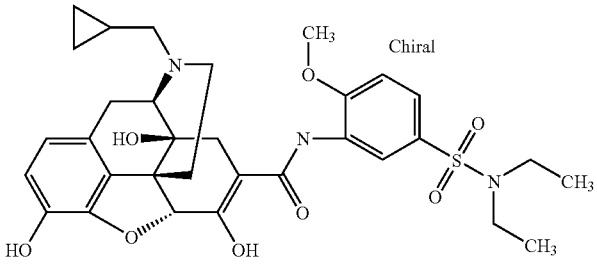 | m/z 626 [M + H]+ 1.74 min** | |
| I-230 | 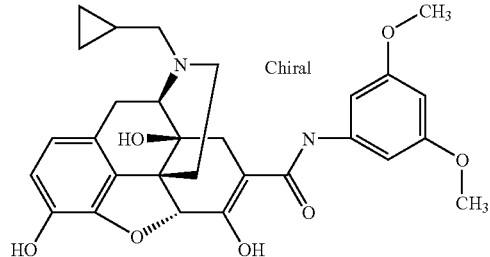 | m/z 521 [M + H]+ 1.56 min** | |
| I-231 | 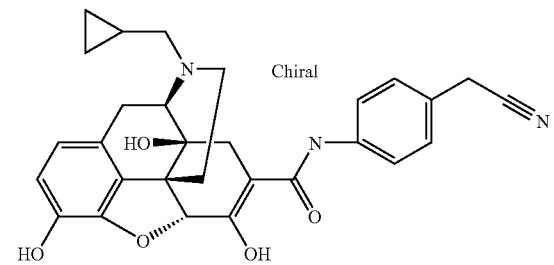 | m/z 500 [M + H]+ 1.40 min** | |
| I-232 | 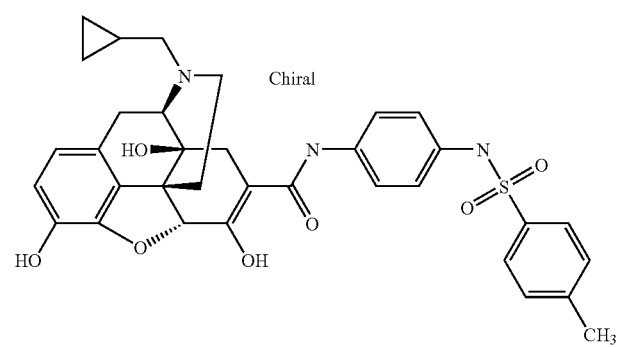 | m/z 630 [M + H]+ 1.72 min** | |

TABLE 57-continued
| Compound No. | Chemical structure | LC/MS*[1] | NMR (1H-NMR (d6-DMSO) δ) |
|---|---|---|---|
| I-233 | 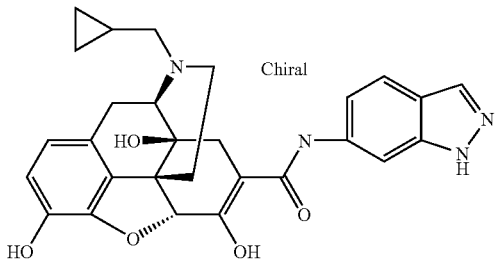 | m/z 501 [M + H]+ 1.25 min** | |
| I-234 | 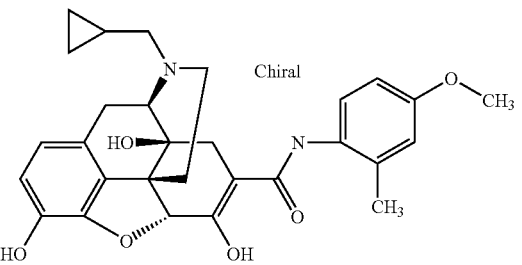 | m/z 505 [M + H]+ 1.46 min** | |
| I-235 | 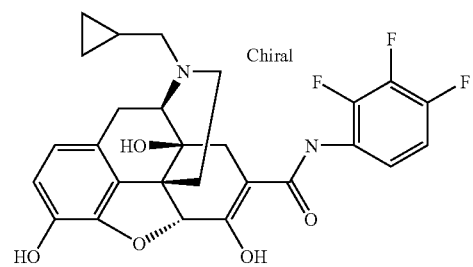 | m/z 515 [M + H]+ 1.56 min** | |
TABLE 58
| Compound No. | Chemical structure | LC/MS*[1] | NMR (1H-NMR (d6-DMSO) δ) |
|---|---|---|---|
| I-236 | 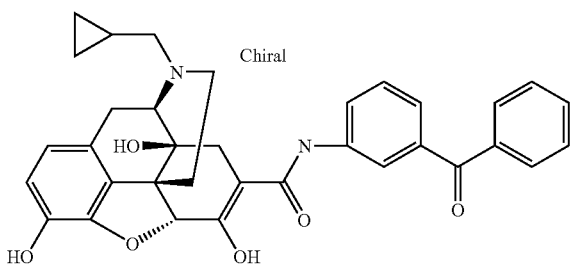 | m/z 565 [M + H]+ 1.77 min** | |
| I-237 | 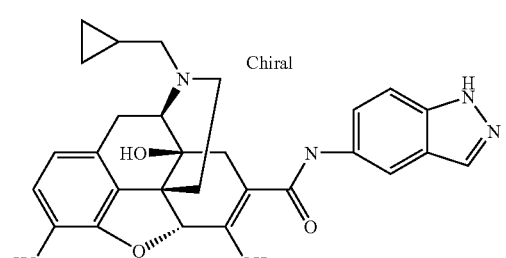 | m/z 501 [M + H]+ 1.17 min** | |

TABLE 58-continued

| Compound No. | Chemical structure | LC/MS*[1] | NMR (1H-NMR (d6-DMSO) δ) |
|---|---|---|---|
| I-238 | 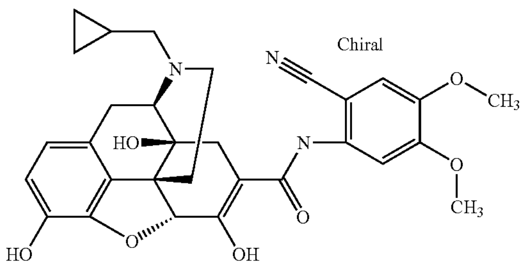 | m/z 546 [M + H]+ 1.29 min** | |
| I-239 | 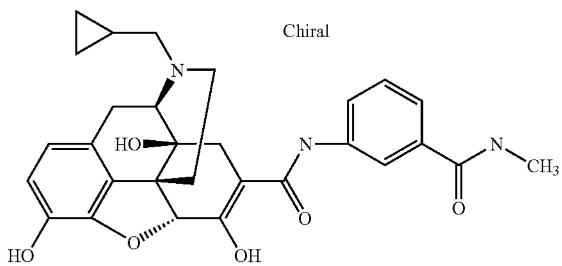 | m/z 518 [M + H]+ 1.21 min** | |
| I-240 | 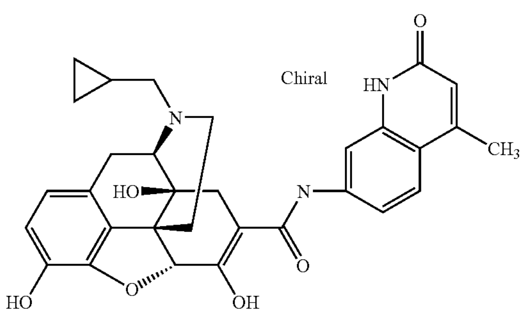 | m/z 542 [M + H]+ 1.31 min** | |
| I-241 | 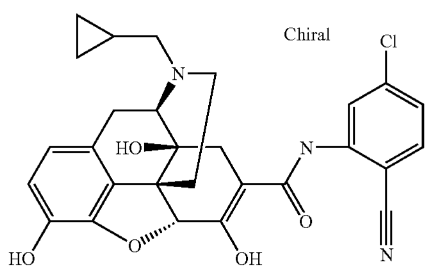 | m/z 520 [M + H]+ 1.50 min** | |
| I-242 | 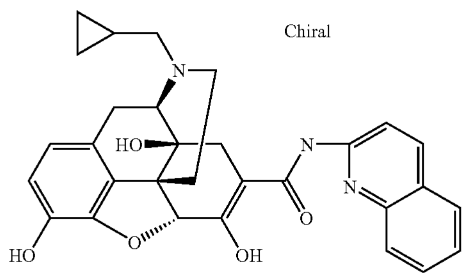 | | |

TABLE 59

| Compound No. | Chemical structure | LC/MS*[1] | NMR (1H-NMR (d6-DMSO) δ) |
|---|---|---|---|
| I-243 | 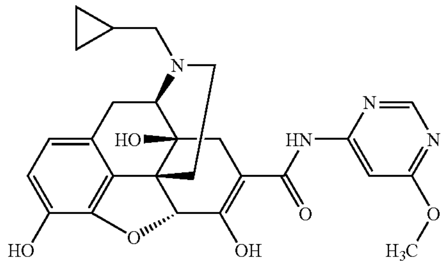 | m/z 493 [M + H]+ 1.05 min | |
| I-244 | 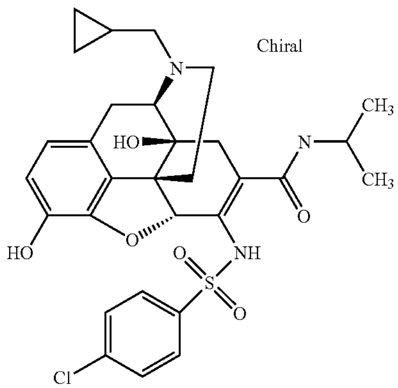 | m/z 460 [M + H]+ 1.02 min | 0.11-0.13 (m, 2 H), 0.48-0.51 (m, 2 H), 0.87 (m, 1 H), 0.95 (d, J = 6.6 Hz, 6 H), 1.48 (d, J = 11.1 Hz, 1 H), 1.88 (d, J = 18.0 Hz, 1 H), 2.10 (s, 3 H), 2.18-2.57 (m, 7 H), 3.04 (d, J = 16.8 Hz, 1 H), 3.19 (brs, 1 H), 3.78 (q, J = 6.9 Hz, 1 H), 4.68 (brs, 1 H), 5.43 (brs, 1 H), 6.49 (d, J = 6.6 Hz, 1 H), 6.51 (d, J = 6.6 Hz, 1 H), 7.35-7.37 (m, 2 H), 7.54 (brs, 1 H), 7.85 (d, J = 6.9 Hz, 2 H), 9.09 (brs, 1 H), 12.4 (brs, 1 H) |
| I-245 | 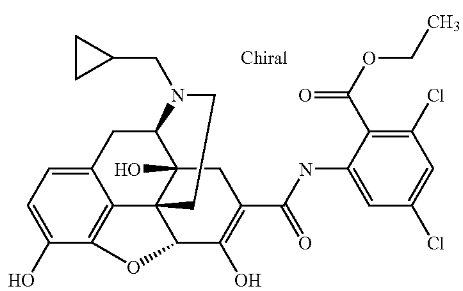 | m/z 601 [M + H]+ 0.76 min | |
| I-246 | 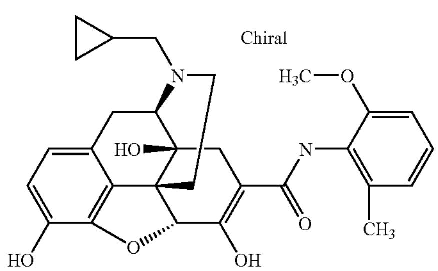 | m/z 505 [M + H]+ 1.38 min** | |
| I-247 | 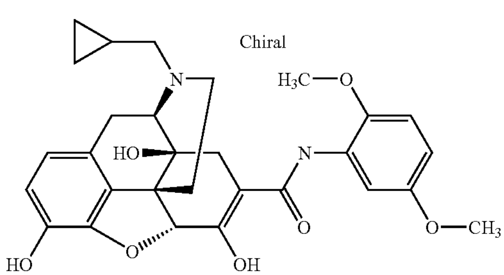 | m/z 521 [M + H]+ 1.58 min** | |

US 8,084,460 B2
175 176
TABLE 60
| Compound No. | Chemical structure | LC/MS*[1] | NMR (1H-NMR (d6-DMSO) δ) |
|---|---|---|---|
| I-248 | 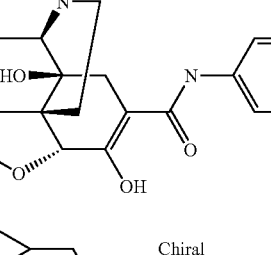 | m/z 493 [M + H]+ 1.69 min** | |
| I-249 | 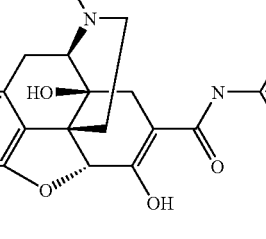 | m/z 479 [M + H]+ 1.55 min** | |
| I-250 | 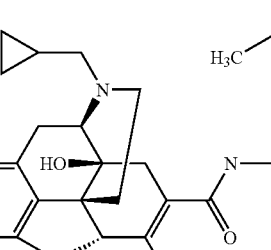 | m/z 519 [M + H]+ 1.74 min** | |
| I-251 | 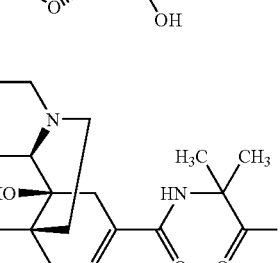 | m/z 512 [M + H]+ 0.38 min | |
| I-252 | 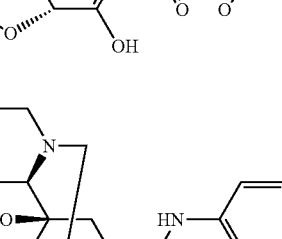 | | 0.10-0.15 (m, 2 H), 0.34-0.38 (m, 2 H), 0.73 (m, 1 H), 1.26 (d, J = 9.6 Hz, 1 H), 1.93-2.54 (m, 10 H), 2.94 (d, J = 18.4 Hz, 1 H), 3.10 (d, J = 6.0 Hz, 1 H), 3.67 (s, 3 H), 3.72 (s, 3 H), 4.58 (s, 1 H), 4.84 (s, 1 H), 6.42 (d, J = 8.0 Hz, 2 H), 6.48 (d, J = 8.0 Hz, 2 H), 6.61 (d, J = 9.3 Hz, 2 H), 6.69 (d, J = 9.2 Hz, 2 H), 7.56 (dd, J = 2.8, 8.8 Hz, 1 H), 7.66 (dd, J = 2.8, 8.8 Hz, 1 H), 8.00 (d, J = 2.4 Hz, 1 H), 8.08 (d, J = 2.0 Hz, 1 H), 8.76 (s, 1 H), 8.97 (s, 1 H), 10.78 (s, 1 H). |

TABLE 61
| Compound No. | Chemical structure |
|---|---|
| I-253 | 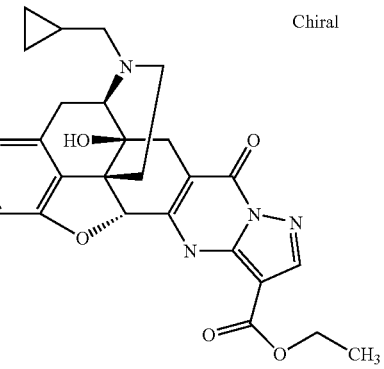 Chiral |
| I-254 | 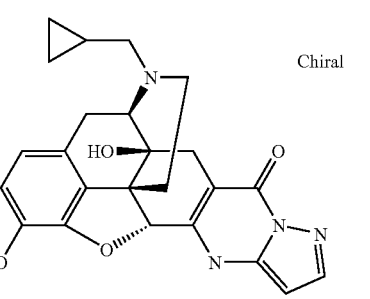 Chiral |
| I-255 | 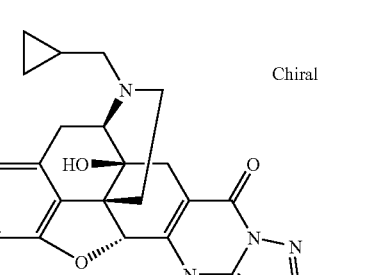 Chiral |
| I-256 | 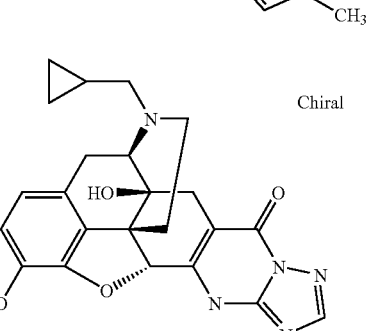 Chiral |
| I-257 | 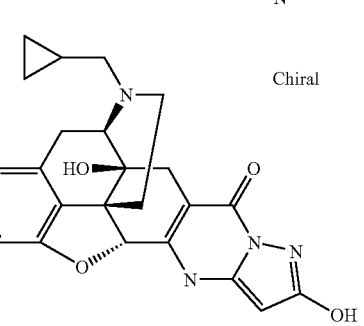 Chiral |
TABLE 62
| Compound No. | Chemical structure |
|---|---|
| I-258 | 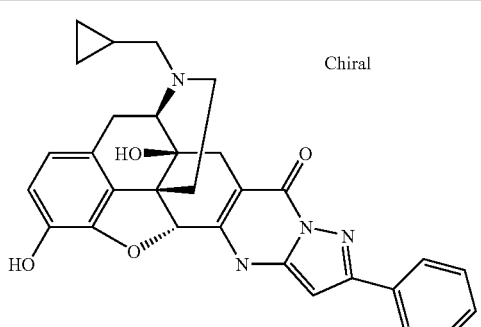 Chiral |
| I-259 | 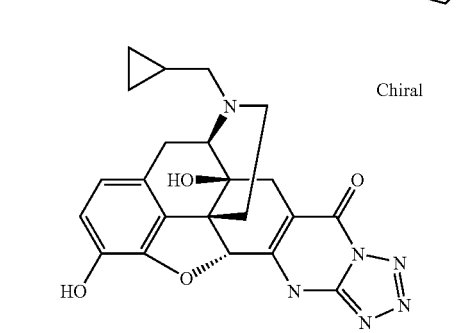 Chiral |
| I-260 | 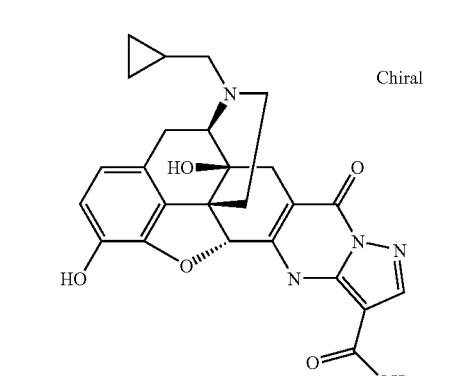 Chiral |
| I-261 | 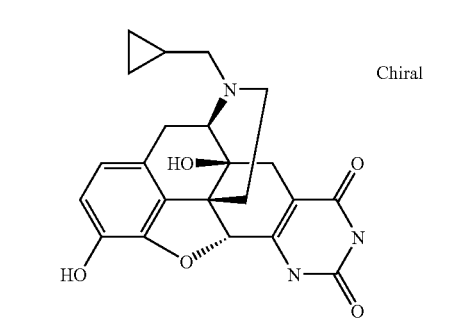 Chiral |

TABLE 62-continued
| Compound No. | Chemical structure |
|---|---|
| I-262 | 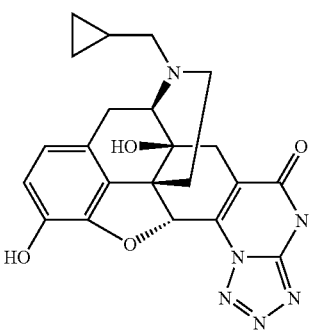 Chiral |
TABLE 63
| Compound No. | Chemical structure |
|---|---|
| I-253 | (structure) Chiral |
| I-254 | (structure) |
| I-255 | (structure) Chiral |
TABLE 64
| Compound No. | Chemical structure | |
|---|---|---|
| I-266 | 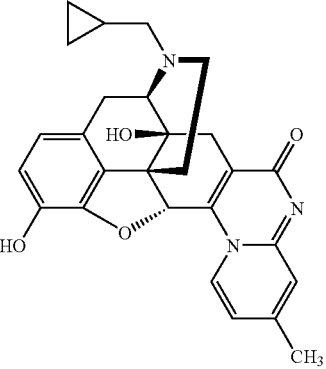 | m/z 457.91 [M + H]+ 0.97 min |
| I-267 | (structure) | m/z 457.91 [M + H]+ 0.62 min |
| I-268 | (structure) | m/z 457.91 [M + H]+ 0.87 min |

TABLE 64-continued

| Compound No. | Chemical structure | |
|---|---|---|
| I-269 | (structure) | m/z 473.91 [M + H]+ 0.69 |
| I-270 | (structure) | m/z 457.91 [M + H]+ 0.97 min |

TABLE 65

| Compound No. | Chemical structure | | LC/MS*[1] |
|---|---|---|---|
| I-271 | (structure) | Chiral | m/z 520 [M + H]+ 1.63 min** |
| I-272 | (structure) | Chiral | m/z 513 [M + H]+ 0.45 min |
| I-273 | (structure) | Chiral | m/z 513 [M + H]+ 0.38 min |

TABLE 65-continued

| Compound No. | Chemical structure | LC/MS*[1] |
|---|---|---|
| I-274 | (Chiral) | m/z 499 [M + H]+ 0.38 min |
| I-275 | (Chiral) | m/z 548 [M + H]+ 0.38 min |

TABLE 66

| Compound No. | Chemical structure | LC/MS*[1] |
|---|---|---|
| I-276 | (Chiral) | m/z 559 [M + H]+ 0.53 min |
| I-277 | (Chiral) | m/z 610 [M + H]+ 0.46 min |

TABLE 66-continued

| Compound No. | Chemical structure | LC/MS*[1] |
|---|---|---|
| I-278 | Chiral | m/z 545 [M + H]+ 0.38 min |
| I-279 | Chiral | m/z 495 [M + H]+ 0.31 min |
| I-280 | Chiral | m/z 545 [M + H]+ 0.97 min |

TABLE 67

| Compound No. | Chemical structure | LC/MS*[1] |
|---|---|---|
| I-281 | Chiral | m/z 531 [M + H]+ 0.92 min |
| I-282 | Chiral | m/z 455 [M + H]+ 0.87 min |

TABLE 67-continued

| Compound No. | Chemical structure | LC/MS*¹ |
|---|---|---|
| I-283 | Chiral | m/z 469 [M + H]+ 0.94 min |
| I-284 | Chiral | m/z 571 [M + H]+ 0.68 min |
| I-285 | Chiral | m/z 509 [M + H]+ 0.32 min |

TABLE 68

| Compound No. | Chemical structure | LC/MS*¹ |
|---|---|---|
| I-286 | Chiral | m/z 471 [M + H]+ 0.32 min |

TABLE 68-continued

| Compound No. | Chemical structure | LC/MS*1 |
|---|---|---|
| I-287 | 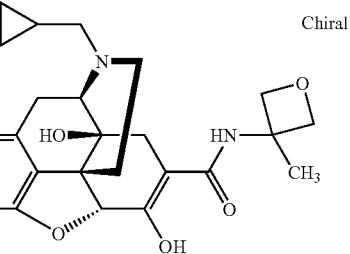 Chiral | m/z 455 [M + H]+ 0.90 min |
| I-288 | 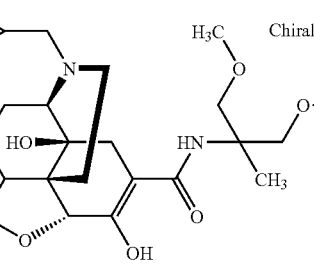 Chiral | m/z 501 [M + H]+ 0.32 min |
| I-289 | 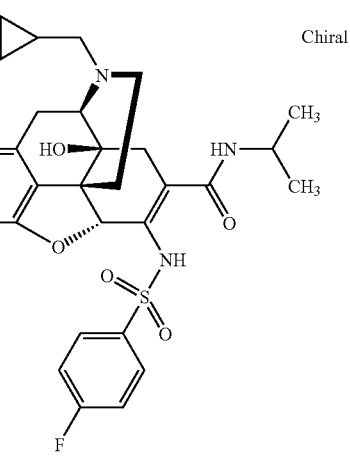 Chiral | m/z 584 [M + H]+ 0.46 min |

(LC/MS conditions of measurements)*1:
Column: Chromolith Flash ROD RP-18e, 25 × 4.6 mm I.D.
Flow Rate: 2 ml/min
UV Detector: 280 nm
Solvent System: [A] = H2O_0.05% HCOOH
[B] = MeOH_0.05% HCOOH
Gradient: 0 min; 90% [A]_10% [B]
0.2 min; 90% [A]_10% [B]
1.0 min; 10% [A]_90% [B]
1.80 min; 10% [A]_90% [B]
Proviso, values with symbol ** follow below conditions of measurement
Column: Phenomenex Luna 5µ C18(2) 100 A, size 50 × 4.60 mm
Gradient: 10%-100% Acetnitrile linear during 3.0 min at 3.0 mL/min

TEST EXAMPLE 1

Binding Assay of Opioid δ Receptor

1) Method of Preparing Membrane Specimen for Binding Assay

A rat cerebrum (Slc: SD) which had been stored at −80° C. was used. To a cerebrum which had been weighed was added a 20-fold amount of ice-cooled 10 mM Tris-HCl buffer (pH 7.0), and the mixture was homogenized (25000 rpm, 30 seconds) with Histocolon (NITI-ON), and centrifuged at 36600×g for 20 minutes. To the resulting pellet was added 15 ml of the same buffer, and the mixture was treated with Histocolon similarly, and centrifuged. This washing work was performed two times. After centrifugation, to the resulting pellet was added 15 mL of a 50 mM Tris-HCl buffer (pH 7.4), and this was treated with Histocolon, and finally resuspended in a 10-fold amount of the same buffer, which was used as a crude membrane fraction (Life Sci. 48, 111-116, 1991). The prepared membrane specimen was frozen and stored at −80° C., and at an assay, the specimen was rapidly thawed, and diluted to about 900 µg/mL with a 50 mM Tris-HCl buffer (pH 7.4) after the centrifugation and Histocolon treatment, and was used in an experiment. For measuring a protein concentration of the membrane specimen, Micro BCA Protein Assay Kit (PIERCE) was used.

2) Method of δ Receptor Binding Assay and Data Analysis

To a solution of 10 μl of the test compound diluted at 10-fold stage was added 10 μl of final 3 nM [$^3$H]-DADLE (51.5 Ci/mmol: PerkinElmer) as a ligand. Into a tube was placed 480 μl of a rat cerebrum membrane fraction to which 100 mM choline chloride, 3 mM MnCl$_2$ and 100 nM DAMGO had been added, and this was incubated at 25° C. for 2 hours. After incubation, this was suction-filtered with a Whatman GF/C filter which had been pre-treated with 0.5% polyethyleneimine, and washed with 2.5 mL of an ice-cooled 10 mM Tris-HCl buffer (pH7.4) four times. After washing, the filter was transferred to a mini vial for liquid scintillation counter, 5 mL of a scintillator (Cleasol I) was added, this was allowed to stand overnight, and the radioactivity was measured for 3 minutes with a liquid scintillation counter Tri-Carb 2200CA (PACKARD). DMSO was used for total binding (Total bound: TB) for data analysis, and 20 μM levallorphan was used for non-specific binding (Non-specific bound: NB), and a Ki value of the test compound was calculated using a KD value (2.93 nM) obtained in advance by Scatchard plot analysis.

Results are shown in Table 69.

TABLE 69

| test compound | Ki (nM) |
|---|---|
| I-3 | 8.76 |
| I-4 | 7.38 |
| I-7 | 7.4 |
| I-10 | 19.92 |
| I-13 | 5.02 |
| I-30 | 5.34 |
| I-39 | 41.8 |
| I-49 | 3.99 |
| I-92 | 5.23 |
| I-118 | 27.65 |
| I-133 | 9.85 |
| I-135 | 9.76 |
| I-145 | 13.87 |
| I-188 | 3.01 |
| I-199 | 12.77 |
| I-208 | 13.28 |
| I-229 | 5.9 |
| I-240 | 11.5 |
| I-243 | 5.2 |
| I-244 | 0.56 |
| I-267 | 41.46 |
| I-283 | 3.73 |
| I-284 | 0.91 |
| I-285 | 5.77 |
| I-286 | 2.46 |
| I-288 | 5.36 |
| I-289 | 0.47 |

From the above results, it is seen that compound (1) has an affinity for an opioid δ receptor.

TEST EXAMPLE 2

Bindind Assay to Opioid μ Receptor

1) Method of Preparing Membrane Specimen for Binding Assay

A rat cerebrum (Slc: SD) which had been stored at −80° C. was used. To a cerebrum which had been weighed was added a 20-fold amount of ice-cooled 10 mM Tris-HCl buffer (pH 7.0), the mixture was homogenized (25000 rpm, 30 seconds) with Histocolon (NITI-ON), and centrifuged at 36600×g for 20 minutes. To the resulting pellet was added 15 ml of the same buffer, and the mixture was treated with Histocoln similarly, and centrifuged. This washing work was performed two times. After centrifugation, to the resulting pellet was added 15 mL of a 50 mM Tris-HCl buffer (pH 7.4), this was treated with Histocolon, and this was finally resuspended in a 10-fold amount of the same buffer, which was used as a crude membrane fraction (Life Sci. 48, 111-116, 1991). The prepared membrane specimen was frozen and stored at −80° C., and at a test, the specimen was rapidly thawed, and diluted to about 900 μg/mL with a 50 mM Tris-HCl buffer (pH 7.4) after the centrifugation and Histocolon treatment, and was used in an experiment. For measuring a protein concentration of the membrane specimen, Micro BCA Protein Assay Kit (PIERCE) was used.

2) Method of μ Receptor Binding Assay and Data Analysis

To a solution of 10 μl of the test compound diluted at 10-fold stage diluted test compound was added 10 μl of final 2 nM [$^3$H]-DAMGO (51.5 Ci/mmol: PerkinElmer) as a ligand, further, 480 μl of a rat cerebrum membrane fraction was placed into a tube, and this was incubated at 25° C. for 2 hours. After incubation, this was suction-filtered with a Whatman GF/C filter which had been pre-treated with 0.5% polyethyleneimine, and washed with 2.5 mL of an ice-cooled 10 mM Tris-HCl buffer (pH 7.4) four times. After washing, the filter was transferred to a mini vial for liquid scintillation counter, 5 mL of a scintillator (Cleasol I) was added, and this was allowed to stand overnight, and the radioactivity was measured for 3 minutes with a liquid scintillation counter Tri-Carb 2200CA (PACKARD). DMSO was used for total binding (Total bound: TB) for data analysis, and 20 μM levallorphan was used for non-specific binding (Non-specific bound: NB), and a Ki value of the test compound was calculated using a KD value (1.72 nM) obtained in advance by Scatchard plot analysis (Anal.Biochem. 107(1), 220-239, 1980).

Results are shown in Table 70.

TABLE 70

| test compound | Ki (nM) |
|---|---|
| I-4 | 5.18 |
| I-10 | 4.05 |
| I-39 | 0.33 |
| I-49 | 16.49 |
| I-118 | 2.29 |
| I-122 | 2.7 |
| I-123 | 1.68 |
| I-124 | 3.9 |
| I-133 | 4.99 |
| I-135 | 1.58 |
| I-138 | 15.53 |
| I-145 | 28.09 |
| I-188 | 17.27 |
| I-199 | 9.45 |
| I-208 | 5.89 |
| I-229 | 1.3 |
| I-240 | 6.85 |
| I-243 | 5.28 |
| I-244 | 11.02 |
| I-267 | 0.84 |
| I-283 | 20.14 |
| I-284 | 1.13 |
| I-285 | 7.29 |
| I-286 | 13.98 |
| I-288 | 14.38 |
| I-289 | 12.95 |

TEST EXAMPLE 3

Mouse Carbon Powder Transport Assay

1) Preparation of Test Diet (Carbon Powder)

Using a 10 w/v % arabic gum aqueous solution, a 5 w/v % active carbon solution was prepared, which was used as a test diet.

2) Animal

A ddY line male mouse (5 to 6 weeks old) was used. The mouse was fasted from about 20 or more hours before assay initiation, and water was given ad lib.

3) Test Compound and Medium

The test compound was dissolved in a solvent (DMAA/Solutol/5% meglumine=15/15/70).

DMAA: N,N-dimethylacetamide
Solutol: Solutol (registered trademark) HS15
Meglumine: D(−)-N-methylglucamine Morphine hydrochloride was dissolved in a physiological saline. The test compound, the above solvent and morphine were all administered at a liquid amount of 10 mL/kg.

4) Assay Method

The test compound 3 mg/kg (test compound administration group) or the solvent (solvent administration group) were subcutaneously administered and, after 15 minutes, amount of 3 mg/kg of morphine was administered to all groups. As a control group, the solvent was subcutaneously administered and, after 15 minutes, a physiological saline was administered.

The test diet 10 mL/kg was orally administered at 15 minutes after administration of morphine. At thirty minutes after administration of the test diet (60 minutes after administration of the test substance), all mice were isolated from esophagus to an ileocecal part near a stomach cardia part. A distance from pyloric part of the stomach to an ileocecal part (full length of small intestine) and a distance until a carbon powder reaching front part (carbon powder movement distance) were measured. The antagonistic activity on the carbon powder transport of inhibitory activity by morphine was calculated as MPE (%) using the following equation. Results are shown in Table 71.

Transport rate (%)=(carbon powder movement distance)/full length of small intestine (cm))×100

M.P.E.(%)={(small intestine transport rate (%) of each individual of test compound administration group−average small intestine transport rate (%) of solvent administration group)/(average small intestine transport rate (%) of control group−average small intestine transport rate (%) of solvent administration group)}×100

TABLE 71

| test compound | M.P.E. (%) |
|---|---|
| I-39 | 52 |
| I-49 | 80 |
| I-118 | 55.6 |
| I-122 | 31.5 |
| I-123 | 44.1 |
| I-124 | 46.6 |
| I-133 | 106.9 |
| I-135 | 59.7 |
| I-138 | 55.8 |
| I-145 | 60.2 |
| I-188 | 74.6 |
| I-199 | 62.8 |
| I-208 | 81.2 |
| I-229 | 39.7 |

TABLE 71-continued

| test compound | M.P.E. (%) |
|---|---|
| I-240 | 36.3 |
| I-243 | 52.6 |
| I-244 | 71.6 |
| I-267 | 60 |
| I-283 | 63.7 |
| I-284 | 79.6 |
| I-285 | 82.5 |
| I-286 | 70.6 |
| I-288 | 101.3 |
| I-289 | 67 |

FORMULATION EXAMPLE 1

A granule containing the following ingredients is prepared.

| Ingredient | Compound represented by formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are passed through a 60 mesh sieve. Corn starch is passed through a 120 mesh sieve. These are mixed with a V-type mixer. To a mixed powder is added a HPC-L (lower viscosity hydroxypropylcellulose) aqueous solution, the materials are kneaded, granulated (extrusion granulation, pore diameter 0.5 to 1 mm), and dried. The resulting dry granule is passed through a sieve using a vibration sieve (12/60 mesh) to obtain a granule.

FORMULATION EXAMPLE 2

A granule for filling into a capsule containing the following ingredients is prepared.

| Ingredient | Compound represented by formula (I) | 15 mg |
|---|---|---|
| | Lactose | 90 mg |
| | Corn starch | 42 mg |
| | HPC-L | 3 mg |
| | | 150 mg |

The compound represented by the formula (I) and lactose are passed through a 60 mesh sieve. Corn starch is passed through a 120 mesh sieve. These are mixed, to a mixed powder is added a HPC-L solution, the materials are kneaded, granulated, and dried. The resulting dry granule is size-adjusted, 150 mg of which is filled into a No. 4 hard gelatin capsule.

FORMULATION EXAMPLE 3

A tablet containing the following ingredients is prepared.

| Ingredient | Compound represented by the formula (I) | 10 mg |
|---|---|---|
| | Lactose | 90 mg |
| | Microcrystalline cellulose | 30 mg |

| | |
|---|---:|
| CMC-Na | 15 mg |
| Magnesium stearate | 5 mg |
| | 150 mg |

The compound represented by the formula (I), lactose, microcrystallinecellulose, CMC-NA (carboxymethylcellulose sodium salt) are passed through a 60 mesh sieve, and mixed. Into a mixed powder is mixed magnesium stearate to obtain a mixed powder for tabletting. The present mixed powder is compressed to obtain 150 mg of a tablet.

FORMULATION EXAMPLE 4

The following ingredients are warmed, mixed, and sterilized to obtain an injectable.

| Ingredient | Compound represented by the formula (I) | 3 mg |
|---|---|---|
| | Nonionic surfactant | 15 mg |
| | Purified water for injection | 1 ml |

INDUSTRIAL APPLICABILITY

The present invention is useful as an agent for alleviating a side effect such as emesis, vomiting and/or constipation.

The invention claimed is:

1. A compound represented by the formula (I):

[Chemical formula 1]

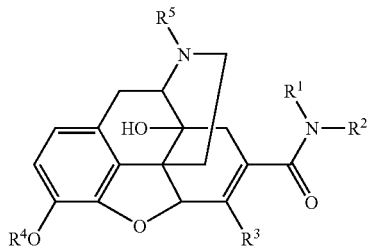

(I)

wherein $R^1$ and $R^2$ are each independently hydrogen, optionally substituted lower alkyl, optionally substituted lower alkenyl, optionally substituted lower alkynyl, optionally substituted lower alkylsulfonyl, optionally substituted acyl, optionally substituted cycloalkyl, optionally substituted cycloalkenyl, optionally substituted aryl, an optionally substituted heterocyclic group, optionally substituted arylsulfonyl, or $R^1$ and $R^2$ are taken together with the nitrogen atom to which they are attached to form optionally substituted heterocycle;

$R^3$ is hydrogen, hydroxy, optionally substituted lower alkyl, optionally substituted lower alkenyl, optionally substituted lower alkynyl, optionally substituted lower alkoxy, mercapto, optionally substituted lower alkylthio, optionally substituted amino, optionally substituted carbamoyl, optionally substituted acyl, optionally substituted acyloxy, optionally substituted aryl, or an optionally substituted heterocyclic group;

a group represented by the formula:

[Chemical Formula 2]

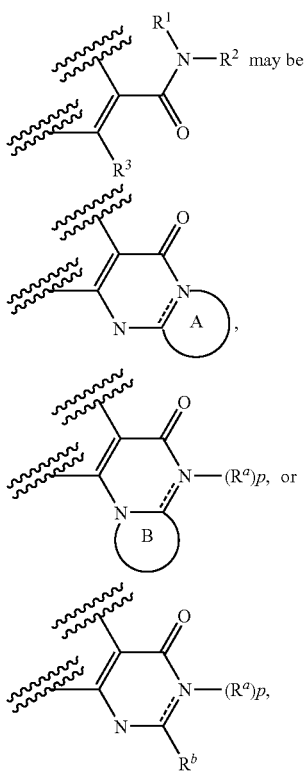

wherein ring A and ring B are each independently optionally substituted nitrogen-containing heterocycle optionally containing additional nitrogen atom, oxygen atom, and/or sulfur atom in the ring;
broken line indicates the presence or the absence of a bond;
when broken line indicates the presence of a bond, p is 0;
when a broken line indicates the absence of a bond, p is 1;
$R^a$ is hydrogen, optionally substituted lower alkyl, optionally substituted lower alkenyl, or optionally substituted lower alkynyl;
and $R^b$ is hydrogen or oxo;
$R^4$ is hydrogen or lower alkyl;
$R^5$ is hydrogen, lower alkyl, cycloalkyl lower alkyl or lower alkenyl, or a pharmaceutically acceptable salt, thereof.

2. The compound according to claim 1, wherein $R^3$ is hydroxy, or a pharmaceutically acceptable salt thereof.

3. The compound according to claim 1, wherein $R^3$ is optionally substituted amino, or a pharmaceutically acceptable salt thereof.

4. The compound in any one of claims 1 to 3, wherein $R^1$ is hydrogen or lower alkyl, $R^2$ is optionally substituted lower alkyl, optionally substituted phenyl, optionally substituted cycloalkyl, or an optionally substituted heterocyclic group, and $R^5$ is cyclopropylmethyl, or a pharmaceutically acceptable salt thereof.

5. A pharmaceutical composition containing a compound in any one of claims 1 to 4, or a pharmaceutically acceptable salt thereof.

6. A composition having an opioid receptor antagonistic activity containing a compound in any one of claims 1 to 4, or a pharmaceutically acceptable salt thereof.

7. A composition for treating and/or preventing emesis, vomiting and/or constipation containing a compound in any one of claims 1 to 4, or a pharmaceutically acceptable salt thereof.

8. A composition for alleviating and/or preventing a side effect induced by a compound having opioid receptor agonistic activity containing a compound in any one of claims 1 to 4, or a pharmaceutically acceptable salt thereof.

9. An agent for treating and/or preventing a side effect according to claim 8, wherein the side effect is emesis, vomiting and/or constipation.

10. A composition for reatment and/or prevention according to claim 8 or 9, wherein the compound having the opioid receptor agonistic activity is morphine, oxycodone, or a pharmaceutically acceptable salt thereof.

11. A composition for analgesic containing
a compound having an opioid receptor agonistic activity,
and an effective amount of compound according to any one of claims 1 to 4, or a pharmaceutically acceptable salt thereof, for alleviating and/or preventing a side effect induced by administrating of the compound having an opioid receptor agonistic activity.

12. A compound represented by the formula (I):

[Chemical formula]

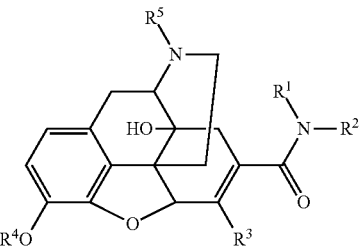

wherein
$R^1$ is hydrogen;
$R^2$ is selected from lower alkyl optionally substituted with lower alkoxy, lower alkoxycarbonyl, or a heterocyclic group optionally substituted with lower alkyl or phenyl; phenyl optionally substituted with lower alkyl, lower alkoxy, halogen, or cyano lower alkyl; cycloalkyl optionally substituted with lower: alkoxycarbonyl or lower alkoxy lower alkyl; or a heterocyclic group optionally substituted with lower alkoxy or oxo;
$R^3$ is hydroxyl;
$R^4$ is hydrogen; and
$R^5$ is cyclopropylmethyl;
or a pharmaceutically acceptable salt thereof.

13. A compound represented by the formula (I):

[Chemical formula]

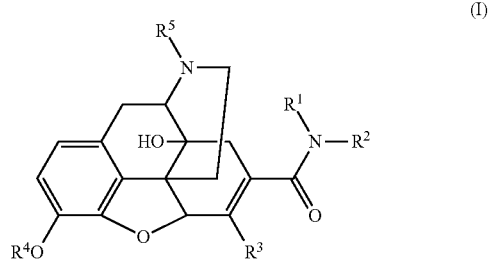

wherein
$R^1$ is hydrogen;
$R^2$ is lower alkyl optionally substituted with lower alkoxy or with a heterocyclic group that is optionally substituted with aryl; phenyl optionally substituted with lower alkyl or with lower alkoxy; cycloalkyl substituted with lower alkylcarbonyl; or a heterocyclic group substituted with lower alkoxy or with aryl;
$R^3$ is hydroxyl;
$R^4$ is hydrogen; and
$R^5$ is cyclopropylmethyl;
or a pharmaceutically acceptable salt thereof.

14. A compound, wherein the compound is

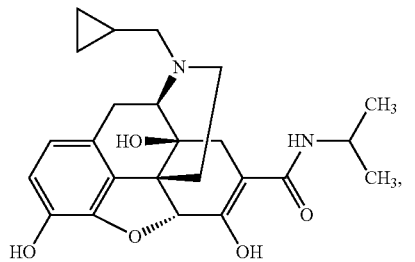

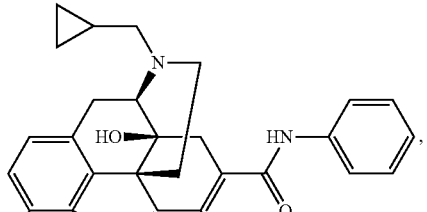

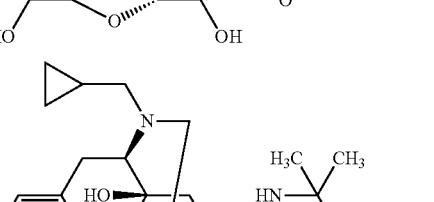

199
-continued
200
-continued
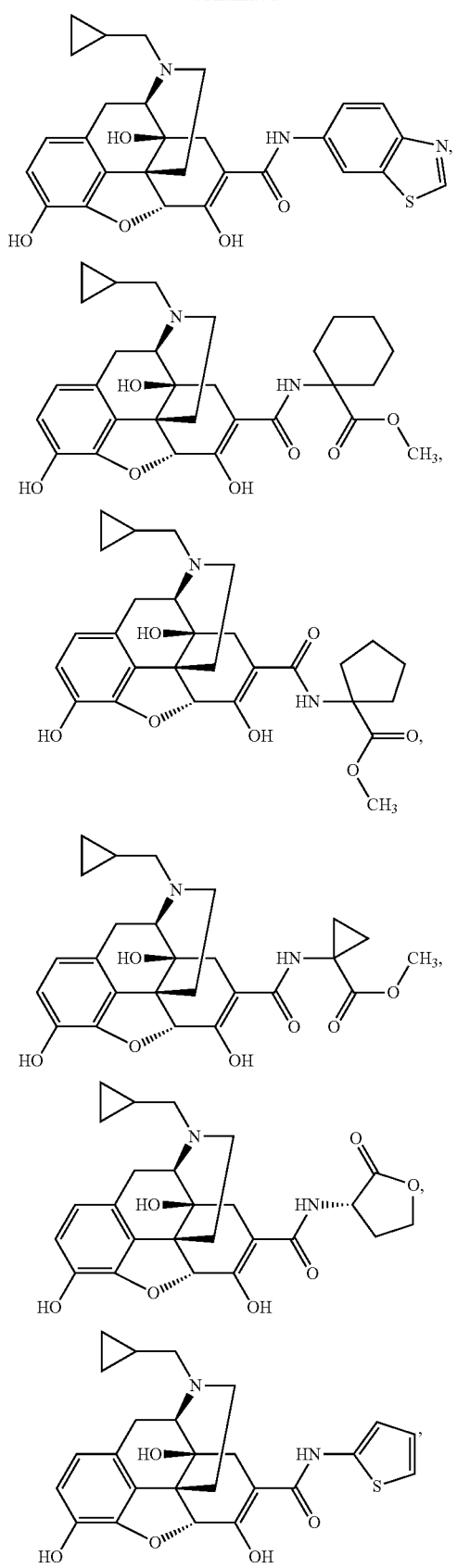
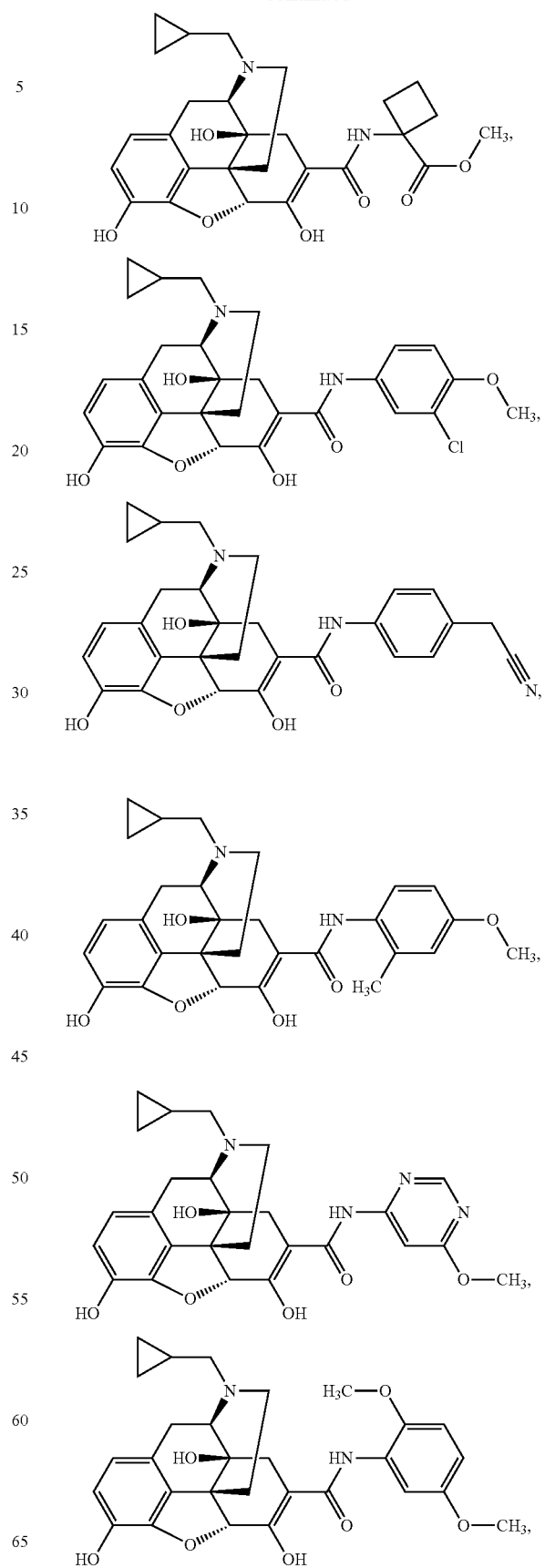

201
-continued
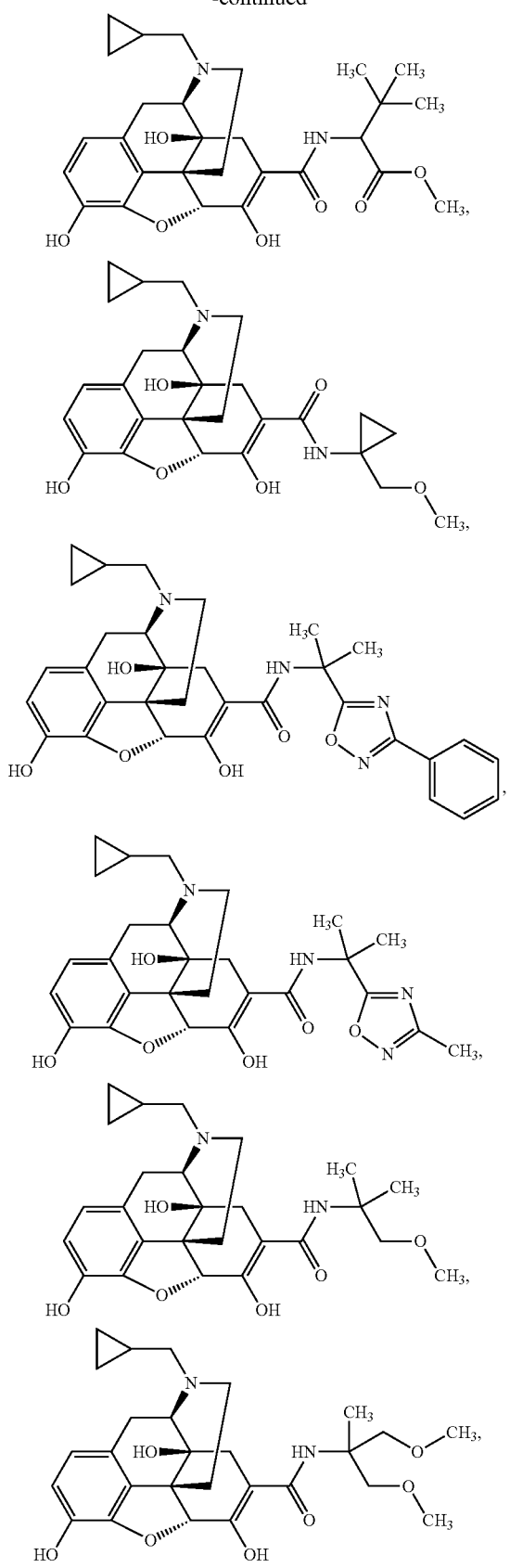
or a pharmaceutically acceptable salt thereof.
202
15. A compound, wherein the compound is
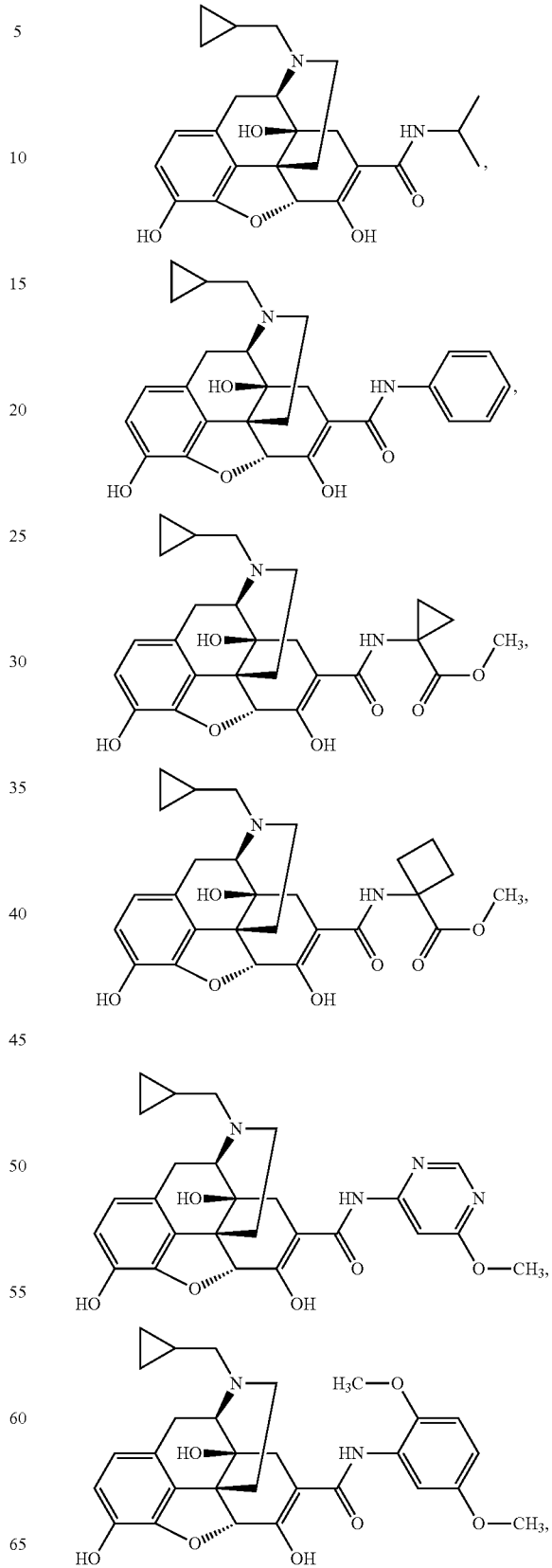

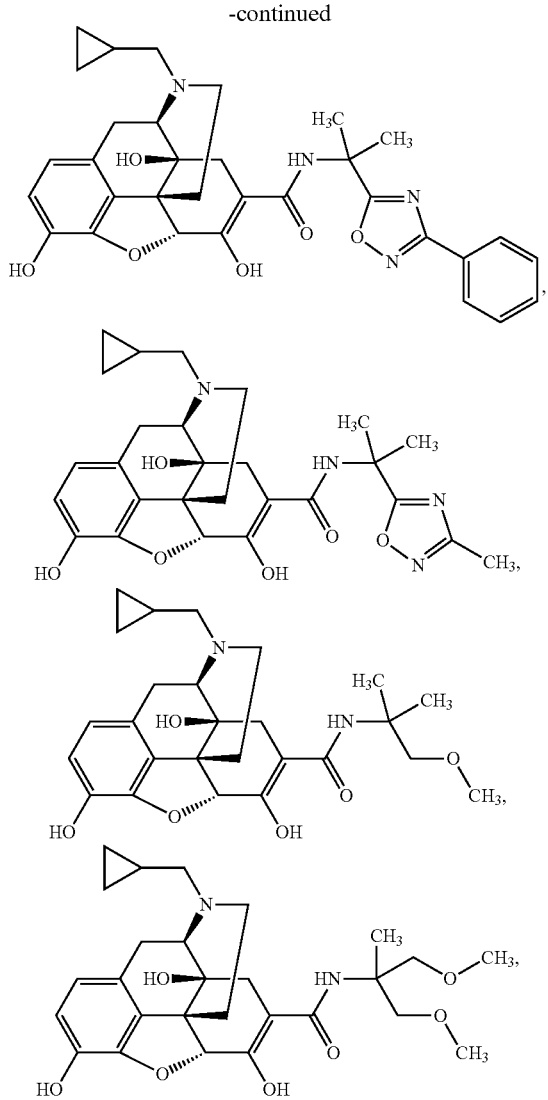

or a pharmaceutically acceptable salt thereof.

16. A composition for analgesic containing:

a compound having an opioid receptor agonistic activity, and an effective amount of compound according to claim 12 or a pharmaceutically acceptable salt thereof, for alleviating and/or preventing a side effect induced by administrating of the compound having an opioid receptor agonistic activity.

17. A composition for analgesic containing:

a compound having an opioid receptor agonistic activity, and an effective amount of compound according to claim 13 or a pharmaceutically acceptable salt thereof, for alleviating and/or preventing a side effect induced by administrating of the compound having an opioid receptor agonistic activity.

18. A composition for analgesic containing:

a compound having an opioid receptor agonistic activity, and an effective amount of compound according to claim 14 or a pharmaceutically acceptable salt thereof, for alleviating and/or preventing a side effect induced by administrating of the compound having an opioid receptor agonistic activity.

19. A composition for analgesic containing:

a compound having an opioid receptor agonistic activity, and an effective amount of compound according to claim 15 or a pharmaceutically acceptable salt thereof, for alleviating and/or preventing a side effect induced by administrating of the compound having an opioid receptor agonistic activity.

* * * * *

UNITED STATES PATENT AND TRADEMARK OFFICE
CERTIFICATE OF CORRECTION

PATENT NO. : 8,084,460 B2
APPLICATION NO. : 11/920851
DATED : December 27, 2011
INVENTOR(S) : Masanao Inagaki et al.

It is certified that error appears in the above-identified patent and that said Letters Patent is hereby corrected as shown below:

On the Title Page, Item (57), in the Abstract, line 14,
"pharmaceutically acceptably salt," should read
--pharmaceutically acceptable salt,--.

In claim 1, column 196, in the structure between lines 3-10,

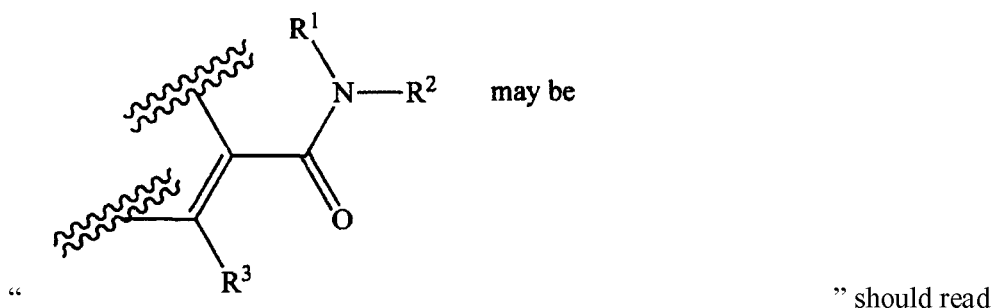

" should read

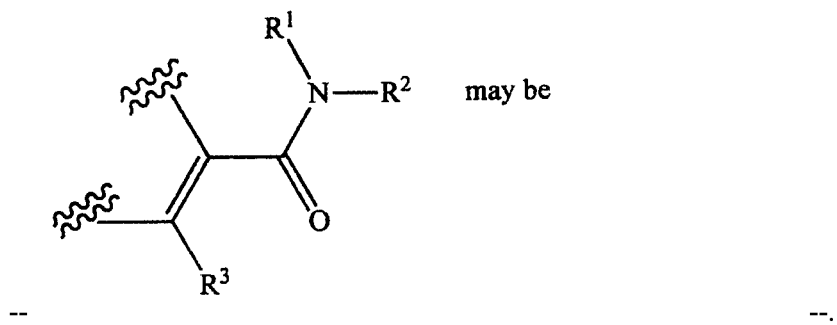

--.

Signed and Sealed this
Seventeenth Day of April, 2012

David J. Kappos
*Director of the United States Patent and Trademark Office*

CERTIFICATE OF CORRECTION (continued)
U.S. Pat. No. 8,084,460 B2

In claim 1, column 196, in the structure between lines 11-17,

" 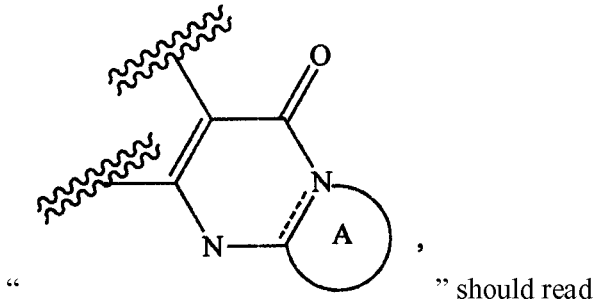 " should read

-- 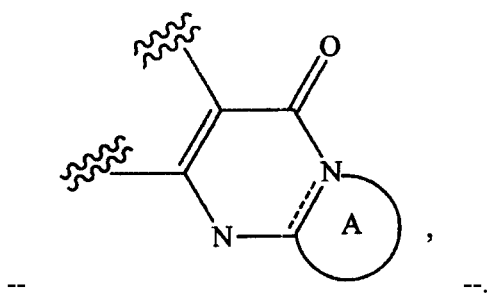 --.

In claim 1, column 196, in the structure between lines 18-2,

" 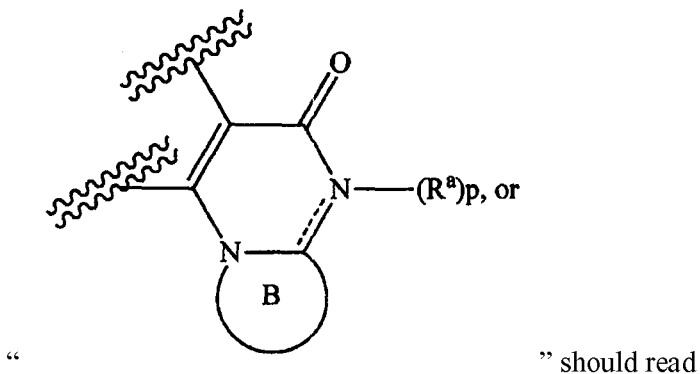 " should read

-- 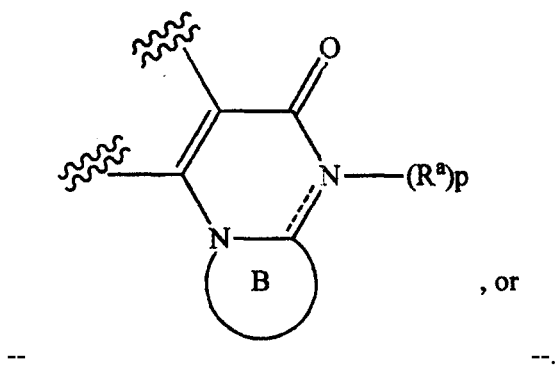, or --.

CERTIFICATE OF CORRECTION (continued)
U.S. Pat. No. 8,084,460 B2

In claim 1, column 196, in the structure between lines 2-33,

" 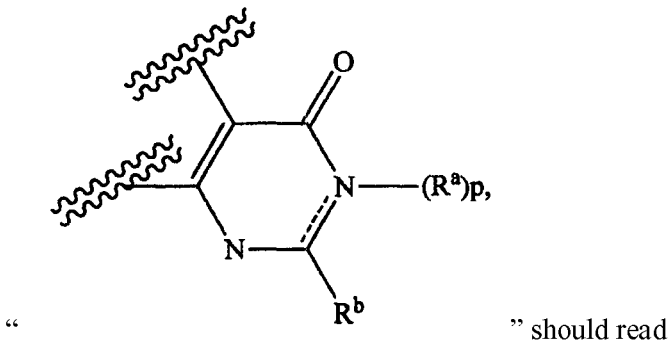 " should read

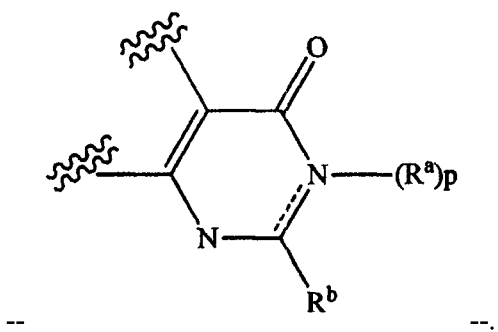

-- --.

In claim 1, column 196, lines 48-49, "acceptable salt, thereof." should read --acceptable salt thereof.--.

In claim 7, column 197, line 3, "claims 1 to 4,or" should read --claims 1 to 4, or--.

In claim 10, column 197, line 12, "forreatment" should read --for treatment--.

In claim 12, column 197, line 60, "lower: alkoxycarbonyl" should read --lower alkoxycarbonyl--.